US007687664B2

(12) United States Patent
Matsuura et al.

(10) Patent No.: US 7,687,664 B2
(45) Date of Patent: Mar. 30, 2010

(54) CARBOXYLIC ACID DERIVATIVE, A SALT THEREOF OR AN ESTER OF THEM, AND MEDICAMENT COMPRISING IT

(75) Inventors: Fumiyoshi Matsuura, Ibaraki (JP); Eita Emori, Ibaraki (JP); Masanobu Shinoda, Ibaraki (JP); Richard Clark, Ibaraki (JP); Shunji Kasai, Ibaraki (JP); Hideki Yoshitomi, Ibaraki (JP); Kazuto Yamazaki, Ibaraki (JP); Takashi Inoue, Ibaraki (JP); Sadakazu Miyashita, Ibaraki (JP); Taro Hihara, Ibaraki (JP)

(73) Assignee: Eisai R&D Management Co., Ltd., Bunkyo-ku, Tokyo (JP)

( * ) Notice: Subject to any disclaimer, the term of this patent is extended or adjusted under 35 U.S.C. 154(b) by 1036 days.

(21) Appl. No.: 10/479,427

(22) PCT Filed: Jun. 4, 2002

(86) PCT No.: PCT/JP02/05511

§ 371 (c)(1), (2), (4) Date: Dec. 3, 2003

(87) PCT Pub. No.: WO02/098840

PCT Pub. Date: Dec. 12, 2002

(65) Prior Publication Data

US 2004/0214888 A1 Oct. 28, 2004

(30) Foreign Application Priority Data

Jun. 4, 2001 (JP) ............................ 2001-168356

(51) Int. Cl.
*C07C 57/34* (2006.01)
*A01N 37/44* (2006.01)
*A01N 43/08* (2006.01)
*A01N 43/10* (2006.01)

(52) U.S. Cl. ........................ 562/489; 514/563; 514/469

(58) Field of Classification Search ................. 548/146, 548/215, 335.5, 365.4, 375; 514/252.1, 265.1, 514/307, 311, 336, 340, 342, 357, 365, 374, 514/378, 399, 400, 406, 469, 522, 538, 557, 514/563, 569; 544/63, 335, 336; 546/231, 546/147, 215; 549/200, 83, 467, 471; 560/12, 560/42, 172, 141; 562/489, 400, 430, 470, 562/490, 456, 469; 564/123, 161, 171, 174
See application file for complete search history.

(56) References Cited

U.S. PATENT DOCUMENTS

| | | | | |
|---|---|---|---|---|
| 5,814,651 | A * | 9/1998 | Duplantier et al. | 514/394 |
| 6,884,821 | B1 * | 4/2005 | Shinoda et al. | 514/563 |
| 7,244,861 | B2 | 7/2007 | Matsuura et al. | |
| 7,253,178 | B2 | 8/2007 | Matsuura et al. | |
| 2004/0102634 | A1 | 5/2004 | Matsuura et al. | |
| 2004/0116708 | A1 | 6/2004 | Harada et al. | |
| 2004/0138271 | A1 | 7/2004 | Matsuura et al. | |
| 2005/0014833 | A1 | 1/2005 | Clark et al. | |

FOREIGN PATENT DOCUMENTS

| | | | | |
|---|---|---|---|---|
| JP | 9-48771 | A | | 2/1997 |
| JP | 11152269 | A | * | 6/1999 |
| WO | WO99/04815 | A1 | | 2/1999 |
| WO | WO99/16758 | A1 | | 4/1999 |
| WO | WO99/18066 | A1 | | 4/1999 |
| WO | WO-99/36393 | A1 | | 7/1999 |
| WO | WO00/64876 | A1 | | 11/2000 |
| WO | WO00/64888 | A1 | | 11/2000 |
| WO | WO00/75103 | A1 | | 12/2000 |
| WO | WO01/25181 | A1 | | 4/2001 |
| WO | WO-01/25189 | A1 | | 4/2001 |
| WO | WO 0125181 | A1 | * | 4/2001 |
| WO | WO01/38325 | A1 | | 5/2001 |
| WO | WO-02/12210 | A1 | | 2/2002 |
| WO | WO-02/34711 | A1 | | 5/2002 |
| WO | WO-02/42273 | A2 | | 5/2002 |
| WO | WO-02/100812 | A1 | | 12/2002 |
| WO | WO-03/055867 | A1 | | 7/2003 |

OTHER PUBLICATIONS

Timothy M Willson, Peter J Brown, Daniel D Sternbach and Brad R Henke The PPARs: From Orphan Receptors to Drug Discovery Journal of Medicinal Chemistry vol. 43, No. 4 Feb. 24, 2000.*

Chinyu, G. S. et al., A novel therapy for colitis utilizing PPAR-gamma ligands to inhigit the epithelial inflammatory response, 1999, The Journal of Clinical Investigation, vol. 104, No. 4, pp. 386.*

Fruchart, J. et al. Peroxisome proliferator-activated receptor-alpha activators regulate gene governing lippoprotein metabolism, vascular inflammation and atheroscierosis, 1999, Current Opinon in Lipidology, vol. 10, pp. 245.*

Na, H-K. et al., Peroxisome proliferator-activated receptor gamma (PPAR-gamma) ligands as bifunctional regulators of cell proliferation, Biochemical Pharmacology, vol. 66 pp. 384.*

Lehmann et al., J. of Bio. Chem., vol. 270, No. 22, pp. 12953-12956, (1995).

(Continued)

*Primary Examiner*—Porfirio Nazario-Gonzalez
*Assistant Examiner*—Yate' K Cutliff
(74) *Attorney, Agent, or Firm*—Birch, Stewart, Kolasch & Birch, LLP

(57) ABSTRACT

The present invention provides novel carboxylic acid derivatives useful as an insulin sensitizer, a salt thereof or a hydrate of them, and a medicament comprising the derivative as the active ingredient. Specifically, it provides a carboxylic acid derivative represented by the following formula (I):

(I)

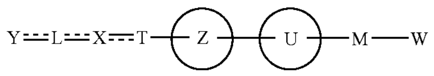

(wherein Y, L, X, T, Z, U, M and W are defined in the specification) and a salt thereof, and ester thereof or a hydrate of them.

25 Claims, No Drawings

OTHER PUBLICATIONS

Willson et al., J. of Medicinal Chem., vol. 43, No. 4, pp. 527-550, (2000).

Barger et al., TCM, vol. 20, No. 6, pp. 238-245, (2000).

Hulin et al., Current Pharm. Design, vol. 2, pp. 85-102, (1996).

Buckle et al., Bio. & Med. Chem. Letters, vol. 6 No. 17, pp. 2121-2126, (1996).

Bastie et al., J. of Bio. Chem., vol. 274, No. 31, pp. 21920-21925, (1999).

Demers et al., Journal of the American Pharmaceutical Association, Scientific Edition, vol. 41, No. 2, 1952, pp. 61-65.

Vasil'eva et al., Database Calpus, "Synthesis and Biological activity of acyl derivatives of 4-aminoantipyrine", 1984, XP002450796.

Aboul-Enein et al., Database Calpus, "Synthesis and biological activity of dibenz[c,e]azepines", 1990, XP002450797.

Richter et al., Tetrahedron Letters, vol. 39, 1998, pp. 8747-8750.

* cited by examiner

CARBOXYLIC ACID DERIVATIVE, A SALT THEREOF OR AN ESTER OF THEM, AND MEDICAMENT COMPRISING IT

TECHNICAL FIELD

The present invention relates to a novel carboxylic acid compound useful for prevention or treatment of hypertension, hyperlipemia and inflammatory disease, a salt thereof or a hydrate of them, and to a medicament comprising it.

PRIOR ART

Diabetes mellitus refers to a durable hyperglycemic condition attributable to the absolute or relative shortage of intrinsic insulin (blood glucose-depressing hormone produced and secreted from Langerhans islet β cells in the pancreas), and in this disease, metabolic abnormalities caused by this condition appear as various morbid states.

Diabetes mellitus is classified roughly into insulin dependent diabetes mellitus (IDDM) that is type 1 diabetes mellitus, for treatment of which insulin administration is absolutely necessary, non insulin dependent diabetes mellitus (NIDDM) that is type 2 diabetes mellitus, and other diabetes mellitus (secondary diabetes mellitus; diabetes mellitus occurs as one symptom of other diseases).

In particular, as life-style is modernized, NIDDM is rapidly increased due to overeating and lack of exercise, thus causing a social problem. While IDDM occurs mainly in infants, NIDDM occurs in middle-aged or elderly persons, to account for the majority of diabetes mellitus in Japan. It is said that NIDDM occurs owing to insulin function-suppressing factors (insulin resistance) such as overeating, lack of exercise, obesity and stress in addition to hereditary factors.

Since excessive intake of calories and obesity resulting from lack of exercise are related to diabetes mellitus as described above, the therapy is based on 3 kinds of therapies, that is, dietary therapy, exercise therapy and chemotherapy.

However, there are not a few cases where dietary therapy and exercise therapy are hardly to conduct because of an increase in the number of persons of advanced age in this aging society in recent years.

In chemotherapy of NIDDM, sulfonyl urea (SU) medicines such as Tolbutamide, Chlorpropamide and Tolazamide and Biguanide (BG) medicines such as Metformin hydrochloride and Buformin have been used as oral blood glucose depressants, but the morbid state of NIDDM is characterized by insulin deficiency and insulin resistance, and it cannot be said that the SU medicines stimulating insulin secretion from pancreatic β cells are effective therapeutic medicines for patients with NIDDM condition, where the insulin secretion potential is well but adequate blood glucose control is not achieved in target organs due to insulin registance, thus permitting hyperglycemia. Further, the BG medicines may permit the onset of lactic acid acidosis, so use of such medicines is limited to a certain extent. Further, these chemicals often caused severe hypoglycemia as a side effect.

To solve these problems, development of chemicals with a new working mechanism is advancing, and thiazolidine derivatives such as Troglitazone, Pioglitazone and Rosiglitazone are called insulin sensitizers, and these chemicals recently attract attention because they can ameliorate insulin resistance (or enhance the action of insulin) and lower blood glucose without promoting secretion of insulin from the pancreas.

It has been revealed that these thiazolidine-type chemicals induce differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953-12956, 1995). By the differentiation of preadipocytes, immature and small adipocytes with less secretion of TNFα, FFA and leptin are increased thus resulting in amelioration of insulin resistance.

Thiazolidine derivatives such as the above Troglitazone, Pioglitazone and Rosiglitazone also act as agonists for PPARγ, to exhibit the effect of ameliorating insulin resistance.

Besides PPARγ, PPAR subtypes such as α, β(δ) etc. have been found, any of which regulate expression of genes involved in lipid metabolism. The homology of each subtype among different biological species is higher than the homology of these subtypes in the same species, and with respect to distribution of each subtype in tissues, PPARγ is located substantially in adipose tissues while PPARα occurs mainly in the liver, heart and kidney, and therefore it was considered that each subtype has an independent function. In recent years, it has been revealed that PPARγ mainly mediates lipid anabolism by promoting expression of a group of genes for LPL, acyl-CoA carboxylase, GPDH etc. to convert glucose into lipid and storing the lipid, while PPARα mediates lipid catabolism by regulating expression of a gene group involved in intake of fatty acids into cells and oxidation thereof to decompose lipid.

Moreover, researches concerning relationships between particular subtypes of PPAR and various diseases have been widely conducted in recent years (J.Med.Chem., 2000, 43(4), 527-550; Trends Cardiovasc. Med., 2000, 10, p 238-245).

As thiazolidine derivatives acting as PPARγ and α dual agonists, compounds disclosed in e.g. JP-A 9-48771 are known.

Further, some compounds are known as insulin sensitizers having a carboxylic acid moiety in their structure (Current Pharmaceutical Design, 2, No. 1, p 85-102, 1996; Bioorganic & Medicinal Chemistry Letters, 6, No. 17, p 2121-2126, 1996; WO200075103; WO9918066; WO9916758).

However, it has been reported that some chemicals acting as PPARγ agonists cause hepatic damage and thus should be carefully used, so chemicals satisfactory in both therapeutic effects and side effects such as toxicity are still not obtained.

Further, compounds having a carboxyl group instead of a thiazolidine group are merely presented in literatures and not marketed. Further, there is no report showing that such compounds can be used as PPARγ and α dual agonists, and as a matter of course, their γ, α and β(δ) triple agonist action is not known. However, it is also estimated that the toxicity of PPARγ agonists described above is the unique one derived from the thiazolidine moiety, and if a compound exhibiting the above action with a new structure in place of the above structure can be found, the compound can be expected to solve the problem of toxicity, and is thus very useful.

The conventional chemicals are still unsatisfactory in respect of neutral fat (triglyceride (TG)) related closely to arteriosclerosis.

Further, the action of PPARβ(δ) to induce differentiation of adipocytes is known (J. Biol. Chem., 274, No. 31, pp. 21920-21925), and by this action, cholesterol levels are reported to be lowered (WO9904815), and if a compound having an agonist action for this subtype can be found, this compound can be expected to exhibit a higher activity than that of the conventional insulin sensitizers and to reduce side effects such as hepatic toxicity.

Furthermore, as a PRAR receptor ligand, diarylic acid derivatives are disclosed in WO00/64888A and triarylic acid derivatives in WO00/64876A.

From the foregoing aspects, there is demand for development of excellent chemicals.

DISCLOSURE OF THE INVENTION

For the purpose of providing a medicament effective in prevention or treatment of hyperglycemia, which satisfies these various requirements, the present inventors made extensive study and, as a result, they found that a carboxylic acid derivative having a novel structure has an excellent anti-hyperglycemia and anti-hyperlipemia action, thus completed the present invention.

That is, the present invention relates to 1) a carboxylic acid compound represented by the formula:

(I)

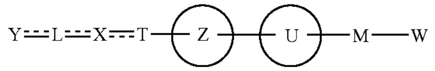

(wherein L represents a single bond, or a C1 to C6 alkylene group, a C2 to C6 alkenylene group or a C2 to C6 alkynylene group, each of which may have one or more substituent groups; M represents a single bond, or a C1 to C6 alkylene group, a C2 to C6 alkenylene group or a C2 to C6 alkynylene group, each of which may have one or more substituent groups; T represents a single bond, or a C1 to C3 alkylene group, a C2 to C3 alkenylene group or a C2 to C3 alkynylene group, each of which may have one or more substituent groups; W represents a carboxyl group; ⎓ represents a single bond or a double bond; X represents a single bond, an oxygen atom, a group represented by —$NR^{X1}CQ^1O$— (wherein $Q^1$ represents an oxygen atom or a sulfur atom; and $R^{X1}$ represents a hydrogen atom, a cyano group, a formyl group, or a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group or a C7 to C19 aromatic acyl group, each of which may have one or more substituent groups, or a C2 to C7 aliphatic alkoxycarbonyl group, or a C7 to C19 aromatic alkoxycarbonyl group), —$OCQ^1NR^{X1}$— ($Q^1$ and $R^{X1}$ each represent the same groups as defined above), —$CQ^1NR^{X1}O$— ($Q^1$ and $R^{X1}$ each represent the same groups as defined above), $ONR^{X1}CQ^1$- ($Q^1$ and $R^{X1}$ each represent the same groups as defined above), —$NR^{X1}CQ^1$- ($Q^1$ and $R^{X1}$ each represent the same groups as defined above), —$CQ^1NR^{X1}$— ($Q^1$ and $R^{X1}$ each represent the same groups as defined above), —$NR^{X1a}CQ^1NR^{X1b}$— ($Q^1$ represents the same group as defined above; and $R^{X1a}$ and $R^{X1b}$ may be the same as or different from each other and each represents a hydrogen atom, a cyano group, a formyl group, or a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group or a C7 to C19 aromatic acyl group, each of which may have one or more substituent groups, a C2 to C7 aliphatic alkoxycarbonyl group, or a C7 to C19 aromatic alkoxycarbonyl group), -$Q^2SO_2$— (wherein $Q^2$ represents an oxygen atom or —$NR^{X10}$— (wherein $R^{X10}$ represents a hydrogen atom, a cyano group, a formyl group, or a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group, or C7 to C19 aromatic acyl group, each of which may have one or more substituent groups, a C2 to C7 aliphatic alkoxycarbonyl group, or a C7 to C19 aromatic alkoxycarbonyl group)) or —$SO_2Q^2$- ($Q^2$ represents the same group as defined above), or a group represented by one of the formulae:

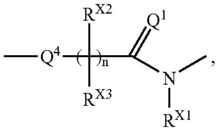,

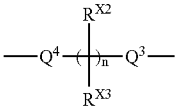,

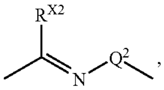,

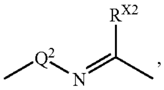,

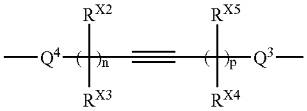,

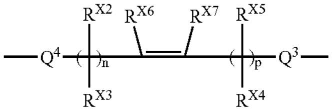,

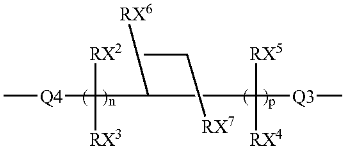 or

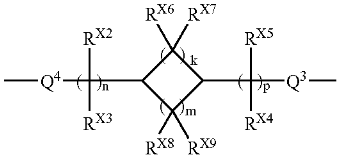

(wherein $Q^1$, $Q^2$ and $R^{X1}$ each represent the same groups as defined above; k is 0 to 5; m is 1 to 5; n and p may be the same as or different from each other and each represents 1 to 5; $R^{X2}$, $R^{X3}$, $R^{X4}$, $R^{X5}$, $R^{X6}$, $R^{X7}$, $R^{X8}$ and $R^{X9}$ may be the same as or different from each other and each represents a hydrogen atom, a hydroxyl group, a cyano group, halogen, a C1 to C6 alkyl group, a C1 to C6 alkoxy group, a C1 to C6 alkylthio group, a C1 to C6 hydroxyalkyl group, a C1 to C6 hydroxyalkoxy group, a C1 to C6 hydroxyalkylthio group, a C1 to C6 aminoalkyl group, a C1 to C6 aminoalkoxy group, a C1 to C6 aminoalkylthio group, a C1 to C6halogenated alkyl group, a C1 to C6 halogenated alkoxy group, a C1 to C6 halogenated alkylthio group, a C2 to C12 alkoxyalkyl group, a C2 to C12 alkoxyalkoxy group, a C2 to C12 alkoxyalkylthio group, a C3 to C7 cycloalkyl group, a C3 to C7 cycloalkyloxy group, a C4 to C13 cycloalkylalkyloxy group, a C3 to C7 cycloalkylthio group, a C2 to C6 alkenyl group, a C2 to C6 alkenyloxy group, a C2 to C6 alkenylthio group, a C2 to C6 alkynyl group, a C2 to C6 alkynyloxy group, a C2 to C6 alkynylthio group, a C6 to C12 aryl group, a C6 to C12 aryloxy group, a C6 to C12 arylthio group, a C7 to C18 alkylaryl group, a C7 to C18 alkylaryloxy group, a C7 to C18 alkylarylthio group, a C7 to C18 aralkyl group, a C7 to C18 aralkyloxy group or a C7 to C18 aralkylthio group, each of which may have one or more substituent groups, or —N ($R^{X11}$) $R^{X12}$— (wherein $R^{X11}$ and $R^{X12}$ may be the same as or different from each other and each represents a hydrogen atom, a cyano group, a formyl group, a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group or a C7 to C19 aromatic acyl group, each of which may have one or more substituent groups, a C2 to C7 aliphatic alkoxycarbonyl group, or a C7 to C19 aromatic alkoxycarbonyl group), provided that $R^{X2}$ and $R^{X3}$, and $R^{X4}$ and $R^{X5}$ may be combined to form a ring; and $Q^3$ and $Q^4$ may be the same as or different from each other and each represents a single bond, an oxygen atom, (O)S(O) or $NR^{X10}$ ($NR^{X10}$ represents the same group as defined above)); Y represents a 5 to 14-membered aromatic group which may have one or more substituent groups and one or more hetero atoms, or a C3 to C7 alicyclic hydrocarbon group; the rings Z and U may be the same as or different from each other and each represents a 5 to 14-membered aromatic group which may have 1 to 4 substituent groups and one or more hetero atoms, and the ring of which may be partially saturated.), or a salt thereof, an ester thereof or a hydrate of them; 2) the carboxylic acid compound according to 1), a salt thereof, an ester thereof or a hydrate of them, wherein in the formula (I), Y is a 5 to 14-membered aromatic group which may have 1 to 4 substituent groups and 1 or more hetero atoms; 3) the carboxylic acid compound according to 1) or 2), a salt thereof, an ester thereof or a hydrate of them, wherein in the formula (I), X represents an oxygen atom, a group represented by —$NR^{X1}CQ^1O$— (wherein $Q^1$ and $R^{X1}$ each represent the same groups as defined above), —$OCQ^1NR^{X1}$— ($Q^1$ and $R^{X1}$ each represent the same groups as defined above), —$NR^{X1}CQ^1$- ($Q^1$ and $R^{X1}$ each represent the same groups as defined above) or —$CQ^1NR^{X1}$— ($Q^1$ and $R^{X1}$ each represent the same groups as defined above), or a group represented by one of the formulae:

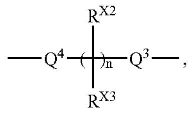
,
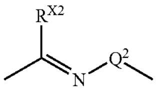
or
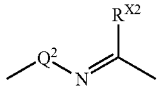

(wherein $Q^1$, $Q^2$, $Q^3$, $Q^4$, k, m, n, p, $R^{X2}$, $R^{X3}$, $R^{X4}$, $R^{X5}$, $R^{X6}$, $R^{X7}$, $R^{X8}$ and $R^{X9}$ each represent the same groups as defined above); 4) the carboxylic acid compound according to any one of 1) to 3), a salt thereof, an ester thereof or a hydrate of them, wherein in the formula (I), X represents an oxygen atom, or a group represented by —$NR^{X1}CQ^1O$— (wherein $Q^1$ and $R^{X1}$ each represent the same groups as defined above), —$OCQ^1NR^{X1}$— ($Q^1$ and $R^{X1}$ each represent the same groups as defined above), —$NR^{X1}CQ^1$- ($Q^1$ and $R^{X1}$ each represent the same groups as defined above) or —$CQ^1NR^{X1}$— ($Q^1$ and $R^{X1}$ each represent the same groups as defined above); 5) the carboxylic acid compound according to any one of 1) to 3), a salt thereof, an ester thereof or a hydrate of them, wherein in the formula (I), L represents a single bond or a C1 to C6 alkylene group which may have one or more substituent groups; X represents a single bond or an oxygen atom; and T represents a C2 to C6 alkynylene group which may have one or more substituent groups; 6) the carboxylic acid compound according to any one of 1) to 3), a salt thereof, an ester thereof or a hydrate of them, wherein in the formula (I), L represents a C2 to C6 alkynylene group which may have one or more substituent groups; X represents a single bond or an oxygen atom; and T represents a single bond or a C1 to C6 alkylene group which may have one or more substituent groups; 7) the carboxylic acid compound according to any one of 1) to 3), a salt thereof, an ester thereof or a hydrate of them, wherein in the formula (I), X represents —$NR^{X1}CQ^1O$— (wherein $Q^1$ represents an oxygen atom; and $R^{X1}$ represents the same group as defined above) or —$OCQ^1NR^{X1}$— ($Q^1$ represents an oxygen atom; and $R^{X1}$ represents the same group as defined above); L represents a single bond or a C1 to C3 alkylene group which may have one or more substituent group; and T represents a single bond or a C1 to C3 alkylene group which may have one or more substituent groups; 8) the carboxylic acid compound according to any one of 1) to 3), a salt thereof, an ester thereof or a hydrate of them, wherein in the formula (I), X is a group represented by one of the formulae:

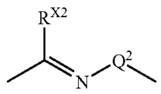
or
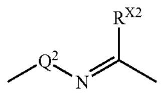

(wherein Q represents an oxygen atom; and $R^{X2}$ represents the same group as defined above); L represents a single bond or a C1 to C3 alkylene group which may have one or more substituent groups; and T represents a single bond or a C1 to C3 alkylene group which may have one or more substituent groups; 9) the carboxylic acid compound according to any one of 1) to 3), a salt thereof, an ester thereof or a hydrate of them, wherein in the formula (I), X is a group represented by the formula:

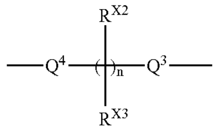

(wherein $Q^3$ and $Q^4$ represent an oxygen atom; and $R^{X2}$ and $R^{X3}$ represent the same groups as defined above, provided that one of $R^{X2}$ and $R^{X3}$ is a group other than hydrogen); L represents a single bond or a C1 to C3 alkylene group which may have one or more substituent groups; T represents a single bond or a C1 to C3 alkylene group which may have one or more substituent groups; 10) the carboxylic acid compound according to any one of 5) to 9), a salt thereof, an ester thereof or a hydrate of them, wherein in the formula (I), M represents a C1 to C6 alkylene group which may have one or more substituent groups; 11) the carboxylic acid compound according to any one of 5) to 10), a salt thereof, an ester thereof or a hydrate of them, wherein in the formula (I), the ring U represents a phenylene group which may have 1 to 4 substituent groups; 12) the carboxylic acid compound according to any one of 5) to 11), a salt thereof, an ester thereof or a hydrate of them, wherein in the formula (I), the ring Z represents a phenylene group which may have 1 to 4 substituent groups; 13) the carboxylic acid compound according to any one of 5) to 12), a salt thereof, an ester thereof or a hydrate of them, wherein in the formula (I), the ring Z and the ring U represent a 1,3-phenylene group which may have 1 to 4 substituent groups; 14) the carboxylic acid compound according to any one of 1) to 3), a salt thereof, an ester thereof or a hydrate of them, wherein in the formula (I), X represents —$NR^{X1}CQ^1$- (wherein $Q^1$ represents an oxygen atom; and $R^{X1}$ represents the same group as defined above) or —$CQ^1NR^{X1}$— ($Q^1$ represents an oxygen atom; and $R^{X1}$ represents the same group as defined above); L represents a single bond or a C1 to C3 alkylene group which may have one or more substituent groups; and T represents a single bond or a C1 to C3 alkylene group which may have one or more substituent groups; 15) the carboxylic acid compound according to any one of 1) to 3), a salt thereof, an ester thereof or a hydrate of them, wherein in the formula (I), L represents a single bond or a C1 to C6 alkylene group which may have one or more substituent groups; X represents an oxygen atom; and T represents a C1 to C6 alkylene group which may have one or more substituent groups; 16) the carboxylic acid compound according to 14) or 15), a salt thereof, an ester thereof or a hydrate of them, wherein in the formula (I), M represents a C1 to C6 alkylene group which may have one or more substituent groups; 17) the carboxylic acid compound according to any one of 14) to 16), a salt thereof, an ester thereof or a hydrate of them, wherein in the formula (I), the ring U represents a phenylene group which may have 1 to 4 substituent groups; 18) the carboxylic acid compound according to any one of 14) to 17), a salt thereof, an ester thereof or a hydrate of them, wherein in the formula (I), the ring z represents a phenylene group which may have 1 to 4 substituent groups; 19) the carboxylic acid compound according to any one of 14) to 18), a salt thereof, an ester thereof or a hydrate of them, wherein in the formula (I), the ring Z and the ring U represent a 1,3-phenylene group which may have 1 to 4 substituent groups; 20) a medicament comprising a carboxylic acid compound represented by the formula:

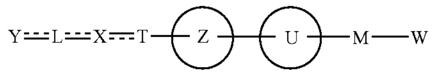

(I)

(wherein L represents a single bond, or a C1 to C6 alkylene group, a C2 to C6 alkenylene group or a C2 to C6 alkynylene group, each of which may have one or more substituent groups; M represents a single bond, or a C1 to C6 alkylene group, a C2 to C6 alkenylene group or a C2 to C6 alkynylene group, each of which may have one or more substituent groups; T represents a single bond, or a C1 to C3 alkylene group, a C2 to C3 alkenylene group or a C2 to C3 alkynylene group, each of which may have one or more substituent groups; W represents a carboxyl group; --- represents a single bond or a double bond; X represents a single bond, an oxygen atom, a group represented by —$NR^{X1}CQ^1O$— (wherein $Q^1$ represents an oxygen atom or a sulfur atom; and $R^{X1}$ represents a hydrogen atom, a cyano group, a formyl group, or a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group or a C7 to C19 aromatic acyl group, each of which may have one or more substituent groups, or a C2 to C7 aliphatic alkoxycarbonyl group, or a C7 to C19 aromatic alkoxycarbonyl group), —$OCQ^1NR^{X1}$— ($Q^1$ and $R^{X1}$ each represent the same groups as defined above), —$CQ^1NR^{X1}O$— ($Q^1$ and $R^{X1}$ each represent the same groups as defined above), $ONR^{X1}CQ^1$- ($Q^1$ and $R^{X1}$ each represent the same groups as defined above), —$NR^{X1}CQ^1$- ($Q^1$ and $R^{X1}$ each represent the same groups as defined above), —$CQ^1NR^{X1}$— ($Q^1$ and $R^{X1}$ each represent the same groups as defined above), —$NR^{X1a}CQ^1NR^{X1b}$— ($Q^1$ represents the same group as defined above; and $R^{X1a}$ and $R^{X1b}$ may be the same as or different from each other and each represents a hydrogen atom, a cyano group, a formyl group, or a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group or a C7 to C19 aromatic acyl group, each of which may have one or more substituent groups, a C2 to C7 aliphatic alkoxycarbonyl group, or a C7 to C19 aromatic alkoxycarbonyl group), -$Q^2SO_2$— (wherein $Q^2$ represents an oxygen atom or —$NR^{X10}$— (wherein $R^{X10}$ represents a hydrogen atom, a cyano group, a formyl group, or a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group, or C7 to C19 aromatic acyl group, each of which may have one or more substituent groups, a C2 to C7 aliphatic alkoxycarbonyl group, or a C7 to C19 aromatic alkoxycarbonyl group)) or —$SO_2Q^2$- ($Q^2$ represents the same group as defined above), or a group represented by one of the formulae:

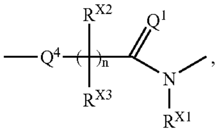
,
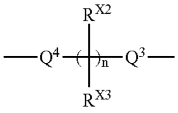
,
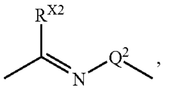
,
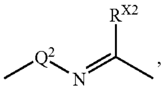
,
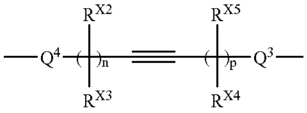
,
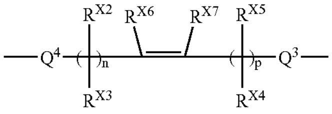
,
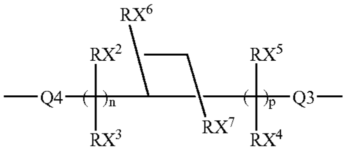
or -continued

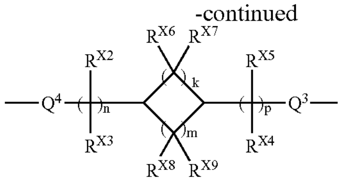

(wherein $Q^1$, $Q^2$ and $R^{X1}$ each represent the same groups as defined above; k is 0 to 5; m is 1 to 5; n and p may be the same as or different from each other and each represents 1 to 5; $R^{X2}$, $R^{X3}$, $R^{X4}$, $R^{X5}$, $R^{X6}$, $R^{X7}$, $R^{X8}$ and $R^{X9}$ may be the same as or different from each other and each represents a hydrogen atom, a hydroxyl group, a cyano group, halogen, a C1 to C6 alkyl group, a C1 to C6 alkoxy group, a C1 to C6 alkylthio group, a C1 to C6 hydroxyalkyl group, a C1 to C6 hydroxyalkoxy group, a C1 to C6 hydroxyalkylthio group, a C1 to C6 aminoalkyl group, a C1 to C6 aminoalkoxy group, a C1 to C6 aminoalkylthio group, a C1 to C6 halogenated alkyl group, a C1 to C6 halogenated alkoxy group, a C1 to C6 halogenated alkylthio group, a C2 to C12 alkoxyalkyl group, a C2 to C12 alkoxyalkoxy group, a C2 to C12 alkoxyalkylthio group, a C3 to C7 cycloalkyl group, a C3 to C7 cycloalkyloxy group, a C4 to C13 cycloalkylalkyloxy group, a C3 to C7 cycloalkylthio group, a C2 to C6 alkenyl group, a C2 to C6 alkenyloxy group, a C2 to C6 alkenylthio group, a C2 to C6 alkynyl group, a C2 to C6 alkynyloxy group, a C2 to C6 alkynylthio group, a C6 to C12 aryl group, a C6 to C12 aryloxy group, a C6 to C12 arylthio group, a C7 to C18 alkylaryl group, a C7 to C18 alkylaryloxy group, a C7 to C18 alkylarylthio group, a C7 to C18 aralkyl group, a C7 to C18 aralkyloxy group or a C7 to C18 aralkylthio group, each of which may have one or more substituent groups, or —$N(R^{X11})R^{X12}$— (wherein $R^{X11}$ and $R^{X12}$ may be the same as or different from each other and each represents a hydrogen atom, a cyano group, a formyl group, a C1 to C6 alkyl group, a C1 to C6 hydroxyalkyl group, a C1 to C6 aminoalkyl group, a C1 to C6 halogenated alkyl group, a C2 to C12 alkoxyalkyl group, a C3 to C7 cycloalkyl group, a C2 to C6 alkenyl group, a C2 to C6 alkynyl group, a C6 to C12 aryl group, a C7 to C18 alkylaryl group, a C7 to C18 aralkyl group, a C2 to C7 aliphatic acyl group or a C7 to C19 aromatic acyl group, each of which may have one or more substituent groups, a C2 to C7 aliphatic alkoxycarbonyl group, or a C7 to C19 aromatic alkoxycarbonyl group), provided that $R^{X2}$ and $R^{X3}$, and $R^{X4}$ and $R^{X5}$ may be combined to form a ring; and $Q^3$ and $Q^4$ may be the same as or different from each other and each represents a single bond, an oxygen atom, (O)S(O) or $NR^{X10}$ ($NR^{X10}$ represents the same group as defined above)); Y represents a 5 to 14-membered aromatic group which may have one or more substituent groups and one or more hetero atoms, or a C3 to C7 alicyclic hydrocarbon group; the rings Z and U may be the same as or different from each other and each represents a 5 to 14-membered aromatic group which may have 1 to 4 substituent groups and one or more hetero atoms, and the ring of which may be partially saturated.), or a salt thereof, an ester thereof or a hydrate of them; 21) the medicament according to 20), which is based on PPAR α and γ dual agonism; 22) the medicament according to 20), which is based on PPAR α, β(δ) and γ triple agonism; 23) the medicament according to 20), which is based on any one of PPAR α, β(δ) and γ agonism; 24) the medicament according to any one of 20) to 23), which is an insulin sensitizer; 25) the medicament according to any one of 20) to 23), which is an agent for preventing or treating diabetes mellitus; 26) the medicament according to any one of 20) to 23), which is an agent for preventing or treating syndrome X; 27) the medicament according to any one of 20) to 23), which is an agent for preventing or treating diabetic complications; 28) the medicament according to any one of 20) to 23), which is an agent for preventing or treating hyperlipemia; 29) the medicament according to any one of 20) to 23), which is a lipid-lowering agent; 30) the medicament according to any one of 20) to 23), which is an agent for preventing or treating obesity; 31) the medicament according to any one of 20) to 23), which is an agent for treating osteoporosis; 32) the medicament according to any one of 20) to 23), which is an anti-inflammatory agent; 33) the medicament according to any one of 20) to 23), which is an agent for preventing or treating a disease of the digestive organs; 34) the medicament according to 33), wherein the disease of the digestive organs is a disease selected from the group consisting of 1) inflammatory diseases of the digestive organs; 2) proliferative diseases of the digestive organs; and 3) ulcerative diseases of the digestive organs; 35) the medicament according to 34), wherein the inflammatory disease of the digestive organs is a disease selected from the group consisting of 1) ulcerative colitis; 2) Crohn's disease; 3) pancreatitis; and (4) gastritis; 36) the medicament according to 34), wherein the inflammatory disease of the digestive organs is ulcerative colitis; 37) the agent for preventing or treating a disease of the digestive organs according to 34), wherein the proliferative diseases of the digestive organs is a disease selected from the group consisting of 1) benign tumor of the digestive organs; 2) digestive polyp; 3) hereditary polyposis syndrome; 4) colon cancer; 5) rectum cancer; and 6) stomach cancer; 38) an agent for preventing or treating a disease against which an insulin sensitizing action is efficacious, which comprises the compound according to any one of 1) to 19) as the active ingredient; 39) the medicament according to any one of 20) to 23), which is an agent for preventing or treating 1) stenocardia and myocardial infarction, and sequelae thereof; 2) senile dementia; or 3) cerebrovascular dementia, and whose action is improving energy metabolism; 40) the medicament according to any one of 20) to 23) which is an immunomodulatory agent; 41) the medicament according to any one of 20) to 23) which is an agent for preventing or treating cancer; 42) a method of preventing or treating a disease against which an insulin sensitizing action is efficacious, which comprises administering to a patient a pharmaceutically effective amount of the carboxylic acid compound according to any one of 1) to 19), a salt thereof, an ester thereof or a hydrate of them; and 43) use of the carboxylic acid compound according to any one of 1) to 19), a salt thereof, an ester thereof or a hydrate of them, for producing an agent for preventing or treating a disease against which an insulin sensitizing action is efficacious.

The salts or esters of the compound of the present invention, or a hydrate of them are preferably those pharmacologically acceptable.

In this specification, the structural formulae of the compounds may, for convenience' sake, indicate a certain isomer, but the present invention encompasses every possible isomer such as geometric isomer, optical isomer based on asymmetric carbon, stereoisomer and tautomer, which can occur in the structures of the compounds of the present invention, and mixtures of these isomers, and therefore, the compounds of the present invention are not limited by the formulae shown for convenience' sake.

Now, the terms used in this specification are described in detail.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a C1 to C6 alkyl group which may have one or more substituent groups, the alkyl group refers to a linear or branched C1 to C6 alkyl group, and specifically it is for example a methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-l-methylpropyl group or 1-ethyl-2-methylpropyl group, preferably a methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group or i-hexyl group, more preferably amethyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, still more preferably amethyl group, ethyl group, n-propyl group, i-propyl group, n-butyl group, i-butyl group, sec-butyl group or t-butyl group, most preferably a methyl group, ethyl group, n-propyl group or i-propyl group.

Herein, the phrase "which may have a substituent" specifically means that the group may be substituted with a substituent such as hydroxyl group; thiol group; nitro group; morpholino group; thiomorpholino group; a halogen atom such as fluorine atom, chlorine atom, bromine atom and iodine atom; nitrile group; azide group; formyl group; alkyl group such as methyl group, ethyl group, propyl group, isopropyl group and butyl group; alkenyl group such as vinyl group, allyl group and propenyl group; alkynyl group such as ethynyl group, butynyl group and propargyl group; alkoxy group such as methoxy group, ethoxy group, propoxy group and butoxy group corresponding to the lower alkyl group; halogenoalkyl group such as fluoromethyl group, difluoromethyl group, trifluoromethyl group and fluoroethyl group; hydroxyalkyl group such as hydroxymethyl group, hydroxyethyl group and hydroxypropyl group; guanidino group; formimidoyl group; acetoimidoyl group; carbamoyl group; thiocarbamoyl group; carbamoylalkyl group such as carbamoylmethyl group and carbamoylethyl group; alkyl carbamoyl group such as methylcarbamoyl group and dimethylcarbamoyl group; carbamide group; alkanoyl group such as acetyl group; amino group; alkylamino group such as methylamino group, ethylamino group and isopropylamino group; dialkylamino group such as dimethylamino group, methylethylamino group and diethylamino group; aminoalkyl group such as aminomethyl group, aminoethyl group and aminopropyl group; carboxyl group; alkoxycarbonyl group such as methoxycarbonyl group, ethoxycarbonyl group and propoxycarbonyl group; alkoxycarbonylalkyl group such as methoxycarbonylmethyl group, ethoxycarbonylmethyl group, propoxycarbonylmethyl group, methoxycarbonylethyl group, ethoxycarbonylethyl group and propoxycarbonylethyl group; alkyloxyalkyl group such as methyloxymethyl group, methyloxyethyl group, ethyloxymethyl group and ethyloxyethyl group; alkylthioalkyl group such as methylthiomethyl group, methylthioethyl group, ethylthiomethyl group and ethylthioethyl group; aminoalkylaminoalkyl group such as aminomethylaminomethyl group and aminoethylaminomethyl group; alkylcarbonyloxy group such as methylcarbonyloxy group, ethylcarbonyloxy group and isopropylcarbonyloxy group; arylalkoxyalkoxyalkyl group such as oxymethyl group and benzyloxyethyloxyethyl group; hydroxyalkoxyalkyl group such as hydroxyethyloxymethyl group and hydroxyethyloxyethyl group; arylalkoxyalkyl group such as benzyloxymethyl group, benzyloxyethyl group and benzyloxypropyl group; quaternary ammonio group such as trimethylammonio group, methylethylmethylammonio group and triethyl ammonio group; cycloalkyl group such as cyclopropyl group, cyclobutyl group, cyclopentyl group and cyclohexyl group; cycloalkenyl group such as cyclopropenyl group, cyclobutenyl group, cyclopentenyl group and cylohexenyl group; aryl group such as phenyl group, pyridinyl group, thienyl group, furyl group and pyrrolyl group; alkylthio group such as methylthio group, ethylthio group, propylthio group and butylthio group; arylthio group such as phenylthio group, pyridinylthio group, thienylthio group, furylthio group and pyrrolylthio group; aryl lower alkyl group such as benzyl group, trityl group and dimethoxytrityl group; substituted sulfonyl group such as sulfonyl group, mesyl group and p-toluene sulfonyl group; aryloyl group such as benzoyl group; halogenoaryl group such as fluorophenyl group and bromophenyl group; and oxyalkoxy group such as methylene dioxy group.

The phrase "which may have one or more substituent groups" means that the mentioned group may have one or more groups arbitrarily selected from these groups, and for example an alkyl group substituted with a hydroxyl group, thiol group, nitro group, morpholino group, thiomorpholino group, halogen atom, nitrile group, azide group, formyl group, amino group, alkylamino group, dialkylamino group, carbamoyl group, sulfonyl group etc.; alkenyl group; alkynyl group; and alkoxy group also fall under the scope of the invention.

Hereinafter, the phrases "which may have a substituent group" and "which may have one or more substituent groups" shall have the above meanings.

When $R^{X2}$, $R^{X3}$, $R^{X4}$, $R^{X5}$, $R^{X6}$, $R^{X7}$, $R^{X8}$ and $R^{X9}$ represents a $C_{1-6}$ alkoxy group which may have one or more substituents, the alkoxy group means a $C_{1-6}$ linear or branched alkoxy group and refers to a group having an oxygen atom bound to the end of the alkyl group. Specific examples thereof include methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group and 1-ethyl-2-methylpropoxy group; preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group and i-hexyloxy group; more preferably methoxy group, ethoxy group, n-propoxy group, i-propoxy group, n-butoxy group, i-butoxy group, sec-butoxy group, t-butoxy group, n-pentyloxy group, i-pentyloxy group, sec-pentyloxy group, t-pentyloxy group, neopentyloxy group, 1-methylbutoxy group, 2-methylbutoxy group, 1,1-dimethylpropoxy group and 1,2-dimethylpropoxy group; further preferably methoxy group, ethoxy group, n-propoxy group, i-propoxy group, n-butoxy group, i-butoxy group, sec-butoxy group and t-butoxy group; and most preferably a methoxy group, ethoxy group, n-propoxy group and i-propoxy group.

When $R^{X2}$, $R^{X3}$, $R^{X4}$, $R^{X5}$, $R^{X6}$, $R^{X7}$, $R^{X8}$ and $R^{X9}$ represented a $C_{1-6}$ alkylthio group which may have one or more substituents, the alkylthio group represents a $C_{1-6}$ linear or branched alkylthio group and refers to a group having a sulfur atom bound to the end of the alkyl group. Specific examples thereof include methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group, i-hexylthio group, 1-methylpentylthio group, 2-methylpentylthio group, 3-methylpentylthio group, 1,1-dimethylbutylthio group, 1,2-dimethylbutylthio group, 2,2-dimethylbutylthio group, 1,3-dimethylbutylthio group, 2,3-dimethylbutylthio group, 3,3-dimethylbutylthio group, 1-ethylbutylthio group, 2-ethylbutylthio group, 1,1,2-trimethylpropylthio group, 1,2,2-trimethylpropylthio group, 1-ethyl-1-methylpropylthio group and 1-ethyl-2-methylpropylthio group, preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group, 1,2-dimethylpropylthio group, n-hexylthio group and i-hexylthio group; more preferably methylthio group, ethylthio group, n-propylthio group, i-propylthio group, n-butylthio group, i-butylthio group, sec-butylthio group, t-butylthio group, n-pentylthio group, i-pentylthio group, sec-pentylthio group, t-pentylthio group, neopentylthio group, 1-methylbutylthio group, 2-methylbutylthio group, 1,1-dimethylpropylthio group and 1,2-dimethylpropylthio group; further preferably methylthio group, ethylthio group, n-propylthio group, i-propylthio group, n-butylthio group, i-butylthio group, sec-butylthio group and t-butylthio group; and most preferably a methylthio group, ethylthio group, n-propylthio group and i-propylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a C1 to C6 hydroxyalkyl group which may have one or more substituent groups, the hydroxyalkyl group refers to a linear or branched C1 to C6 alkyl group substituted at a substitutable position with a hydroxyl group. Specifically, for example, a hydroxymethyl group, 2-hydroxyethyl group and 1-hydroxyethyl group may be proposed.

Similarly, when $R^{X2}$, $R^{X3}$, $R^{X4}$, $R^{X5}$, $R^{X6}$, $R^{X7}$, $R^{X8}$ and $R^{X9}$ represent a C1 to C6 hydroxyalkoxy group which may have one or more substituent groups, the hydroxyalkoxy group refers to a linear or branched C1 to C6 alkoxy group substituted at a substitutable position with a hydroxy group. Specifically, for example, a hydroxymethoxy group, 2-hydroxyethoxy group and 1-hydroxyethoxy group may be proposed.

Similarly, when $R^{X2}$, $R^{X3}$, $R^{X4}$, $R^{X5}$, $R^{X6}$, $R^{X7}$, $R^{X8}$ and $R^{X9}$ represent a C1 to C6 hydroxyalkylthio group which may have one or more substituent groups, the hydroxyalkylthio group refers to a linear or branched C1 to C6 alkylthio group substituted at a substitutable position with a hydroxyl group. Specifically, for example, a hydroxymethylthio group, 2-hydroxyethylthio group and 1-hydroxyethylthio group may be proposed.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a C1 to C6 aminoalkyl group which may have one or more substituent groups, the aminoalkyl group refers to a linear or branched C1 to C6 alkyl group substituted at a substitutable position with an amino group. Specifically, for example, an aminomethyl group, 2-aminoethyl group and 1-aminoethyl group may be proposed.

Similarly, when $R^{X2}$, $R^{X3}$, $R^{X4}$, $R^{X5}$, $R^{X6}$, $R^{X7}$, $R^{X8}$ and $R^{X9}$ represent a C1 to C6aminoalkoxy group which may have one or more substituent groups, the aminoalkoxy group refers to a linear or branched C1 to C6 alkoxy group substituted at a substitutable position with an amino group. Specifically, for example, an aminomethoxy group, 2-aminoethoxy group and 1-aminoethoxy group may be proposed.

Similarly, when $R^{X2}$, $R^{X3}$, $R^{X4}$, $R^{X5}$, $R^{X6}$, $R^{X7}$, $R^{X8}$ and $R^{X9}$ represent a C1 to C6 aminoalkylthio group which may have one or more substituent groups, the aminoalkylthio group refers to a linear or branched C1 to C6 alkylthio group substituted at a substitutable position with an amino group. Specifically, for example, an aminomethylthio group, 2-aminoethylthio group and 1-aminoethylthio group may be proposed.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a halogeno $C_{1-6}$ alkyl group which may have one or more substituents, the halogenoalkyl group represents a group having the $C_{1-6}$ linear or branched alkyl group substituted at substitutable sites with one or more halogen atoms. Herein, the halogen atoms refer to fluorine atom, chlorine atom, bromine atom and iodine atom. Specific examples of such a group include fluoromethyl group, trifluoromethyl group, 2-fluoroethyl group and 1-fluoroethyl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{1-6}$ halogenated alkoxy group which may have one or more substituents, the halogenated alkoxy group represents a group having the $C_{1-6}$ linear or branched alkoxy group substituted at substitutable sites with one or more halogen atoms. Specific examples thereof include fluoromethoxy group, trifluoromethoxy group, 2-fluoroethoxy group and 1-fluoroethoxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{1-6}$ halogenated alkylthio group which may have one or more substituents, the halogenated alkylthio group represents a group having the $C_{1-6}$ linear or branched alkylthio group substituted at substitutable sites with one or more halogen atoms. Specific examples thereof include fluoromethylthio group, trifluoromethylthio group, 2-fluoroethylthio group and 1-fluoroethylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{2-12}$ alkoxyalkyl group which may have one or more substituents, the alkoxyalkyl group represents a group having the $C_{1-6}$ linear or branched alkyl group substituted at a substitutable site with the $C_{1-6}$ linear or branched alkoxy group. Specific examples thereof include methoxymethyl group, ethoxymethyl group, 1-methoxyethyl group, 2-methoxyethyl group, 1-ethoxyethyl group and 2-ethoxyethyl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{2-12}$ alkoxyalkoxy group which may have one or more substituents, the alkoxyalkoxy group represents a group having the $C_{1-6}$ linear or branched alkoxy group substituted at a substitutable site with the $C_{1-6}$linear or branched alkoxy group. Specific examples thereof include methoxymethoxy group, ethoxymethoxy group, 1-methoxyethoxy group, 2-methoxyethoxy group, 1-ethoxyethoxy group and 2-ethoxyethoxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{2-12}$ alkoxyalkylthio group which may have one or more substituents, the alkoxyalkylthio group represents a group having the $C_{1-6}$ linear or branched alkylthio group substituted at a substitutable site with the $C_{16}$ linear or branched alkoxy group. Specific examples thereof include methoxymethylthio group, ethoxymethylthio group, 1-methoxyethylthio group, 2-methoxyethylthio group, 1-ethoxyethylthio group and 2-ethoxyethylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{3-7}$ cycloalkyl group which may have one or more substituents, the cycloalkyl group means a $C_{3-7}$ cyclicalkyl group, and specific examples thereof include cyclopropyl group, cyclobutyl group, cyclopentyl group, cyclohexyl group and cycloheptyl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{3-7}$ cycloalkyloxy group which may have one or more substituents, the cycloalkyloxy group refers to a group having an oxygen atom bound to the end of the $C_{3-7}$ cyclic alkyl group, and specific examples thereof include cyclopropyloxy group, cyclobutyloxy group, cyclopentyloxy group, cyclohexyloxy group and cycloheptyloxy group.

Similarly, when $R^{X2}$, $R^{X3}$, $R^{X4}$, $R^{X5}$, $R^{X6}$, $R^{X7}$, $R^{X8}$ and $R^{X9}$ represent $C_{3-7}$ cycloalkylthio group which may have one or more substituents, the cycloalkylthio group refers to a group having a sulfur atom bound to the end of the $C_{3-7}$ cycloalkyl group, and specific examples thereof include cyclopropylthio group, cyclobutylthio group, cyclopentylthio group, cyclohexylthio group and cycloheptylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{2-6}$ alkenyl group which may have one or more substituents, the alkenyl group is a $C_{2-6}$ linear or branched alkenyl group and refers to a compound residue having a double bond in the alkyl group containing 2 or more carbon atoms. Specific examples of thereof include ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,1-dimethyl-1-butene-1-yl group, 1,2-dimethyl-1-butene-1-yl group, 1,3-dimethyl-1-butene-1-yl group, 2,2-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 2,2-dimethyl-2-butene-1-yl group, 3,3-dimethyl-2-butene-1-yl group, 1,1-dimethyl-3-butene-1-yl group, 1,2-dimethyl-3-butene-1-yl group, 1,3-dimethyl-3-butene-1-yl group, 2,2-dimethyl-3-butene-1-yl group, 3,3-dimethyl-3-butene-1-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-pentene-1-yl group, 2-pentene-1-yl group, 3-pentene-1-yl group, 4-pentene-1-yl group, 1-pentene-2-yl group, 2-pentene-2-yl group, 3-pentene-2-yl group, 4-pentene-2-yl group, 1-pentene-3-yl group, 2-pentene-3-yl group, 1-methyl-1-pentene-1-yl group, 2-methyl-1-pentene-1-yl group, 3-methyl-1-pentene-1-yl group, 4-methyl-1-pentene-1-yl group, 1-methyl-2-pentene-1-yl group, 2-methyl-2-pentene-1-yl group, 3-methyl-2-pentene-1-yl group, 4-methyl-2-pentene-1-yl group, 1-methyl-3-pentene-1-yl group, 2-methyl-3-pentene-1-yl group, 3-methyl-3-pentene-1-yl group, 4-methyl-3-pentene-1-yl group, 1-methyl-4-pentene-1-yl group, 2-methyl-4-pentene-1-yl group, 3-methyl-4-pentene-1-yl group, 4-methyl-4-pentene-1-yl group, 1-methyl-1-pentene-2-yl group, 2-methyl-1-pentene-2-yl group, 3-methyl-1-pentene-2-yl group, 4-methyl-1-pentene-2-yl group, 1-methyl-2-pentene-2-yl group, 2-methyl-2-pentene-2-yl group, 3-methyl-2-pentene-2-yl group, 4-methyl-2-pentene-2-yl group, 1-methyl-3-pentene-2-yl group, 2-methyl-3-pentene-2-yl group, 3-methyl-3-pentene-2-yl group, 4-methyl-3-pentene-2-yl group, 1-methyl-4-pentene-2-yl group, 2-methyl-4-pentene-2-yl group, 3-methyl-4-pentene-2-yl group, 4-methyl-4-pentene-2-yl group, 1-methyl-1-pentene-3-yl group, 2-methyl-1-pentene-3-yl group, 3-methyl-1-pentene-3-yl group, 4-methyl-1-pentene-3-yl group, 1-methyl-2-pentene-3-yl group, 2-methyl-2-pentene-3-yl group, 3-methyl-2-pentene-3-yl group, 4-methyl-2-pentene-3-yl group, 1-hexene-1-yl group, 1-hexene-2-yl group, 1-hexene-3-yl group, 1-hexene-4-yl group, 1-hexene-5-yl group, 1-hexene-6-yl group, 2-hexene-1-yl group, 2-hexene-2-yl group, 2-hexene-3-yl group, 2-hexene-4-yl group, 2-hexene-5-yl group, 2-hexene-6-yl group, 3-hexene-1-yl group, 3-hexene-2-yl group and 3-hexene-3-yl group; preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, 3-methyl-3-butene-1-yl group, 1-ethyl-1-butene-1-yl group, 2-ethyl-1-butene-1-yl group, 3-ethyl-1-butene-1-yl group, 1-ethyl-2-butene-1-yl group, 2-ethyl-2-butene-1-yl group, 3-ethyl-2-butene-1-yl group, 1-ethyl-3-butene-1-yl group, 2-ethyl-3-butene-1-yl group, 3-ethyl-3-butene-1-yl group, 1,1-dimethyl-1-butene-1-yl group, 1,2-dimethyl-1-butene-1-yl group, 1,3-dimethyl-1-butene-1-yl group, 2,2-dimethyl-1-butene-1-yl group, 3,3-dimethyl-1-butene-1-yl group, 1,1-dimethyl-2-butene-1-yl group, 1,2-dimethyl-2-butene-1-yl group, 1,3-dimethyl-2-butene-1-yl group, 2,2-dimethyl-2-butene-1-yl group, 3,3-dimethyl-2-butene-1-yl group, 1,1-dimethyl-3-butene-1-yl group, 1,2-dimethyl-3-butene-1-yl group, 1,3-dimethyl-3-butene-1-yl group, 2,2-dimethyl-3-butene-1-yl group and 3,3-dimethyl-3-butene-1-yl group; more preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group, 2-butene-2-yl group, 1-methyl-1-propene-1-yl group, 2-methyl-1-propene-1-yl group, 1-methyl-2-propene-1-yl group, 2-methyl-2-propene-1-yl group, 1-methyl-1-butene-1-yl group, 2-methyl-1-butene-1-yl group, 3-methyl-1-butene-1-yl group, 1-methyl-2-butene-1-yl group, 2-methyl-2-butene-1-yl group, 3-methyl-2-butene-1-yl group, 1-methyl-3-butene-1-yl group, 2-methyl-3-butene-1-yl group, and 3-methyl-3-butene-1-yl group; and most preferably ethenyl group, 1-propene-1-yl group, 2-propene-1-yl group, 3-propene-1-yl group, 1-butene-1-yl group, 1-butene-2-yl group, 1-butene-3-yl group, 1-butene-4-yl group, 2-butene-1-yl group and 2-butene-2-yl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{2-6}$ alkenyloxy group which may have one or more substituents, the alkenyloxy group refers to a group having an oxygen atom bound to the end of the $C_{2-6}$ linear or branched alkenyl group. Specific examples thereof include ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group, 3-methyl-3-butene-1-yloxy group, 1-ethyl-1-butene-1-yloxy group, 2-ethyl-1-butene-1-yloxy group, 3-ethyl-1-butene-1-yloxy group, 1-ethyl-2-butene-1-yloxy group, 2-ethyl-2-butene-1-yloxy group, 3-ethyl-2-butene-1-yloxy group, 1-ethyl-3-butene-1-yloxy group, 2-ethyl-3-butene-1-yloxy group, 3-ethyl-3-butene-1-yloxy group, 1,1-dimethyl-1-butene-1-yloxy group, 1,2-dimethyl-1-butene-1-yloxy group, 1,3-dimethyl-1-butene-1-yloxy group, 2,2-dimethyl-1-butene-1-yloxy group, 3,3-dimethyl-1-butene-1-yloxy group, 1,1-dimethyl-2-butene-1-yloxy group, 1,2-dimethyl-2-butene-1-yloxy group, 1,3-dimethyl-2-butene-1-yloxy group, 2,2-dimethyl-2-butene-1-yloxy group, 3,3-dimethyl-2-butene-1-yloxy group, 1,1-dimethyl-3-butene-1-yloxy group, 1,2-dimethyl-3-butene-1-yloxy group, 1,3-dimethyl-3-butene-1-yloxy group, 2,2-dimethyl-3-butene-1-yloxy group, 3,3-dimethyl-3-butene-1-yloxy group, 1-pentene-1-yloxy group, 2-pentene-1-yloxy group, 3-pentene-1-yloxy group, 4-pentene-1-yloxy group, 1-pentene-2-yloxy group, 2-pentene-2-yloxy group, 3-pentene-2-yloxy group, 4-pentene-2-yloxy group, 1-pentene-3-yloxy group, 2-pentene-3-yloxy group, 1-pentene-1-yloxy group, 2-pentene-1-yloxy group, 3-pentene-1-yloxy group, 4-pentene-1-yloxy group, 1-pentene-2-yloxy group, 2-pentene-2-yloxy group, 3-pentene-2-yloxy group, 4-pentene-2-yloxy group, 1-pentene-3-yloxy group, 2-pentene-3-yloxy group, 1-methyl-1-pentene-1-yloxy group, 2-methyl-1-pentene-1-yloxy group, 3-methyl-1-pentene-1-yloxy group, 4-methyl-1-pentene-1-yloxy group, 1-methyl-2-pentene-1-yloxy group, 2-methyl-2-pentene-1-yloxy group, 3-methyl-2-pentene-1-yloxy group, 4-methyl-2-pentene-1-yloxy group, 1-methyl-3-pentene-1-yloxy group, 2-methyl-3-pentene-1-yloxy group, 3-methyl-3-pentene-1-yloxy group, 4-methyl-3-pentene-1-yloxy group, 1-methyl-4-pentene-1-yloxy group, 2-methyl-4-pentene-1-yloxy group, 3-methyl-4-pentene-1-yloxy group, 4-methyl-4-pentene-1-yloxy group, 1-methyl-1-pentene-2-yloxy group, 2-methyl-1-pentene-2-yloxy group, 3-methyl-1-pentene-2-yloxy group, 4-methyl-1-pentene-2-yloxy group, 1-methyl-2-pentene-2-yloxy group, 2-methyl-2-pentene-2-yloxy group, 3-methyl-2-pentene-2-yloxy group, 4-methyl-2-pentene-2-yloxy group, 1-methyl-3-pentene-2-yloxy group, 2-methyl-3-pentene-2-yloxy group, 3-methyl-3-pentene-2-yloxy group, 4-methyl-3-pentene-2-yloxy group, 1-methyl-4-pentene-2-yloxy group, 2-methyl-4-pentene-2-yloxy group, 3-methyl-4-pentene-2-yloxy group, 4-methyl-4-pentene-2-yloxy group, 1-methyl-1-pentene-3-yloxy group, 2-methyl-1-pentene-3-yloxy group, 3-methyl-1-pentene-3-yloxy group, 4-methyl-1-pentene-3-yloxy group, 1-methyl-2-pentene-3-yloxy group, 2-methyl-2-pentene-3-yloxy group, 3-methyl-2-pentene-3-yloxy group, 4-methyl-2-pentene-3-yloxy group, 1-hexene-1-yloxy group, 1-hexene-2-yloxy group, 1-hexene-3-yloxy group, 1-hexene-4-yloxy group, 1-hexene-5-yloxy group, 1-hexene-6-yloxy group, 2-hexene-1-yloxy group, 2-hexene-2-yloxy group, 2-hexene-3-yloxy group, 2-hexene-4-yloxy group, 2-hexene-5-yloxy group, 2-hexene-6-yloxy group, 3-hexene-1-yloxy group, 3-hexene-2-yloxy group and 3-hexene-3-yloxy group; preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group, 3-methyl-3-butene-1-yloxy group, 1-ethyl-1-butene-1-yloxy group, 2-ethyl-1-butene-1-yloxy group, 3-ethyl-1-butene-1-yloxy group, 1-ethyl-2-butene-1-yloxy group, 2-ethyl-2-butene-1-yloxy group, 3-ethyl-2-butene-1-yloxy group, 1-ethyl-3-butene-1-yloxy group, 2-ethyl-3-butene-1-yloxy group, 3-ethyl-3-butene-1-yloxy group, 1,1-dimethyl-1-butene-1-yloxy group, 1,2-dimethyl-1-butene-1-yloxy group, 1,3-dimethyl-1-butene-1-yloxy group, 2,2-dimethyl-1-butene-1-yloxy group, 3,3-dimethyl-1-butene-1-yloxy group, 1,1-dimethyl-2-butene-1-yloxy group, 1,2-dimethyl-2-butene-1-yloxy group, 1,3-dimethyl-2-butene-1-yloxy group, 2,2-dimethyl-2-butene-1-yloxy group, 3,3-dimethyl-2-butene-1-yloxy group, 1,1-dimethyl-3-butene-1-yloxy group, 1,2-dimethyl-3-butene-1-yloxy group, 1,3-dimethyl-3-butene-1-yloxy group, 2,2-dimethyl-3-butene-1-yloxy group and 3,3-dimethyl-3-butene-1-yloxy group; more preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group, 2-butene-2-yloxy group, 1-methyl-1-propene-1-yloxy group, 2-methyl-1-propene-1-yloxy group, 1-methyl-2-propene-1-yloxy group, 2-methyl-2-propene-1-yloxy group, 1-methyl-1-butene-1-yloxy group, 2-methyl-1-butene-1-yloxy group, 3-methyl-1-butene-1-yloxy group, 1-methyl-2-butene-1-yloxy group, 2-methyl-2-butene-1-yloxy group, 3-methyl-2-butene-1-yloxy group, 1-methyl-3-butene-1-yloxy group, 2-methyl-3-butene-1-yloxy group and 3-methyl-3-butene-1-yloxy group; further preferably ethenyloxy group, 1-propene-1-yloxy group, 2-propene-1-yloxy group, 3-propene-1-yloxy group, 1-butene-1-yloxy group, 1-butene-2-yloxy group, 1-butene-3-yloxy group, 1-butene-4-yloxy group, 2-butene-1-yloxy group and 2-butene-2-yloxy group; and most preferably ethenyloxy group, 1-propene-1-yloxy group, 2-propene-1-yloxy group and 3-propene-1-yloxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{2-6}$ alkenylthio group which may have one or more substituents, the alkenylthio group refers to a group having sulfur atom bound to the end of the $C_{2-6}$ linear or branched alkenyl group, and specific examples thereof include ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group, 3-methyl-3-butene-1-ylthio group, 1-ethyl-1-butene-1-ylthio group, 2-ethyl-1-butene-1-ylthio group, 3-ethyl-1-butene-1-ylthio group, 1-ethyl-2-butene-1-ylthio group, 2-ethyl-2-butene-1-ylthio group, 3-ethyl-2-butene-1-ylthio group, 1-ethyl-3-butene-1-ylthio group, 2-ethyl-3-butene-1-ylthio group, 3-ethyl-3-butene-1-ylthio group, 1,1-dimethyl-1-butene-1-ylthio group, 1,2-dimethyl-1-butene-1-ylthio group, 1,3-dimethyl-1-butene-1-ylthio group, 2,2-dimethyl-2-butene-1-ylthio group, 3,3-dimethyl-1-butene-1-ylthio group, 1,1-dimethyl-2-butene-1-ylthio group, 1,2-dimethyl-2-butene-1-ylthio group, 1,3-dimethyl-2-butene-1-ylthio group, 2,2-dimethyl-1-butene-1-ylthio group, 3,3-dimethyl-2-butene-1-ylthio group, 1,1-dimethyl-3-butene-1-ylthio group, 1,2-dimethyl-3-butene-1-ylthio group, 1,3-dimethyl-3-butene-1-ylthio group, 2,2-dimethyl-3-butene-1-ylthio group, 3,3-dimethyl-3-butene-1-ylthio group, 1-pentene-1-ylthio group, 2-pentene-1-ylthio group, 3-pentene-1-ylthio group, 4-pentene-1-ylthio group, 1-pentene-2-ylthio group, 2-pentene-2-ylthio group, 3-pentene-2-ylthio group, 4-pentene-2-ylthio group, 1-pentene-3-ylthio group, 2-pentene-3-ylthio group, 1-pentene-1-ylthio group, 2-pentene-1-ylthio group, 3-pentene-1-ylthio group, 4-pentene-1-ylthio group, 1-pentene-2-ylthio group, 2-pentene-2-ylthio group, 3-pentene-2-ylthio group, 4-pentene-2-ylthio group, 1-pentene-3-ylthio group, 2-pentene-3-ylthio group, 1-methyl-1-pentene-1-ylthio group, 2-methyl-1-pentene-1-ylthio group, 3-methyl-1-pentene-1-ylthio group, 4-methyl-1-pentene-1-ylthio group, 1-methyl-2-pentene-1-ylthio group, 2-methyl-2-pentene-1-ylthio group, 3-methyl-2-pentene-1-ylthio group, 4-methyl-2-pentene-1-ylthio group, 1-methyl-3-pentene-1-ylthio group, 2-methyl-3-pentene-1-ylthio group, 3-methyl-3-pentene-1-ylthio group, 4-methyl-3-pentene-1-ylthio group, 1-methyl-4-pentene-1-ylthio group, 2-methyl-4-pentene-1-ylthio group, 3-methyl-4-pentene-1-ylthio group, 4-methyl-4-pentene-1-ylthio group, 1-methyl-1-pentene-2-ylthio group, 2-methyl-1-pentene-2-ylthio group, 3-methyl-1-pentene-2-ylthio group, 4-methyl-1-pentene-2-ylthio group, 1-methyl-2-pentene-2-ylthio group, 2-methyl-2-pentene-2-ylthio group, 3-methyl-2-pentene-2-ylthio group, 4-methyl-2-pentene-2-ylthio group, 1-methyl-3-pentene-2-ylthio group, 2-methyl-3-pentene-2-ylthio group, 3-methyl-3-pentene-2-ylthio group, 4-methyl-3-pentene-2-ylthio group, 1-methyl-4-pentene-2-ylthio group, 2-methyl-4-pentene-2-ylthio group, 3-methyl-4-pentene-2-ylthio group, 4-methyl-4-pentene-2-ylthio group, 1-methyl-1-pentene-3-ylthio group, 2-methyl-1-pentene-3-ylthio group, 3-methyl-1-pentene-3-ylthio group, 4-methyl-1-pentene-3-ylthio group, 1-methyl-2-pentene-3-ylthio group, 2-methyl-2-pentene-3-ylthio group, 3-methyl-2-pentene-3-ylthio group, 4-methyl-2-pentene-3-ylthio group, 1-hexene-1-ylthio group, 1-hexene-2-ylthio group, 1-hexene-3-ylthio group, 1-hexene-4-ylthio group, 1-hexene-5-ylthio group, 1-hexene-6-ylthio group, 2-hexene-1-ylthio group, 2-hexene-2-ylthio group, 2-hexene-3-ylthio group, 2-hexene-4-ylthio group, 2-hexene-5-ylthio group, 2-hexene-6-ylthio group, 3-hexene-1-ylthio group, 3-hexene-2-ylthio group and 3-hexene-3-ylthio group; preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group, 3-methyl-3-butene-1-ylthio group, 1-ethyl-1-butene-1-ylthio group, 2-ethyl-1-butene-1-ylthio group, 3-ethyl-1-butene-1-ylthio group, 1-ethyl-2-butene-1-ylthio group, 2-ethyl-2-butene-1-ylthio group, 3-ethyl-2-butene-1-ylthio group, 1-ethyl-3-butene-1-ylthio group, 2-ethyl-3-butene-1-ylthio group, 3-ethyl-3-butene-1-ylthio group, 1,1-dimethyl-1-butene-1-ylthio group, 1,2-dimethyl-1-butene-1-ylthio group, 1,3-dimethyl-1-butene-1-ylthio group, 2,2-dimethyl-1-butene-1-ylthio group, 3,3-dimethyl-1-butene-1-ylthio group, 1,1-dimethyl-2-butene-1-ylthio group, 1,2-dimethyl-2-butene-1-ylthio group, 1,3-dimethyl-2-butene-1-ylthio group, 2,2-dimethyl-2-butene-1-ylthio group, 3,3-dimethyl-2-butene-1-ylthio group, 1,1-dimethyl-3-butene-1-ylthio group, 1,2-dimethyl-3-butene-1-ylthio group, 1,3-dimethyl-3-butene-1-ylthio group, 2,2-dimethyl-3-butene-1-ylthio group and 3,3-dimethyl-3-butene-1-ylthio group; more preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group, 2-butene-2-ylthio group, 1-methyl-1-propene-1-ylthio group, 2-methyl-1-propene-1-ylthio group, 1-methyl-2-propene-1-ylthio group, 2-methyl-2-propene-1-ylthio group, 1-methyl-1-butene-1-ylthio group, 2-methyl-1-butene-1-ylthio group, 3-methyl-1-butene-1-ylthio group, 1-methyl-2-butene-1-ylthio group, 2-methyl-2-butene-1-ylthio group, 3-methyl-2-butene-1-ylthio group, 1-methyl-3-butene-1-ylthio group, 2-methyl-3-butene-1-ylthio group and 3-methyl-3-butene-1-ylthio group; further preferably ethenylthio group, 1-propene-1-ylthio group, 2-propene-1-ylthio group, 3-propene-1-ylthio group, 1-butene-1-ylthio group, 1-butene-2-ylthio group, 1-butene-3-ylthio group, 1-butene-4-ylthio group, 2-butene-1-ylthio group and 2-butene-2-ylthio group; and most preferably ethenylthio group, 1-propene-1-ylthio group, 2-propene-1-ylthio group and 3-propene-1-ylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{2-6}$ alkynyl group which may have one or more substituents, the alkynyl group is a $C_{2-6}$ linear or branched alkynyl group and refers to a compound residue having a triple bond in the alkyl group containing 2 or more carbon atoms. Specific examples thereof include ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group, 3-methyl-3-butyn-1-yl group, 1-ethyl-1-butyn-1-yl group, 2-ethyl-1-butyn-1-yl group, 3-ethyl-1-butyn-1-yl group, 1-ethyl-2-butyn-1-yl group, 2-ethyl-2-butyn-1-yl group, 3-ethyl-2-butyn-1-yl group, 1-ethyl-3-butyn-1-yl group, 2-ethyl-3-butyn-1-yl group, 3-ethyl-3-butyn-1-yl group, 1,1-dimethyl-1-butyn-1-yl group, 1,2-dimethyl-1-butyn-1-yl group, 1,3-dimethyl-1-butyn-1-yl group, 2,2-dimethyl-1-butyn-1-yl group, 3,3-dimethyl-1-butyn-1-yl group, 1,1-dimethyl-2-butyn-1-yl group, 1,2-dimethyl-2-butyn-1-yl group, 1,3-dimethyl-2-butyn-1-yl group, 2,2-dimethyl-2-butyn-1-yl group, 3,3-dimethyl-2-butyn-1-yl group, 1,1-dimethyl-3-butyn-1-yl group, 1,2-dimethyl-3-butyn-1-yl group, 1,3-dimethyl-3-butyn-1-yl group, 2,2-dimethyl-3-butyn-1-yl group, 3,3-dimethyl-3-butyn-1-yl group, 1-pentyn-1-yl group, 2-pentyn-1-yl group, 3-pentyn-1-yl group, 4-pentyn-1-yl group, 1-pentyn-2-yl group, 2-pentyn-2-yl group, 3-pentyn-2-yl group, 4-pentyn-2-yl group, 1-pentyn-3-yl group, 2-pentyn-3-yl group, 1-pentyn-1-yl group, 2-pentyn-1-yl group, 3-pentyn-1-yl group, 4-pentyn-1-yl group, 1-pentyn-2-yl group, 2-pentyn-2-yl group, 3-pentyn-2-yl group, 4-pentyn-2-yl group, 1-pentyn-3-yl group, 2-pentyn-3-yl group, 1-methyl-1-pentyn-1-yl group, 2-methyl-1-pentyn-1-yl group, 3-methyl-1-pentyn-1-yl group, 4-methyl-1-pentyn-1-yl group, 1-methyl-2-pentyn-1-yl group, 2-methyl-2-pentyn-1-yl group, 3-methyl-2-pentyn-1-yl group, 4-methyl-2-pentyn-1-yl group, 1-methyl-3-pentyn-1-yl group, 2-methyl-3-pentyn-1-yl group, 3-methyl-3-pentyn-1-yl group, 4-methyl-3-pentyn-1-yl group, 1-methyl-4-pentyn-1-yl group, 2-methyl-4-pentyn-1-yl group, 3-methyl-4-pentyn-1-yl group, 4-methyl-4-pentyn-1-yl group, 1-methyl-1-pentyn-2-yl group, 2-methyl-1-pentyn-2-yl group, 3-methyl-1-pentyn-2-yl group, 4-methyl-1-pentyn-2-yl group, 1-methyl-2-pentyn-2-yl group, 2-methyl-2-pentyn-2-yl group, 3-methyl-2-pentyn-2-yl group, 4-methyl-2-pentyn-2-yl group, 1-methyl-3-pentyn-2-yl group, 2-methyl-3-pentyn-2-yl group, 3-methyl-3-pentyn-2-yl group, 4-methyl-3-pentyn-2-yl group, 1-methyl-4-pentyn-2-yl group, 2-methyl-4-pentyn-2-yl group, 3-methyl-4-pentyn-2-yl group, 4-methyl-4-pentyn-2-yl group, 1-methyl-1-pentyn-3-yl group, 2-methyl-1-pentyn-3-yl group, 3-methyl-1-pentyn-3-yl group, 4-methyl-1-pentyn-3-yl group, 1-methyl-2-pentyn-3-yl group, 2-methyl-2-pentyn-3-yl group, 3-methyl-2-pentyn-3-yl group, 4-methyl-2-pentyn-3-yl group, 1-hexyn-1-yl group, 1-hexyn-2-yl group, 1-hexyn-3-yl group, 1-hexyn-4-yl group, 1-hexyn-5-yl group, 1-hexyn-6-yl group, 2-hexyn-1-yl group, 2-hexyn-2-yl group, 2-hexyn-3-yl group, 2-hexyn-4-yl group, 2-hexyn-5-yl group, 2-hexyn-6-yl group, 3-hexyn-1-yl group, 3-hexyn-2-yl group and 3-hexyn-3-yl group; preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group, 3-methyl-3-butyn-1-yl group, 1-ethyl-1-butyn-1-yl group, 2-ethyl-1-butyn-1-yl group, 3-ethyl-1-butyn-1-yl group, 1-ethyl-2-butyn-1-yl group, 2-ethyl-2-butyn-1-yl group, 3-ethyl-2-butyn-1-yl group, 1-ethyl-3-butyn-1-yl group, 2-ethyl-3-butyn-1-yl group, 3-ethyl-3-butyn-1-yl group, 1,1-dimethyl-1-butyn-1-yl group, 1,2-dimethyl-1-butyn-1-yl group, 1,3-dimethyl-1-butyn-1-yl group, 2,2-dimethyl-1-butyn-1-yl group, 3,3-dimethyl-1-butyn-1-yl group, 1,1-dimethyl-2-butyn-1-yl group, 1,2-dimethyl-2-butyn-1-yl group, 1,3-dimethyl-2-butyn-1-yl group, 2,2-dimethyl-2-butyn-1-yl group, 3,3-dimethyl-2-butyn-1-yl group, 1,1-dimethyl-3-butyn-1-yl group, 1,2-dimethyl-3-butyn-1-yl group, 1,3-dimethyl-3-butyn-1-yl group, 2,2-dimethyl-3-butyn-1-yl group and 3,3-dimethyl-3-butyn-1-yl group; more preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group, 2-butyn-2-yl group, 1-methyl-1-propyn-1-yl group, 2-methyl-1-propyn-1-yl group, 1-methyl-2-propyn-1-yl group, 2-methyl-2-propyn-1-yl group, 1-methyl-1-butyn-1-yl group, 2-methyl-1-butyn-1-yl group, 3-methyl-1-butyn-1-yl group, 1-methyl-2-butyn-1-yl group, 2-methyl-2-butyn-1-yl group, 3-methyl-2-butyn-1-yl group, 1-methyl-3-butyn-1-yl group, 2-methyl-3-butyn-1-yl group and 3-methyl-3-butyn-1-yl group; further preferably ethynyl group, 1-propyn-1-yl group, 2-propyn-1-yl group, 3-propyn-1-yl group, 1-butyn-1-yl group, 1-butyn-2-yl group, 1-butyn-3-yl group, 1-butyn-4-yl group, 2-butyn-1-yl group and 2-butyn-2-yl group; and most preferably ethynyl group, 1-propyn-1-yl group, 2-propyn-1-yl group and 3-propyn-1-yl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{2-6}$ alkynyloxy group which may have one or more substituents, the alkynyloxy group refers to a group having oxygen atom bound to the end of the $C_{2-6}$linear or branched alkynyl group, and specific examples thereof include ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group, 3-methyl-3-butyn-1-yloxy group, 1-ethyl-1-butyn-1-yloxy group, 2-ethyl-1-butyn-1-yloxy group, 3-ethyl-1-butyn-1-yloxy group, 1-ethyl-2-butyn-1-yloxy group, 2-ethyl-2-butyn-1-yloxy group, 3-ethyl-2-butyn-1-yloxy group, 1-ethyl-3-butyn-1-yloxy group, 2-ethyl-3-butyn-1-yloxy group, 3-ethyl-3-butyn-1-yloxy group, 1,1-dimethyl-1-butyn-1-yloxy group, 1,2-diethyl-1-butyn-1-yloxy group, 1,3-dimethyl-1-butyn-1-yloxy group, 2,2-dimethyl-1-butyn-1-yloxy group, 3,3-dimethyl-1-butyn-1-yloxy group, 1,1-dimethyl-2-butyn-1-yloxy group, 1,2-dimethyl-2-butyn-1-yloxy group, 1,3-dimethyl-2-butyn-1-yloxy group, 2,2-dimethyl-2-butyn-1-yloxy group, 3,3-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group, 3,3-dimethyl-3-butyn-1-yloxy group, 1-pentyn-1-yloxy group, 2-pentyn-1-yloxy group, 3-pentyn-1-yloxy group, 4-pentyn-1-yloxy group, 1-pentyn-2-yloxy group, 2-pentyn-2-yloxy group, 3-pentyn-2-yloxy group, 4-pentyn-2-yloxy group, 1-pentyn-3-yloxy group, 2-pentyn-3-yloxy group, 1-pentyn-1-yloxy group, 2-pentyn-1-yloxy group, 3-pentyn-1-yloxy group, 4-pentyn-1-yloxy group, 1-pentyn-2-yloxy group, 2-pentyn-2-yloxy group, 3-pentyn-2-yloxy group, 4-pentyn-2-yloxy group, 1-pentyn-3-yloxy group, 2-pentyn-3-yloxy group, 1-methyl-1-pentyn-1-yloxy group, 2-methyl-1-pentyn-1-yloxy group, 3-methyl-1-pentyn-1-yloxy group, 4-methyl-1-pentyn-1-yloxy group, 1-methyl-2-pentyn-1-yloxy group, 2-methyl-2-pentyn-1-yloxy group, 3-methyl-2-pentyn-1-yloxy group, 4-methyl-2-pentyn-1-yloxy group, 1-methyl-3-pentyn-1-yloxy group, 2-methyl-3-pentyn-1-yloxy group, 3-methyl-3-pentyn-1-yloxy group, 4-methyl-3-pentyn-1-yloxy group, 1-methyl-4-pentyn-1-yloxy group, 2-methyl-4-pentyn-1-yloxy group, 3-methyl-4-pentyn-1-yloxy group, 4-methyl-4-pentyn-1-yloxy group, 1-methyl-1-pentyn-2-yloxy group, 2-methyl-1-pentyn-2-yloxy group, 3-methyl-1-pentyn-2-yloxy group, 4-methyl-1-pentyn-2-yloxy group, 1-methyl-2-pentyn-2-yloxy group, 2-methyl-2-pentyn-2-yloxy group, 3-methyl-2-pentyn-2-yloxy group, 4-methyl-2-pentyn-2-yloxy group, 1-methyl-3-pentyn-2-yloxy group, 2-methyl-3-pentyn-2-yloxy group, 3-methyl-3-pentyn-2-yloxy group, 4-methyl-3-pentyn-2-yloxy group, 1-methyl-4-pentyn-2-yloxy group, 2-methyl-4-pentyn-2-yloxy group, 3-methyl-4-pentyn-2-yloxy group, 4-methyl-4-pentyn-2-yloxy group, 1-methyl-1-pentyn-3-yloxy group, 2-methyl-1-pentyn-3-yloxy group, 3-methyl-1-pentyn-3-yloxy group, 4-methyl-1-pentyn-3-yloxy group, 1-methyl-2-pentyn-3-yloxy group, 2-methyl-2-pentyn-3-yloxy group, 3-methyl-2-pentyn-3-yloxy group, 4-methyl-2-pentyn-3-yloxy group, 1-hexyn-1-yloxy group, 1-hexyn-2-yloxy group, 1-hexyn-3-yloxy group, 1-hexyn-4-yloxy group, 1-hexyn-5-yloxy group, 1-hexyn-6-yloxy group, 2-hexyn-1-yloxy group, 2-hexyn-2-yloxy group, 2-hexyn-3-yloxy group, 2-hexyn-4-yloxy group, 2-hexyn-5-yloxy group, 2-hexyn-6-yloxy group, 3-hexyn-1-yloxy group, 3-hexyn-2-yloxy group and 3-hexyn-3-yloxy group; preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group, 3-methyl-3-butyn-1-yloxy group, 1-ethyl-1-butyn-1-yloxy group, 2-ethyl-1-butyn-1-yloxy group, 3-ethyl-1-butyn-1-yloxy group, 1-ethyl-2-butyn-1-yloxy group, 2-ethyl-2-butyn-1-yloxy group, 3-ethyl-2-butyn-1-yloxy group, 1-ethyl-3-butyn-1-yloxy group, 2-ethyl-3-butyn-1-yloxy group, 3-ethyl-3-butyn-1-yloxy group, 1,1-dimethyl-1-butyn-1-yloxy group, 1,2-dimethyl-1-butyn-1-yloxy group, 1,3-dimethyl-1-butyn-1-yloxy group, 2,2-dimethyl-1-butyn-1-yloxy group, 3,3-dimethyl-1-butyn-1-yloxy group, 1,1-dimethyl-2-butyn-1-yloxy group, 1,2-dimethyl-2-butyn-1-yloxy group, 1,3-dimethyl-2-butyn-1-yloxy group, 2,2-dimethyl-2-butyn-1-yloxy group, 3,3-dimethyl-2-butyn-1-yloxy group, 1,1-dimethyl-3-butyn-1-yloxy group, 1,2-dimethyl-3-butyn-1-yloxy group, 1,3-dimethyl-3-butyn-1-yloxy group, 2,2-dimethyl-3-butyn-1-yloxy group and 3,3-dimethyl-3-butyn-1-yloxy group; more preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group, 2-butyn-2-yloxy group, 1-methyl-1-propyn-1-yloxy group, 2-methyl-1-propyn-1-yloxy group, 1-methyl-2-propyn-1-yloxy group, 2-methyl-2-propyn-1-yloxy group, 1-methyl-1-butyn-1-yloxy group, 2-methyl-1-butyn-1-yloxy group, 3-methyl-1-butyn-1-yloxy group, 1-methyl-2-butyn-1-yloxy group, 2-methyl-2-butyn-1-yloxy group, 3-methyl-2-butyn-1-yloxy group, 1-methyl-3-butyn-1-yloxy group, 2-methyl-3-butyn-1-yloxy group and 3-methyl-3-butyn-1-yloxy group; further preferably ethynyloxy group, 1-propyn-1-yloxy group, 2-propyn-1-yloxy group, 3-propyn-1-yloxy group, 1-butyn-1-yloxy group, 1-butyn-2-yloxy group, 1-butyn-3-yloxy group, 1-butyn-4-yloxy group, 2-butyn-1-yloxy group and 2-butyn-2-yloxy group; and most preferably ethynyloxy group, 1-propyn-1-yloxy group, 2-propyn-1-yloxy group and 3-propyn-1-yloxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{2-6}$ alkynylthio group which may have one or more substituents, the alkynylthio group refers to a group having sulfur atom bound to the end of the $C_{2-6}$ linear or branched alkynyl group, and specific examples thereof include ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group, 3-methyl-3-butyn-1-ylthio group, 1-ethyl-1-butyn-1-ylthio group, 2-ethyl-1-butyn-1-ylthio group, 3-ethyl-1-butyn-1-ylthio group, 1-ethyl-2-butyn-1-ylthio group, 2-ethyl-2-butyn-1-ylthio group, 3-ethyl-2-butyn-1-ylthio group, 1-ethyl-3-butyn-1-ylthio group, 2-ethyl-3-butyn-1-ylthio group, 3-ethyl-3-butyn-1-ylthio group, 1,1-dimethyl-1-butyn-1-ylthio group, 1,2-dimethyl-1-butyn-1-ylthio group, 1,3-dimethyl-1-butyn-1-ylthio group, 2,2-dimethyl-1-butyn-1-ylthio group, 3,3-dimethyl-1-butyn-1-ylthio group, 1,1-dimethyl-2-butyn-1-ylthio group, 1,2-dimethyl-2-butyn-1-ylthio group, 1,3-dimethyl-2-butyn-1-ylthio group, 2,2-dimethyl-2-butyn-1-ylthio group, 3,3-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group, 3,3-dimethyl-3-butyn-1-ylthio group, 1-pentyn-1-ylthio group, 2-pentyn-1-ylthio group, 3-pentyn-1-ylthio group, 4-pentyn-1-ylthio group, 1-pentyn-2-ylthio group, 2-pentyn-2-ylthio group, 3-pentyn-2-ylthio group, 4-pentyn-2-ylthio group, 1-pentyn-3-ylthio group, 2-pentyn-3-ylthio group, 1-pentyn-1-ylthio group, 2-pentyn-1-ylthio group, 3-pentyn-1-ylthio group, 4-pentyn-1-ylthio group, 1-pentyn-2-ylthio group, 2-pentyn-2-ylthio group, 3-pentyn-2-ylthio group, 4-pentyn-2-ylthio group, 1-pentyn-3-ylthio group, 2-pentyn-3-ylthio group, 1-methyl-1-pentyn-1-ylthio group, 2-methyl-1-pentyn-1-ylthio group, 3-methyl-1-pentyn-1-ylthio group, 4-methyl-1-pentyn-1-ylthio group, 1-methyl-2-pentyn-1-ylthio group, 2-methyl-2-pentyn-1-ylthio group, 3-methyl-2-pentyn-1-ylthio group, 4-methyl-2-pentyn-1-ylthio group, 1-methyl-3-pentyn-1-ylthio group, 2-methyl-3-pentyn-1-ylthio group, 3-methyl-3-pentyn-1-ylthio group, 4-methyl-3-pentyn-1-ylthio group, 1-methyl-4-pentyn-1-ylthio group, 2-methyl-4-pentyn-1-ylthio group, 3-methyl-4-pentyn-1-ylthio group, 4-methyl-4-pentyn-1-ylthio group, 1-methyl-1-pentyn-2-ylthio group, 2-methyl-1-pentyn-2-ylthio group, 3-methyl-1-pentyn-2-ylthio group, 4-methyl-1-pentyn-2-ylthio group, 1-methyl-2-pentyn-2-ylthio group, 2-methyl-2-pentyn-2-ylthio group, 3-methyl-2-pentyn-2-ylthio group, 4-methyl-2-pentyn-2-ylthio group, 1-methyl-3-pentyn-2-ylthio group, 2-methyl-3-pentyn-2-ylthio group, 3-methyl-3-pentyn-2-ylthio group, 4-methyl-3-pentyn-2-ylthio group, 1-methyl-4-pentyn-2-ylthio group, 2-methyl-4-pentyn-2-ylthio group, 3-methyl-4-pentyn-2-ylthio group, 4-methyl-4-pentyn-2-ylthio group, 1-methyl-1-pentyn-3-ylthio group, 2-methyl-1-pentyn-3-ylthio group, 3-methyl-1-pentyn-3-ylthio group, 4-methyl-1-pentyn-3-ylthio group, 1-methyl-2-pentyn-3-ylthio group, 2-methyl-2-pentyn-3-ylthio group, 3-methyl-2-pentyn-3-ylthio group, 4-methyl-2-pentyn-3-ylthio group, 1-hexyn-1-ylthio group, 1-hexyn-2-ylthio group, 1-hexyn-3-ylthio group, 1-hexyn-4-ylthio group, 1-hexyn-5-ylthio group, 1-hexyn-6-ylthio group, 2-hexyn-1-ylthio group, 2-hexyn-2-ylthio group, 2-hexyn-3-ylthio group, 2-hexyn-4-ylthio group, 2-hexyn-5-ylthio group, 2-hexyn-6-ylthio group, 3-hexyn-1-ylthio group, 3-hexyn-2-ylthio group and 3-hexyn-3-ylthio group; preferably ethynylthio group, 1-propyn-1-ylthio group, 2-propyn-1-ylthio group, 3-propyn-1-ylthio group, 1-butyn- 1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group, 3-methyl-3-butyn-1-ylthio group, 1-ethyl-1-butyn-1-ylthio group, 2-ethyl-1-butyn-1-ylthio group, 3-ethyl-1-butyn-1-ylthio group, 1-ethyl-2-butyn-1-ylthio group, 2-ethyl-2-butyn-1-ylthio group, 3-ethyl-2-butyn-1-ylthio group, 1-ethyl-3-butyn-1-ylthio group, 2-ethyl-3-butyn-1-ylthio group, 3-ethyl-3-butyn-1-ylthio group, 1,1-dimethyl-1-butyn-1-ylthio group, 1,2-dimethyl-1-butyn-1-ylthio group, 1,3-dimethyl-1-butyn-1-ylthio group, 2,2-dimethyl-1-butyn-1-ylthio group, 3,3-dimethyl-1-butyn-1-ylthio group, 1,1-dimethyl-2-butyn-1-ylthio group, 1,2-dimethyl-2-butyn-1-ylthio group, 1,3-dimethyl-2-butyn-1-ylthio group, 2,2-dimethyl-2-butyn-1-ylthio group, 3,3-dimethyl-2-butyn-1-ylthio group, 1,1-dimethyl-3-butyn-1-ylthio group, 1,2-dimethyl-3-butyn-1-ylthio group, 1,3-dimethyl-3-butyn-1-ylthio group, 2,2-dimethyl-3-butyn-1-ylthio group and 3,3-dimethyl-3-butyn-1-ylthio group; more preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group, 2-butyn-2-ylthio group, 1-methyl-1-propyn-1-ylthio group, 2-methyl-1-propyn-1-ylthio group, 1-methyl-2-propyn-1-ylthio group, 2-methyl-2-propyn-1-ylthio group, 1-methyl-1-butyn-1-ylthio group, 2-methyl-1-butyn-1-ylthio group, 3-methyl-1-butyn-1-ylthio group, 1-methyl-2-butyn-1-ylthio group, 2-methyl-2-butyn-1-ylthio group, 3-methyl-2-butyn-1-ylthio group, 1-methyl-3-butyn-1-ylthio group, 2-methyl-3-butyn-1-ylthio group and 3-methyl-3-butyn-1-ylthio group; further preferably ethynylthio group, 1-propyn-1-ylthio group, 2-propyn-1-ylthio group, 3-propyn-1-ylthio group, 1-butyn-1-ylthio group, 1-butyn-2-ylthio group, 1-butyn-3-ylthio group, 1-butyn-4-ylthio group, 2-butyn-1-ylthio group and 2-butyn-2-ylthio group; and most preferably ethynylthio group, 1-propyn-1-ylthio group, 2-propyn-1-ylthio group and 3-propyn-1-ylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{6-12}$ aryl group which may have one or more substituents, the aryl group refers to an aromatic cyclic group, and specific examples thereof include phenyl group, 1-naphthyl group, 2-naphthyl group, as-indacenyl group, s-indacenyl group and acenapthylenyl group; preferably phenyl group, 1-naphthyl group and 2-naphthyl group; more preferably phenyl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{6-12}$ aryloxy group which may have one or more substituents, the aryloxy group refers to a group having an oxygen atom bound to the end of the $C_{6-12}$ aryl group, and specific examples thereof include phenyloxy group, 1-naphthyloxy group, 2-naphthyloxy group, as-indacenyloxy group, s-indacenyloxy group and acenapthylenyloxy group; preferably phenyloxy group, 1-naphthyloxy group and 2-naphthyloxy group; more preferably phenyloxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{6-12}$ arylthio group which may have one or more substituents, the arylthio group refers to a group having a sulfur atom bound to the end of the $C_{6-12}$ aryl group, and specific examples thereof include phenylthio group, 1-naphthylthio group, 2-naphthylthio group, as-indacenylthio group, s-indacenylthio group and acenapthylenylthio group; preferably phenylthio group, 1-naphthylthio group and 2-naphthylthio group; more preferably phenylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{7-18}$ alkylaryl group which may have one or more substituents, the alkylaryl group refers to a group having the $C_{6-12}$ aryl group substituted at a substitutable site with the $C_{1-6}$ alkyl group. Specific examples thereof include tolyl group, xylyl group, cumenyl group, mesityl group, cymenyl group and styryl group; preferably tolyl group, xylyl group, cumenyl group, mesityl group, cymenyl group and styryl group; more preferably tolyl group, xylyl group, cumenyl group and mesityl group; and further preferably tolyl group, xylyl group and cumenyl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{7-18}$ alkylaryloxy group which may have one or more substituents, the alkylaryloxy group refers to a group having an oxygen atom bound to the end of the $C_{7-18}$ alkylaryl group. Specific examples thereof include o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group, 2,5-cymenyl-1-oxy group, o-styryloxy group, m-styryloxy group and p-styryloxy group; preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, 2,3-cymenyl-1-oxy group, 2,4-cymenyl-1-oxy group, 2,5-cymenyl-1-oxy group, o-styryloxy group, m-styryloxy group and p-styryloxy group; more preferably o-tolyloxy group, m-tolyloxy group, p-tolyloxy group, 2,3-xylyl-1-oxy group, 2,4-xylyl-1-oxy group, 2,5-xylyl-1-oxy group, o-cumenyloxy group, m-cumenyloxy group, p-cumenyloxy group, mesityloxy group, o-styryloxy group, m-styryloxy group and p-styryloxy group; more preferably o-tolyloxy group, m-tolyloxy group, p-tolyloxy group, 2,3-xylyl-1-oxy group, 2,4-xylyl-1-oxy group, 2,5-xylyl-1-oxy group and mesityloxy group; and most preferably o-tolyloxy group, m-tolyloxy group and p-tolyloxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{7-18}$ alkylarylthio group which may have one or more substituents, the alkylarylthio group refers to a group having a sulfur atom bound to the end of the $C_{7-18}$ alkylaryl group. Specific examples thereof include o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group, 2,5-cymenyl-1-thio group, o-styrylthio group, m-styrylthio group and p-styrylthio group; preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, 2,3-cymenyl-1-thio group, 2,4-cymenyl-1-thio group, 2,5-cymenyl-1-thio group, o-styrylthio group, m-styrylthio group and p-styrylthio group; more preferably o-tolylthio group, m-tolylthio group, p-tolylthio group, 2,3-xylyl-1-thio group, 2,4-xylyl-1-thio group, 2,5-xylyl-1-thio group, o-cumenylthio group, m-cumenylthio group, p-cumenylthio group, mesitylthio group, o-styrylthio group, m-styrylthio group and p-styrylthio group; further preferably o-tolylthio group, m-tolylthio group, p-tolylthio group, 2,3-xylyl-1-thio group, 2,4-xylyl-1-thio group, 2,5-xylyl-1-thio group and mesitylthio group; and most preferably o-tolylthio group, m-tolylthio group and p-tolylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$, $R^{X9}$ and $R^{X10}$ represent a $C_{7-18}$ aralkyl group which may have one or more substituents, the aralkyl group refers to a group having the $C_{1-6}$ alkyl group substituted at a substitutable site with the $C_{6-12}$ aryl group. Specific examples thereof include benzyl group, phenetyl group, 3-phenylpropyl group, 4-phenylbutyl group, 5-phenylpentyl group, 6-phenylhexyl group, 1-naphthylmethyl group, 2-naphthylmethyl group, 1-naphthylethyl group, 2-naphthylethyl group, 1-naphthylpropyl group and 2-naphthylpropyl group; preferably benzyl group, phenetyl group, 3-phenylpropyl group, 4-phenylbutyl group, 5-phenylpentyl group, 6-phenylhexyl group, 1-naphthylmethyl group, 2-naphthylmethyl group, 1-naphthylethyl group, 2-naphthylethyl group, 1-naphthylpropyl group and 2-naphthylpropyl group; more preferably benzyl group, phenetyl group, 3-phenylpropyl group, 4-phenylbutyl group, 5-phenylpentyl group, 6-phenylhexyl group, 1-naphthylmethyl group and 2-naphthylmethyl group; further preferably benzyl group, phenetyl group, 3-phenylpropyl group and 4-phenylbutyl group; and most preferably benzyl group and phenetyl group.

Similarly, when $R^{X2}$, $R^{X3}$, $R^{X4}$, $R^{X5}$, $R^{X6}$, $R^{X7}$, $R^{X8}$ and $R^{X9}$ represent a $C_{7-18}$ aralkyloxy group which may have one or more substituents, the aralkyloxy group refers to a group having an oxygen atom bound to the $C_{7-18}$ aralkyl group. Specific examples thereof include benzyloxy group, phenetyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; preferably benzyloxy group, phenetyloxy group, 3-phenylpropyloxy group, 4-phenylbutyloxy group, 5-phenylpentyloxy group, 6-phenylhexyloxy group, 1-naphthylmethyloxy group, 2-naphthylmethyloxy group, 1-naphthylethyloxy group, 2-naphthylethyloxy group, 1-naphthylpropyloxy group and 2-naphthylpropyloxy group; more preferably benzyloxy group, phenetyloxy group, 3-phenylpropyloxy group, 4-phenylbutyloxy group, 5-phenylpentyloxy group, 6-phenylhexyloxy group, 1-naphthylmethyloxy group and 2-naphthylmethyloxy group; further preferably benzyloxy group, phenetyloxy group, 3-phenylpropyloxy group and 4-phenylbutyloxy group; and most preferably benzyloxy group and phenetyloxy group.

Similarly, when $R^{X2}$, $R^{X3}$, $R^{X4}$, $R^{X5}$, $R^{X6}$, $R^{X7}$, $R^{X8}$ and $R^{X9}$ represent a $C_{7-18}$ aralkylthio group which may have one or more substituents, the aralkylthio group refers to a group having a sulfur atom bound to the end of the $C_{7-18}$ aralkyl group. Specific examples thereof include benzylthio group, phenetylthio group, 3-phenylpropylthio group, 4-phenylbutylthio group, 5-phenylpentylthio group, 6-phenylhexylthio group, 1-naphthylmethylthio group, 2-naphthylmethylthio group, 1-naphthylethylthio group, 2-naphthylethylthio group, 1-naphthylpropylthio group and 2-naphthylpropylthio group; preferably benzylthio group, phenetylthio group, 3-phenylpropylthio group, 4-phenylbutylthio group, 5-phenylpentylthio group, 6-phenylhexylthio group, 1-naphthylmethylthio group, 2-naphthylmethylthio group, 1-naphthylethylthio group, 2-naphthylethylthio group, 1-naphthylpropylthio group and 2-naphthylpropylthio group; more preferably benzylthio group, phenetylthio group, 3-phenylpropylthio group, 4-phenylbutylthio group, 5-phenylpentylthio group, 6-phenylhexylthio group, 1-naphthylmethylthio group and 2-naphthylmethylthio group; further preferably benzylthio group, phenetylthio group, 3-phenylpropylthio group and 4-phenylbutylthio group; and most preferably benzylthio group and phenetylthio group.

When $R^{X1}$, $R^{X1a}$, $R^{X1b}$, $R^{X2}$, $R^{X3}$, $R^{X4}$, $R^{X5}$, $R^{X6}$, $R^{X7}$, $R^{X8}$ and $R^{X9}$ represent a $C_{4-13}$ cycloalkylalkyloxy group which may have one or more substituents, the cycloalkylalkyloxy group refers to a group having the linear or branched $C_{1-6}$ alkoxy group wherein a substitutable site is substituted with the $C_{3-7}$ cyclic alkyl group, and specific examples thereof include cyclopropylmethoxy group, cyclobutylmethoxy group, cyclopentylmethoxy group, cyclohexylmethoxy group, cycloheptylmethoxy group, 1-cyclopropylethoxy group, 2-cyclopropylethoxy group, 1-cyclopropyl-n-propoxy group, 2-cyclopropyl-n-propoxy group, 3-cyclopropyl-n-propoxy group, cyclopropyl-i-propoxy group, cyclopropyl-n-butoxy group, cyclopropyl-i-butoxy group, cyclopropyl-sec-butoxy group, cyclopropyl-t-butoxy group, cyclopropyl-n-pentyloxy group, cyclopropyl-i-pentyloxy group, cyclopropyl-sec-pentyloxy group, cyclopropyl-t-pentyloxy group and cyclopropyl-neopentyloxy group; more preferably cyclopropyl-methoxy group, cyclopropyl-ethoxy group, cyclopropyl-n-propoxy group, cyclopropyl-i-propoxy group, cyclopropyl-n-butoxy group, cyclopropyl-i-butoxy group, cyclopropyl-sec-butoxy group, cyclopropyl-t-butoxy group, cyclopropyl-n-pentyloxy group, cyclopropyl-i-pentyloxy group, cyclopropyl-sec-pentyloxy group, cyclopropyl-t-pentyloxy group, cyclopropyl-neopentyloxy group; and most preferably cyclopropyl-methoxy group, cyclopropyl-ethoxy group, cyclopropyl-n-propoxy group, cyclopropyl-i-propoxy group and the like.

Herein, specific examples of "hetero atom" include oxygen atom, sulfuratom, nitrogenatom, phosphorus, arsenic, antimony, silicon, germanium, tin, lead, boron, mercury and the like, oxygen atom, sulfur atom, nitrogen atom and phosphorus are preferred, and oxygen atom, sulfur atom and nitrogen atom are more preferred.

Hereinafter, when expressed as "which may have a hetero atom", the hetero atom is as defined above.

When Y, ring Z and ring U represent a 5 to 14-membered aromatic group which may have one or more hetero atoms", the aromatic group means the $C_{6-12}$ aryl group, or the $C_{6-12}$ aryl groups wherein a substitutable site is substituted with the $C_{1-6}$ aliphatic hydrocarbon group, and specific examples of which include phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group, 2-naphthylmethyl group, 1-naphthylethyl group, 2-naphthylethyl group, as-indacenyl group, s-indacenyl group, acenaphthylenyl group and the like. Phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group, 2-naphthylmethyl group, 1-naphthylethyl group, 2-naphthylethyl group, as-indacenyl group, s-indacenyl group and acenaphthylenyl group are preferred; phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group, cinnamylidene group, 3-phenylpropyl group, 4-phenylbutyl group, 5-phenylpentyl group, 6-phenylhexyl group, 1-naphthyl group, 2-naphthyl group, 1-naphthylmethyl group and 2-naphthylmethyl group are more preferred; phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group, phenethyl group, α-methylbenzyl group, benzhydryl group, trityl group, benzylidene group, styryl group, cinnamyl group and cinnamylidene group are still preferred; phenyl group, o-tolyl group, m-tolyl group, p-tolyl group, 2,3-xylyl group, 2,4-xylyl group, 2,5-xylyl group, mesityl group, cymenyl group, o-cumenyl group, m-cumenyl group, p-cumenyl group, benzyl group and phenethyl group are further preferred; and phenyl group, o-tolyl group, m-tolyl group, p-tolyl group, 2,3-xylyl group, 2,4-xylyl group, 2,5-xylyl group and benzyl group are most preferred. Therefore, specific examples of the aromatic group having a hetero atom include furyl group, thienyl group, pyrrolyl group, pyridyl group, quinolyl group, isoquinolyl group, cinnolyl group, quinazolyl group, quinoxalyl group, indolyl group, indazolyl group, oxazolyl group, isoxazolyl group, thiazolyl group, isothiazolyl group, imidazolyl group, pyrazolyl group, furazanyl group, pyridazinyl group, pyrimidyl group, pyrazyl group and the like.

When rings Z and U represent a 5 to 14-membered aromatic group whose ring may be partially saturated", the aromatic group means 9 to 14-membered aromatic group wherein two or three rings are condensed, with 1 or 2 rings being nonaromatic, and specific examples of which include dihydrobenzofuranyl group, phthalanyl group, chromanyl group, chromanonyl group, isochromanyl group, tetrahydronaphthalenyl group, dihydrobenzothiophenyl group, indolinyl group, isatinyl group, indanyl group, indanonyl group, tetranonyl group, coumarinyl group, naphthoquinonyl group and anthraquinonyl group; preferably dihydrobenzofuranyl group, phthalanyl group, chromanyl group, chromanonyl group, tetrahydronaphthalenyl group and indanyl group; and more preferably dihydrobenzofuranyl group and chromanyl group.

The expression "Y represents a $C_{3-7}$ alicyclic hydrocarbon" refers to that the alicyclic hydrocarbon group means a $C_{3-7}$ cyclic aliphatic hydrocarbon group, and specific examples of which include cyclopropyl group, cyclobutyl group, cyclopentyl group, cyclohexyl group, cycloheptyl group, cyclopropenyl group, cyclobutenyl group, cyclopentenyl group, cyclohexenyl group, cycloheptenyl group and the like. Cyclopropyl group, cyclobutyl group, cyclopentyl group, cyclohexyl group, cycloheptyl group, cyclopropenyl group, cyclobutenyl group, cyclopentenyl group, cyclohexenyl group and cycloheptenyl group are preferred; cyclopropyl group, cyclobutyl group, cyclopentyl group, cyclohexyl group and cycloheptyl group are more preferred; cyclopropyl group, cyclobutyl group, cyclopentyl group and cyclohexyl group are still preferred; and cyclopropyl group, cyclobutyl group and cyclopentyl group are most preferred. Therefore, specific examples of the alicyclic hydrocarbon having a hetero atom include pyrrolynyl group, pyrrolidinyl group, imidazolinyl group, imidazolidinyl group, pyrazolinyl group, pyrazolidinyl group, piperidinyl group, piperazinyl group, morpholinyl group, dihydrofuranyl group and tetrahydrofuranyl group, with dihydrofuranyl group and tetrahydrofuranyl group being preferred.

When L represents a single bond, the compounds of the invention are exemplified by carboxylic acid derivatives having group X bound via a single bond to the group Y, represented by the following formula:

(II)

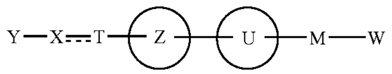

(wherein each symbol has the same meaning as defined above), a salts thereof, an ester thereof or a hydrate of them.

When M represents a single bond, the compounds of the invention are exemplified by carboxylic acid derivatives represented by the following formula:

(III)

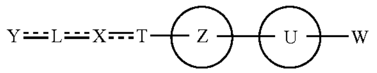

(wherein each symbol has the same meaning as defined above), a salt thereof, an ester thereof or a hydrate of them.

When T represents a single bond, the compounds of the invention are exemplified by carboxylic acid derivatives represented by the following formula:

(IV)

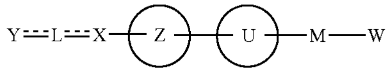

(wherein each symbol has the same meaning as defined above), a salt thereof, an ester thereof or a hydrate of them.

When X represents a single bond, the compounds of the invention are exemplified by carboxylic acid derivatives represented by the following formula:

(V)

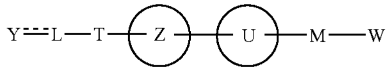

(wherein each symbol has the same meaning as defined above), a salt thereof, an ester thereof or a hydrate of them.

When L, T and M represent a C1 to C6 alkylene group which may have one or more substituent groups, the alkylene group refers to a divalent group derived by removing one hydrogen atom from the above-described C1 to C6 alkyl group, and specifically it is for example a methylene group, ethylene group, 1-methylethylene group, 2-methylethylene group, 1-ethylethylene group, 2-ethylethylene group, 1,1-dimethylethylene group, 1,2-dimethylethylene group, propylene group, 1-methylpropylene group, 2-methylpropylene group, 3-methylpropylene group, 1-ethylpropylene group, 2-ethylpropylene group, 3-ethylpropylene group, 1,1-dimethylpropylene group, 1,2-dimethylpropylene group, 1,3-dimethylpropylene group, 1,1-diethylpropylene group, 1,2-diethylpropylene group, 1,3-diethylpropylene group, trimethylene group, 1-methyltrimethylene group, 1-ethyltrimethylene group, 2-methyltrimethylene group, 1,1-dimethyltrimethylene group, tetramethylene group, pentamethylene group or hexamethylene group. It is preferably a methylene group, ethylene group, 2-methylethylene group, 2-ethylethylene group, propylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group or hexamethylene group, more preferably a methylene group, ethylene group, 2-methylethylene group, propylene group, 2-ethylethylene group, 1,1-dimethylethylene group, 1,2-dimethylethylene group, trimethylene group, 1-methyltrimethylene group, 1-ethyltrimethylene group, 2-methyltrimethylene group or 1,1-dimethyltrimethylene group, more preferably a methylene group, ethylene group, 2-methylethylene group, propylene group, 2-ethylethylene group, 1,1-dimethylethylene group, 1,2-dimethylethylene group or trimethylene group, most preferably a methylene group, ethylene group, methylethylene group or propylene group.

Similarly, when T represents a $C_{1-3}$ alkylene group which may have one or more substituents, the alkylene group means a bivalent group derived by removing one hydrogen atom from the $C_{1-3}$ alkyl group, and specific examples of which include the $C_{1-3}$ alkylene group as recited above. Methylene group, ethylene group and propylene group are preferred; methylene group and ethylene group are more preferred; and methylene group is most preferred.

When L, T and M represent a C2 to C6 alkenylene group which may have one or more substituent groups, the alkenylene group refers to a divalent group derived by removing one hydrogen atom from the above-described C2 to C6 alkenyl group, and specifically it is for example a vinylene group, 1-methylvinylene group, 2-methylvinylene group, 1-ethylvinylene group, 2-ethylvinylene group, propenylene group, 1-methylpropenylene group, 2-methylpropenylene group, 3-methylpropenylene group, 1-ethylpropenylene group, 2-ethylpropenylene group, 3-ethylpropenylene group, butenylene group, pentenylene group or hexenylene group. Preferably it is a vinylene group, 1-methylvinylene group, 2-methylvinylene group, 1-ethylvinylene group, 2-ethylvinylene group, propenylene group, 1-methylpropenylene group, 2-methylpropenylene group, 3-methylpropenylene group, 1-ethylpropenylene group, 2-ethylpropenylene group, 3-ethylpropenylene group, butenylene group or pentenylene group, more preferably a vinylene group, 1-methylvinylene group, 2-methylvinylene group, 1-ethylvinylene group, 2-ethylvinylene group, propenylene group, 1-methylpropenylene group, 2-methylpropenylene group, 3-methylpropenylene group, 1-ethylpropenylene group, 2-ethylpropenylene group or 3-ethylpropenylene group, still more preferably a vinylene group, 1-methylvinylene group, 2-methylvinylene group, 1-ethylvinylene group or 2-ethylvinylene group, most preferably a vinylene group.

When L and T represent a C2 to C6 alkynylene group which may have one or more substituent groups, the alkynylene group refers to a divalent group derived by removing one hydrogen atom from the above-described C2to C6alkynyl group, and specifically it is for example an ethynylene group, propynylene group, butynylene group, pentynylene group or hexynylene group. It is preferably an ethynylene group, propynylene group, butynylene group or pentynylene group, more preferably an ethynylene group, propynylene group or butynylene group, still more preferably a butynylene group or propynylene group, most preferably a propynylene group.

Similarly, when M represents a C2 to C6 alkynylene group which may have one or more substituent groups, the alkynylene group means a divalent group derived by removing one hydrogen atom from the above-described C2 to C6 alkynyl group, and specifically it is the above-described C2 to C6 alkynylene group. It is preferably an ethynylene group or propynylene group, more preferably an ethynylene group.

When $R^{X1}$, $R^{X1a}$, $R^{X1b}$, $R^{X10}$, $R^{X11}$ and $R^{X12}$ represent a $C_{2-7}$ aliphatic acyl group which may have one or more substituents, the aliphatic acyl group represents the $C_{1-6}$ alkyl group, the $C_{2-6}$ alkenyl group or the $C_{2-6}$ alkynyl group wherein a carbonyl group is bound to their terminal end, and specific examples of which include acetyl group, propionyl group, butyryl group, isobutyryl group, valeryl group, isovaleryl group, pivaloyl group, hexanoyl group, octanoyl group, acryloyl group, methacryloyl group, crotonoyl group and the like. Acetyl group, propionyl group, butyryl group, isobutyryl group, valeryl group, isovaleryl group, pivaloyl group, hexanoyl group, octanoyl group, acryloyl group, methacryloyl group and crotonoyl group are preferred; acetyl group, propionyl group, butyryl group, isobutyryl group, valeryl group, isovaleryl group, pivaloyl group, hexanoyl group and octanoyl group are more preferred; acetyl group, propionyl group, butyryl group and isobutyryl group are still preferred; and acetyl group and propionyl group are most preferred.

When $R^{X1}$, $R^{X1a}$, $R^{X1b}$, $R^{X10}$, $R^{X11}$ and $R^{X12}$ represent a $C_{7-19}$ aromatic acyl group which may have one or more substituents, the $C_{5-12}$ aromatic acyl group means the $C_{5-12}$ aryl group wherein a carbonyl group or a group derived by removing one hydrogen atom from the $C_{2-7}$ aliphatic acyl group is bound to their terminal end, and specific examples of which include benzoyl group, o-toluoyl group, m-toluoyl group, p-toluoyl group, cinnamoyl group, 1-naphthoyl group, 2-naphthoyl group and the like. Benzoyl group, o-toluoyl group, m-toluoyl group, p-toluoyl group, cinnamoyl group, 1-naphthoyl group and 2-naphthoyl group are preferred; benzoyl group, o-toluoyl group, m-toluoyl group, p-toluoyl group and cinnamoyl group are more preferred; benzoyl group and cinnamoyl group are still preferred; and benzoyl group is most preferred.

When $R^{X1}$, $R^{X1a}$, $R^{X1b}$, $R^{X10}$, $R^{X11}$ and $R^{X12}$ represent a C2 to C7 aliphatic alkoxycarbonyl group which may have one or more substituent groups, the aliphatic alkoxycarbonyl group refers to a C1 to C6 alkoxy group, C2 to C6 alkenyloxy group or C2 to C6 alkynyloxy group having a carbonyl group bound to the terminal thereof, and specifically it is a methoxycarbonyl group, ethoxycarbonyl group, propyloxycarbonyl group, butoxycarbonyl group, i-butoxycarbonyl group, t-butoxycarbonyl group, pentyloxycarbonyl group, hexyloxycarbonyl group, octyloxycarbonyl group, allyloxycarbonyl group, methallyloxycarbonyl group or crotyloxycarbonyl group. It is preferably a methoxycarbonyl group, ethoxycarbonyl group, propyloxycarbonyl group, butoxycarbonyl group, i-butoxycarbonyl group, t-butoxycarbonyl group, pentyloxycarbonyl group, hexyloxycarbonyl group, octyloxycarbonyl group or allyloxycarbonyl group, more preferably a methoxycarbonyl group, ethoxycarbonyl group, propyloxycarbonyl group, butoxycarbonyl group, i-butoxycarbonyl group, t-butoxycarbonyl group, pentyloxycarbonyl group, hexyloxycarbonyl group or octyloxycarbonyl group, more preferably a methoxycarbonyl group, ethoxycarbonyl group, propyloxycarbonyl group, butoxycarbonyl group or i-butoxycarbonyl group, most preferably a methoxycarbonyl group, ethoxycarbonyl group or propyloxycarbonyl group.

When $R^{X1}$, $R^{X1a}$, $R^{X1b}$, $R^{X10}$, $R^{X11}$ and $R^{X12}$ represent a C7 to C19 aromatic alkoxycarbonyl group which may have one or more substituent groups, the aromatic alkoxycarbonyl group refers to a C5 to C12 aryl group having a carbonyl group bound to the terminal thereof or a group derived from by removing one hydrogen atom from the above-described C2 to C7 aliphatic alkoxycarbonyl group. Specifically, for example, a phenoxycarbonyl group, o-tolyloxycarbonyl group, m-tolyloxycarbonyl group, p-tolyloxycarbonyl group, 1-naphthyloxycarbonyl group and 2-naphthyloxycarbonyl group may be proposed. It is preferably a phenoxycarbonyl group, o-tolyloxycarbonyl group, m-tolyloxycarbonyl group, p-tolyloxycarbonyl group or 1-naphthyloxycarbonyl group, more preferably a phenoxycarbonyl group, o-tolyloxycarbonyl group or m-tolyloxycarbonyl group, still more preferably a phenoxycarbonyl group or o-tolyloxycarbonyl group, most preferably a phenoxycarbonyl group.

represents a single bond or a double bond. Therefore, compounds of the present invention represented by the following formula (I):

(I)

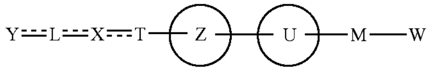

(wherein each symbol represents a group as defined above) comprehend carboxylic acid compound represented by the following formulae:

(Ia)

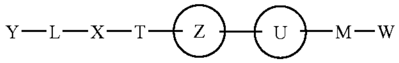

(Ib)

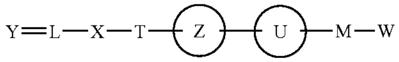

(Ic)

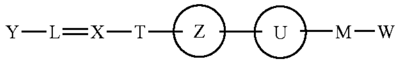

(Id)

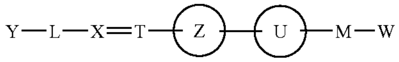

(Ie)

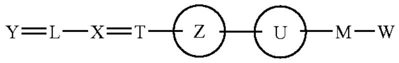

(If)

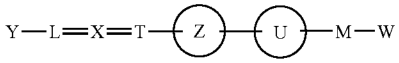

(Ig)

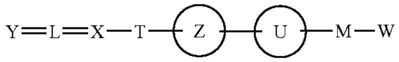

(Ih)

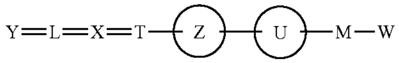

(wherein symbols are as described above), a salt thereof, an ester thereof or a hydrate of them.

The group represented by the formula:

(wherein each symbol represents a group as defined above) and the group represented by the formula:

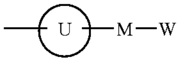

(wherein each symbol represents a group as defined above) are bound with each other on the ring Z via from 2 to 8 atoms. In the case where such wording is used, "bound with each other on the ring Z via from 2 to 8 atoms" represents the following cases.

For example, when the ring Z is benzene, and 2 atoms are involved in binding, the formula is as follows:

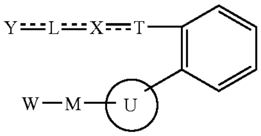

wherein each symbol represents a group as defined above.

When the ring Z is anthracene, and 8 atoms are involved in binding, the formula is as follows:

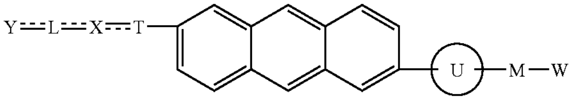

(wherein each symbol represents a group as defined above). Therefore, those defined by the ring Z, the group represented by the formula:

(wherein each symbol represents a group as defined above) and the group represented by the formula:

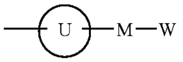

(wherein each symbol represents a group as defined above) may be bound in any positions. Preferably the compound represented by the formula:

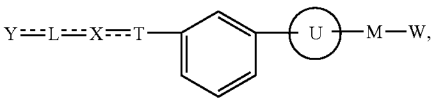

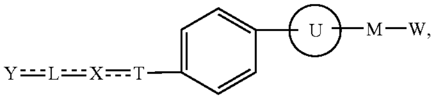

-continued

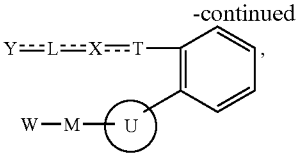

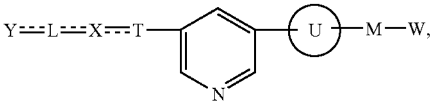

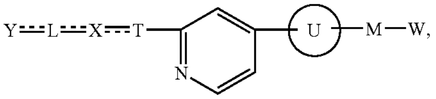

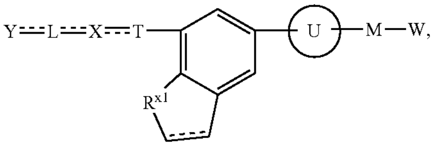

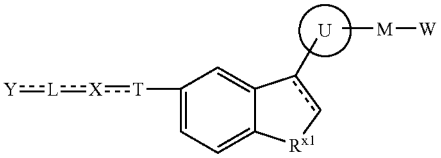

and

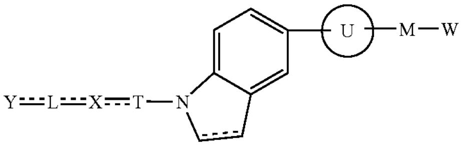

(wherein each symbol represents a group as defined above, and the aromatic group may further have 1 to 4 substituents), and more preferably the formula:

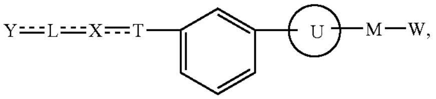

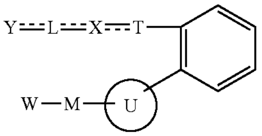

and

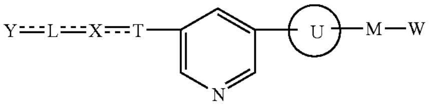

(wherein each symbol represents a group as defined above, and the aromatic group may further have 1 to 4 substituents).

The group represented by the formula:

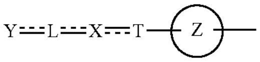

(wherein each symbol represents a group as defined above) and the group represented by the formula:

-M-W (wherein each symbol represents a group as defined above) are bound with each other on the ring U via from 2 to 8 atoms. In the case where such wording is used, "bound with each other on the ring U via from 2 to 8 atoms" represents the following cases. For example, when the ring U is benzene, and 2 atoms are involved in binding, the formula is as follows:

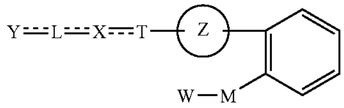

(wherein each symbol represents a group as defined above), and when the ring Z is anthracene, and 8 atoms are involved in binding, the formula is as follows:

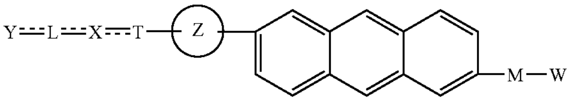

(wherein each symbol represents a group as defined above). Therefore, those defined by the ring U, the group represented by the formula:

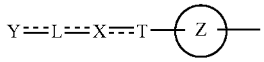

(wherein each symbol represents a group as defined above) and the group represented by the formula:

-M-W (wherein each symbol represents a group as defined above) may be bound in any positions. Preferably the compound represented by the formula:

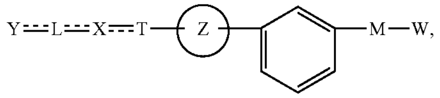

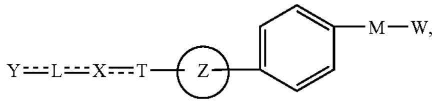

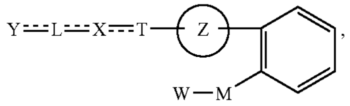

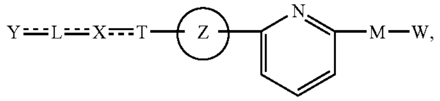

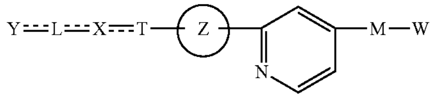

-continued and

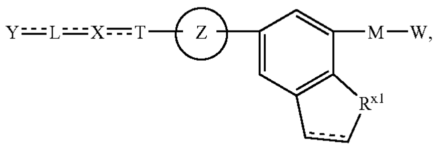

(wherein each symbol represents a group as defined above, and the aromatic group may further have 1 to 4 substituents), and more preferably the formula:

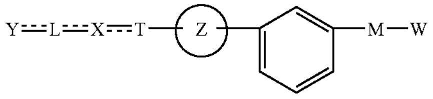

and

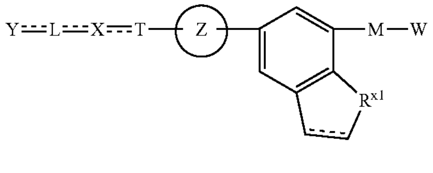

(wherein each symbol represents a group as defined above, and the aromatic group may further have 1 to 4 substituents).

"Salts" used herein are not particularly limited with regard to the kind, and specific examples include additive salts of inorganic acid such as hydrofluoride, hydrochloride, sulfate, nitrate, perchlorate, phosphate, carbonate, bicarbonate, hydrobromide or hydroiodide; additive salts of organic carboxylic acid such as acetate, maleate, fumarate, oxalate, lactate, tartrate or trifluoroacetate; additive salts of organic sulfonic acid such as methanesulfonate, trifluoromethanesulfonate, ethanesulfonate, hydroxymethanesulfonate, hydroxyethanesulfonate, benzensufonate, toluenesulfonate or taurine salt and the like; additive salts of amine such as trimethylamine salt, triethylamine salt, pyridine salt, procaine salt, picoline salt, dicyclohexylamine salt, N,N'-dibenzyldiaminoethane salt, N-methylglucamine salt, diethanolamine salt, triethanolamine salt, tris (hydroxymethylamino)methane salt or phenethylbenzyl amine salt; additive salts of alkaline metal such as sodium salt or potassium salt; additive salts of alkaline earth metal such as magnesium salt or calcium salt; and additive salts of amino acid such as arginine salt, lysine salt, serine salt, glycine salt, aspartate or glutamate and the like. Pharmaceutically acceptable salts are preferred.

Pharmaceutically acceptable salts are not particularly limited with regard to the kind, and specific examples include additive salts of inorganic acid such as hydrochloride, sulfate, carbonate, bicarbonate, hydrobromide or hydroiodide; additive salts of organic carboxylic acid such as acetate, maleate, lactate, tartrateortrifluoroacetate; additive salts of organic sulfonic acid such as methanesulfonate, hydroxymethanesulfonate, hydroxyethanesulfonate, benzensufonate, toluenesulfonate or taurine salt; additive salts of amine such as trimethylamine salt, triethylamine salt, pyridine salt, procaine salt, picoline salt, dicyclohexylamine salt, N,N'-dibenzyldiaminoethane salt, N-methylglucamine salt, diethanolamine salt, triethanolamine salt, tris(hydroxymethylamino)methane salt or phenethyl benzyl amine; additive salts of alkaline metal such as sodium salt or potassium salt; additive salts of amino acid such as arginine salt, lysine salt, serine salt, glycine salt, aspartate or glutamate.

"Ester" used in the present invention refers to esters of carboxyl group of W in the general formula (I). These are not particularly limited in so far as they are commonly used in organic synthesis, and physiologically acceptable ester groups which are hydrolyzed under physiological conditions are comprehended. Specific examples include $C_{1-6}$ alkyl groups, $C_{6-12}$ aryl groups, $C_{7-20}$ aralkyl groups such as benzyl group, $C_{7-20}$ heteroarylalkyl groups, 4-methoxybenzyl group, alkanoyloxyalkyl groups such as acetoxymethyl group, propionyloxymethyl group or pivaloxymethyl group, alkoxycarbonyloxyalkyl groups such as methoxycarbonyloxymethyl group, ethoxycarbonyloxymethyl group or 2-methoxycarbonyloxyethyl group, (5-methyl-2-oxo-1,3-dioxo-4-yl)methyl group and the like.

It is to be noted that if the carboxylic acid derivative having the above general formula (I), a salt pharmacologically acceptable salt thereof or a pharmacologically acceptable ester thereof form solvates, all such solvates are comprehended in the present invention.

The compound of the present invention represented by the formula (I):

(I)

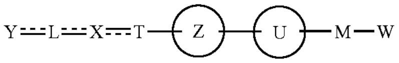

(wherein each symbol represents a group as defined above) can be synthesized in a conventional method, and can be synthesized, for example, in the manner as described below.

GENERAL PRODUCTION EXAMPLE A

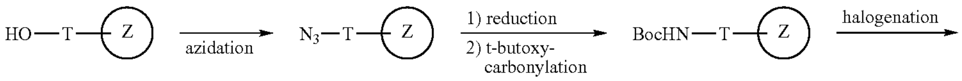

1a 2a 3a

-continued

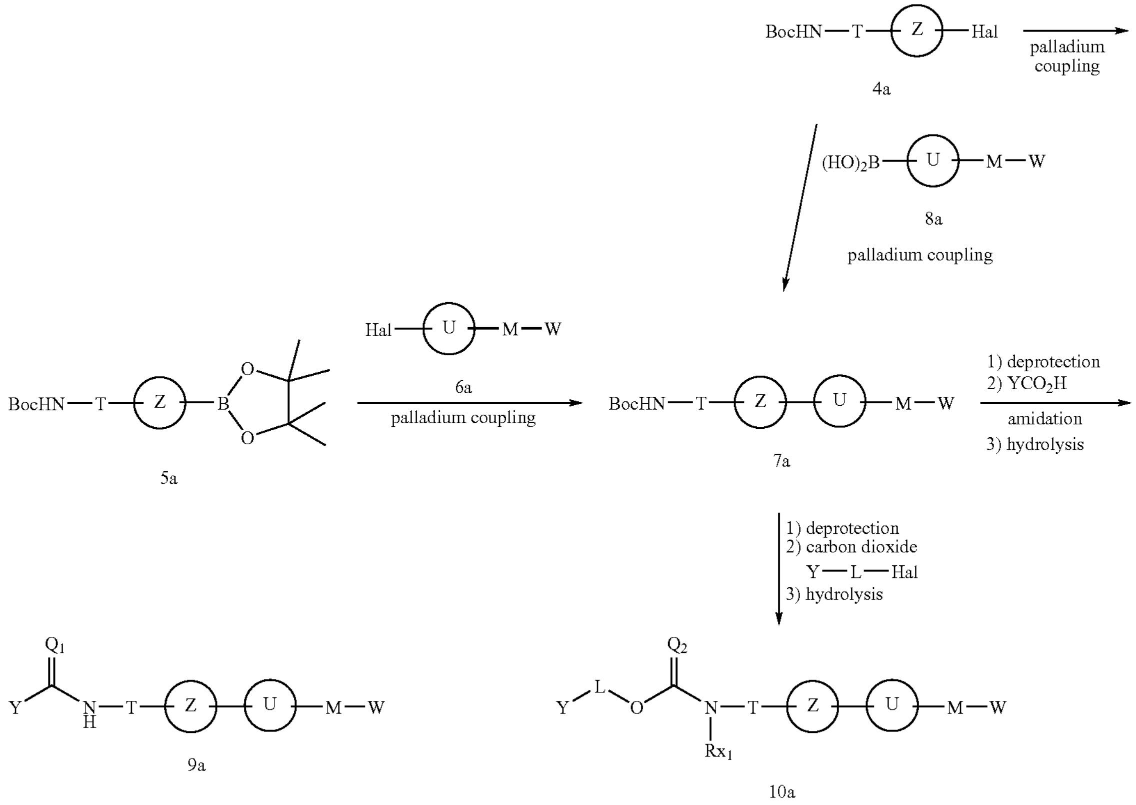

4a
8a
6a
5a
7a
9a
10a

In the reaction scheme, each symbol represents the same groups as defined above, and Hal represents a halogen.

The compound of the formula (2a) is obtained by azidating the compound of the formula (1a).

The reaction conditions are not particularly limited, but preferably the compound of the formula (1a) is reacted with diphenyl phosphoryl azide at a temperature of −20 to 150° C. in the presence of an organic base such as lithium hydroxide, sodium hydroxide, potassium hydroxide, lithium carbonate, sodium carbonate, potassium carbonate, cesium carbonate, lithium hydride, sodium hydride, potassium hydride or diazabicyclo[5.4.0]undecene in an organic solvent such as N,N-dimethylformamide, N-methylpyrrolidone, dioxane, tetrahydrofuran -or toluene.

The compound of the formula (3a) is obtained by reducing the compound of the formula (2a) and then converting the formed amino group into a t-butoxycarbonylamino group.

The reaction conditions are not particularly limited, but preferably the compound of the formula (2a) is reacted in the presence of a metal catalyst such as palladium-carbon, platinum oxide or Raney's nickel and t-butyl dicarbonate in a hydrogen atmosphere at a temperature of 0 to 150° C. in a solvent such as methanol, ethanol, propanol, dimethyl sulfoxide, N,N-dimethylformamide, N-methylpyrrolidone, dioxane, tetrahydrofuran or toluene.

The compound of the formula (4a) can be obtained by halogenating the compound of the formula (3a).

The reaction conditions are not particularly limited, but preferably the compound of the formula (4a) is reacted with a halogenating reagent such as chlorine, bromine, iodine, N-chlorosuccinimide, N-bromosuccinimide or N-iodosuccinimide in an organic solvent such as methanol, ethanol, propanol, dimethyl sulfoxide, N,N-dimethylformamide, N-methylpyrrolidone, dioxane, tetrahydrofuranoracetonitrile. The reaction temperature is preferably −0° C. to 50° C.

The compound of the formula (5a) is obtained by reacting bispinacolate diboron with the compound of the formula (4a).

The reaction conditions are not particularly limited, but preferably the compound of the formula (4a) is reacted in the presence of 0.0001 to 0.5 mol equivalent copper halide, 0.0001 to 0.5 mol equivalent palladium catalyst such as tetrakistriphenyl phosphine palladium, dichlorobistriphenyl phosphine palladium or dichlorodiphenyl ferrocenyl palladium and a base such as triethylamine, N,N-diisopropylethylamine, butylamine, tributylamine, lithiumhydroxide, sodiumhydroxide, potassium hydroxide, lithium carbonate, sodium carbonate, potassium carbonate, cesium carbonate, lithium hydride, sodium hydride, potassium hydride, sodium acetate or potassium acetate at a temperature of 0 to 150° C. in a solvent such as methanol, ethanol, propanol, dimethyl sulfoxide, N,N-dimethylformamide, N-methylpyrrolidone, dioxane, tetrahydrofuran, dimethoxyethane or toluene.

The compound of the formula (7a) is obtained by reacting the compound of the formula (5a) with the compound of the formula (6a), or by reacting the compound of the formula (4a) with the compound of the formula (8a).

The reaction conditions are in accordance with those of the production example for the compound of the formula (5a) in Production Example A.

The compound of the formula (9a) is obtained by deprotecting the compound of the formula (7a), then amidating the product and hydrolyzing an intramolecular ester.

The reaction conditions for deprotection are not particularly limited, and the desired compound is obtained by reaction with an acid such as hydrogen chloride or trifluoroacetic acid at 0 to 150° C. in an organic solvent such as dichloromethane, chloroform, tetrahydrofuran or dioxane.

The reaction conditions for amidation are not particularly limited, and the desired compound is obtained by reaction with a suitable carboxylic acid at a temperature of 0 to 150° C. in the presence of a condensing agent such as diphenylphosphoryl acid azide, diethylphosphoric acid cyanide or dicyclohexyl carbodiimide and a base such as triethylamine, N,N-diisopropylethylamine, tributylamine, sodium bicarbonate or potassium bicarbonate in a solvent such as N,N-dimethylformamide, N-methylpyrrolidone, dioxane, tetrahydrofuran, toluene, dichloromethane or chloroform.

The reaction conditions for hydrolysis are not particularly limited, and the desired compound is obtained by reaction with an aqueous solution of lithium hydroxide, sodium hydroxide or potassium hydroxide at a temperature of 0 to 150° C. in a solvent such as methanol, ethanol, propanol, dimethyl sulfoxide, N,N-dimethylformamide, N-methylpyrrolidone, dioxane or tetrahydrofuran.

The compound of the formula (10a) is obtained by deprotecting the compound of the formula (7a), then allowing carbon dioxide and Y—L-Hal to act on the product to form its corresponding carbamate, and hydrolyzing an intramolecular ester.

The reaction conditions for deprotection are in accordance with those of the production example for the compound of the formula (9a) in Production Example A.

The reaction conditions for synthesizing the carbamate are not particularly limited, and the reaction was carried out according to the literature (*J. Org. Chem.* 2000, 66, 1035).

The reaction conditions for hydrolysis are in accordance with the production example for the formula (9a) in Production Example A.

GENERAL PRODUCTION EXAMPLE B

In the reaction scheme, each symbol represents the same groups as defined above, and Hal represents a halogen.

The compound of the formula (2b) is obtained by halogenating the compound of the formula (1b).

The reaction conditions are in accordance with those of the production example for the formula (4a) in Production Example A.

The compound of the formula (4b) is obtained by palladium-coupling the compound of the formula (2b) with the compound of the formula (3b).

The reaction conditions are in accordance with those of the production example for the formula (5a) in Production Example A.

The compound of the formula (6b) is obtained by palladium-coupling the compound of the formula (5b) with the compound of the formula (3b).

The reaction conditions are in accordance with those of the production example for the formula (5a) in Production Example A.

The compound of the formula (4b) is obtained by reducing the compound of the formula (6b).

The reaction conditions are not particularly limited, and the compound of the formula (4b) is obtained by reacting the compound of the formula (6b) with a reducing agent such as diborane in a solvent such as dimethyl sulfoxide, N,N-dimethylformamide, N-methylpyrrolidone, dioxane or tetrahydrofuran. The reaction temperature is preferably a temperature of 0 to 150° C. Alternatively, the compound of the formula (4b) can also be obtained by reacting the compound of the formula (6b) with chlorocarbonate ester in a solvent such as dimethyl sulfoxide, N,N-dimethylformamide, N-methylpyrrolidone, dioxane or tetrahydrofuran to form a mixed acid anhydride, and then reacting it with a reducing agent such as lithium borohydride, sodium borohydride or potassium borohydride. The reaction temperature is preferably a temperature of 0 to 150° C.

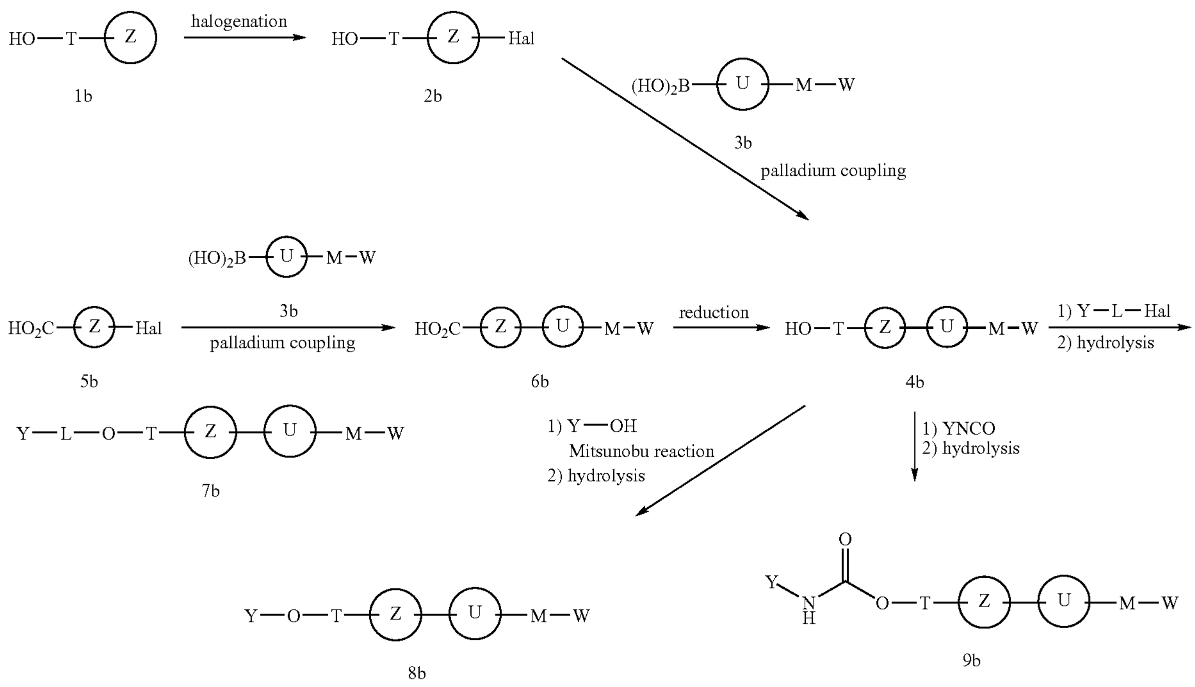

The compound of the formula (7b) is obtained by alkylating the compound of the formula (4b) and then hydrolyzing an intramolecular ester.

The reaction conditions for the alkylation are not particularly limited, and the compound formula (4b) can be reacted for example at a temperature of 0 to 150° C. in the presence of a base such as lithium hydroxide, sodium hydroxide, potassium hydroxide, lithium carbonate, sodium carbonate, potassium carbonate, cesium carbonate, lithium hydride, sodium hydride or potassium hydride in a solvent such as methanol, ethanol, propanol, dimethyl sulfoxide, N,N-dimethylformamide, N-methylpyrrolidone, dioxane, tetrahydrofuran or toluene.

The reaction conditions for the hydrolysis are in accordance with those of the production example for the formula (9a) in Production Example A.

The compound of the formula (8b) is obtained by subjecting the compound of the formula (4b) to Mitsunobu reaction and then hydrolyzing an intramolecular ester.

The reaction conditions for Mitunobu reaction are not particularly limited, and the compound of the formula (4b) is reacted with diethyl azodicarboxylate or diisopropyl azodicarboxylate in the presence of an organophosphorus reagent such as triphenyl phosphine, tributyl phosphine, trimethyl phosphine or triethyl phosphine in a solvent such as dimethyl sulfoxide, N,N-dimethylformamide, N-methylpyrrolidone, dioxane, tetrahydrofuran or toluene. The reaction temperature is preferably −78 to 150° C.

The reaction conditions for the hydrolysis are in accordance with those of the production example for the formula (9a) in Production Example A.

The compound of the formula (9b) is obtained by reacting the compound of the formula (4b) with Y—NCO to form its corresponding carbamate, and then hydrolyzing an intramolecular ester.

The reaction conditions for synthesizing the carbamate are not particularly limited, and the compound of the formula (9b) is obtained by reacting an organic base such as pyridine or triethylamine with the compound of the formula (4b) at 0 to 150° C. in an organic solvent such as tetrahydrofuran, toluene, ether or dioxane.

The reaction conditions for the hydrolysis are in accordance with those of the production example for the formula (9a) in Production Example A.

GENERAL PRODUCTION EXAMPLE C

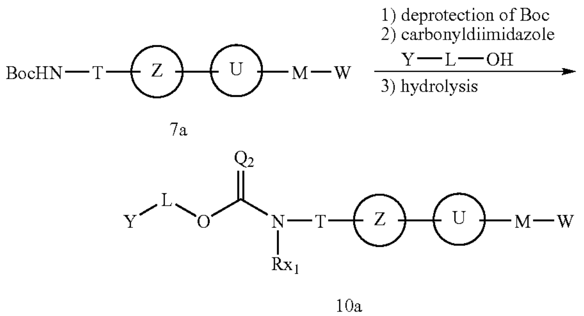

7a

10a wherein each symbol represents the same groups as defined above.

The compound of the formula (10a) in General Synthesis Method A is obtained by deprotecting a Boc group in the compound of the formula (7a) in General Synthesis Method A, then converting the product into its corresponding carbamate and hydrolyzing the product.

The reaction conditions for deprotection and hydrolysis are in accordance with those of the production example for the compound of the formula (9a) in Production Example C.

The carbamate is also obtained by reacting carbonyldimizazole with Y—L—OH at a temperature of 0 to 50° C. in a solvent such as dichloromethane, chloroform, tetrahydrofuran, toluene or acetonitrile and then reacting the product at a temperature of 0 to 50° C. with an amine obtained by deprotecting the compound of the formula (7g).

GENERAL PRODUCTION EXAMPLE D

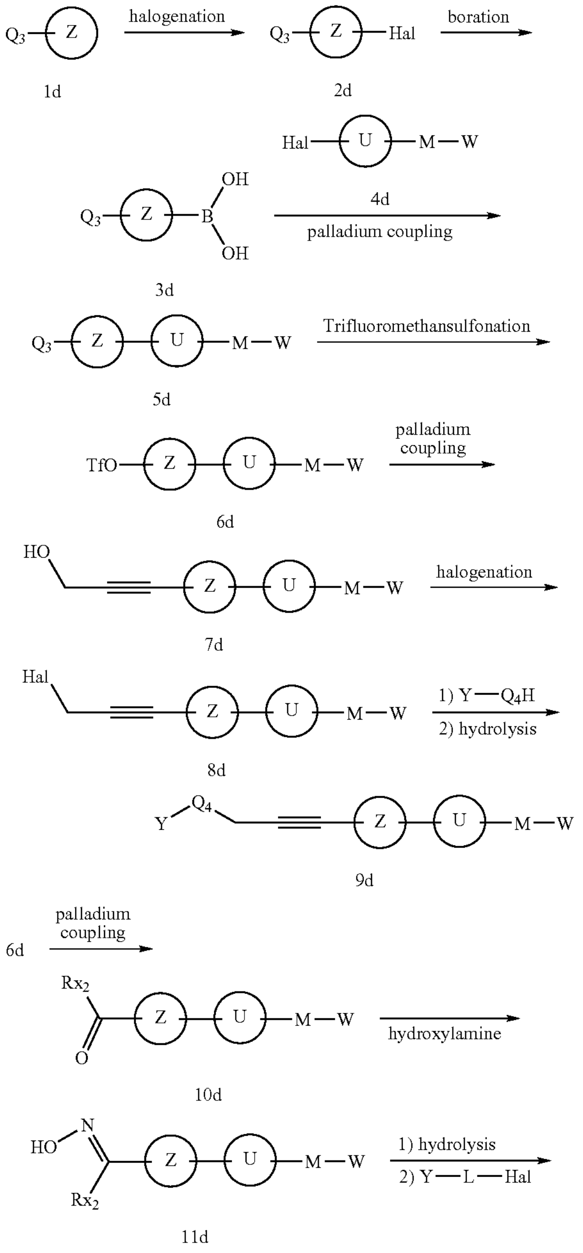

1d

2d

3d

5d

6d

7d

8d

9d

6d

10d

11d

-continued

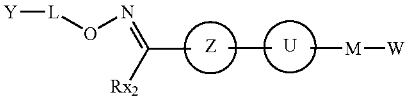

12d wherein each symbol represents the same groups as defined above, Hal represents a halogen, and Tf represents a trifluoromethanesulfonyl group.

The compound of the formula (2d) is obtained by halogenating the compound of the formula (1d).

The reaction conditions are not particularly limited, and preferably the compound of the formula (1d) is reacted with a halogenating reagent such as chlorine, bromine, iodine, N-chlorosuccinimide, N-bromosuccinimide or N-iodosuccinimide in an organic solvent such as methanol, ethanol, propanol, dimethyl sulfoxide, N,N-dimethylformamide, N-methylpyrrolidone, dioxane, tetrahydrofuranoracetonitrile. The reaction temperature is preferably −0 to 50° C.

The compound of the formula (3d) is obtained by borating the compound of the formula (2d).

The reaction conditions are not particularly limited, and the compound of the formula (3b) is obtained by reacting bispinacolate diboron with the compound of the formula (2d) at a temperature of 0 to 150° C. in the presence of 0.0001 to 0.5 mol equivalent palladium catalyst such as tetrakistriphenyl phosphine palladium, dichlorobistriphenylphosphine palladium or dichlorodiphenyl ferrocenyl palladium and a base such as triethylamine, N,N-diisopropylethylamine, butylamine, tributylamine, lithium hydroxide, sodium hydroxide, potassium hydroxide, lithium carbonate, sodium carbonate, potassium carbonate, cesium carbonate, lithium hydride, sodium hydride, potassium hydride, sodium acetate or potassium acetate in a solvent such as methanol, ethanol, propanol, dimethyl sulfoxide, N,N-dimethylformamide, N-methylpyrrolidone, dioxane, tetrahydrofuran, dimethoxyethane or toluene, or by metalizing the halogen of the compound of the formula (2d) with butyl lithium etc. in an organic solvent such as tetrahydrofuran or ether, and reacting the metalate with trialkoxy borane.

The compound of the formula (5d) is obtained by reacting the compound of the formula (3d) with the compound of the formula (4d).

The reaction conditions are not particularly limited, and preferably the compound of the formula (3d) is reacted with the compound of the formula (4d) for example at a temperature of 0 to 150° C. in the presence of 0.0001 to 0.5 mol equivalent palladium catalyst such as tetrakistriphenyl phosphine palladium, dichlorobistriphenyl phosphine palladium or dichlorodiphenyl ferrocenyl palladium and a base such as triethylamine, N,N-diisopropylethylamine, butylamine, tributylamine, lithium hydroxide, sodium hydroxide, potassium hydroxide, lithium carbonate, sodium carbonate, potassium carbonate, cesium carbonate, lithium hydride, sodium hydride, potassium hydride, sodium acetate, potassium acetate or potassium phosphate in a solvent such as methanol, ethanol, propanol, dimethylsulfoxide, N,N-dimethylformamide, N-methylpyrrolidone, dioxane, tetrahydrofuran, dimethoxyethane or toluene.

The compound of the formula (6d) is obtained by trifluoromethansulfonation of the compound of the formula (5d) The reaction conditions are not particularly limited, and the compound of the formula (6d) can be synthesized by reacting the compound of the formula (5d) at a temperature of 0 to 150° C. with N,N-bistrifluoromethyl aniline, trifluoromethanesulfonic anhydride or trifluoromethanesulfonyl chloride in the presence of an organic base such as triethylamine, N,N-diisopropylethylamine or tributylamine in a solvent such as pyridine, dichloromethane or chloroform.

The compound of the formula (7d) is obtained by reacting the compound of the formula (6d) with propargyl alcohol.

The reaction conditions are not particularly limited, and the compound of the formula (6d) is reacted with propargyl alcohol preferably at a temperature of 0 to 150° C. in the presence of 0.0001 to 0.5 mol equivalent copper halide, 0.0001 to 0.5 mol equivalent palladium catalyst such as tetrakistriphenyl phosphine palladium, dichlorobistriphenylphosphine palladium or dichlorodiphenyl ferrocenyl palladium and a base such as triethylamine, N,N-diisopropylethylamine, butylamine, tributylamine, lithium hydroxide, sodium hydroxide, potassium hydroxide, lithium carbonate, sodium carbonate, potassium carbonate, cesium carbonate, lithium hydride, sodium hydride, potassium hydride, sodium acetate or potassium acetate in a solvent suchasmethanol, ethanol, propanol, dimethyl sulfoxide, N,N-dimethylformamide, N-methylpyrrolidone, dioxane, tetrahydrofuran, dimethoxyethane or toluene.

The compound of the formula (8d) is obtained by halogenating the compound of the formula (7d).

The reaction conditions are not particularly limited, and the compound of the formula (8d) is obtained by reacting the compound of the formula (7d) with phosphorus oxychloride, thionyl chloride, phosphorus trichloride or phosphorus tribromide in a solvent such as dioxane, tetrahydrofuran or dimethoxyethane. The reaction temperature is 0 to 150° C. Further, triphenyl phosphine can also be used in combination with carbon tetrachloride, carbon tetrabromide, N-bromosuccinimide etc.

The compound of the formula (9d) is obtained by alkylating the compound of the formula (8d) with Y-Q4-H, and then hydrolyzing the product.

The reaction conditions are in accordance with those of the production example for the formula (7b) in General Production Example B.

The compound of the formula (10d) is obtained by palladium-coupling the compound of the formula (9d) with the compound of the formula (6d).

The reaction conditions are not particularly limited, and the compound of the formula (10d) is synthesized by reacting the compound of the formula (6d) at a temperature of 0 to 150° C. with 1,1-ethoxyvinyl tributyl tin, butyl vinyl ether etc. in the presence of 0.0001 to 0.5 mol equivalent palladium catalyst such as tetrakistriphenyl phosphine palladium and dichlorobistriphenyl phosphine palladium and lithium chloride in a solvent such as dioxane, tetrahydrofuran, dimethoxyethane or toluene.

The compound of the formula (11d) is obtained by reacting the compound of the formula (10d) with hydroxylamine.

The reaction conditions are not particularly limited, and the compound of the formula (11d) can be synthesized by reacting the compound of the formula (10d) with hydroxylamine at a temperature of 0 to 150° C. in a solvent such as methanol, ethanol, propanol, dimethyl sulfoxide, N,N-dimethylformamide, N-methylpyrrolidone, dioxane, tetrahydrofuran or toluene. An acid such as acetic acid, trifluoroacetic acid or hydrogen chloride may also be present.

The compound of the formula (12d) is obtained by hydrolyzing the compound of the formula (11d), and the subsequent alkylation with Y—L-Hal.

The reaction conditions for hydrolysis are not particularly limited, and the desired compound is obtained by reaction in an aqueous solution of lithium hydroxide, sodium hydroxide or potassium hydroxide at a temperature of 0 to 150° C. in a solvent such as methanol, ethanol, propanol, dimethyl sulfoxide, N,N-dimethylformamide, N-methylpyrrolidone, dioxane or tetrahydrofuran.

The reaction conditions for the alkylation are in accordance with those of the production example for the formula (7b) in General Production Example B.

GENERAL PRODUCTION EXAMPLE E

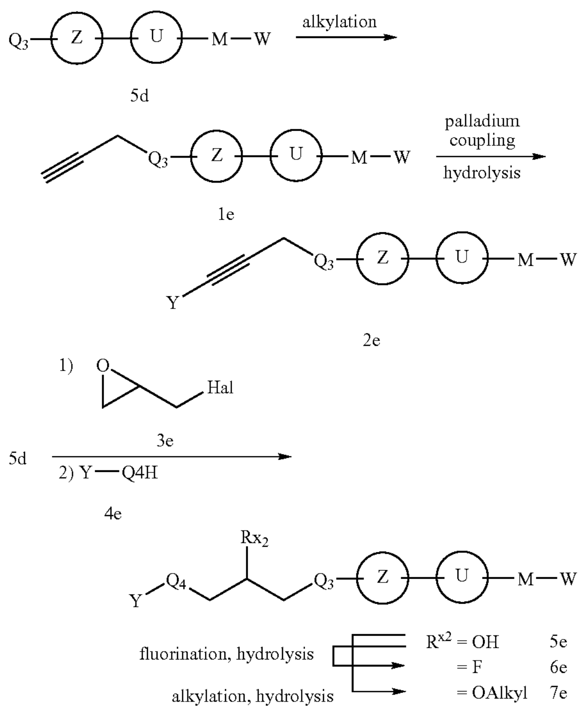

5d 1e 2e 3e 4e 5e 6e 7e wherein each symbol represents the same groups as defined above, Hal represents an eliminating group such as halogen or sulfonate, Tf represents a trifluoromethanesulfonyl group, and Alkyl represents an alkyl group.

The compound of the formula (1e) is obtained by alkylating the compound of the formula (5d) in General Production Example D with propargyl bromide.

The reaction conditions are in accordance with those of the production example for the formula (7b) in General Production Example B.

The compound of the formula (2e) is obtained by palladium-coupling the compound of the formula (1e).

The reaction conditions are in accordance with the production example for the compound of the formula (7d) in General Production Example D.

The compound of the formula (5e) is obtained by alkylating the compound of the formula (5d) in General Production Example D with the compound of the formula (3e) and then alkylating the formed epoxide with the compound of the formula (4e).

The conditions for the alkylation of the compounds of the formulae (3e) and (4e) are in accordance with those of the production example for the compound of the formula (7b) in General Production Example B.

The compound of the formula (6e) is obtained by fluorinating the compound of the formula (5e) and then hydrolyzing an intramolecular ester.

The reaction conditions for the fluorination are not particularly limited, and the compound of the formula (6e) is obtained by reacting at a temperature of 0 to 150° C. with a reagent such as diethylaminosulfur trifluoride in a solvent such as dichloromethane or chloroform.

The reaction conditions for the hydrolysis are in accordance with the production example of the formula (9a) in Production Example A.

The compound of the formula (7e) is obtained by alkylating the compound of the formula (6e) and then hydrolyzing an intramolecular ester.

The reaction conditions for alkylation are in accordance with the production example of the formula (7b) in General Production Example B.

The reaction conditions for hydrolysis are in accordance with the production example of the formula (9a) in Production Example A.

Although compounds of the present invention can be synthesized in the above methods, they may be also synthesized in commonly used general organic synthesizing methods. As for protecting groups for a hydroxyl group which may be used herein, any hydroxyl groups are possible without limitation insofar as they are protected by groups which are generally known as a protecting group for a hydroxyl group in organic synthesis, and specific examples of protecting groups for a hydroxyl group include lower alkylsilyl groups such as trimethylsilyl group or t-butyldimethylsilyl; lower alkoxymethyl groups such as methoxymethyl group or 2-methoxyethoxymethyl group; tetrahydropyranyl group; aralkyl groups such as benzyl group, p-methoxybenzyl group, 2,4-dimethoxybenzyl group, o-nitrobenzyl group, p-nitrobenzyl group or trityl group; acyl groups such as formyl group or acetyl group; lower alkoxycarbonyl groups such as t-butoxycarbonyl group, 2-iodoethoxycarbonyl group or 2,2,2-trichloroethoxycarbonyl group; alkenyloxycarbonyl groups such as 2-propenyloxycarbonyl group, 2-chloro-2-propenyloxycarbonyl group, 3-methoxycarbonyl-2-propenyloxycarbonyl group, 2-methyl-2-propenyloxycarbonyl group, 2-butenyloxycarbonyl group or cinnamyloxycarbonyl group; aralkyloxycarbonyl groups such as benzyloxycarbonyl group, p-methoxybenzyloxycarbonyl group, o-nitrobenzyloxycarbonyl group or p-nitrobenzyloxycarbonyl group and the like.

These protecting groups may be eliminated by conventional methods such as hydrolysis and reduction depending on the kind of the employed protecting group.

Although compounds of the present invention can be synthesized by the methods as described above, they may be also synthesized in commonly used general organic synthesizing methods. Specific examples of protecting groups for an amino group which may be used herein include, but not limited to, any groups which are generally known as a protecting group for an amino group in organic synthesis. For example, substituted or unsubstituted lower alkanoyl groups such as formyl group, acetyl group, chloroacetyl group, dicholroacetyl group, propionyl group, phenylacetyl group, phenoxyacetyl group or thienylacetyl group; substituted or unsubstituted lower alkoxycarbonyl groups such as benzyloxycarbonyl group, t-butoxycarbonyl group or p-nitrobenzyloxycarbonyl group; substituted lower alkyl groups such as methyl group, t-butyl group, 2,2,2-trichloroethyl group, trityl group, p-methoxybenzyl group, p-nitrobenzyl group, diphenylmethyl group or pivaloyloxymethyl group; substituted silyl groups such as trimethylsilyl group or t-butyldimethylsilyl group; substituted silylalkoxyalkyl groups such as trimethylsilylmethoxymethyl group, trimethylsilylethoxymethyl group, t-butyldimethylsilylmethoxymethyl group or t-butyldimethylsilylethoxymethyl group; substituted or unsubstituted benzylidene groups such as benzylidene group, salicylidene group, p-nitrobenzylidene group, m-chlorobenzylidene group, 3,5-di(t-butyl)-4-hydroxybenzylidene group or 3,5-di(t-butyl)benzylidene group may be proposed.

These protecting groups may be eliminated by conventional methods such as hydrolysis and reduction depending on the kind of the employed protecting group.

Although compounds of the present invention can be synthesized in the above methods, they may be also synthesized in commonly used general organic synthesizing methods. As for protecting groups for a carboxyl group which may be used herein, any carboxyl groups are possible without limitation insofar as they are protected by groups which are generally known as a protecting group for a carboxyl group in organic synthesis, and specific examples of a protecting group for a carboxyl group include linear or branched lower alkyl groups of from 1 to 4 carbon atoms such as methyl group, ethyl group, isopropyl group or t-butyl group; halogeno lower alkyl groups such as 2-iodoethyl group or 2,2,2-trichloroethyl group; lower alkoxymethyl groups such as methoxymethyl group, ethoxymethyl group or isobutoxymethyl group; lower aliphatic acyloxymethyl groups such as butylyloxymethyl group or pivaloyloxymethyl group; 1-lower alkoxycarbonyloxyethyl groups such as 1-methoxycarbonyloxyethyl group or 1-ethoxycarbonyloxyethyl group; aralkyl groups such as benzyl, p-methoxybenzyl group, o-nitrobenzyl group or p-nitrobenzyl group; benzhydryl group; phthalidyl group, etc.

Elimination of such a protective group can be carried out in a conventional method such as hydrolysis and reduction etc, depending on the type of the protective group used.

Although compounds of the present invention can be synthesized by the methods as described above, they may be synthesized in commonly used general organic synthesizing methods. Specific examples of solvents which may be used herein include, but not limited to, any solvents which do not inhibit the reaction and are generally used in organic synthesis, for example, lower alcohols such as methanol, ethanol, propanol or butanol; polyalcohols such as ethylene glycol or glycerin; ketones such as acetone, methyl ethyl ketone, diethyl ketone or cyclohexanone; ethers such as diethyl ether, isopropyl ether, tetrahydrofuran, dioxane, 2-methoxyethanol or 1,2-dimethoxyethane; nitriles such as acetonitrile or propionitrile; esters such as methyl acetate, ethyl acetate, isopropyl acetate, butyl acetate or diethyl phthalate; hydrocarbon halides such as dichloromethane, chloroform, carbon tetrachloride, 1,2-dichloroethane, trichloroethylene or tetrachloroethylene; aromatic compounds such as benzene, toluene, xylene, monochlorobenzene, nitrobenzene, indene, pyridine, quinoline, collidine or phenol; hydrocarbons such as pentane, cyclohexane, hexane, heptane, octane, isooctane, petroleumbenzine or petroleumether; amines such as ethanolamine, diethylamine, triethylamine, pyrrolidine, piperidine, piperazine, morpholine, aniline, dimethylaniline , benzylamine or toluidine; amides such as formamide, N-methylpyrrolidone, N,N-dimethylimidazolone, N,N-dimethylacetamide or N,N-dimethylformamide; phosphate amides such as hexamethylphosphate triamide or hexamethylphosphite triamide; water; and mixed solvents of one or more kinds of commonly used solvents. The mixing ratio is not particularly limited.

Although compounds of the present invention can be synthesized by the methods as described above, they may be synthesized in commonly used general organic synthesizing methods. Specific examples of bases which may be used herein include, but not limited to, any bases which do not inhibit the reaction and are generally used in organic synthesis, for example, sodium carbonate, sodium hydrogencarbonate, potassium carbonate, sodium hydride, potassium hydride, potassium t-butoxide, pyridine, dimethylaminopyridine, trimethylamine, triethylamine, N, N-diisopropylethylmine, N-methylmorpholine, N-methyl pyrrolidine, N-methyl piperidine, N,N-dimethyianiline, 1,8-diazabicyclo[5,4,0]undec-7-ene (DBU), pyridine, 4-dimethylaminopyridine, picoline, lutidine , quinoline, isoquinoline, sodium hydroxide, potassium hydroxide, lithium hydroxide, butyl lithium, sodium or potassium alcoholates such as sodium methylate, potassium methylate or sodium ethylate, and the like.

Although compounds of the present invention can be synthesized by the methods as described above, they may be synthesized in commonly used general organic synthesizing methods. Specific examples of reducing agents which may be used herein include, but not limited to, any reducing agents which do not inhibit the reaction and are generally used in organic synthesis, for example, $NaBH_4$, $LiBH_4$, $Zn(BH_4)_2$, $Me_4NBH(OAc)_3$, $NaBH_3CN$, Selectride, Super Hydride ($LiBHEt_3$), $LiAlH_4$, DIBAL, $LiAlH$ $(t\text{-}BuO)_3$, Red-al, binap, as well as catalysts such as platinum, palladium, rhodium, ruthenium, nickel and the like.

After the reaction is completed, the product can be purified if necessary by usual methods such as column chromatography on silica gel or adsorption resin, or by re-crystallization from a suitable solvent.

The medicament according to the present invention improves insulin resistance by the agonism of PPAR as described above, and the present invention can be applied not only as an insulin sensitizer but also as various medicaments based on PPAR (α, β, γ) agonism (based on e.g. PPAR α and γ dual agonism, PPAR α, β(δ) and γ triple agonism, or either one of PPAR α, β(δ) and γ agonism).

For example, the relationship of PPAR not only with insulin resistance but also with blood lipid or inflammatory diseases is known (Current Opinion in Lipidol. 10:245-257, 1999; Jiang, C., et al., PPAR-gamma agonists inhibit production of monocyte inflammatorycytokines, Nature 391:82-86 (1998); Jackson, S. M., et al., Peroxisome proliferator-activated receptor activators target human endothelial cells to inhibit leukocyte-endothelial cell interaction., Arterioscler. Thromb. Vasc. Biol. 19: 2094-2104 (1999); Su, C. G., et al., A novel therapy for colitis utilizing PPAR-gamma ligands to inhibit the epithelial inflammatory response., J Clin Invest 1999 August ; 104(4):383-9; Ricote, M., et al., The peroxisome proliferator-activated receptor-gamma is a negative regulator of macrophage activation., Nature 1998 Jan. 1; 391 (6662):79-82), and the medicament of the present invention can be applied to diseases against which it is reported to be effective in these literatures.

The dose of the pharmaceutical preparation of the present invention, though being varied depending on the severeness of symptom, age, sex, body weight, administration form and the type of disease, is usually 100 μg to 10 g/day/adult, and this dose is administered in one or divided portions.

The administration form of the medicament of the present invention is not particularly limited, and it can be administered orally or parenterally by an ordinarily used method.

For manufacturing of the medicament, ordinarily used fillers, binders, lubricants, coloring agents, flavoring agents and if necessary stabilizers, emulsifiers, absorption promoters, surfactants etc. can be used, and ingredients used generally as starting materials for medicament are compounded in a usual manner.

These ingredients include e.g. animal and vegetable oils (such as soybean oil, tallow and synthetic glyceride), hydrocarbons (such as liquid paraffin, squalene and solid paraffin), ester oils (such as octyldodecyl myristate and isopropyl myristate), higher alcohols (such as cetostearyl alcohol and behenyl alcohol), silicon resin, silicon oil, surfactants (polyoxyethylene fatty ester, sorbitan fatty ester, glycerin fatty ester, polyoxyethylene sorbitan fatty ester, polyoxyethylene hardened castor oil and polyoxyethylene-polyoxypropylene block copolymer), water-soluble polymers (such as hydroethyl cellulose, polyacrylic acid, carboxyvinyl polymer, polyethylene glycol, polyvinyl pyrrolidone and methyl cellulose), alcohols (such as ethanol and isopropanol), polyvalent alcohols (such as glycerin, propylene glycol, dipropylene glycol and sorbitol), sugars (such as glucose and sucrose), inorganic powder (such as silicic anhydride, aluminum magnesium silicate and aluminum silicate), and pure water. For pH adjustment, it is possible to use inorganic acids (such as hydrochloric acid and phosphoric acid), alkali metal salt of inorganic acid (such as sodium phosphate), inorganic bases (such as sodium hydroxide), organic acids (such as lower fatty acids, citric acid and lactic acid), alkali metal salts of organic acid (such as sodium citrate and sodium lactate) and organic bases (such as arginine and ethanolamine). If necessary, preservatives, antioxidants etc. can be added.

Hereinafter, pharmacological experiment examples are shown to show the usefulness of this invention.

EXPERIMENT EXAMPLE 1

Measurement of Blood Glucose Reduction, Blood Triglyceride Reduction and Blood Non-Esterified Fatty Acids Reduction A chemical suspended in 0.5% methyl cellulose was orally administered via a sonde into male db/db mice (Nippon Charles River, Yokohama, JP) once a day (30 mg/kg/day). Before treatment and after 4 and 9 days treatment, blood was collected though a tail vein after the mice were fasted for 1 hour, respectively. On Day 10, an oral glucose loading test was conducted; in this test, the mice were fasted overnight from the previous day, and in the next morning, 2 g/kg glucose was given to the mice. Plasma glucose, triglycerides (TG), non-esterified fatty acid (NEFA) can be measured by using commercial kits that is, Glucose C-II Test Waco (Wade name) (Wako Pure Chemical Industries, Ltd., Tokyo), Determiner L TG II (trade name) (Kyowa Medex, Tokyo) and NEFA C-Test Wako (Wako Pure Chemical Industries, Ltd., Tokyo), respectively. Compounds of the present invention showed excellent blood glucose reduction, blood triglyceride reduction and blood non-esterified fatty acid reduction.

EXPERIMENT EXAMPLE 2

Measurement of Transcriptional Activity

A GAL4-PPAR LBD chimera expression vector was constructed by ligating human PPAR 167-468 (PPAR α), 138-440 (NUC-1) and 174-475 (PPARγ) amino acid regions (LBD: Ligand Binding Domain) to a yeast transcriptional factor GAL4 1-147 amino acid region. As the reporter gene, PLAP (Placental Alkaline Phosphatase) was used, and this was ligated downstream of a TK promoter containing a 5-copy GAL4 DNA binding element to construct a vector. As host cells, CV-1 (ATCC CCL-70) was used. That is, CV-1 cells were spread at a density of $5\times10^5$ cells on a 35-mm dish and cultured in 10% FCS/DMEM for 24 hours, and using FuGENE 6 transfection reagent, the cells were co-transfected with the GAL4-PPAR LBD expression vector and GAL4 DBD-TK-PLAP expression vector. 24 hours after this transfection, the cells were spread again on a 96-well plate at a density of $1\times10^4$/well and further cultured for 24 hours. After 24 hours, the medium was exchanged with DMEM containing 10% FCS, which was previously treated at 65° C. for inactivating intrinsic alkaline phosphatase, and a test compound was added at an arbitrary concentration. The transcriptional activity was determined in terms of PLAP activity secreted 24 hours after addition of the compound, to calculate $EC_{50}$. The results are shown in Table 1.

TABLE 1

| | Transcriptional activity, EC50 (unit: μM) | | |
|---|---|---|---|
| | PPAR α | PPAR β | PPAR γ |
| Ex 11 | <0.0001 | 0.176 | 0.711 |
| Ex 21 | 0.045 | 0.116 | 0.043 |
| Ex 141 | NA | NA | 0.031 |
| Ex 199 | 0.538 | 0.00035 | 0.136 |
| Ex 220 | 0.75 | 0.0005 | 0.058 |
| Ex 257 | 0.029 | NA | NA |
| Ex 263 | NA | 0.00048 | 1.157 |
| Ex 267 | 0.622 | 0.018 | 0.468 |
| Ex 302 | 0.003 | 0.074 | 0.7 |
| Ex 365 | 1.56 | 1.144 | 0.15 |
| Ex 351 | 1.824 | 0.16 | 1.415 |
| Ex 361 | 0.719 | <0.0001 | 0.654 |
| Ex 375 | 0.653 | 0.102 | 1.285 |

The PLAP activity was determined after adding 50 μl assay buffer and 50 μl chemoluminescence substrate to 10 μl culture supernatant and incubating the mixture at room temperature for 1 hour. In this way, transcription activities with respect to PPARα, PPARβ(δ) and PPARγ could be determined. The compounds of the present invention showed an excellent transcriptional activity.

As described above, the compounds of the present invention have an excellent blood glucose and blood lipid-ameliorating action and are very useful as anti-diabetes agents, anti-hyperlipemia agents and insulin sensitizers.

EXPERIMENT EXAMPLE 3

Anti-inflammatory Effect

Experimental colitis was induced to female ICR mice (10 mice/group, Charles River Japan, Yokohama) by giving 4% dextran sodium in drinking water for 5 days. After 8 days, the mice were grouped into sections from “0” (normal) to “4” (severe) based on change in diarrhea, hematochezia and weight loss as described by Cooper H S et al., (Laboratory Invest (69), pp. 238-249, 1993) and the average of the values was used as the Disease Activity Index for colitis. Each test compound was suspended in a 0.5% methylcellulose solution and administered to the mice orally once a day via a sonde from the day when the induction of colitis was initiated. The compounds of the present invention had an excellent anti-inflammatory effect.

EXAMPLES

Hereinafter, the present invention will be described specifically in more detail by reference to Examples, but the present invention is not limited to these Examples.

Example 1

3-(3-{[(2,4-dichlorobenzoyl)amino]methyl}-4-methoxyphenyl)benzoic Acid

Production Example 1a t-Butyl N-(2-methoxybenzyl)carbamate

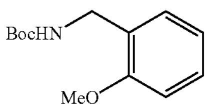

2-Methoxybenzylamine (13.0 g) was dissolved in 80 ml of tetrahydrofuran, and then a solution of 16 g of t-butyl dicarbonate in tetrahydrofuran (20 ml) was added thereto. The mixture was stirred at room temperature for 1 hour, and then the solvent was evaporated. The residue was dissolved in ethyl acetate and successively washed with 1N hydrochloric acid and brine. The organic layer was dried over anhydrous magnesium sulfate, and then the solvent was evaporated to give 19.0 g of the title compound.

$^1$H-NMR ($CDCl_3$).

δ: 1.45 (s, 9H) 3.84 (s, 3H) 4.27-4.33 (m, 2H) 5.01 (br, 1H) 6.84 (d, J=8.8 Hz, 1H) 6.94 (t, J=8.8 Hz, 1H) 7.23-7.29 (m, 2H).

MS m/e (ESI) 440 ($MH^+$).

Production Example 1b t-Butyl N-(5-bromo-2-methoxybenzyl)carbamate

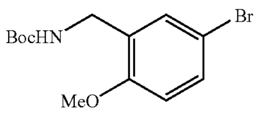

t-Butyl N-(2-methoxybenzyl)carbamate (6.04 g) was dissolved in 50 ml of acetonitrile, and 4.6 g of N-bromosuccinimide was added thereto. The mixture was stirred at room temperature for 3 hours, and then the solvent was evaporated. The residue was dissolved in ethyl acetate and successively washed with water and brine. The organic layer was dried over anhydrous magnesium sulfate, and the solvent was evaporated. The residue was washed with a mixed solvent of t-butyl methyl ether and hexane, to give 6.97 g of the title compound.

$^1$H-NMR ($CDCl_3$).

δ: 1.45 (s, 9H) 3.62 (s, 3H) 4.26 (d, J=6.4 Hz, 2H) 4.97 (br, 1H) 6.72 (d, J=8.8 Hz, 1H) 7.34 (dd, 1H, J=2.8, 11.2 Hz) 7.35 (s, 1H).

Production Example 1c t-Butyl N-[2-methoxy-5-(4,4,5,5-tetramethyl-1,3,2-dioxaborolan-2-yl)benzyl]carbamate

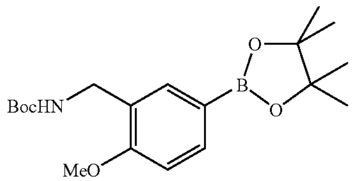

10 g of 4-Bromo-2-[(N-t-butoxycarbonylamino)methyl] anisole, 10 g of bis(pinacolato)diboron, 800 mg of dichlorobistriphenyl phosphinoferrocene palladium and 10 g of potassium acetate were dissolved in 95 ml of dimethyl sulfoxide, and the mixture was stirred at 100° C. for 24 hours in a nitrogen atmosphere. The reaction mixture was diluted with ethyl acetate and water, and filtered through Celite. The filtrate was washed with water and brine and dried over anhydrous magnesium sulfate, and the solvent was evaporated. The residues was purified by silica gel column, to give 7.012 g of the title compound in the 4:1 hexane-ethyl acetate fraction.

$^1$H-NMR ($CDCl_3$).

δ: 1.33 (s, 12H) 1.45 (s, 9H) 3.86 (s, 3H) 4.32 (d, J=5.2 Hz, 2H) 4.96 (br, 1H) 6.86 (d, J=8.0 Hz, 1H) 7.70 (s, 1H) 7.72 (dd, J=1.6, 8.4 Hz, 1H).

Production Example 1d

3-(3-{[(t-Butoxycarbonyl)amino]methyl}-4-methoxyphenyl)benzoate

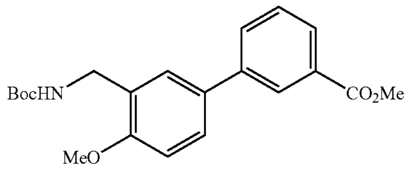

213 mg of t-Butyl N-[2-methoxy-5-(4,4,5,5-tetramethyl-1,3,2-dioxaborolan-2-yl)benzyl]carbamate, 151 mg of methyl 3-bromobenzoate, 30 mg of dichlorobistriphenylphosphinoferrocene palladium and 400 mg of potassium carbonate were dissolved in 5 ml of dimethoxyethane, and the mixture was heated under reflux for 5.5 hours in a nitrogen atmosphere. The reaction mixture was filtered through Celite, and the filtrate was evaporated. The residue was purified by silica gel column, to give 215 mg of methyl title compound in the 4:1 hexane-ethyl acetate fraction.

$^1$H-NMR ($CDCl_3$).

δ: 1.46 (s, 9H) 3.90 (s, 3H) 3.95 (s, 3H) 4.38 (brd, J=6.0 Hz, 2H) 5.06 (br, 1H) 6.95 (d, J=8.4 Hz, 1H) 7.48 (t, J=8.0 Hz, 1H) 7.51 (s, 1H) 7.52 (d, J=7.6 Hz, 1H) 7.76 (dd, J=2.0, 6.4 Hz, 1H) 7.97 (d, J=9.2 Hz, 1H) 8.22 (t, J=1.6 Hz, 1H).

Example 1e 3-(3-{[(2,4-Dichlorobenzoyl)amino]methyl}-4-methoxyphenyl)benzoic Acid

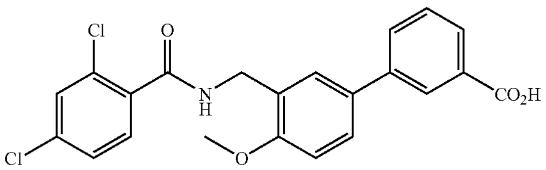

1 mL of 4N HCl/dioxane was added to 30 mg of 3-(3-{[(t-butoxycarbonyl)amino]methyl}-4-methoxyphenyl)benzoate, and the mixture was left at room temperature for 1 hour. The reaction mixture was concentrated, and the residue was dissolved in 0.4 mL N,N-dimethylformamide. To 0.2 mL of aliquot of the solution were added 9 mg of 2,4-dichlorobenzoic acid, 6 mg of diethyl cyanophosphonate and 9 mg of triethylamine, and the mixture was left overnight at room temperature. The reaction mixture was diluted with water and extracted with ethyl acetate. The organic layer was concentrated, then the residue was dissolved in 0.4 mL of ethanol, 0.1 mL of 5 N aqueous sodium hydroxide was added thereto, and the mixture was stirred at 50 to 60° C. for 1 hour. The reaction mixture was concentrated and then neutralized with 1 N hydrochloric acid. The reaction mixture was extracted with ethyl acetate and then purified by HPLC using a reverse phase system column and a water-acetonitrile-trifluoroacetic acid eluent, to give 1.97 mg of the title compound.

MS m/e (ESI) 430 ($MH^+$).

Example 2

3-(3-{[(4-Chloro-2-fluorobenzoyl)amino]methyl}-4-methoxyphenyl)benzoic Acid

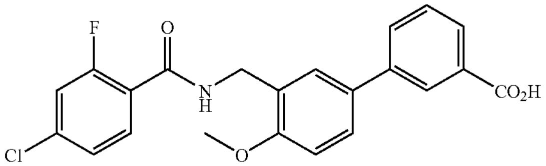

The title compound was obtained in the same way as Example 1e) except for using 4-chloro-2-fluorobenzoic acid.

MS m/e (ESI) 414 ($MH^+$).

Example 3

3-(3-{[(4-Trifluoromethyl-2-fluorobenzoyl)amino]methyl}-4-methoxyphenyl)benzoic Acid

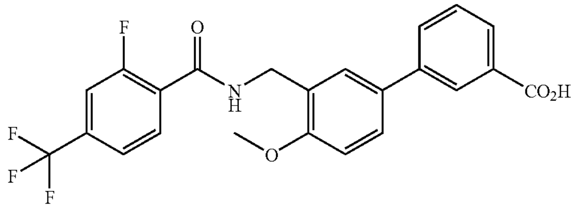

The title compound was obtained in the same way as Example 1e) except for using 4-trifluoromethyl-2-fluorobenzoic acid.

$^1$H-NMR ($CDCl_3$).

δ: 3.95 (s, 3H) 4.74 (d, J=4.8 Hz, 2H) 7.11 (d, J=8.8HZ, 1H) 7.40 (d, J=7.6 Hz, 1H) 7.46-7.53 (m, 4H) 7.57 (dd, J=2.4, 8.4 Hz, 1H) 7.62 (d, J=2.4 Hz, 1H) 7.72-7.75 (m, 1H) 7.98-8.01 (m, 1H) 8.22 (t, J=8.0 Hz, 1H) 8.26 (s, 1H).

MS m/e (ESI) 448 ($MH^+$).

Example 4

3-(3-{[(4-Cyclohexylbenzoyl)amino]methyl}-4-methoxyphenyl)benzoic Acid

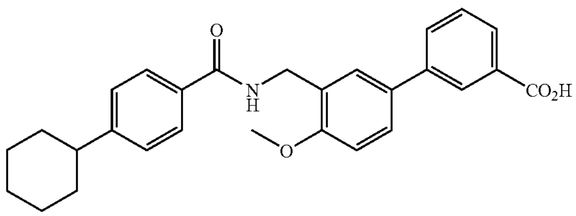

The title compound was obtained in the same way as Example 1e) except for using 4-cyclohexylbenzoic acid.

MS m/e (ESI) 444 ($MH^+$).

Example 5

3-(3-{[(4-Propoxy-2-chlorobenzoyl)amino]methyl}-4-methoxyphenyl)benzoic Acid

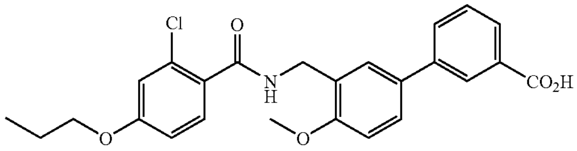

The title compound was obtained in the same way as Example 1e) except for using 4-propoxy-2-chlorobenzoic acid.

$^1$H-NMR ($CDCl_3$).

δ: 0.95 (t, J=7.2 Hz, 3H) 1.71 (q, J=7.2 Hz, 2H) 3.86 (s, 3H) 3.97 (t, J=6.4 Hz, 2H) 4.44 (d, J=5.6 Hz, 2H) 6.95 (dd, J=2.4, 8.4 Hz, 1H) 7.04 (d, J=2.4 Hz, 1H) 7.10 (d, J=8.4 Hz, 1H) 7.41 (d, 8.4 Hz, 1H) 7.55 (t, J=7.6 Hz, 1H) 7.59 (dd, J=2,4, 8.4 Hz, 1H) 7.63 (d, J=2.0 Hz, 1H) 7.83 (d, J=8.0 Hz, 1H) 7.86 (d, J=8.0 Hz, 1H) 8.14 (s, 1H) 8.78 (t, J=6.0 Hz, 1H).

MS m/e (ESI) 454 ($MH^+$).

Example 6

3-(3-{[(4-Isopropoxy-2-chlorobenzoyl)amino]methyl}-4-methoxyphenyl)benzoic Acid

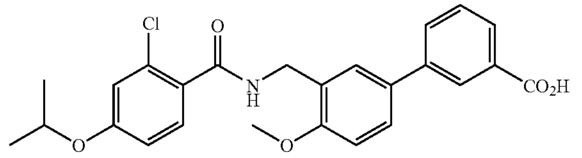

The title compound was obtained in the same way as Example 1e) except for using 4-isopropoxy-2-chlorobenzoic acid.

MS m/e (ESI) 454 ($MH^+$).

Example 7

3-(3-{[(4-Cyclopentyloxy-2-chlorobenzoyl)amino]methyl}-4-methoxyphenyl)benzoic Acid

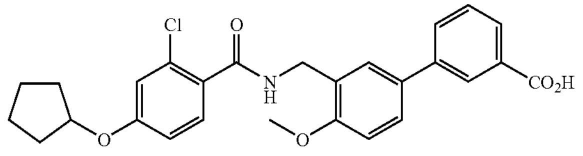

The title compound was obtained in the same way as Example 1e) except for using 4-pentyloxy-2-chlorobenzoic acid.

$^1$H-NMR ($CDCl_3$).

δ: 1.58-1.67 (m, 2H) 1.63-1.96 (m, 6H) 3.93 (s, 3H) 4.72 (d, J=5.6 HZ, 2H) 4.75 (m, 1H) 6.81 (dd, J=2.4, 8.8 Hz, 1H) 6.86 (d, J=2.4 Hz, 1H) 6.98 (d, J=8.4 Hz, 1H) 7.04 (br, 1H) 7.51 (t, J=7.6 Hz, 1H) 7.56 (dd, J=2.4, 8.0 Hz, 1H) 7.66 (d, J=2.4 Hz, 1H) 7.76 (d, J=8.8 Hz, 1H) 7.78-7.82 (m, 1H) 8.01-8.04 (m, 1H) 8.30 (s, 1H).

MS m/e (ESI) 480 ($MH^+$).

Example 8

3-{4-Methoxy-3-[({[4-methyl-2-(4-methylphenyl)-1,3-thiazol-5-yl]carbonyl}amino)methyl]phenyl}benzoic Acid

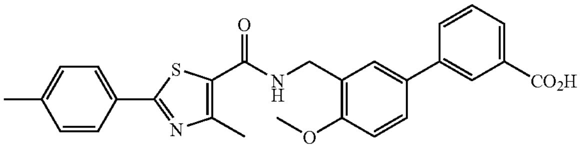

The title compound was obtained in the same way as Example 1e) except for using 4-methyl-2-(4-methylphenyl)-1,3-thiazol-5-carboxylic Acid.

MS m/e (ESI) 473 ($MH^+$).

Example 9

3-{4-Methoxy-3-[({[4-methyl-2-(2-chlorophenyl)-1,3-thiazol-5-yl]carbonyl}amino)methyl]phenyl}benzoic acid

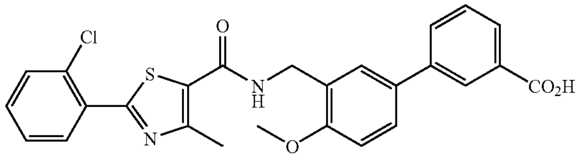

The title compound was obtained in the same way as Example 1e) except for using 4-methyl-2-(2-chlorophenyl)-1,3-thiazol-5-carboxylic Acid.

MS m/e (ESI) 493 ($MH^+$).

Example 10

3-{4-Methoxy-3-[({[4-methyl-2-(2,4-dichlorophenyl)-1,3-thiazol-5-yl]carbonyl}amino)methyl]phenyl}benzoic acid

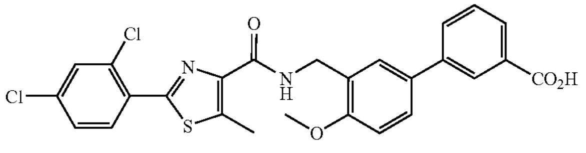

The title compound was obtained in the same way as Example 1e) except for using 4-methyl-2-(2,4-dichlorophenyl)-1,3-thiazol-5-carboxylic Acid.

MS m/e (ESI) 527 ($MH^+$).

Example 11

3-{4-Methoxy-3-[({[4-methyl-2-(4-chlorophenyl)-1,3-thiazol-5-yl]carbonyl}amino)methyl]phenyl}benzoic acid

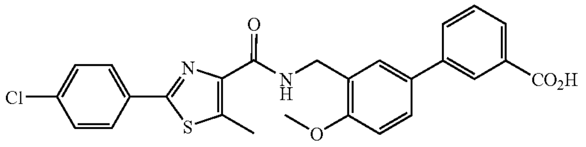

The title compound was obtained in the same way as Example 1e) except for using 4-methyl-2-(4-chlorophenyl)-1,3-thiazol-5-carboxylic acid.

MS m/e (ESI) 493 ($MH^+$).

Example 12

3-{4-Methoxy-3-[({[4-methyl-2-(2-thienyl)-1,3-thiazol-5-yl]carbonyl}amino)methyl]phenyl}benzoic acid

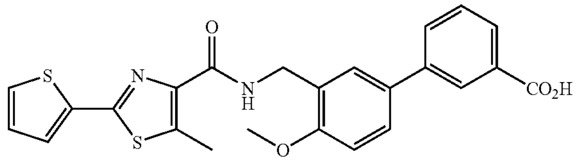

The title compound was obtained in the same way as Example 1e) except for using 4-methyl-2-(2-thienyl)-1,3-thiazol-5-carboxylic acid.

MS m/e (ESI) 465 ($MH^+$).

Example 13

3-{3-[({[5-(2-Chlorophenyl)-3-isoxazoyl]-carbonyl}amino)methyl]-4-methoxyphenyl}benzoic acid

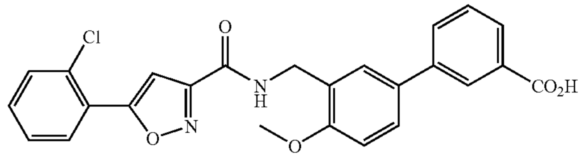

The title compound was obtained in the same way as Example 1e) except for using 5-(2-chlorophenyl) -3-isoxazolecarboxylic acid.

MS m/e (ESI) 463 ($MH^+$).

Example 14

3-(3-{[(2,4-Dichlorobenzoyl)amino]methyl}-4-methoxyphenyl)-6-fluorobenzoic acid

Production Example 14a

Methyl 3-(3-{[(t-butoxycarbonyl)amino]methyl}-4-methoxyphenyl)-6-fluorobenzoate

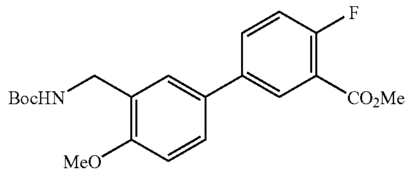

The title compound was obtained in the same way as Production Example 1d) except for using methyl 2-fluoro-5-bromobenzoate.

$^1$H-NMR ($CDCl_3$).

δ: 1.45 (s, 9H) 3.89 (s, 3H) 3.96 (s, 3H) 4.36 (brd, J=5.6 Hz, 2H) 5.07 (br, 1H) 6.93 (d, J=8.4 Hz, 1H) 7.18 (dd, J=8.8, 9.2 Hz, 1H) 7.44 (d, J=2.4 Hz, 1H) 7.47 (s, 1H) 7.67 (ddd, J=2.4, 4.8, 8.8 Hz, 1H) 8.09 (dd, J=2.4, 6.8 Hz, 1H).

Example 14b 3-(3-{[(2,4-Dichlorobenzoyl)amino]methyl}-4-methoxyphenyl)-6-fluorobenzoic acid

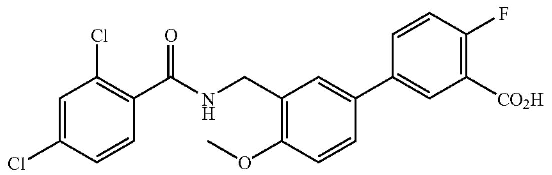

The title compound was obtained in the same way as Example 1e) except for using methyl 3-(3-{[(t-butoxycarbonyl)amino]methyl}-4-methoxyphenyl)-6-fluorobenzoate.

MS m/e (ESI) 448 ($MH^+$).

Example 15

3-(3-{[(4-Chloro-2-fluorobenzoyl)amino]-methyl}-4-methoxyphenyl)-6-fluorobenzoic acid

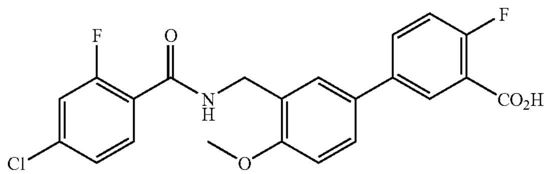

The title compound was obtained in the same way as Example 14b) except for using 4-chloro-2-fluorobenzoic acid.

MS m/e (ESI) 432 ($MH^+$).

Example 16

3-(3-{[(4-Trifluoromethyl-2-fluorobenzoyl)amino]methyl}-4-methoxyphenyl)-6-fluorobenzoic acid

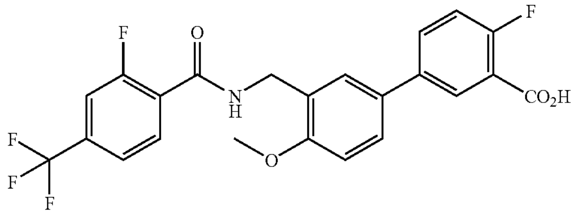

The title compound was obtained in the same way as Example 14b) except for using 4-trifluoromethyl-2-fluorobenzoic acid.

MS m/e (ESI) 466 ($MH^+$).

Example 17

3-(3-{[(4-Propoxy-2-chlorobenzoyl)amino]methyl}-4-methoxyphenyl)-6-fluorobenzoic acid

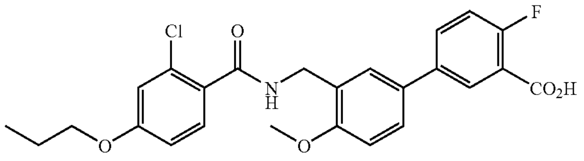

The title compound was obtained in the same way as Example 14b) except for using 4-propoxy-2-chlorobenzoic acid.

$^1$H-NMR ($CDCl_3$).

δ: 0.95 (t, J=7.2 Hz, 3H) 1.71 (q, J=6.8 Hz, 2H) 3.86 (s, 3H) 3.97 (t, J=6.4 Hz, 2H) 4.43 (d, J=5.6 Hz, 2H) 6.95 (dd, J=2.0, 8.4 Hz, 1H) 7.03 (d, J=2.0 Hz, 1H) 7.09 (d, J=8.4 Hz, 1H) 7.36 (d, 9.2 Hz, 1H) 7.40 (d, J=8.0 Hz, 1H) 7.56 (d, J=8.4 Hz, 1H) 7.58 (s, 1H) 7.78-7.84 (m, 1H) 8.02 (dd, J=2.0, 6.8 Hz, 1H) 8.76 (t, J=6.0 Hz, 1H).

MS m/e (ESI) 472 ($MH^+$).

Example 18

3-(3-{[(4-Isopropoxy-2-chlorobenzoyl)amino]-methyl}-4-methoxyphenyl)-6-fluorobenzoic acid

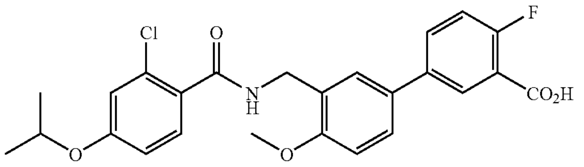

The title compound was obtained in the same way as Example 14b) except for using 4-isopropoxy-2-chlorobenzoic acid.

MS m/e (ESI) 472 ($MH^+$).

Example 19

3-(3-{[(2,4-Dichlorobenzoyl)amino]methyl}-4-methoxyphenyl)-6-chlorobenzoic acid

Production Example 19a

Methyl 3-(3-{[(t-butoxycarbonyl)amino]methyl}-4-methoxyphenyl)-6-chlorobenzoate

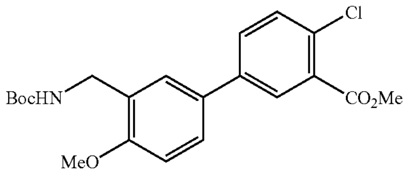

The title compound was obtained in the same way as Production Example 1d) except for using methyl 2-chloro-5-bromobenzoate.

$^1$H-NMR ($CDCl_3$).

δ: 1.45 (s, 9H) 3.89 (s, 3H) 3.96 (s, 3H) 4.35 (brs, 2H) 5.05 (br, 1H) 6.93 (d, J=8.8 Hz, 1H) 7.45-7.49 (m, 3H) 7.59 (dd, J-2.4, 8.4 Hz, 1H) 7.99 (d, J=2.4 Hz, 1H).

Example 19b 3-(3-{[(2,4-Dichlorobenzoyl)amino]methyl}-4-methoxyphenyl)-6-chlorobenzoic acid

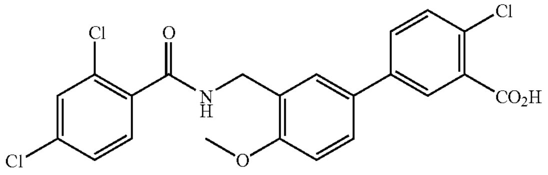

The title compound was obtained in the same way as Example 1e) except for using methyl 3-(3-{[(t-butoxycarbonyl)amino]methyl}-4-methoxyphenyl)-6-chlorobenzoate.

MS m/e (ESI) 464 ($MH^+$).

Example 20

2-Chloro-5-[4-methoxy-3-({[(4-methyl-2-phenyl-1,3-thiazol-5-yl)carbonyl]amino}methyl)phenyl]benzoic acid

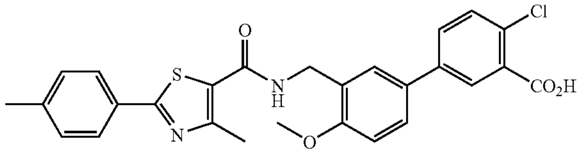

The title compound was obtained in the same way as Example 19b) except for using 4-methyl-2-(4-methylphenyl)-1,3-thiazol-5-carboxylic acid.

MS m/e (ESI) 507 ($MH^+$).

Example 21

3-(3-{[(2,4-Dichlorobenzoyl)amino]methyl}-4-methoxyphenyl)-6-methylbenzoic Acid

Production Example 21a

Methyl 3-(3-{[(t-butoxycarbonyl)amino]methyl}-4-methoxyphenyl)-6-methylbenzoate

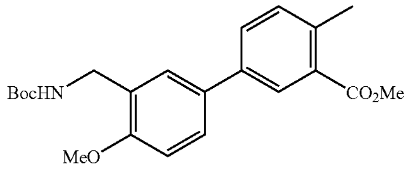

The title compound was obtained in the same way as Production Example 1d) except for using methyl 2-methyl-5-bromobenzoate.

$^1$H-NMR ($CDCl_3$).

δ: 1.46 (s, 9H) 2.61 (s, 3H) 3.89 (s, 3H) 3.92 (s, 3H) 4.37 (brd, J=5.2 Hz, 2H) 5.06 (br, 1H) 6.93 (d, J=8.4 Hz, 1H) 7.29 (d, J=8.0 Hz, 1H) 7.48 (dd, J=2.4, 8.4 Hz, 1H) 7.50 (s, 1H) 7.58 (dd, J=2.4, 8.0 Hz, 1H) 8.10 (dd, J=2.0 Hz, 1H).

Example 21b 3-(3-{[(2,4-Dichlorobenzoyl)amino]methyl}-4-methoxyphenyl)-6-methylbenzoic Acid

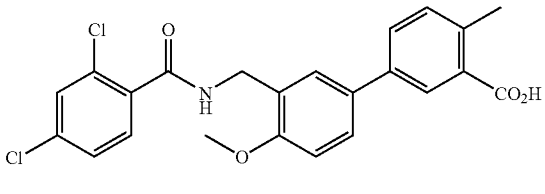

The title compound was obtained in the same way as Example 1e) except for using methyl 3-(3-{[(t-butoxycarbonyl)amino]methyl}-4-methoxyphenyl)-6-methylbenzoate.

$^1$H-NMR ($CDCl_3$).

δ: 2.64 (s, 3H) 3.91 (s, 3H) 4.69 (d, J=6.0 Hz, 2H) 6.96 (d, J=8.4 Hz, 1H) 7.14 (br, 1H) 7.28 (d, J=8.0 Hz, 1H) 7.31 (dd, 2.0, 8.4 Hz, 1H) 7.41 (d, J=2.0 Hz, 1H) 7.54 (dd, J=2.4, 8.8 Hz, 1H) 7.58 (dd, J=2.0, 7.6 Hz, 1H) 7.62 (s, 1H) 7.63 (d, J=6.4 Hz, 1H) 8.17 (d, J=2.0 Hz, 1H).

MS m/e (ESI) 444 ($MH^+$).

Example 22

3-(3-{[(4-Trifluoromethyl-2-fluorobenzoyl)amino]methyl}-4-methoxyphenyl)-6-methylbenzoic Acid

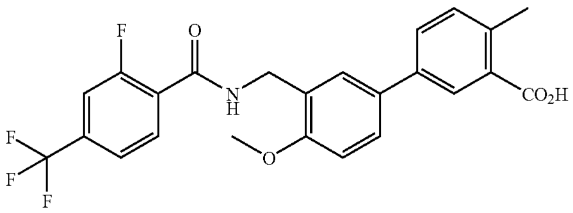

The title compound was obtained in the same way as Example 21b) except for using 4-trifluoromethyl-2-fluorobenzoic acid.

MS m/e (ESI) 462 ($MH^+$).

Example 23

3-(3-{[(4-propoxy-2-chlorobenzoyl)amino]methyl}-4-methoxyphenyl)-6-methylbenzoic Acid

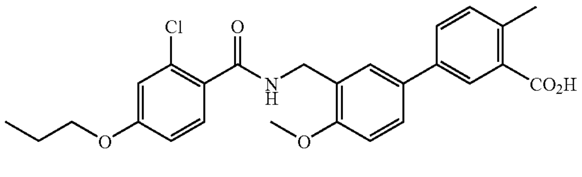

The title compound was obtained in the same way as Example 21b) except for using 4-propoxy-2-chlorobenzoic acid.

$^1$H-NMR ($CDCl_3$).

δ: 0.95 (t, J=7.2 Hz, 3H) 1.71 (q, J=6.4 Hz, 2H) 2.52 (s, 3H) 3.85 (s, 3H) 3.97 (t, J=6.8 Hz, 2H) 4.43 (d, J=4.8 Hz, 2H) 6.96 (dd, J=2.4, 8.8 HZ, 1H) 7.04 (d, J=2.4 Hz, 1H) 7.08 (d, J=8.8 Hz, 1H) 7.35 (d, 8.0 Hz, 1H) 7.40 (d, J=8.4 Hz, 1H) 7.55 (dd, J=2.0, 8.4 Hz, 1H) 7.60 (d, J=2.0 Hz, 1H) 7.66 (dd, J=2.0, 7.6 Hz, 1H) 8.03 (d, J=2.0 Hz, 1H) 8.77 (t, J=6.0 Hz, 1H).

MS m/e (ESI) 468 ($MH^+$).

Example 24

3-{4-Methoxy-3-[({[4-methyl-2-(4-methylphenyl)-1,3-thiazol-5-yl]carbonyl}amino)methyl]-phenyl}-6-methylbenzoic Acid

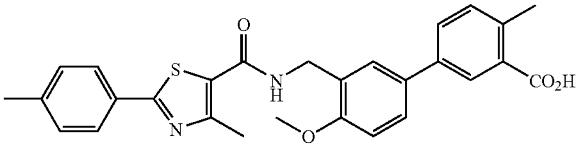

The title compound was obtained in the same way as Example 21b) except for using 4-methyl-2-(4-methylphenyl)-1,3-thiazol-5-carboxylic Acid.

MS m/e (ESI) 487 ($MH^+$).

Example 25

3-(3-{[(2, 4-dichlorobenzoyl)amino]methyl}-4-methoxyphenyl)-6-methoxybenzoic Acid Production Example 25a Methyl 3-(3-{[(t-butoxycarbonyl)amino]methyl}-4-methoxyphenyl)-6-methoxybenzoate

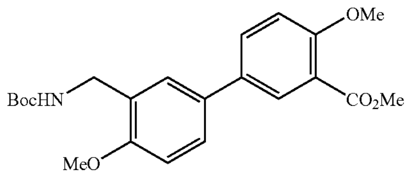

The title compound was obtained in the same way as Production Example 1d) except for using methyl 2-methoxy-5-bromobenzoate.

$^1$H-NMR ($CDCl_3$).

δ: 1.46 (s, 9H) 3.88 (s, 3H) 3.92 (s, 3H) 3.94 (s, 3H) 4.35 (brs, 2H) 5.06 (br, 1H) 6.92 (d, J=8.0 Hz, 1H) 7.03 (d, J=8.8 Hz, 1H) 7.44 (dd, J=2.4, 10.8 Hz, 1H) 7.46 (s, 1H) 7.65 (dd, J=2.4, 8.8 Hz, 1H) 7.98 (d, J=2.4 Hz, 1H).

Example 25b 3-(3-{[(2,4-Dichlorobenzoyl)amino]methyl}-4-methoxyphenyl)-6-methoxybenzoic Acid

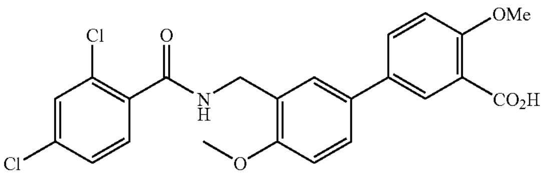

The title compound was obtained in the same way as Example 1e) except for using methyl 3-(3-{[(t-butoxycarbonyl)amino]methyl}-4-methoxyphenyl)-6-methoxybenzoate.

MS m/e (ESI) 460 ($MH^+$).

Example 26

3-(3-{[(4-Chloro-2-fluorobenzoyl)amino]-methyl}-4-methoxyphenyl)-6-methoxybenzoic Acid

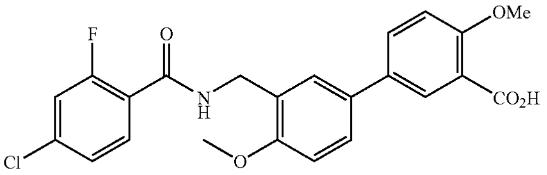

The title compound was obtained in the same way as Example 25b) except for using 4-chloro-2-fluorobenzoic acid.

MS m/e (ESI) 444 ($MH^+$).

Example 27

3-(3-{[(4-Trifluoromethyl-2-fluorobenzoyl)amino]methyl}-4-methoxyphenyl).-6-methoxybenzoic Acid

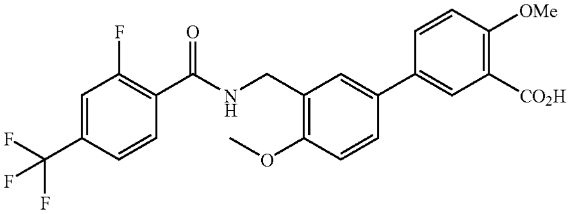

The title compound was obtained in the same way as Example 25b) except for using 4-trifluoromethyl-2-fluorobenzoic acid.

MS m/e (ESI) 478 ($MH^+$).

Example 28

3-(3-{[(4-Cyclohexylbenzoyl)amino]methyl}-4-methoxyphenyl)-6-methoxybenzoic Acid

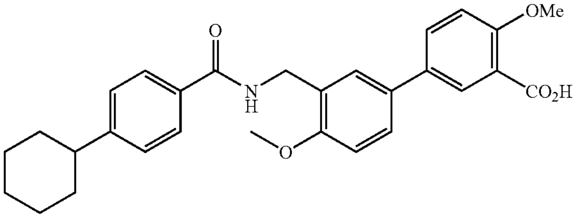

The title compound was obtained in the same way as Example 25b) except for using 4-cyclohexylbenzoic acid.

MS m/e (ESI) 474 ($MH^+$).

Example 29

3-(3-{[(4-Propoxy-2-chlorobenzoyl)amino]-methyl}-4-methoxyphenyl)-6-methoxybenzoic Acid

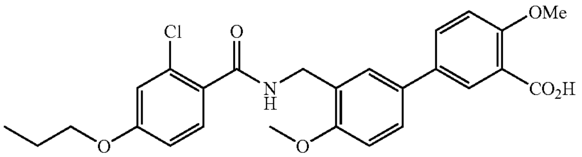

The title compound was obtained in the same way as Example 25b) except for using 4-propoxy-2-chlorobenzoic acid.

$^1$H-NMR ($CDCl_3$).

δ: 0.95 (t, J=7.2 Hz, 3H) 1.71 (q, J=6.8 Hz, 2H) 3.83 (s, 3H) 3.84 (s, 3H) 3.97 (t, J=6.4 Hz, 2H) 4.42 (d, J=5.6 Hz, 2H) 6.95 (dd, J=2.4, 8.4 HZ, 1H) 7.03 (d, J=2.4 Hz, 1H) 7.05 (d, J=8.4 Hz, 1H) 7.18 (d, 8.8 Hz, 1H) 7.40 (d, J=8.4 Hz, 1H) 7.51 (dd, J=2.4, 8.8 Hz, 1H) 7.55 (d, J=2.0 Hz, 1H) 7.71 (dd, J=2.4, 8.8 Hz, 1H) 7.84 (d, J=2.4 Hz, 1H) 8.76 (t, J=6.4 Hz, 1H).

MS m/e (ESI) 484 ($MH^+$).

Example 30

3-(3-{[(4-Isopropoxy-2-chlorobenzoyl)amino]methyl}-4-methoxyphenyl)-6-methoxybenzoic Acid

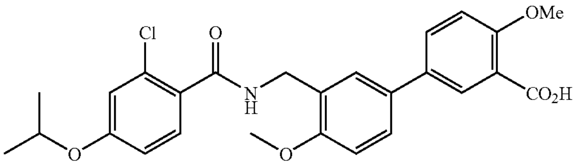

The title compound was obtained in the same way as Example 25b) except for using 4-isopropoxy-2-chlorobenzoic acid.

MS m/e (ESI) 484 ($MH^+$).

Example 31

3-(3-{[(4-Cyclopentyloxy-2-chlorobenzoyl)amino] methyl}-4-methoxyphenyl)-6-methoxybenzoic Acid

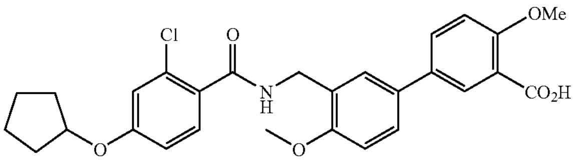

The title compound was obtained in the same way as Example 25b) except for using 4-pentyloxy-2-chlorobenzoic acid.

MS m/e (ESI) 510 ($MH^+$).

Example 32

3-{4-Methoxy-3-[({[4-methyl-2-(4-methylphenyl)-1, 3-thiazol-5-yl]carbonyl}amino)methyl]-phenyl}-6-methoxybenzoic Acid

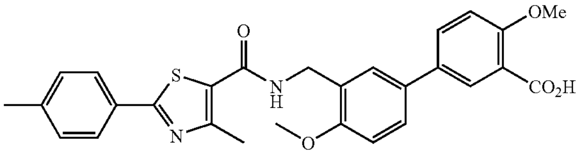

The title compound was obtained in the same way as Example 25b) except for using 4-methyl-2-(4-methylphenyl)-1,3-thiazol-5-carboxylic Acid.

MS m/e (ESI) 503 ($MH^+$).

Example 33

3-{4-Methoxy-3-[([4-methyl-2-(2-chlorophenyl)-1, 3-thiazol-5-yl]carbonyl}amino)methyl]-phenyl}-6-methoxybenzoic Acid

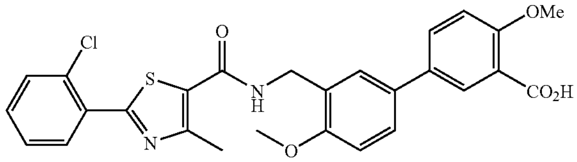

The title compound was obtained in the same way as Example 25b) except for using 4-methyl-2-(2-chlorophenyl)-1,3-thiazol-5-carboxylic Acid.

MS m/e (ESI) 493 ($MH^+$).

Example 34

3-{4-Methoxy-3-[({[4-methyl-2-(2,4-dichlorophenyl)-1,3-thiazol-5-yl]carbonyl}amino)methyl]-phenyl}-6-methoxybenzoic Acid

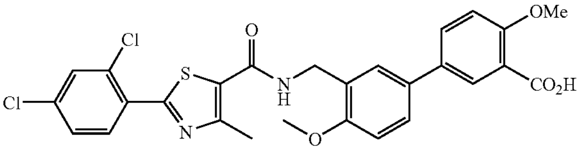

The title compound was obtained in the same way as Example 25b) except for using 4-methyl-2-(2,4-dichlorophenyl)-1,3-thiazol-5-carboxylic Acid.

MS m/e (ESI) 527 ($MH^+$).

Example 35

3-{4-Methoxy-3-[({[4-methyl-2-(4-chlorophenyl)-1, 3-thiazol-5-yl]carbonyl}amino)methyl]-phenyl}-6-methoxybenzoic Acid

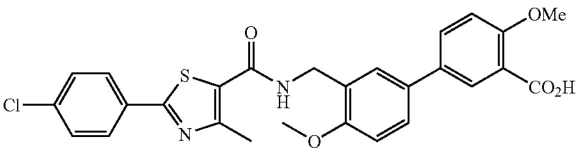

The title compound was obtained in the same way as Example 25b) except for using 4-methyl-2-(4-chlorophenyl)-1,3-thiazol-5-carboxylic Acid.

MS m/e (ESI) 493 ($MH^+$).

Example 36

3-{4-Methoxy-3-[({[4-methyl-2-(2-thienyl)-1,3-thiazol-5-yl]carbonyl}amino)methyl]phenyl}-6-methoxybenzoic Acid

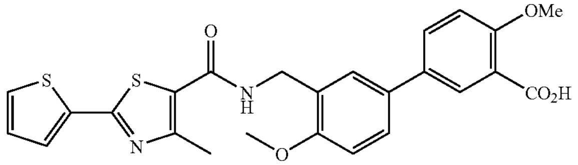

The title compound was obtained in the same way as Example 25b) except for using 4-methyl-2-(4-thienylphenyl)-1,3-thiazol-5-carboxylic Acid.

MS m/e (ESI) 495 ($MH^+$).

Example 37

3-{3-[({[5-(2-Chlorophenyl)-3-isoxazoyl]carbonyl}amino)methyl]-4-methoxyphenyl}-6-methoxybenzoic Acid

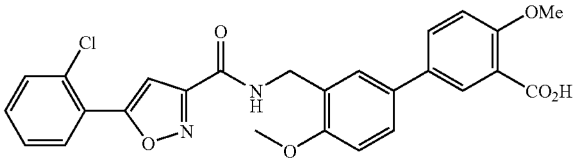

The title compound was obtained in the same way as Example 25b) except for using 5-(2-chlorophenyl)-3-isoxazolecarboxylic Acid.

MS m/e (ESI) 493 ($MH^+$).

Example 38

3-(3-{[(2,4-Dichlorobenzoyl)amino]methyl}-4-methoxyphenyl)-6-isopropoxybenzoic Acid Production Example 38a 3-{[(t-Butoxycarbonyl)amino]-methyl}-4-methoxyphenylboronic Acid

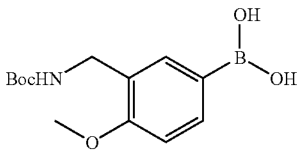

9.99 g of 4-Bromo-2-[(N-t-butoxycarbonylamino)methyl]-anisole was dissolved in 200 ml of tetrahydrofuran, and the mixture was cooled to −68° C. in a nitrogen atmosphere. 44 ml of butyl lithium (1.6 M) in hexane was added dropwise through a syringe. The mixture was stirred at −68° C. for 0.5 hour, and then 11 ml of triisopropyl boronate was added thereto all at once. The temperature of the reaction mixture was increased gradually to −54° C., and 1 N hydrochloric acid was added to the reaction mixture. The reaction mixture was extracted with ethyl acetate, the organic layer was successively washed with 1N hydrochloric acid and brine, dried over anhydrous magnesium sulfate, and the solvent was evaporated. The residue was purified by silica gel column, to give 4.80 g of the title compound in the 3:2→1:1 hexane-ethyl acetate fraction.

Production Example 38b

Methyl 3-(3-{[(t-butoxycarbonyl)amino]methyl}-4-methoxyphenyl)-6-isopropoxybenzoate

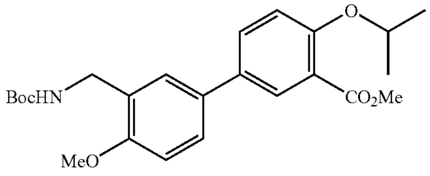

230 mg of 3-{[(t-Butoxycarbonyl)amino]methyl}-4-methoxyphenylboronic acid, 197 mg of methyl 2-isopropoxy-5-chlorobenzoate, 30 mg of dichlorobistriphenylphosphinoferrocene nickel and 570 mg of potassium phosphate were dissolved in dioxane, and the mixture was stirred overnight at 95° C. in a nitrogen atmosphere. The reaction mixture was filtered through Celite, and the filtrate was evaporated. The residue was purified by a silica gel column, to give 194 mg of the title compound in the 5:1 hexane-ethyl acetate fraction.

$^1$H-NMR ($CDCl_3$).

δ: 1.39 (d, J=6.0 Hz, 6H) 1.45 (s, 9H) 3.88 (s, 3H) 3.91 (s, 3H) 4.35 (brs, 2H) 4.61 (sept, J=6.0 Hz, 1H) 5.06 (br, 1H) 6.91 (d, J=8.8 Hz, 1H) 7.03 (d, J=8.8 Hz, 1H) 7.45 (dd, J=2.4, 10.4 Hz, 1H) 7.46 (s, 1H) 7.60 (dd, J=2.4, 8.8 Hz, 1H) 7.94 (d, J=2.4 Hz, 1H).

Example 38c 3-(3-{[(2,4-Dichlorobenzoyl)amino]methyl}-4-methoxyphenyl)-6-isopropoxybenzoic Acid

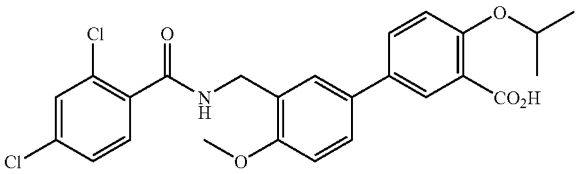

The title compound was obtained in the same way as Example 1e) except for using methyl 3-(3-{[(t-butoxycarbonyl)amino]methyl}-4-methoxyphenyl)-6-isopropoxybenzoate.

MS m/e (ESI) 488 ($MH^+$).

Example 39

3-{4-Methoxy-3-[({[4-methyl-2-(4-methylphenyl)-1,3-thiazol-5-yl]carbonyl}amino)methyl]-phenyl}-6-isopropoxybenzoic Acid

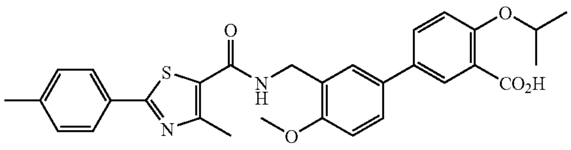

The title compound was obtained in the same way as Example 38c) except for using 4-methyl-2-(4-methylphenyl)-1,3-thiazol-5-carboxylic Acid.

MS m/e (ESI) 531 ($MH^+$).

Example 40

5-(3-{[(2,4-Dichlorobenzoyl)amino]methyl}-4-methoxyphenyl)-2,3-dihydrobenzo[b]furan-7-carboxylic Acid Production Example 40a Methyl 5-(3-{[(t-butoxycarbonyl)amino]methyl}-4-methoxyphenyl)-2,3-dihydrobenzo[b]furan-7-carboxylate

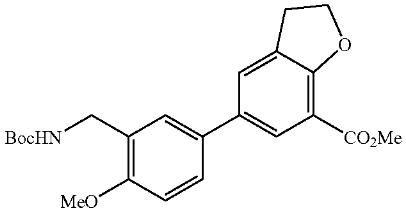

The title compound was obtained in the same way as Production Example 1d) except for using 5-bromo-7-carboxymethylbenzotetrahydrofuran.

$^1$H-NMR ($CDCl_3$).

δ: 1.46 (s, 9H) 3.28 (t, J=8.8 Hz, 2H) 3.88 (s, 3H) 3.93 (s, 3H) 4.36 (brd, J=5.6 Hz, 2H) 4.77 (t, J=8.8 Hz, 2H) 5.06 (br, 1H) 6.91 (d, J=8.8 Hz, 1H) 7.44 (dd, J=2.4, 10.8 Hz, 1H) 7.45 (s, 1H) 7.55 (s, 1H) 6.90 (t, J=1.2 Hz, 1H).

Example 40b 5-(3-{[(2,4-Dichlorobenzoyl)amino]methyl}-4-methoxyphenyl)-2,3-dihydrobenzo[b]furan-7-carboxylic Acid

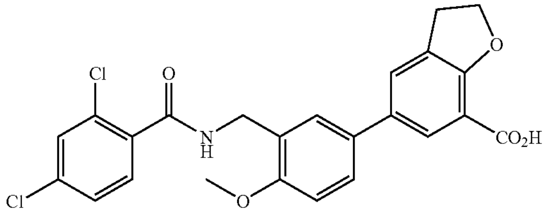

The title compound was obtained in the same way as Example 1e) except for using 5-(3-[(t-butoxycarbonyl) amino]methyl}-4-methoxyphenyl)-2,3-dihydrobenzo[b]furan-7-carboxylate.

MS m/e (ESI) 472 ($MH^+$).

Example 41

3-{4-Methoxy-3-[({[4-methyl-2-(4-methylphenyl)-1,3-thiazol-5-yl]carbonyl}amino)methyl]-phenyl}-2,3-dihydrobenzo[b]furan-7-carboxylic Acid

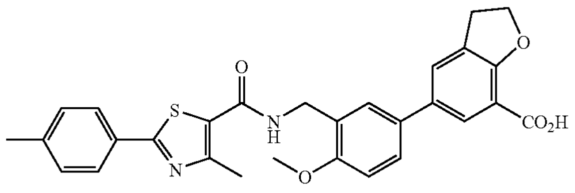

The title compound was obtained in the same way as Example 40b) except for using 4-methyl-2-(4-methylphenyl)-1,3-thiazol-5-carboxylic Acid.

MS m/e (ESI) 515 ($MH^+$).

Example 42

3-(3-{[(2,4-Dichlorobenzoyl)amino]methyl}-4-methoxyphenyl)-5-fluorobenzoic Acid

Production Example 42a

Methyl 3-(3-{[(t-butoxycarbonyl)amino]methyl}-4-methoxyphenyl)-5-fluorobenzoate

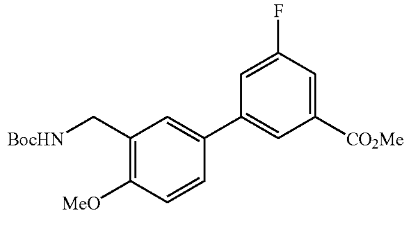

The title compound was obtained in the same way as Production Example 1d) except for using methyl 3-bromo-5-fluorobenzoate.

$^1$H-NMR ($CDCl_3$).

δ: 1.46 (s, 9H) 3.90 (s, 3H) 3.96 (s, 3H) 4.37 (brs, 2H) 5.07 (br, 1H) 6.95 (d, J=8.8 Hz, 1H) 7.44 (dt, J=1.6, 9.6 Hz, 1H) 7.51 (dd, J=2.4, 10.4 Hz, 1H) 7.52 (s, 1H) 7.64 (dd, J=1.6, 8.8 Hz, 1H) 8.03 (t, J=1.6 Hz, 1H).

Example 42b 3-(3-{[(2,4-Dichlorobenzoyl)amino]methyl}-4-methoxyphenyl)-5-fluorobenzoic Acid

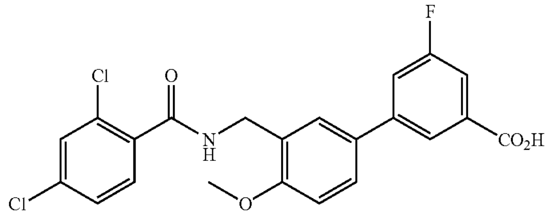

The title compound was obtained in the same way as Example 1e) except for using methyl 3-(3-{[(t-butoxycarbonyl)amino]methyl}-4-methoxyphenyl)-5-fluorobenzoate.

MS m/e (ESI) 448 ($MH^+$).

Example 43

3-(3-{[(4-chloro-2-fluorobenzoyl)amino]-methyl}-4-methoxyphenyl)-5-fluorobenzoic Acid

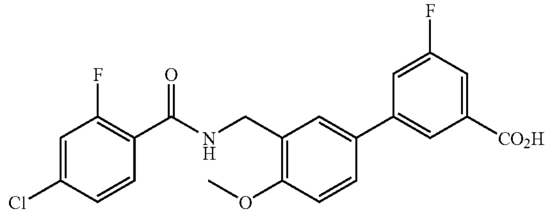

The title compound was obtained in the same way as Example 42b) except for using 4-chloro-2-fluorobenzoic acid.

MS m/e (ESI) 432 ($MH^+$).

Example 44

3-(3-{[(4-Trifluoromethyl-2-fluorobenzoyl)amino] methyl}-4-methoxyphenyl)-5-fluorobenzoic Acid

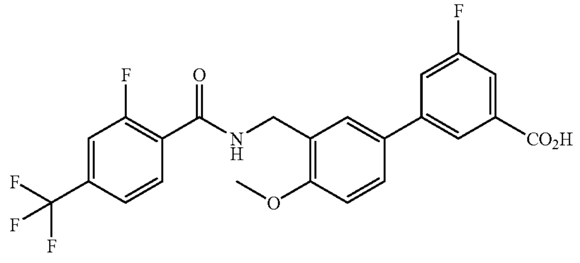

The title compound was obtained in the same way as Example 42b) except for using 4-trifluoromethyl-2-fluorobenzoic acid.

MS m/e (ESI) 466 ($MH^+$).

Example 45

3-(3-{[(4-Propoxy-2-chlorobenzoyl)amino]-methyl}-4-methoxyphenyl)-5-fluorobenzoic Acid

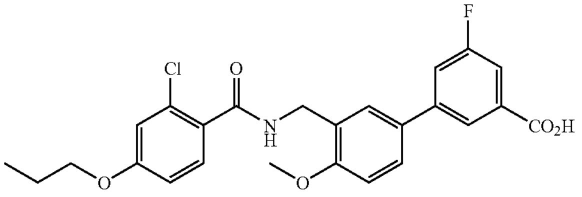

The title compound was obtained in the same way as Example 42b) except for using 4-propoxy-2-chlorobenzoic acid.

MS m/e (ESI) 472 ($MH^+$).

Example 46

3-(3-{[(4-Isopropoxy-2-chlorobenzoyl)amino]-methyl}-4-methoxyphenyl)-5-fluorobenzoic Acid

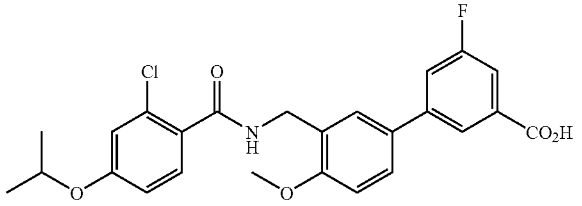

The title compound was obtained in the same way as Example 42b) except for using 4-isopropoxy-2-chlorobenzoic acid.

MS m/e (ESI) 472 ($MH^+$).

Example 47

3-{4-Methoxy-3-[({[4-methyl-2-(4-methylphenyl)-1,3-thiazol-5-yl]carbonyl}amino)methyl]-phenyl}-5-fluorobenzoic Acid

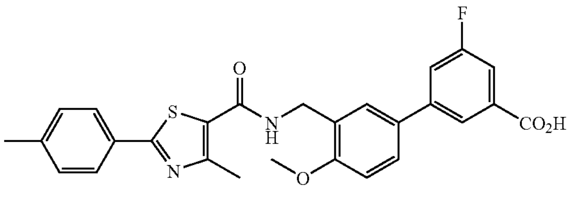

The title compound was obtained in the same way as Example 42b) except for using 4-methyl-2-(4-methylphenyl)-1,3-thiazol-5-carboxylic Acid.

MS m/e (ESI) 491 ($MH^+$).

Example 48

3-(3-{[(2,4-Dichlorobenzoyl)amino]methyl}-4-methoxyphenyl)-4-fluorobenzoic Acid

Production Example 48a

Methyl 3-(3-{[(t-butoxycarbonyl)amino]methyl}-4-methoxyphenyl)-4-fluorobenzoate

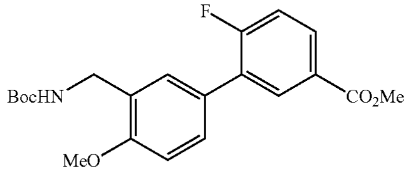

The title compound was obtained in the same way as Production Example 1d) except for using methyl 3-bromo-4-fluorobenzoate.

$^1$H-NMR ($CDCl_3$).

δ: 1.45 (s, 9H) 3.90 (s, 3H) 3.93 (s, 3H) 4.36 (brs, 2H) 5.04 (br, 1H) 6.95 (d, J=8.8 Hz, 1H) 7.18 (dd, J=8.8, 10.4 Hz, 1H) 7.46-7.48 (m, 2H) 7.97 (ddd, J=2.0, 4.8, 8.4 Hz, 1H) 8.12 (dd, J=2.0, 7.6 Hz, 1H).

Example 48b

3-(3-{[(2,4-Dichlorobenzoyl)amino]methyl}-4-methoxyphenyl)-4-fluorobenzoic Acid

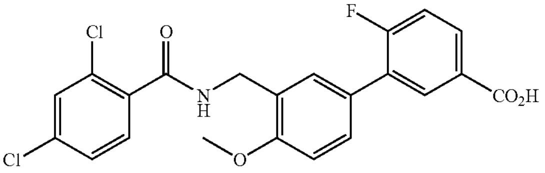

The title compound was obtained in the same way as Example 1e) except for using methyl 3-(3-{[(t-butoxycarbonyl)amino]methyl}-4-methoxyphenyl)-4-fluorobenzoate.

MS m/e (ESI) 448 ($MH^+$).

Example 49

3-(3-{[(4-Chloro-2-fluorobenzoyl)amino]-methyl}-4-methoxyphenyl)-4-fluorobenzoic Acid

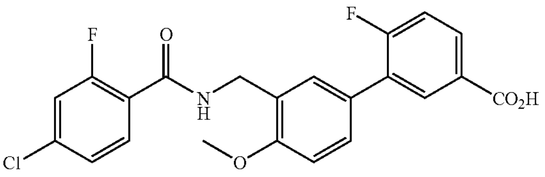

The title compound was obtained in the same way as Example 48b) except for using 4-chloro-2-fluorobenzoic acid.

MS m/e (ESI) 432 ($MH^+$).

Example 50

3-(3-{[(4-Trifluoromethyl-2-fluorobenzoyl)amino]methyl}-4-methoxyphenyl)-4-fluorobenzoic Acid

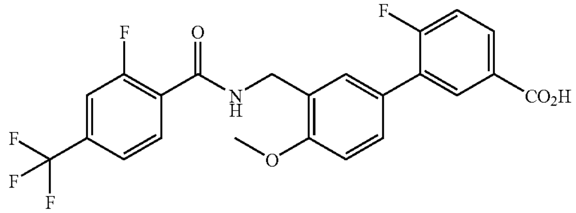

The title compound was obtained in the same way as Example 48b) except for using 4-trifluoromethyl-2-fluorobenzoic acid.

MS m/e (ESI) 466 ($MH^+$).

Example 51

3-(3-{[(4-Propoxy-2-chlorobenzoyl)amino]-methyl}-4-methoxyphenyl)-4-fluorobenzoic Acid

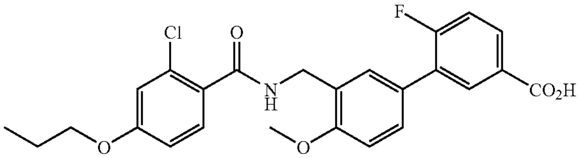

The title compound was obtained in the same way as Example 48b) except for using 4-propoxy-2-chlorobenzoic acid.

MS m/e (ESI) 472 ($MH^+$).

Example 52

3-(3-{[(4-Isopropoxy-2-chlorobenzoyl)amino]methyl}-4-methoxyphenyl)-4-fluorobenzoic Acid

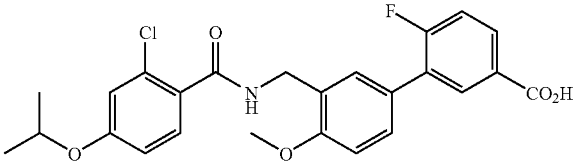

The title compound was obtained in the same way as Example 48b) except for using 4-isopropoxy-2-chlorobenzoic acid.

MS m/e (ESI) 472 ($MH^+$).

Example 53

3-{4-Methoxy-3-[({[4-methyl-2-(4-methylphenyl)-1,3-thiazol-5-yl]carbonyl}amino)methyl]-phenyl}-4-fluorobenzoic Acid

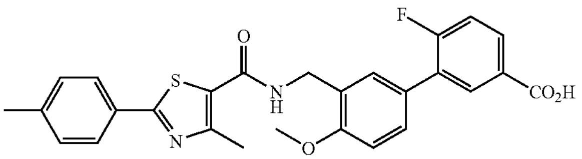

The title compound was obtained in the same way as Example 42b) except for using 4-methyl-2-(4-methylphenyl)-1,3-thiazol-5-carboxylic Acid.

MS m/e (ESI) 491 ($MH^+$).

Example 54

3-(3-{[(2,4-Dichlorobenzoyl)amino]methyl}-4-methoxyphenyl)-4-chlorobenzoic Acid

Production Example 54a

Methyl-3-(3-{[(t-butoxycarbonyl)-amino]methyl}-4-methoxyphenyl)-4-chlorobenzoate

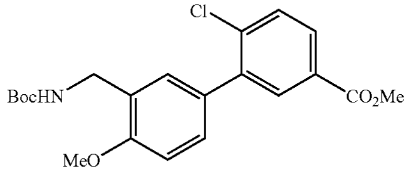

The title compound was obtained in the same way as Production Example 1d) except for using methyl 3-bromo-4-chlorobenzoate.

$^1$H-NMR ($CDCl_3$).

δ: 1.45 (s, 9H) 3.90 (s, 3H) 3.92 (s, 3H) 4.37 (brd, J=4.8 Hz, 2H) 5.03 (br, 1H) 6.94 (d, J=8.8 Hz, 1H) 7.36 (d, J=7.6 Hz, 2H) 7.52 (d, J=8.8 Hz, 1H) 7.91 (dd, J=2.0, 8.0 Hz, 1H) 7.99 (d, J=2.0 Hz, 1H).

Example 54b 3-(3-{[(2,4-Dichlorobenzoyl)amino]methyl}-4-methoxyphenyl)-4-chlorobenzoic Acid

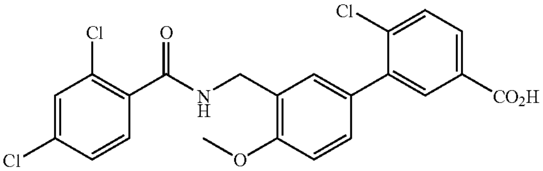

The title compound was obtained in the same way as Example 1e) except for using methyl 3-(3-{[(t-butoxycarbonyl)amino]methyl}-4-methoxyphenyl)-4-chlorobenzoate.

MS m/e (ESI) 464 ($MH^+$).

Example 55

3-(3-{[(4-Chloro-2-fluorobenzoyl)amino]methyl}-4-methoxyphenyl)-4-chlorobenzoic Acid

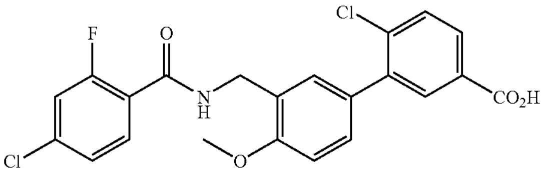

The title compound was obtained in the same way as Example 54b) except for using 4-chloro-2-fluorobenzoic acid.

MS m/e (ESI) 448 ($MH^+$).

Example 56

3-(3-{[(4-Trifluoromethyl-2-fluorobenzoyl)amino] methyl}-4-methoxyphenyl)-4-chlorobenzoic Acid

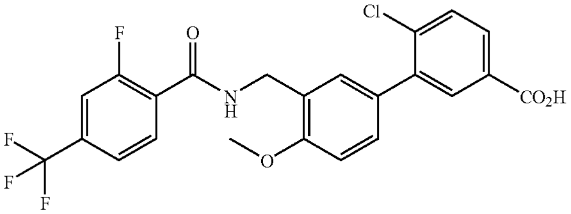

The title compound was obtained in the same way as Example 54b) except for using 4-trifluoromethyl-2-fluorobenzoic acid.

MS m/e (ESI) 482 ($MH^+$).

Example 57

3-(3-{[(4-Propoxy-2-chlorobenzoyl)amino]-methyl}-4-methoxyphenyl)-4-chlorobenzoic Acid

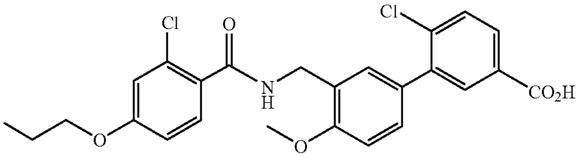

The title compound was obtained in the same way as Example 54b) except for using 4-propoxy-2-chlorobenzoic acid.

MS m/e (ESI) 488 ($MH^+$).

Example 58

3-(3-{[(4-Isopropoxy-2-chlorobenzoyl)amino]-methyl}-4-methoxyphenyl)-4-chlorobenzoic acid

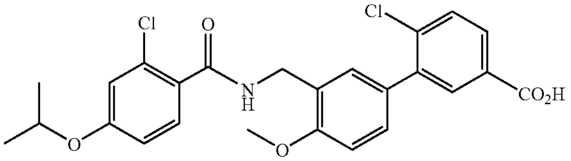

The title compound was obtained in the same way as Example 54b) except for using 4-isopropoxy-2-chlorobenzoic acid.

MS m/e (ESI) 488 ($MH^+$).

Example 59

3-{4-Methoxy-3-[({[4-methyl-2-(4-methylphenyl)-1,3-thiazol-5-yl]carbonyl}amino)methyl]-phenyl}-4-chlorobenzoic Acid

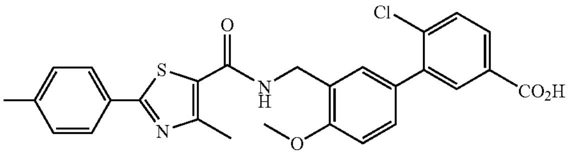

The title compound was obtained in the same way as Example 54b) except for using 4-methyl-2-(4-methylphenyl)-1,3-thiazol-5-carboxylic Acid.

MS m/e (ESI) 507 ($MH^+$).

Example 60

3-(3-{[(2,4-Dichlorobenzoyl)amino]methyl}-4-methoxyphenyl)-4-methylbenzoic Acid

Production Example 60a

Methyl 3-(3-{[(t-butoxycarbonyl)amino]methyl}-4-methoxyphenyl)-4-methylbenzoate

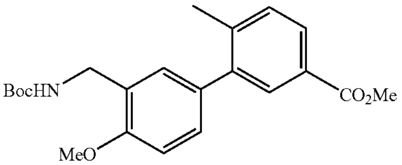

The title compound was obtained in the same way as Production Example 1d) except for using methyl 3-bromo-4-methylbenzoate.

$^1H$-NMR ($CDCl_3$).

δ: 1.44 (s, 9H) 2.31 (s, 3H) 3.90 (s, 3H) 3.92 (s, 3H) 4.35 (brd, J=5.2 Hz, 2H) 5.03 (br, 1H) 6.92 (d, J=8.4 Hz, 1H) 7.21 (dd, J=2.0, 8.4 Hz, 1H) 7.24 (s, 1H) 7.32 (d, J=8.0 Hz, 1H) 7.88 (s, 1H) 7.89 (dd, J=1.6, 8.0 Hz, 1H).

Example 60b 3-(3-{[(2,4-Dichlorobenzoyl)amino]methyl}-4-methoxyphenyl)-4-methylbenzoic Acid

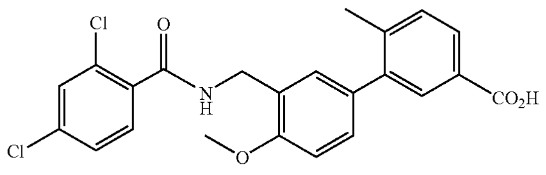

The title compound was obtained in the same way as Example 1e) except for using methyl 3-(3-{[(t-butoxycarbonyl)-amino]methyl}-4-methoxyphenyl)-4-methylbenzoate.

MS m/e (ESI) 444 ($MH^+$).

Example 61

3-(3-{[(4-Chloro-2-fluorobenzoyl)amino]methyl}-4-methoxyphenyl)-4-methylbenzoic Acid

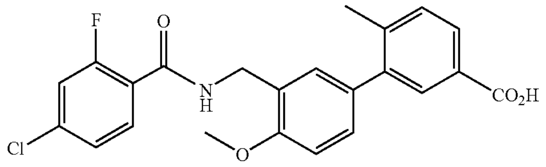

The title compound was obtained in the same way as Example 60b) except for using 4-chloro-2-fluorobenzoic acid.

MS m/e (ESI) 428 ($MH^+$).

Example 62

3-(3-{[(4-Trifluoromethyl-2-fluorobenzoyl)amino]methyl}-4-methoxyphenyl)-4-methylbenzoic Acid

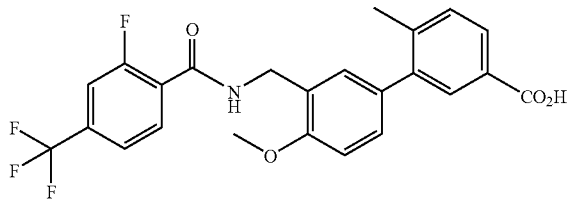

The title compound was obtained in the same way as Example 60b) except for using 4-fluoro-2-fluorobenzoic acid.

MS m/e (ESI) 462 ($MH^+$).

Example 63

3-(3-{[(4-Propoxy-2-chlorobenzoyl)amino]-methyl}-4-methoxyphenyl)-4-methylbenzoic Acid

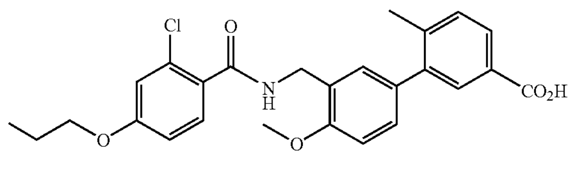

The title compound was obtained in the same way as Example 60b) except for using 4-propoxy-2-chlorobenzoic acid.

MS m/e (ESI) 468 ($MH^+$).

Example 64

3-(3-{[(4-Isopropoxy-2-chlorobenzoyl)amino]-methyl}-4-methoxyphenyl)-4-methylbenzoic Acid

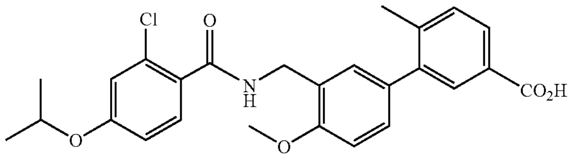

The title compound was obtained in the same way as Example 60b) except for using 4-isopropoxy-2-chlorobenzoic acid.

MS m/e (ESI) 468 ($MH^+$).

Example 65

3-{4-Methoxy-3-[({[4-methyl-2-(4-methylphenyl)-1,3-thiazol-5-yl]carbonyl}amino)methyl]-phenyl}-4-methylbenzoic Acid

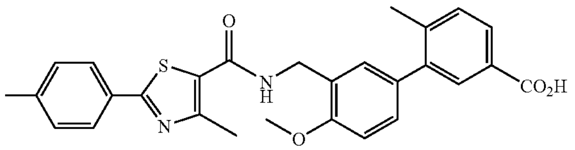

The title compound was obtained in the same way as Example 60b) except for using 4-methyl-2-(4-methylphenyl)-1,3-thiazol-5-carboxylic Acid.

MS m/e (ESI) 487 ($MH^+$).

Example 66

3-(3-{[(2,4-Dichlorobenzoyl)amino]methyl}-4-methoxyphenyl)-2-fluorobenzoic Acid

Production Example 66a

Methyl 3-(3-{[(t-butoxycarbonyl)amino]methyl}-4-methoxyphenyl)-2-fluorobenzoate

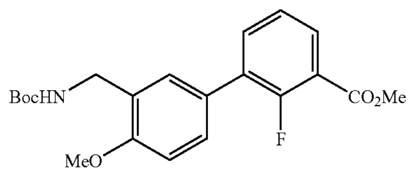

The title compound was obtained in the same way as Production Example 1d) except for using methyl 3-bromo-2-fluorobenzoate.

$^1$H-NMR ($CDCl_3$).

δ: 1.45 (s, 9H) 3.90 (s, 3H) 3.95 (s, 3H) 4.36 (brd, J=6.0 Hz, 2H) 5.04 (br, 1H) 6.94 (d, J=8.4 Hz, 1H) 7.24 (t, J=7.6 Hz, 1H) 7.44 (s, 1H) 7.46 (s, 1H) 7.57 (dt, J=2.0, 8.8 Hz, 1H) 7.86 (d, J=1.6, 7.6 Hz, 1H).

Example 66b 3-(3-{[(2,4-Dichlorobenzoyl)amino]methyl}-4-methoxyphenyl)-2-fluorobenzoic Acid

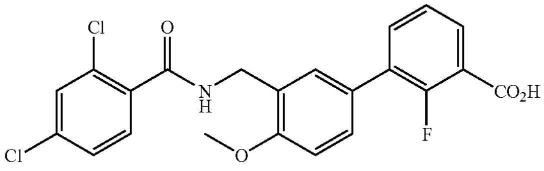

The title compound was obtained in the same way as Example 1e) except for using methyl 3-(3-{[(t-butoxycarbonyl)amino]methyl}-4-methoxyphenyl)-2-fluorobenzoate.

MS m/e (ESI) 448 ($MH^+$).

Example 67

3-(3-{[(4-Chloro-2-fluorobenzoyl)amino]-methyl}-4-methoxyphenyl)-2-fluorobenzoic Acid

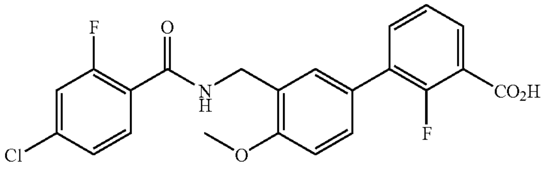

The title compound was obtained in the same way as Example 66b) except for using 4-chloro-2-fluorobenzoic acid.

MS m/e (ESI) 432 ($MH^+$).

Example 68

3-(3-{[(4-Trifluoromethyl-2-fluorobenzoyl)amino]methyl}-4-methoxyphenyl)-2-fluorobenzoic Acid

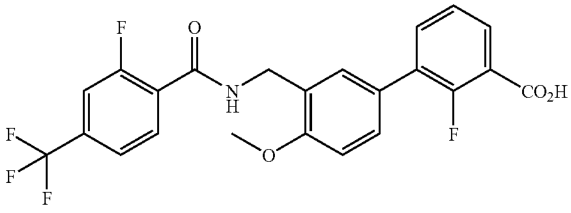

The title compound was obtained in the same way as Example 66b) except for using 4-trifluoromethyl-2-fluorobenzoic acid.

MS m/e (ESI) 466 ($MH^+$).

Example 69

3-(3-{[(4-Propoxy-2-chlorobenzoyl)amino]-methyl}-4-methoxyphenyl)-2-fluorobenzoic Acid

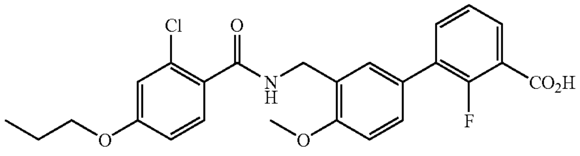

The title compound was obtained in the same way as Example 66b) except for using 4-propoxy-2-chlorobenzoic acid.

$^1$H-NMR ($CDCl_3$).

δ: 0.93 (t, J=7.6 Hz, 3H) 1.70 (q, J=6.8 Hz, 2H) 3.82 (s, 3H) 3.96(t, J=6.4 Hz, 2H) 4.43 (d, J=5.2 Hz, 2H) 6.92 (dd, J=2.4, 8.4 HZ, 1H) 7.02 (d, J=2.8 Hz, 1H) 7.11 (d, J=8.8 Hz, 1H) 7.33 (t, 7.6 Hz, 1H) 7.38 (d, J=8.4 Hz, 1H) 7.43 (d, J=8.4 Hz, 1H) 7.49 (s, 1H) 7.62 (dt, J=2.0, 7.6 Hz, 1H) 7.78 (dt, J=2.0, 7.6 Hz, 1H) 8.72 (t, J=5.6 Hz, 1H).

MS m/e (ESI) 472 ($MH^+$).

Example 70

3-(3-{[(4-Isopropoxy-2-chlorobenzoyl)amino]-methyl}-4-methoxyphenyl)-2-fluorobenzoic Acid

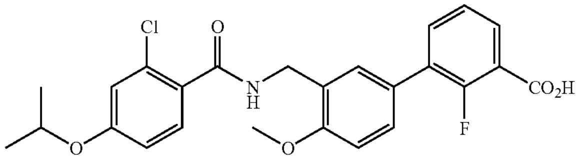

The title compound was obtained in the same way as Example 66b) except for using 4-isopropoxy-2-chlorobenzoic acid.

MS m/e (ESI) 472 ($MH^+$).

Example 71

3-(3-{[(2,4-Dichlorobenzoyl)amino]methyl}-4-methoxyphenyl)-4-methyl-6-fluorobenzoic Acid Production Example 71a Methyl 3-(3-{[(t-butoxycarbonyl)amino]methyl}-4-methoxyphenyl)-4-methyl-6-fluorobenzoate

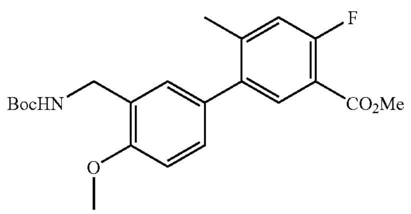

The title compound was obtained in the same way as Production Example 1d) except for using methyl 3-bromo-4-methyl-6-fluorobenzoate.

Example 71b 3-(3-{[(2,4-Dichlorobenzoyl)amino]methyl}-4-methoxyphenyl)-4-methyl-6-fluorobenzoic Acid

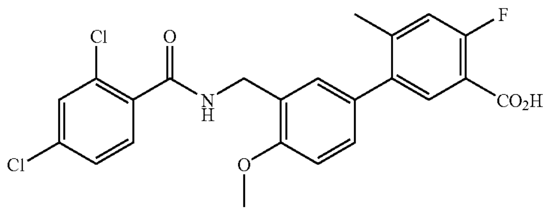

The title compound was obtained in the same way as Example 1e) except for using methyl 3-(3-{[(t-butoxycarbonyl)amino]methyl}-4-methoxyphenyl)-4-methyl-6-fluorobenzoate.

MS m/e (ESI) 462 ($MH^+$).

Example 72

3-(3-{[(4-Chloro-2-fluorobenzoyl)amino]-methyl}-4-methoxyphenyl)-4-methyl-6-fluorobenzoic Acid

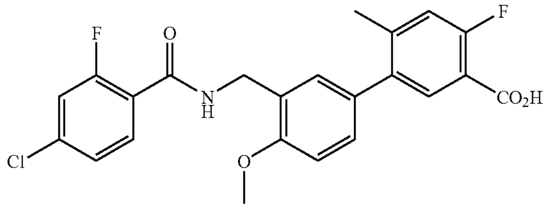

The title compound was obtained in the same way as Example 71b) except for using 4-chloro-2-fluorobenzoic acid.

MS m/e (ESI) 446 ($MH^+$).

Example 73

3-(3-{[(4-Trifluoromethyl-2-fluorobenzoyl)amino]methyl}-4-methoxyphenyl)-4-methyl-6-fluorobenzoic Acid

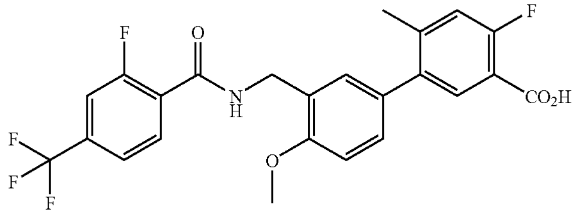

The title compound was obtained in the same way as Example 71b) except for using 4-trifluoromethyl-2-fluorobenzoic acid.

MS m/e (ESI) 480 ($MH^+$).

Example 74

3-(3-{[(4-Propoxy-2-chlorobenzoyl)amino]methyl}-4-methoxyphenyl)-4-methyl-6-fluorobenzoic Acid

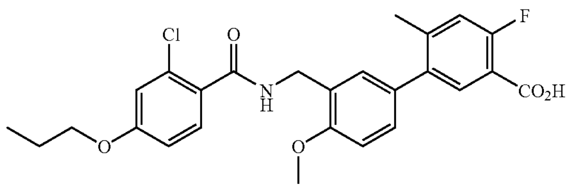

The title compound was obtained in the same way as Example 71b) except for using 4-propoxy-2-chlorobenzoic acid.

MS m/e (ESI) 486 ($MH^+$).

Example 75

3-(3-{[(4-Isopropoxy-2-chlorobenzoyl)amino]-methyl}-4-methoxyphenyl)-4-methyl-6-fluorobenzoic Acid

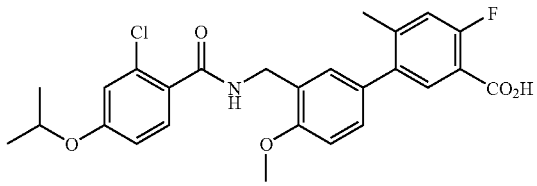

The title compound was obtained in the same way as Example 71b) except for using 4-isopropoxy-2-chlorobenzoic acid.

MS m/e (ESI) 486($MH^+$).

Example 76

6-(3-{[(2,4-Dichlorobenzoyl)amino]methyl}-4-methoxyphenyl)-2-pyridinecarboxylic Acid Production Example 76a Methyl 6-(3-{[(3,3-dimethylbutanoyl)amino]methyl}-4-methoxyphenyl)-2-pyridinecarboxylate

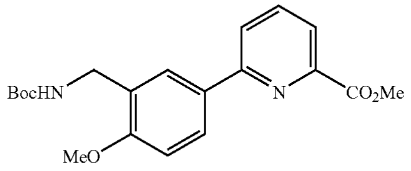

The title compound was obtained in the same way as Production Example 1d) except for using methyl 6-bromo-2-pyridinecarboxylate.

$^1H$-NMR ($CDCl_3$).

δ: 1.47 (s, 9H) 3.92 (s, 3H) 3.99 (s, 3H) 4.38 (brs, 2H) 5.10 (br, 1H) 6.99 (d, J=8.4 Hz, 1H) 7.53 (dd, J=2.4, 10.4 Hz, 1H) 7.54 (s, 1H) 8.44 (t, J=2.0 Hz, 1H) 8.97 (d, J=2.0 Hz, 1H) 9.14 (s, 1H).

Example 76b 6-(3-{[(2,4-Dichlorobenzoyl)amino]methyl}-4-methoxyphenyl)-2-pyridinecarboxylic Acid

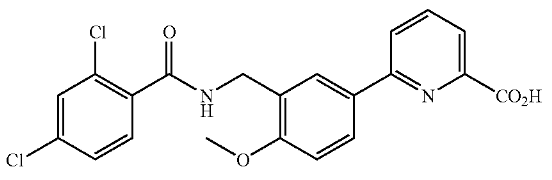

The title compound was obtained in the same way as Example 1e) except for using methyl 6-(3-{[(3,3-dimethylbutanoyl)amino]methyl}-4-methoxyphenyl)-2-pyridinecarboxylate.

MS m/e (ESI) 431 ($MH^+$).

Example 77

2-(3-{[(2,4-Dichlorobenzoyl)amino]methyl}-4-methoxyphenyl)isonicotinic Acid

Production Example 77a

Methyl 6-(3-{[(3,3-dimethylbutanoyl)amino]methyl}-4-methoxyphenyl)isonicotinate

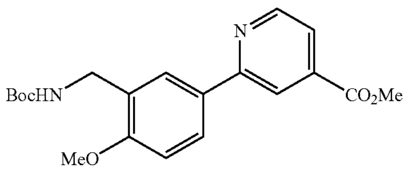

The title compound was obtained in the same way as Production Example 1d) except for using methyl 2-chloroisonicotinate.

$^1$H-NMR ($CDCl_3$).

δ: 1.46 (s, 9H) 3.93 (s, 3H) 4.01 (s, 3H) 4.39 (brs, 2H) 5.13 (br, 1H) 7.00 (d, J=8.4 Hz, 1H) 7.82 (d, J=4.8 Hz, 1H) 7.93 (d, J=2.4 Hz, 1H) 7.97 (dd, J=2.4, 8.4 Hz, 1H) 8.29 (s, 1H) 8.88 (d, J=5.2 Hz, 1H).

Example 77b 2-(3-{[(2,4-Dichlorobenzoyl)amino]methyl}-4-methoxyphenyl)isonicotinic Acid

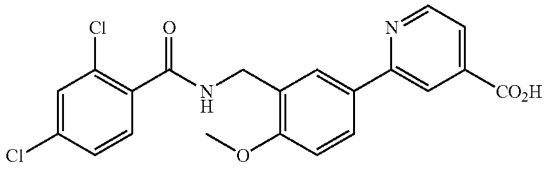

The title compound was obtained in the same way as Example 1e) except for using methyl 6-(3-{[(3,3-dimethylbutanoyl)amino]methyl}-4-methoxyphenyl)isonicotinate.

MS m/e (ESI) 431 ($MH^+$).

Example 78

2-(3-{[(4-Trifluoromethyl-2-fluorobenzoyl)amino]methyl}-4-methoxyphenyl)isonicotinic Acid

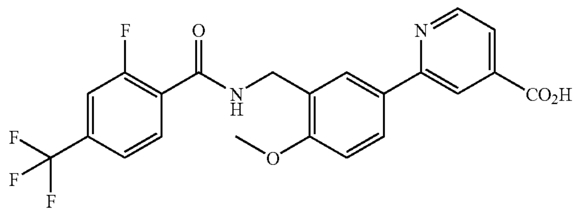

The title compound was obtained in the same way as Example 77b) except for using 4-trifluoromethyl-2-fluorobenzoic acid.

MS m/e (ESI) 449 ($MH^+$).

Example 79

2-(3-{[(4-Propoxy-2-chlorobenzoyl)amino]methyl}-4-methoxyphenyl)isonicotinic Acid

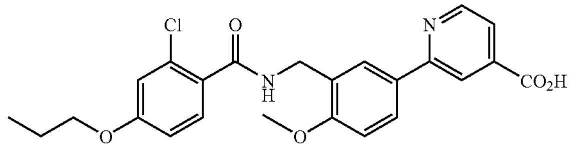

The title compound was obtained in the same way as Example 77b) except for using 4-propoxy-2-chlorobenzoic acid.

MS m/e (ESI) 455 ($MH^+$).

Example 80

5-(3-{[(2,4-Dichlorobenzoyl)amino]methyl}-4-methoxyphenyl)nicotinic Acid

Production Example 80a

Methyl 6-(3-{[(3,3-dimethylbutanoyl)amino]methyl}-4-methoxyphenyl)nicotinate

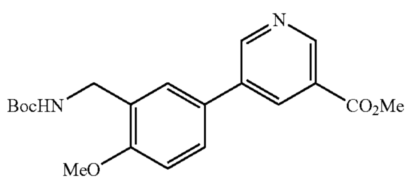

The title compound was obtained in the same way as Production Example 1d) except for using methyl 5-bromonicotinate.

$^1$H-NMR ($CDCl_3$).

δ: 1.46 (s, 9H) 3.91 (s, 3H) 3.99 (s, 3H) 4.38 (brd, J=4.8 Hz, 2H) 5.08 (br, 1H) 6.98 (d, J=8.8 Hz, 1H) 7.52 (dd, J=2.4, 10.4 Hz, 1H) 7.54 (s, 1H) 8.44 (t, J=2.4 Hz, 1H) 8.96 (d, J=2.0 Hz, 1H) 9.14 (d, J=1.6 Hz, 1H).

Example 80b 5-(3-{[(2,4-Dichlorobenzoyl)amino]methyl}-4-methoxyphenyl)nicotinic Acid

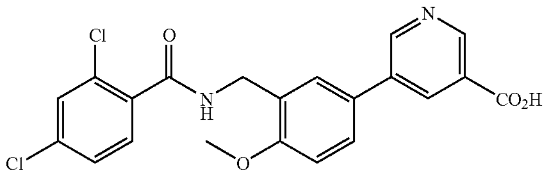

The title compound was obtained in the same way as Example 1e) except for using methyl 6-(3-{[(3,3-dimethylbutanoyl)-amino]methyl}-4-methoxyphenyl)nicotinate.

MS m/e (ESI) 431 ($MH^+$).

Example 81

5-(3-{[(2,4-Dichlorobenzoyl)amino]methyl}-4-methoxyphenyl)-2-floic Acid

Production Example 81a

Methyl 5-(3-{[(t-butoxycarbonyl)amino]methyl}-4-methoxyphenyl)-2-floate

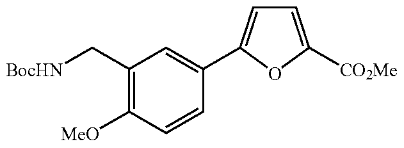

The title compound was obtained in the same way as Production Example 1d) except for using methyl 5-bromo-2-floate.

$^1$H-NMR ($CDCl_3$).

δ: 1.45 (s, 9H) 3.88 (s, 3H) 3.91 (s, 3H) 4.34 (brd, J=5.6 Hz, 2H) 5.05 (br, 1H) 6.62 (d, J=3.6 Hz, 1H) 6.90 (d, J=8.8 Hz, 1H) 7.23 (d, J=3.6 Hz, 1H) 7.65 (d, J=2.4 Hz, 1H) 7.70 (dd, J=2.0, 8.4 Hz, 1H).

Example 81b 5-(3-{[(2,4-Dichlorobenzoyl)amino]methyl}-4-methoxyphenyl)-2-floic Acid

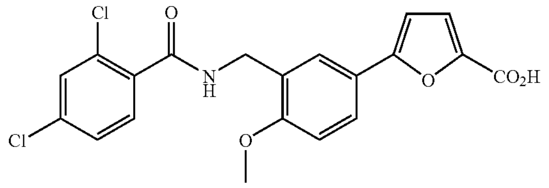

The title compound was obtained in the same way as Example 1e) except for using methyl 5-(3-{[(t-butoxycarbonyl)amino]methyl}-4-methoxyphenyl)-2-floate.

MS m/e (ESI) 420 ($MH^+$).

Example 82

5-[4-Methoxy-3-({[(4-methyl-2-phenyl-1,3-thiazol-5-yl)carbonyl]amino}methyl)phenyl]-2-floic Acid

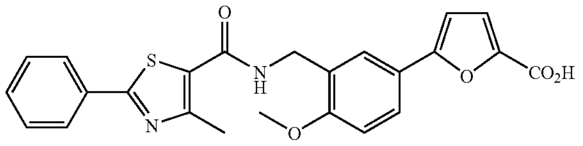

The title compound was obtained in the same way as Example 81b) except for using 4-methyl-2-(phenyl)-1,3-thiazol-5-carboxylic Acid.

MS m/e (ESI) 449 ($MH^+$).

Example 83

4-(3-{[(2,4-Dichlorobenzoyl)amino]methyl}-4-methoxyphenyl)-2-thiophenecarboxylic Acid Production Example 83a Methyl 4-(3-{[(t-butoxycarbonyl)amino]methyl}-4-methoxyphenyl)-2-thiophenecarboxylate

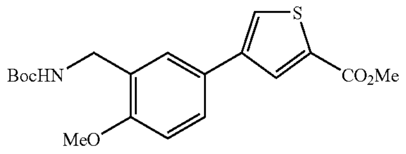

The title compound was obtained in the same way as Production Example 1d) except for using methyl 4-bromo-2-thiophenecarboxylate.

$^1$H-NMR ($CDCl_3$).

δ: 1.45 (s, 9H) 3.88 (s, 3H) 3.91 (s, 3H) 4.34 (s, 2H) 6.90 (d, J=8.0 Hz, 1H) 7.45-7.51 (m, 2H) 7.55 (d, J=1.6 Hz, 1H) 8.03 (d, J=1.6 Hz, 1H).

Example 83b 4-(3-{[(2,4-Dichlorobenzoyl)amino]methyl}-4-methoxyphenyl)-2-thiophenecarboxylic Acid

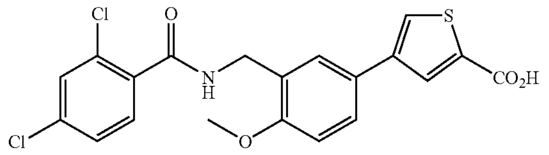

The title compound was obtained in the same way as Example 1e) except for using methyl 4-(3-{[(t-butoxycarbonyl)amino]methyl}-4-methoxyphenyl)-2-thiophenecarboxylate.

MS m/e (ESI) 436 ($MH^+$).

Example 84

4-(3-{[(4-Chloro-2-fluorobenzoyl)amino]-methyl}-4-methoxyphenyl)-2-thiophenecarboxylic Acid

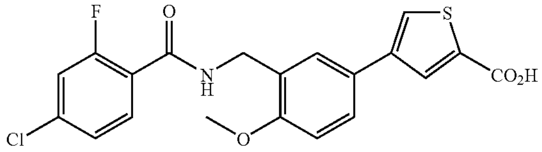

The title compound was obtained in the same way as Example 83b) except for using 4-chloro-2-fluorobenzoic acid.

MS m/e (ESI) 420 ($MH^+$).

Example 85

4-(3-{[(4-Trifluoromethyl-2-fluorobenzoyl)amino] methyl}-4-methoxyphenyl)-2-thiophenecarboxylic Acid

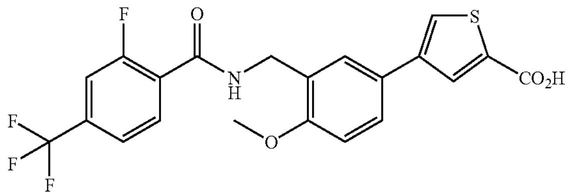

The title compound was obtained in the same way as Example 83b) except for using 4-trifluoromethyl-2-fluorobenzoic acid.

MS m/e (ESI) 454 ($MH^+$).

Example 86

4-(3-{[(4-Propoxy-2-chlorobenzoyl)amino]-methyl}-4-methoxyphenyl)-2-thiophenecarboxylic Acid

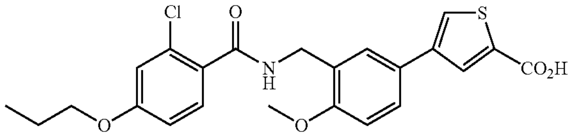

The title compound was obtained in the same way as Example 83b) except for using 4-propoxy-2-chlorobenzoic acid.

MS m/e (ESI) 460 ($MH^+$).

Example 87

4-(3-{[(4-Isopropoxy-2-chlorobenzoyl)amino]methyl}-4-methoxyphenyl)-2-thiophenecarboxylic Acid

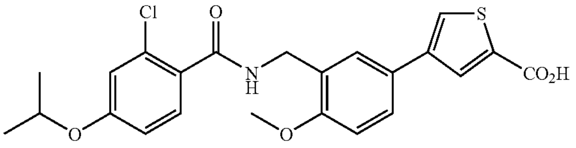

The title compound was obtained in the same way as Example 83b) except for using 4-isopropoxy-2-chlorobenzoic acid.

MS m/e (ESI) 460 ($MH^+$).

Example 88

2-(3-{[(2,4-Dichlorobenzoyl)amino]methyl}-4-methoxyphenyl)-4-methyl-1,3-thiazol-5-carboxylic Acid Production Example 88a Methyl 2-(3-{[(t-butoxycarbonyl)amino]methyl}-4-methoxyphenyl)-4-methyl-1,3-thiazol-5-carboxylate

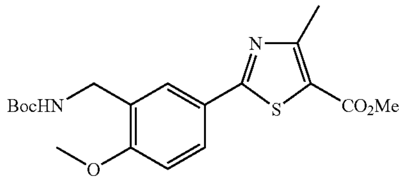

The title compound was obtained in the same way as Production Example 1d) except for using methyl 2-bromo-4-methyl-1,3-thiazol-5-carboxylate.

$^1$H-NMR ($CDCl_3$)

δ: 1.46 (s, 9H) 2.98 (s, 3H) 3.90 (s, 3H) 3.96 (s, 3H) 4.35 (d, J=6.0 Hz, 2H) 5.03 (br, 1H) 6.90 (d, J=8.8 Hz, 1H) 7.79 (s, 1H) 7.84 (dd, J=2.4, 8.4 Hz, 1H).

Example 88b 2-(3-{[(2,4-Dichlorobenzoyl)amino]methyl}-4-methoxyphenyl)-5-methyl-1,3-thiazol-4-carboxylic Acid

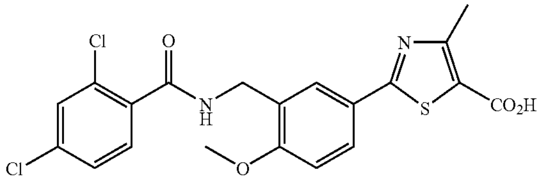

The title compound was obtained in the same way as Example 1e) except for using methyl 2-(3-{[(t-butoxycarbonyl)amino]methyl}-4-methoxyphenyl)-4-methyl-1,3-thiazol-5-carboxylate.

MS m/e (ESI) 451 ($MH^+$).

Example 89

2-{4-Methoxy-3-[({[4-methyl-2-(4-methylphenyl)-1,3-thiazol-5-yl]carbonyl}amino)methyl]-phenyl}-4-methyl-1,3-thiazol-5-carboxylic Acid

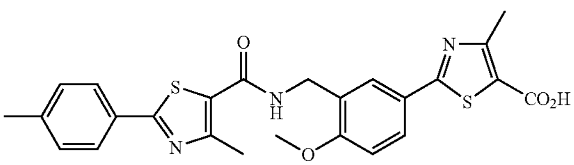

The title compound was obtained in the same way as Example 88b) except for using 4-methyl-2-(4-methylphenyl)-1,3-thiazol-5-carboxylic Acid.

MS m/e (ESI) 480 ($MH^+$).

Example 90

3-(3-{[(4-Propoxy-2-chlorobenzoyl)amino]-methyl}-4-hydroxyphenyl)benzoic Acid

Production Example 90a 2-(Benzyloxy)-5-bromophenyl]methanol

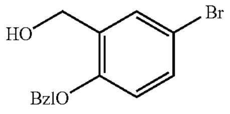

3-Bromo-2-hydroxybenzyl alcohol (100 g) was dissolved in 1 L of N,N-dimethylformamide, and 84 g of benzyl bromide and 80 g of potassium carbonate were added successively to the solution. The mixture was stirred overnight at room temperature, the reaction mixture was filtered through Celite, and the filtrate was diluted with ethyl acetate. The organic layer was washed with water and a saturated aqueous solution of sodium chloride, dried over anhydrous magnesium sulfate, and the solvent was evaporated, to give 140.3 g of the title compound.

$^1$H-NMR ($CDCl_3$).

δ: 2.21(br, 1H) 4.69 (s, 2H) 5.09 (s, 2H) 6.81 (d, J=8.8 Hz, 1H) 7.33-7.40 (m, 6H) 7.45 (d, J=2.4 Hz, 1H).

Production Example 90b t-Butyl N-[2-(benzyloxy)-5-bromobenzyl]carbamate

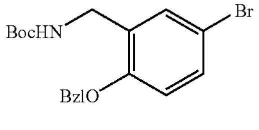

[2-(Benzyloxy)-5-bromophenyl]methanol (140.3 g) was dissolved in 700 ml of toluene, 160 g of diphenyl phosphorazide and 85 g of diazabicyclodecene were successively added to the solution, and the mixture was stirred overnight at room temperature. 1 L of ethyl acetate was added thereto, and the reaction mixture was successively washed with water and brine, dried over anhydrous magnesium sulfate, and the solvent was removed to give 157 g of 1-[2-(benzyloxy)-5-bromobenzyl]-1,2-triazadien-2-ium. 47.23 g of the product was dissolved in 500 ml of tetrahydrofuran and 20 ml of water, 42 g of triphenyl phosphine was added thereto, and the mixture was stirred overnight. 28 g of t-butyl dicarbonate was added thereto and stirred at room temperature for 1 hour, and 3 ml of 30% aqueous hydrogen peroxide was added thereto. The solvent was concentrated and the residue was suspended in diethyl ether and filtered. The filtrate was evaporated, and the residue was purified by silica gel column, to give 47.645 g of the title compound in the 15:1→10:1 hexane-ethyl acetate fraction.

$^1$H-NMR ($CDCl_3$).

δ: 1.45 (s, 9H) 4.32 (s, 2H) 4.95 (br, 1H) 5.07 (s, 2H) 6.78 (d, J=8.8 Hz, 1H) 7.31 (dd, J=2.4, 8.8 Hz, 1H) 7.34-7.40 (m, 6H)

Production Example 90c t-Butyl N-[2-benzyloxy-5-(4,4,5,5-tetramethyl-1,3,2-dioxaborolan-2-yl)benzyl]carbamate

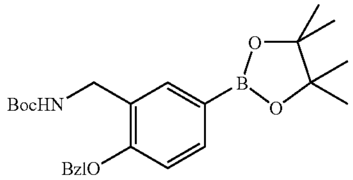

The title compound was obtained in the same way as Production Example 1c) except for using t-butyl N-[2-(benzyloxy)-5-bromobenzyl]carbamate.

$^1$H-NMR ($CDCl_3$).

δ: 1.33 (s, 12H) 1.44 (s, 9H) 4.38 (brd, J=5.2 Hz, 2H) 4.97 (br, 1H) 5.14 (s, 2H) 6.92 (d, J=8.0 Hz, 1H) 7.31-7.43 (m, 5H) 7.70 (dd, J=1.6, 8.0 Hz, 1H) 7.72 (d, J=3.2 Hz, 1H).

Production Example 90d

Methyl 3-(3-{[(t-butoxycarbonyl)amino]methyl}-4-benzyloxyphenyl)benzoate

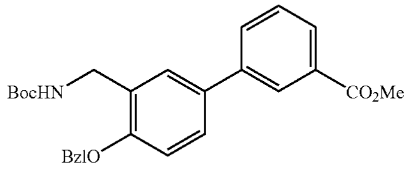

The title compound was obtained in the same way as Production Example 1d) except for using t-butyl N-[2-benzyloxy-5-(4,4,5,5-tetramethyl-1,3,2-dioxaborolan-2-yl)benzyl]carbamate.

$^1$H-NMR ($CDCl_3$).

δ: 1.45 (s, 9H) 3.95 (s, 3H) 4.44 (brd, J=4.8 Hz, 2H) 5.05 (br, 1H) 5.16 (s, 2H) 7.01 (d, J=8.4 Hz, 1H) 7.33-7.50 (m, 7H) 7.53 (s, 1H) 7.74 (dt, J=1.6, 8.0 Hz, 1H) 7.97 (d, J=6.4 Hz, 1H) 8.22 (t, J=0.9 Hz, 1H).

Example 90e 3-(3-{[(4-Propoxy-2-chlorobenzoyl)amino]methyl}-4-hydroxyphenyl)benzoic Acid

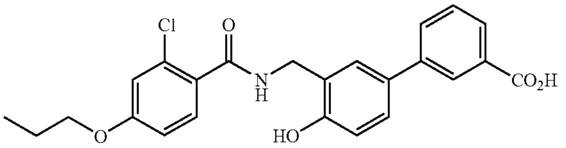

Methyl 3-(3-{[(t-butoxycarbonyl)amino]methyl}-4-benzyloxyphenyl)benzoate (2.062 g) was dissolved in 30 ml of methanol, 500 mg of 10% palladium-carbon was added thereto, and the mixture was stirred overnight at room temperature in a hydrogen atmosphere. The reaction mixture was filtered through Celite and the filtrate was concentrated, to give 1.825 g of 3-(3-{[(t-butoxycarbonyl)amino]methyl}-4-hydroxyphenyl)benzoate. The title compound was obtained in the same way as Example 1e) except for using this product.

MS m/e (ESI) 440 ($MH^+$).

Example 91

3-(3-{[(2,4-Dichlorobenzoyl)amino]methyl}-4-ethoxyphenyl)benzoic Acid

Production Example 91a

Methyl 3-(3-{[(t-butoxycarbonyl)amino]methyl}-4-ethoxyphenyl)benzoate

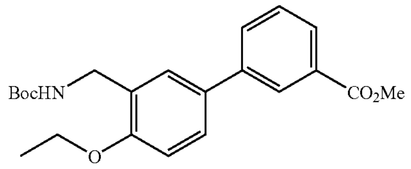

Methyl 3-(3-{[(t-butoxycarbonyl)amino]methyl}-4-benzyloxyphenyl)benzoate (2.062 g) was dissolved in 30 ml methanol, 500 mg of 10% palladium-carbon was added thereto, the mixture was stirred overnight at room temperature in a hydrogen atmosphere. The reaction mixture was filtered through Celite, and the filtrate was concentrated to give 1.825 g of 3-(3-{[(t-butoxycarbonyl)amino]methyl}-4-hydroxyphenyl)benzoate. 396 mg of the product was dissolved in 5 ml acetonitrile, 0.5 ml iodoethane and 500 mg cesium carbonate were added successively thereto, and the mixture was stirred overnight at room temperature. The reaction mixture was filtered through Celite, and the filtrate was evaporated. The residue was purified by silica gel column, to give 365 mg of the title compound in the 7:1→5:1 hexane-ethyl acetate fraction.

$^1$H-NMR ($CDCl_3$).

δ: 1.46 (s, 9H) 1.47 (t, J=7.0 Hz, 3H) 3.95 (s, 3H) 4.11 (q, J=6.8 Hz, 2H) 4.39 (brd, J=5.6 Hz, 2H) 5.05 (br, 1H) 6.93 (d, J=8.4 Hz, 1H) 7.46-7.52 (m, 3H) 7.74 (dt, J=1.2, 8.0 Hz, 1H) 7.97 (dd, J=1.2, 7.6 Hz, 1H) 8.22 (t, J=1.6 Hz, 1H).

Example 91b 3-(3-{[(2,4-Dichlorobenzoyl)amino]methyl}-4-ethoxyphenyl)benzoic Acid

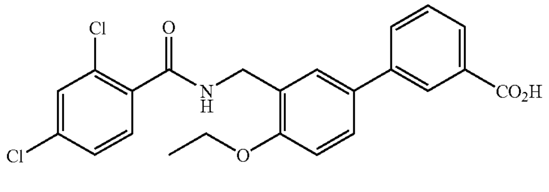

The title compound was obtained in the same way as Example 1e) except for using methyl 3-(3-{[(t-butoxycarbonyl)amino]methyl}-4-ethoxyphenyl)benzoate.

MS m/e (ESI) 444 (MH$^+$).

Example 92

3-(3-{[(4-Chloro-2-fluorobenzoyl)amino]methyl}-4-ethoxyphenyl)benzoic Acid

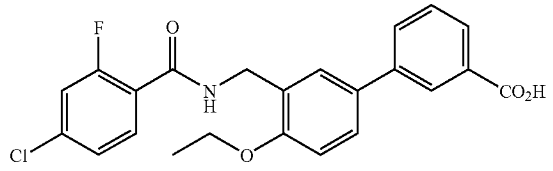

The title compound was obtained in the same way as Example 91b) except for using 4-chloro-2-fluorobenzoic acid.

MS m/e (ESI) 428 (MH$^+$).

Example 93

3-(3-{[(4-Trifluoromethyl-2-fluorobenzoyl)amino]methyl}-4-ethoxyphenyl)benzoic Acid

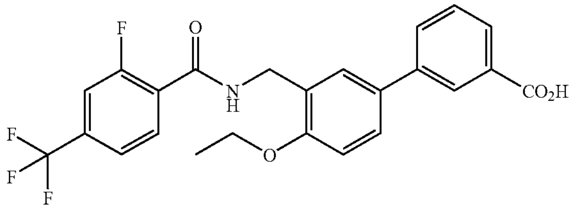

The title compound was obtained in the same way as Example 91b) except for using 4-trifluoromethyl-2-fluorobenzoic acid.

$^1$H-NMR ($CDCl_3$).

δ: 1.37 (t, J=7.2 Hz, 3H) 4.12 (q, J=7.2 Hz, 2H) 4.51 (d, J=5.6 Hz, 2H) 7.10 (d, J=8.8 HZ, 1H) 7.54 (d, J=8.0 Hz, 1H) 7.57 (d, J=8.0 Hz, 1H) 7.67 (d, J=8.0 Hz, 1H) 7.79-7.87 (m, 5H) 8.14 (t, J=2.0 Hz, 1H) 9.00 (t, J=6.0 Hz, 1H).

MS m/e (ESI) 462 (MH$^+$).

Example 94

3-(3-{[(4-Propoxy-2-chlorobenzoyl)amino]methyl}-4-ethoxyphenyl)benzoic Acid

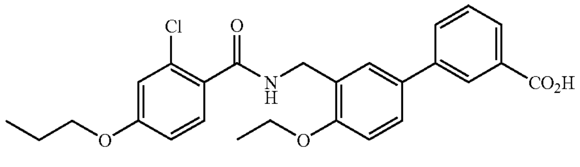

The title compound was obtained in the same way as Example 91b) except for using 4-propoxy-2-chlorobenzoic acid.

MS m/e (ESI) 468 (MH$^+$).

Example 95

3-(3-{[(4-Isopropoxy-2-chlorobenzoyl)amino]methyl}-4-ethoxyphenyl)benzoic Acid

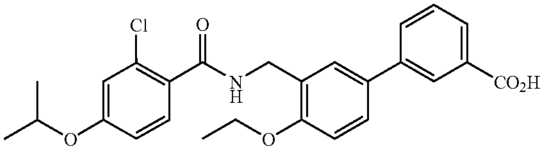

The title compound was obtained in the same way as Example 91b) except for using 4-isopropoxy-2-chlorobenzoic acid.

MS m/e (ESI) 468 ($MH^+$).

Example 96

3-(3-{[(4-Chlorobenzoyl)amino]methyl}-4-ethoxyphenyl)benzoic Acid

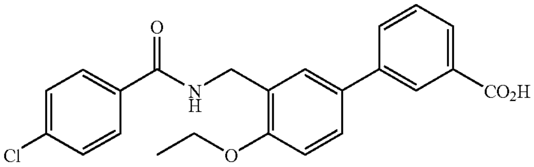

The title compound was obtained in the same way as Example 91b) except for using 4-chlorobenzoic acid.

MS m/e (ESI) 410 ($MH^+$).

Example 97

3-(3-{[(2-Chlorobenzoyl)amino]methyl}-4-ethoxyphenyl)benzoic Acid

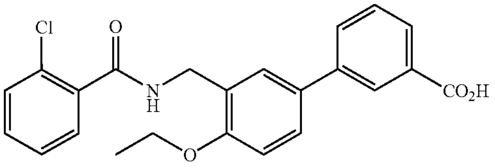

The title compound was obtained in the same way as Example 91b) except for using 2-chlorobenzoic acid.

MS m/e (ESI) 410 ($MH^+$).

Example 98

3-{4-Ethoxy-3-[({[4-methyl-2-(4-methylphenyl)-1,3-thiazol-5-yl]carbonyl}amino)methyl]phenyl}benzoic Acid

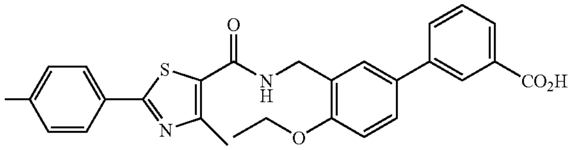

The title compound was obtained in the same way as Example 91b) except for using 4-methyl-2-(4-methylphenyl)-1,3-thiazol-5-carboxylic Acid MS m/e (ESI) 487 ($MH^+$). .

Example 99

3-(3-{[(2,4-Dichlorobenzoyl)amino]methyl}-4-isopropoxyphenyl)benzoic Acid

Production Example 99

Methyl 3-(3-{[(t-butoxycarbonyl)amino]methyl}-4-isopropoxyphenyl)benzoate

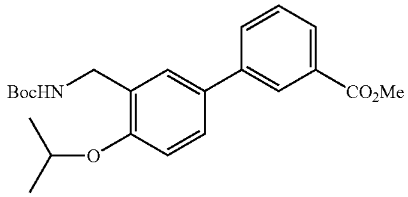

The title compound was obtained in the same way as Production Example 91a) except for using 2-iodopropane.

$^1$H-NMR ($CDCl_3$).

δ: 1.39 (d, J=6.0 Hz, 6H) 1.59 (s, 9H) 3.95 (s, 3H) 4.37 (brd, J=5.6 Hz, 2H) 4.64 (sept, J=6.4 Hz, 1H) 5.02 (br, 1H) 6.95 (d, J=8.4 Hz, 1H) 7.46-7.52 (m, 3H) 7.74 (ddd, J=1.2, 2.0, 8.0 Hz, 1H) 7.97 (dt, J=1.2, 7.6 Hz, 1H) 8.22 (t, J=1.6 Hz, 1H)

Example 99b 3-(3-{[(2,4-Dichlorobenzoyl)amino]methyl}-4-isopropoxyphenyl)benzoic Acid

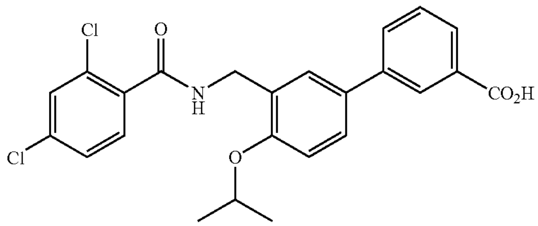

The title compound was obtained in the same way as Example 1e) except for using methyl 3-(3-{[(t-butoxycarbonyl)amino]methyl}-4-isopropoxyphenyl)benzoate.

MS m/e (ESI) 458 ($MH^+$).

Example 100

3-(3-{[(4-Chloro-2-fluorobenzoyl)amino]methyl}-4-isopropoxyphenyl)benzoic Acid

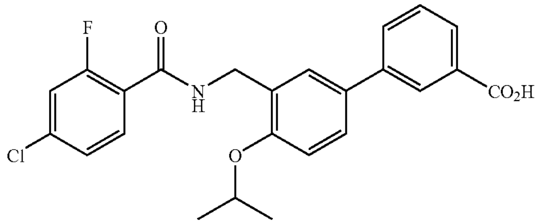

The title compound was obtained in the same way as Example 99b) except for using 4-chloro-2-fluorobenzoic acid MS m/e (ESI) 442 ($MH^+$). .

Example 101

3-(3-{[(4-Trifluoromethyl-2-fluorobenzoyl)amino]methyl}-4-isopropoxyphenyl)benzoic Acid

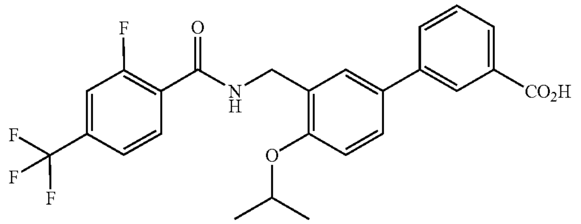

The title compound was obtained in the same way as Example 99b) except for using 4-trifluoromethyl-2-fluorobenzoic acid.

MS m/e (ESI) 476 ($MH^+$).

Example 102

3-(3-{[(4-Propoxy-2-chlorobenzoyl)amino]methyl}-4-isopropoxyphenyl)benzoic Acid

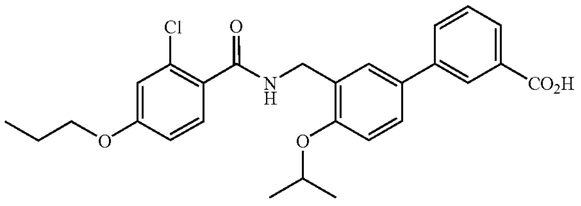

The title compound was obtained in the same way as Example 99b) except for using 4-propoxy-2-chlorobenzoic acid.

MS m/e (ESI) 482 ($MH^+$).

Example 103

3-(3-{[(4-Isopropoxy-2-chlorobenzoyl)amino]methyl}-4-isopropoxyphenyl)benzoic Acid

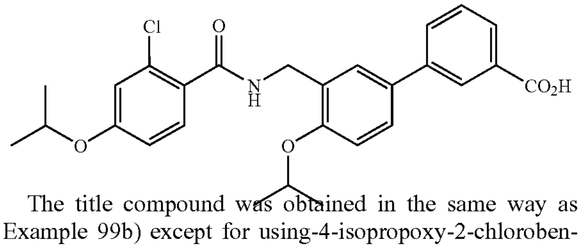

The title compound was obtained in the same way as Example 99b) except for using-4-isopropoxy-2-chlorobenzoic acid.

$^1$H-NMR ($CDCl_3$).

δ: 1.33 (d, J=6.0 Hz, 6H) 1.41 (d, J=6.0 Hz, 6H) 4.46 (sept, J=6.0 Hz, 1H) 4.68 (sept, J=6.0 Hz, 1H) 4.72 (d, J=6.0 Hz, 2H) 6.82 (dd, J=2.4, 8.8 Hz, 1H) 6.88 (d, J=2.4 Hz, 1H) 6.98 (d, J=2.4 Hz, 1H) 7.05 (t, J=5.6 Hz, 1H) 7.50 (t, J=7.6 Hz, 1H) 7.53 (dd, J=2.4, 8.8 Hz, 1H) 7.66 (d, J=2.4 Hz, 1H) 7.78 (d, J=8.8 Hz, 1H) 7.79-7.81 (m, 1H) 8.02 (dt, J=1.2, 8.0 Hz, 1H) 8.30 (t, J=1.6 Hz, 1H).

MS m/e (ESI) 482 ($MH^+$).

Example 104

3-(3-{[(4-Chlorobenzoyl)amino]methyl}-4-isopropoxyphenyl)benzoic Acid

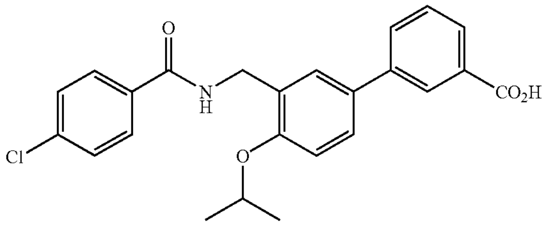

The title compound was obtained in the same way as Example 99b) except for using 4-chlorobenzoic acid.

MS m/e (ESI) 424 ($MH^+$).

Example 105

3-(3-{[(2-Chlorobenzoyl)amino]methyl}-4-isopropoxyphenyl)benzoic Acid

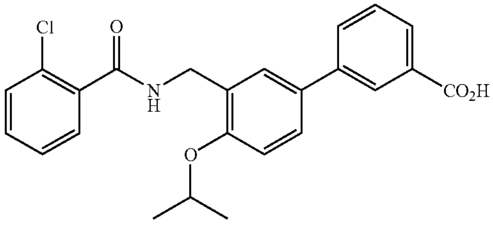

The title compound was obtained in the same way as Example 99b) except for using 2-chlorobenzoic acid.

MS m/e (ESI) 424 ($MH^+$).

Example 106

3-{4-Isopropoxy-3-[({[4-methyl-2-(4-methylphenyl)-1,3-thiazol-5-yl]carbonyl}amino)methyl]-phenyl}benzoic Acid

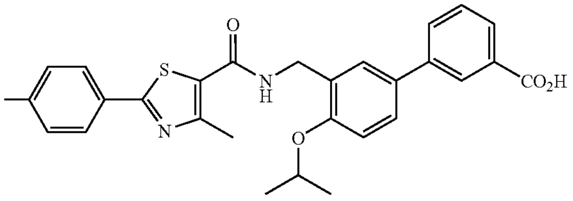

The title compound was obtained in the same way as Example 99b) except for using 4-methyl-2-(4-methylphenyl)-1,3-thiazol-5-carboxylic Acid.

MS m/e (ESI) 501 ($MH^+$).

Example 107

3-(3-{[(2,4-Dichlorobenzoyl)amino]methyl}-4-propoxyphenyl)benzoic Acid

Production Example 107a

Methyl 3-(3-{[(t-butoxycarbonyl)amino]methyl}-4-propoxyphenyl)benzoate

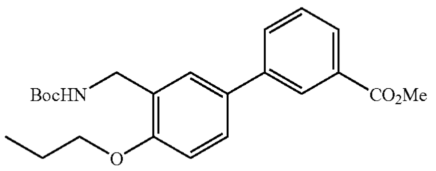

The title compound was obtained in the same way as Production Example 91a) except for using 1-iodopropane.

$^{1}$H-NMR ($CDCl_3$).

δ: 1.08 (t, J=7.2 Hz, 3H) 1.46 (s, 9H) 1.86 (sept, J=7.2 Hz, 2H) 3.95 (s, 3H) 4.01 (t, J=7.2 Hz, 2H) 4.39 (brd, J=5.2 Hz, 2H) 5.05 (br, 1H) 6.93 (d, J=8.4 Hz, 1H) 7.46-7.52 (m, 3H) 7.74 (ddd, J=1.2, 2.0, 7.6 Hz, 1H) 7.97 (dt, J=1.6, 7.6 Hz, 1H) 8.22 (t, J=1.6 Hz, 1H).

Example 107b 3-(3-{[(2,4-Dichlorobenzoyl)amino]methyl}-4-propoxyphenyl)benzoic Acid

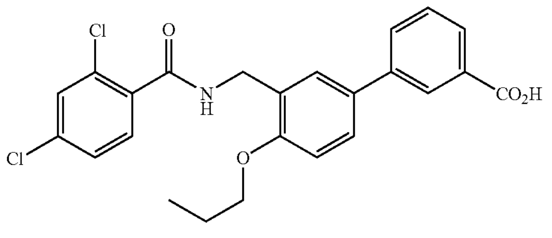

The title compound was obtained in the same way as Example 1e) except for using methyl 3-(3-{[(t-butoxycarbonyl)amino]methyl}-4-propoxyphenyl)benzoate.

MS m/e (ESI) 458 ($MH^+$).

Example 108

3-(3-{[(4-Chloro-2-fluorobenzoyl)amino]methyl}-4-propoxyphenyl)benzoic Acid

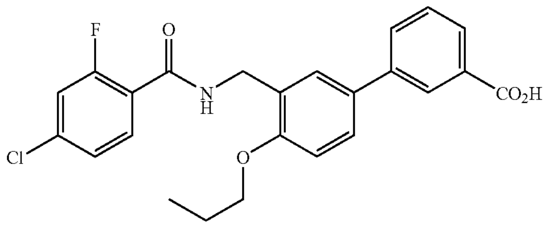

The title compound was obtained in the same way as Example 107b) except for using 4-chloro-2-fluorobenzoic acid.

MS m/e (ESI) 442 ($MH^+$).

Example 109

3-(3-{[(4-Trifluoromethyl-2-fluorobenzoyl)amino]methyl}-4-propoxyphenyl)benzoic Acid

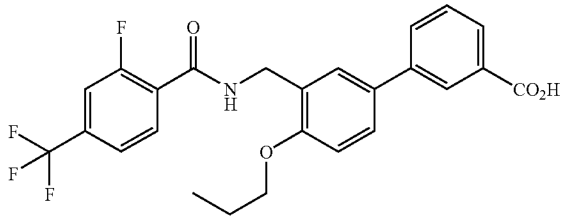

The title compound was obtained in the same way as Example 107b) except for using 4-trifluoromethyl-2-fluorobenzoic acid.

$^{1}$H-NMR ($CDCl_3$).

δ: 1.02 (t, J=7.6 Hz, 3H) 1.78 (q, J=6.4 Hz, 2H) 4.03 (t, J=6.0 Hz, 2H) 4.53 (d, J=5.6 Hz, 2H) 7.09 (d, J=8.4 HZ, 1H) 7.51 (t, J=8.0 Hz, 1H) 7.58 (dd, J=2.0, 8.4 Hz, 1H) 7.59 (s, 1H) 7.67 (d, J=8.0 Hz, 1H) 7.77-7.86 (m, 4H) 8.14 (s, 1H) 9.00 (t, J=5.6 Hz, 1H).

MS m/e (ESI) 476 ($MH^+$).

Example 110

3-(3-{[(4-Propoxy-2-chlorobenzoyl)amino]methyl}-4-propoxyphenyl)benzoic Acid

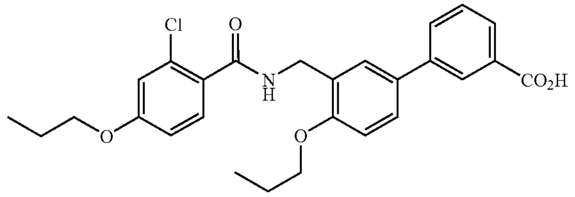

The title compound was obtained in the same way as Example 107b) except for using 4-propoxy-2-chlorobenzoic acid.

MS m/e (ESI) 482 ($MH^+$).

Example 111

3-(3-{[(4-Isopropoxy-2-chlorobenzoyl)amino]methyl}-4-propoxyphenyl)benzoic Acid

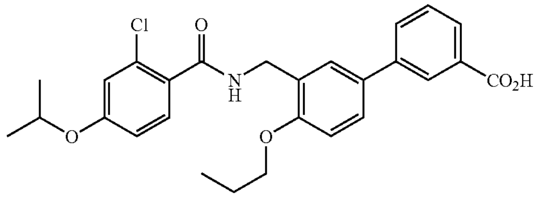

The title compound was obtained in the same way as Example 107b) except for using 4-isopropoxy-2-chlorobenzoic acid.

MS m/e (ESI) 482 ($MH^+$).

Example 112

3-(3-{[(4-Chlorobenzoyl)amino]methyl}-4-propoxyphenyl)benzoic Acid

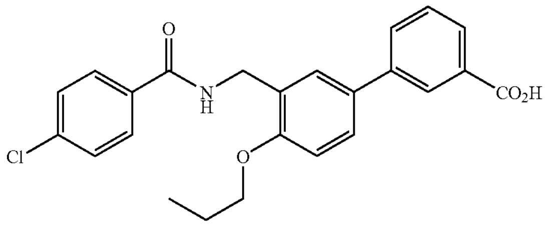

The title compound was obtained in the same way as Example 107b) except for using 4-chlorobenzoic acid.

MS m/e (ESI) 424 ($MH^+$).

Example 113

3-(3-{[(2-Chlorobenzoyl)amino]methyl}-4-propoxyphenyl)benzoic Acid

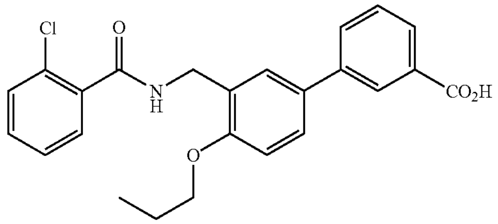

The title compound was obtained in the same way as Example 107b) except for using 2-chlorobenzoic acid.

MS m/e (ESI) 424 ($MH^+$).

Example 114

3-{4-Propoxy-3-[({[4-methyl-2-(4-methylphenyl)-1,3-thiazol-5-yl]carbonyl}amino)methyl]phenyl}benzoic Acid

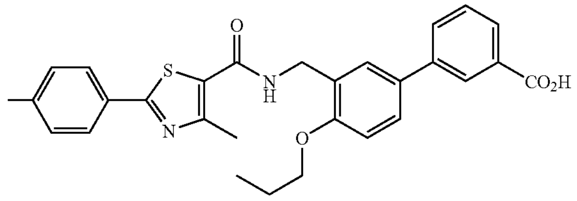

The title compound was obtained in the same way as Example 107b) except for using 4-methyl-2-(4-methylphenyl)-1,3-thiazol-5-carboxylic Acid. MS m/e (ESI) 501 ($MH^+$).

Example 115

3-(3-{[(2,4-Dichlorobenzoyl)amino]methyl}-4-chlorophenyl)benzoic Acid

Production Example 115a

5-Bromo-2-chlorophenyl)methanol

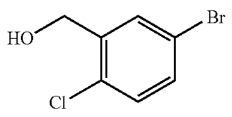

5-Bromo-2-chlorobenzoic acid (12 g) was dissolved in 60 ml of tetrahydrofuran, and 148.3 g of boran/tetrahydrofuran complex (1 M tetrahydrofuran solution) was added thereto. The mixture was stirred at room temperature for 2.5 days. 1 N hydrochloric acid was added thereto, then the reaction mixture was extracted with ethyl acetate. The organic layer was washed with water and a saturated aqueous sodium chloride solution and dried over anhydrous magnesium sulfate, and the solvent was evaporated, to give 11.46 g of the title compound.

$^1$H-NMR ($CDCl_3$).

δ: 1.96 (br, 1H) 4.76 (s, 2H) 7.22 (d, J=8.4 Hz, 1H) 7.36 (dd, J=2.4, 8.4 Hz, 1H) 7.67 (d, J=2.1 Hz, 1H).

Production Example 115b

4-Bromo-2-(azidomethyl)chlorobenzene

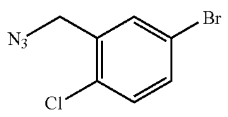

(5-Bromo-2-chlorophenyl)methanol (8.187 g) was dissolved in 100 ml of toluene, 12.2 g of diphenylposhorazide and 6.52 ml of diazabicycloundecene were added successively, and the mixture was stirred overnight at room temperature. After ethyl acetate was added thereto, the reaction mixture was successively washed with water and brine, dried over anhydrous magnesium sulfate, and the solvent was removed. The residue was purified by silica gel column, to give 9.75 g of the title compound in the 50:1 hexane-ethyl acetate fraction.

$^1$H-NMR ($CDCl_3$).

δ: 4.48 (s, 2H) 7.28 (d, J=8.4 Hz, 1H) 7.41 (dd, J=2.4, 8.4 Hz, 1H) 7.56 (d, J=2.4 Hz, 1H).

Production Example 115c t-Butyl N-(5-bromo-2-chlorobenzyl)carbamate

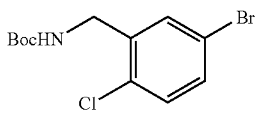

The title compound was obtained in the same way as Production Example 90b) except for using 4-bromo-2-(azidomethyl)chlorobenzene.

$^1$H-NMR ($CDCl_3$).

δ: 1.46 (s, 9H) 4.37 (brd, J=6.0 Hz, 2H) 5.00 (br, 1H) 7.21 (d, J=8.4 Hz, 1H) 7.34 (dd, J=2.4, 8.4 Hz, 1H) 7.50 (d, J=2.4 Hz, 1H).

Production Example 115d t-Butyl N-[2-chloro-5-(4,4,5,5-tetramethyl-1,3,2-dioxaborolan-2-yl)benzyl]carbamate

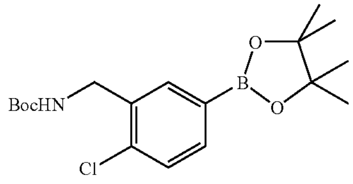

The title compound was obtained in the same way as Production Example 1c) except for using t-butyl N-(5-bromo-2-chlorobenzyl)carbamate.

$^1$H-NMR ($CDCl_3$).

δ: 1.33 (s, 12H) 1.46 (s, 9H) 4.42 (brd, J=5.2 Hz, 2H) 4.94 (br, 1H) 7.36 (d, J=7.6 Hz, 1H) 7.64 (dd, J=1.2, 7.6 Hz, 1H) 7.77 (s, 1H).

Production Example 115e

Methyl 3-(3-{[(t-butoxycarbonyl)amino]methyl}-4-chlorophenyl)benzoate

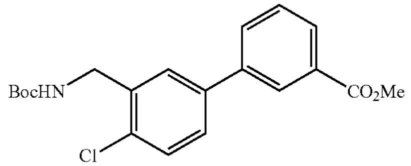

The title compound was obtained in the same way as Production Example 1d) except for using t-butyl N-[2-chloro-5-(4,4,5,5-tetramethyl-1,3,2-dioxaborolan-2-yl)benzyl]carbamate.

$^1$H-NMR ($CDCl_3$).

δ: 1.59 (s, 9H) 3.95 (s, 3H) 4.48 (brd, J=6.0 Hz, 2H) 5.05 (br, 1H) 7.43-7.52 (m, 2H) 7.53 (d, J=8.0 Hz, 1H) 7.61 (s, 1H) 7.75 (dt, J=1.6, 8.0 Hz, 1H) 8.04 (d, J=7.6 Hz, 1H) 8.23 (s, 1H).

Example 115f

3-(3-{[(2,4-Dichlorobenzoyl)amino]methyl}-4-chlorophenyl)benzoic Acid

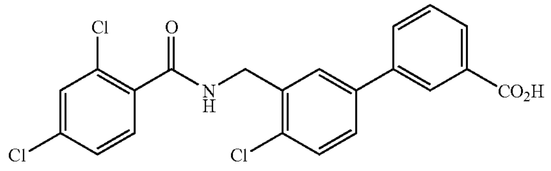

The title compound was obtained in the same way as Example 1e) except for using methyl 3-(3-{[(t-butoxycarbonyl)amino]methyl}-4-chlorophenyl)benzoate. MS m/e (ESI) 434 ($MH^+$).

Example 116

3-(3-{[(4-Trifluoromethyl-2-fluorobenzoyl)amino]methyl}-4-chlorophenyl)benzoic Acid

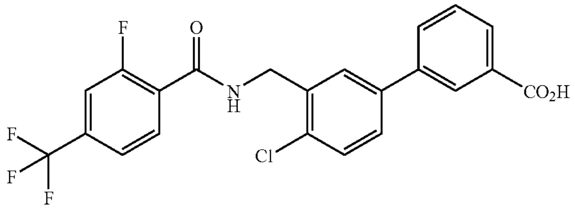

The title compound was obtained in the same way as Example 115f) except for using 4-trifluoromethyl-2-fluorobenzoic acid.

MS m/e (ESI) 452 ($MH^+$).

Example 117

3-(3-{[(4-Propoxy-2-chlorobenzoyl)amino]methyl}-4-chlorophenyl)benzoic Acid

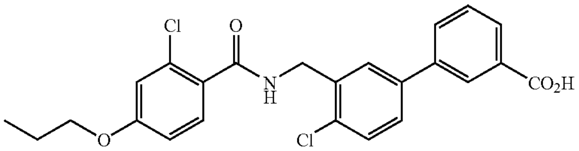

The title compound was obtained in the same way as Example 115f) except for using 4-propoxy-2-chlorobenzoic acid.

MS m/e (ESI) 458 ($MH^+$).

Example 118

3-(3-{[(2,4-Dichlorobenzoyl)amino]methyl}phenyl)benzoic Acid

Production Example 118a

Methyl 3-(3-{[(t-butoxycarbonyl)amino]methyl}phenyl)benzoate

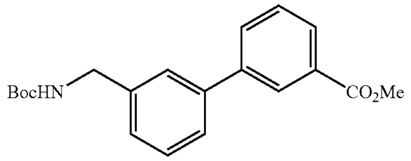

Methyl 3-(3-{[(t-butoxycarbonyl)amino]methyl}-4-chlorophenyl)benzoate (199 mg) was dissolved in 3 ml of methanol, 100 mg of 10% palladium-carbon was added thereto, and the mixture was stirred at room temperature for 3 days in a hydrogen atmosphere. The reaction mixture was filtered through Celite, and the filtrate was evaporated. The residue was dissolved in ethyl acetate, then washed with a saturated aqueous sodium bicarbonate solution, dried over anhydrous magnesium sulfate, and the solvent was evaporated, to give 182 mg of the title compound $^1$H-NMR ($CDCl_3$). .

δ: 1.48 (s, 9H) 3.95 (s, 3H) 4.40 (brd, J=5.6 Hz, 2H) 4.92 (br, 1H) 7.31 (d, J=7.6 Hz, 1H) 7.43 (t, J=7.6 Hz, 1H) 7.52-7.53 (m, 3H) 7.78 (dt, J=1.0, 7.2 Hz, 1H) 8.03 (dt, J=1.2, 8.0 Hz, 1H) 8.26 (t, J=1.2 Hz, 1H).

Example 118b 3-(3-{[(2,4-Dichlorobenzoyl)amino]methyl}phenyl) benzoic Acid

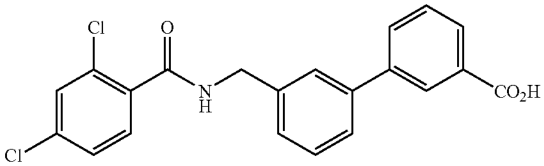

The title compound was obtained in the same way as Example 1e) except for using methyl 3-(3-{[(t-butoxycarbonyl)amino]methyl}phenyl)benzoate.

MS m/e (ESI) 400 ($MH^+$).

Example 119

3-(3-{[(4-Trifluoromethyl-2-fluorobenzoyl)amino] methyl}phenyl)benzoic Acid

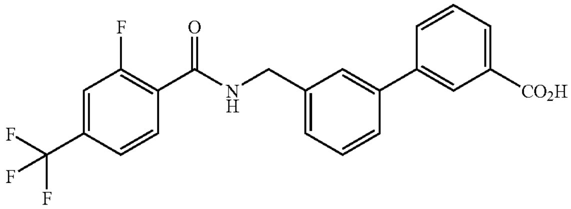

The title compound was obtained in the same way as Example 118b) except for using 4-trifluoromethyl-2-fluorobenzoic acid.

MS m/e (ESI) 418 ($MH^+$).

Example 120

3-(3-{[(4-Propoxy-2-chlorobenzoyl)amino] methyl}phenyl)benzoic Acid

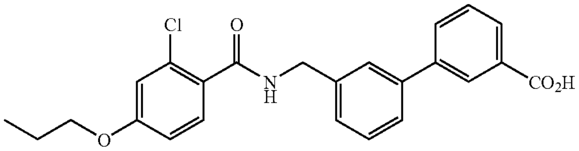

The title compound was obtained in the same way as Example 118b) except for using 4-propoxy-2-chlorobenzoic acid.

MS m/e (ESI) 424 ($MH^+$).

Example 121

3-(5-{[(2,4-Dichlorobenzoyl)amino]methyl}-6-ethoxy-3-pyridyl)benzoic Acid

Production Example 121a

2-Ethoxy-3-pyridyl)methanol

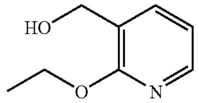

2-Ethoxynicotinic acid (10.07 g) was dissolved in 120 ml of tetrahydrofuran, and 10 ml of triethylamine and 6.83 ml of ethyl chlorocarbonate were added successively, and the mixture was stirred at room temperature for 1.5 hours. The reaction mixture was filtered, and an aqueous suspension of 3.5 g of sodium borohydride was added to the filtrate under ice-cooling. The mixture was stirred for 1 hour at room temperature, water was added thereto, and the mixture was extracted with ethyl acetate. The organic layer was dried over anhydrous magnesium sulfate, and the solvent was evaporated. The residue was purified by silica gel column, to give 7.18 g of the title compound in the 2:1 hexane-ethyl acetate fraction.

$^1$H-NMR ($CDCl_3$).

δ: 1.41 (t, J=7.2 Hz, 3H) 2.41 (br, 1H) 4.43 (q, J=7.2 Hz, 2H) 4.65 (brs, 2H) 6.87 (dd, J=4.8, 7.2 Hz, 1H) 7.57 (ddd, J=0.8, 2.0, 7.2 Hz, 1H) 8.08 (dd, J=1.6, 4.8 Hz, 1H).

Production Example 121b 1-(2-Ethoxy-3-pyridyl)-1,2-triazadien-2-ium

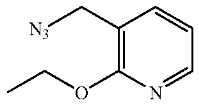

The title compound was obtained in the same way as Production Example 90b) except for using (2-ethoxy-3-pyridyl) methanol.

$^1$H-NMR ($CDCl_3$).

δ: 1.42 (t, J=6.8 Hz, 3H) 4.34 (s, 2H) 4.43 (q, J=7.6 Hz, 2H) 6.87 (dd, J=4.8, 6.8 Hz, 1H) 7.53 (dq, J=0.8, 7.2 Hz, 1H) 8.12 (dd, J=2.0, 5.2 Hz, 1H).

Production Example 121c t-Butyl N-[(5-bromo-2-methoxy-3-pyridyl)methyl]carbamate

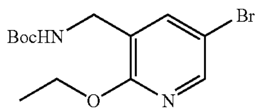

6.02 g of 1-(2-ethoxy-3-pyridyl)-1,2-triazadien-2-ium and 7 g of t-butyl dicarbonate were dissolved in 200 ml of ethyl acetate, then 2 g of 10% palladium-carbon was added thereto, and the mixture was stirred at room temperature for 3 hours in a hydrogen atmosphere. The reaction mixture was filtered through Celite, and the filtrate was evaporated. The residue was purified by silica gel column, to give 7.54 g of N-[(2-methoxy-3-pyridyl)methyl]carbamate in the 8:1→4:1 hexane-ethyl acetate fraction. This product was dissolved in 70 ml of acetonitrile, then 5.32 g of N-bromosuccinimide was added thereto, and the mixture was stirred at room temperature for 3 hours. The solvent was evaporated, the residue was dissolved in ethyl acetate, and successively washed with water and brine. The organic layer was dried over anhydrous magnesium sulfate, and the solvent was removed. The residue was purified by silica gel column, to give 5.26 g of the title compound in the 10:1 hexane-ethyl acetate fraction.

$^1$H-NMR ($CDCl_3$).

δ: 1.38 (t, J=4.8 Hz, 3H) 1.46 (s, 9H) 4.23 (brd, J=6.0 Hz, 2H) 4.38 (q, J=7.6 Hz, 2H) 5.01 (br, 1H) 7.61 (d, J=2.0 Hz, 1H) 8.08 (d, J=2.4 Hz, 1H).

Production Example 121d

Methyl 3-(5-{[(t-butoxycarbonyl)amino]methyl}-6-ethoxy-3-pyridyl)benzoate

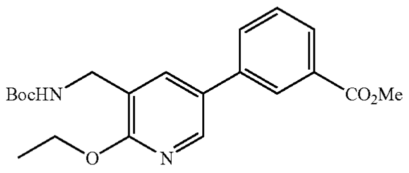

1.108 g of N-[(5-bromo-2-methoxy-3-pyridyl)methyl]carbamate, 660 mg of 3-[carboxymethyl]boronic acid, 193 mg of tetrakistriphenyl phosphine palladium and 1.85 g of potassium carbonate were dissolved in 15 ml of toluene, and the mixture was stirred at 90° C. overnight in a nitrogen atmosphere. The reaction mixture was filtered through Celite, and the filtrate was evaporated. The residue was purified by silica gel column, to give 1.008 g of the title compound in the 3:1 hexane-ethyl acetate fraction.

$^1$H-NMR ($CDCl_3$).

δ: 1.44 (t, J=7.2 Hz, 3H) 1.46 (s, 9H) 3.95 (s, 3H) 4.34 (brd, J=6.0 Hz, 2H) 4.46 (q, J=7.2 Hz, 2H) 5.10 (br, 1H) 7.51 (t, J=7.6 Hz, 1H) 7.71 (dt, J=1.6, 7.6 Hz, 1H) 7.77 (s, 1H) 8.01 (dt, J=1.6, 5.2 Hz, 1H) 8.20 (t, J=1.6 Hz, 1H) 8.30 (d, J=2.8 Hz, 1H).

Example 121e 3-(5-{[(2,4-Dichlorobenzoyl)amino]methyl}-6-ethoxy-3-pyridyl)benzoic Acid

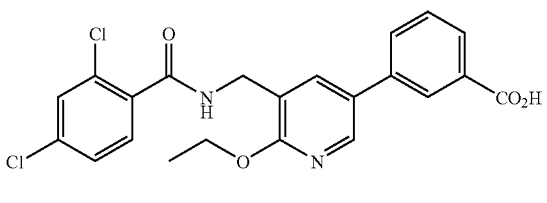

The title compound was obtained in the same way as Example 1e) except for using methyl 3-(5-{[(t-butoxycarbonyl)amino]methyl}-6-ethoxy-3-pyridyl)benzoate.

M S m/e (ESI) 445 ($MH^+$).

Example 122

3-(5-{[(4-Chloro-2-fluorobenzoyl)amino]methyl}-6-ethoxy-3-pyridyl)benzoic Acid

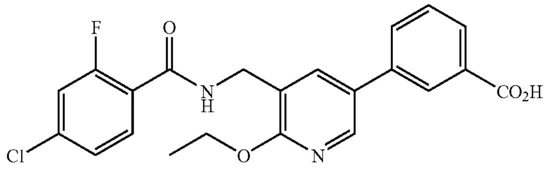

The title compound was obtained in the same way as Example 121e) except for using 4-chloro-2-fluorobenzoic acid.

MS m/e (ESI) 429 ($MH^+$).

Example 123

3-(5-{[(4-Trifluoromethyl-2-fluorobenzoyl)amino]methyl}-6-ethoxy-3-pyridyl)benzoic Acid

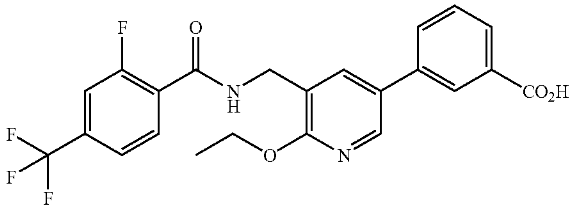

The title compound was obtained in the same way as Example 121e) except for using 4-trifluoromethyl-2-fluorobenzoic acid.

MS m/e (ESI) 463 ($MH^+$).

Example 124

3-(5-{[(4-Propoxy-2-chlorobenzoyl)amino]methyl}-6-ethoxy-3-pyridyl)benzoic Acid

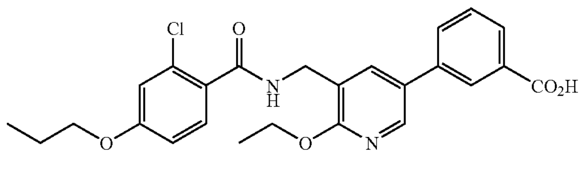

The title compound was obtained in the same way as Example 121e) except for using 4-propoxy-2-chlorobenzoic acid.

MS m/e (ESI) 469 ($MH^+$).

Example 125

3-(5-{[(4-Isopropoxy-2-chlorobenzoyl)amino]methyl}-6-ethoxy-3-pyridyl)benzoic Acid

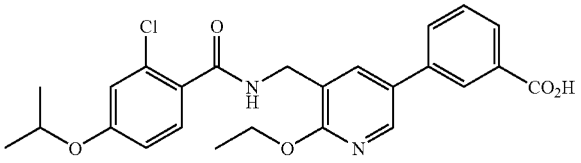

The title compound was obtained in the same way as Example 121e) except for using 4-isopropoxy-2-chlorobenzoic acid.

MS m/e (ESI) 469 ($MH^+$).

Example 126

3-(7-{[(2,4-Dichlorobenzoyl)amino]methyl}-2,3-dihydro-benzo[b]furan-5-yl)

Production Example 126a

5-Bromo-2,3-dihydrobenzo[b]furan

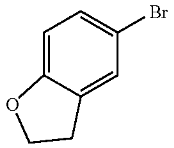

Dihydrobenzofuran (9.34 g) was dissolved in 130 ml of acetonitrile, 13.9 g of N-bromosuccinimide was added thereto and the mixture was stirred at room temperature for 3 hours. The solvent was evaporated, then the residue was dissolved in ethyl acetate and successively washed with water and brine. The organic layer was dried over anhydrous magnesium sulfate and the solvent was removed, to give 15.94 g of the title compound.

$^1$H-NMR ($CDCl_3$).

δ: 3.02 (t, J=8.8 Hz, 2H) 4.57 (t, J=8.8 Hz, 2H) 6.66 (d, J=8.0 Hz, 1H) 7.12-7.21 (m, 1H) 7.28-7.29 (m, 1H).

Production Example 126b

5-Bromo-2,3-dihydrobenzo[b]furan-7-carboaldehyde

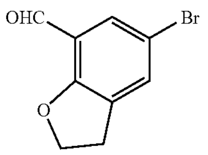

5-Bromo-2,3-dihydrobenzo[b]furan (15.94 g) was dissolved in 200 ml of trifluoroacetic acid, and 22.5 g of hexamethylenetetramine was added thereto, and the mixture was stirred at 50° C. overnight. The solvent was evaporated, then the residue was dissolved in ethyl acetate and successively washed with water, a saturated aqueous sodium bicarbonate solution and brine. The organic layer was dried over anhydrous magnesium sulfate, and the solvent was removed. The residue was purified by silica gel column, to give 11.42 g of the title compound in the 4:1 hexane-ethyl acetate fraction.

$^1$H-NMR ($CDCl_3$).

δ: 3.26 (t, J=8.8 Hz, 2H) 4.76 (t, J=8.8 Hz, 2H) 7.49 (dt, J=1.2, 3.2 Hz, 1H) 7.69 (dt, J=0.8, 2.8, 1H) 10.12 (s, 1H).

Production Example 126c

5-Bromo-2,3-dihydrobenzo[b]furan-7-yl)methyl Acide

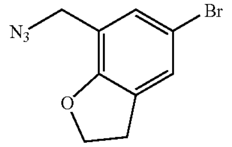

5-Bromo-2,3-dihydrobenzo[b]furan-7-carbaldehyde (11.42 g), was dissolved in 50 ml of tetrahydrofuran and 50 ml of ethanol, then 2 g of sodium borohydride was added thereto, and the mixture was stirred overnight at room temperature. 1 N hydrochloric acid was added to the reaction mixture which was then extracted with ethyl acetate. The organic layer was dried over anhydrous magnesium sulfate, and the solvent was removed, to give (5-bromo-2,3-dihydrobenzo[b]furan-7-yl)methanol. This product was treated in the same way as Production Example 90b) to give 12.6 g of the title compound.

$^1$H-NMR ($CDCl_3$).

δ: 3.23 (t, J=8.8 Hz, 2H) 4.27 (s, 2H) 4.62 (t, J=8.8 Hz, 2H) 7.19-7.20 (m, 1H) 7.26-7.28 (m, 1H).

Production Example 126d t-Butyl N-[(5-bromo-2,3-dihydrobenzo[b]furan-7-yl)methyl]carbamate

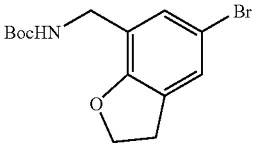

The title compound was obtained in the same way as Production Example 90b) except for using (5-bromo-2,3-dihydrobenzo[b]furan-7-yl)methylazide.

$^1$H-NMR ($CDCl_3$).

δ: 1.59 (s, 9H) 3.20 (t, J=8.8 Hz, 2H) 4.23 (brd, J=5.6 Hz, 2H) 4.58 (t, J=8.8 Hz, 2H) 4.96 (br, 1H) 7.17 (s, 1H) 7.21 (t, J=0.9 Hz, 1H).

Production Example 126e

Methyl 3-(7-{[(t-butoxycarbonyl)amino]methyl}-2,3-dihydrobenzo[b]furan-5-yl)benzoate

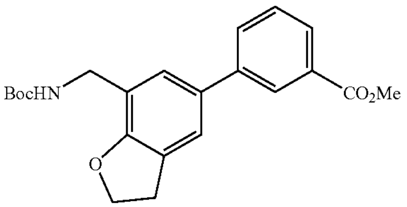

The title compound was obtained in the same way as Production Example-121d) except for using t-butyl—N-[(5-bromo-2,3-dihydrobenzo[b]furan-7-yl)methyl]carbamate.

$^1$H-NMR ($CDCl_3$).

δ: 1.46 (s, 9H) 3.28 (t, J=8.8 Hz, 2H) 3.94 (s, 3H) 4.34 (brd, J=4.8 Hz, 2H) 4.65 (t, J=8.8 Hz, 2H) 5.05 (br, 1H) 7.32 (s, 1H) 7.38 (s, 1H) 7.47 (t, J=7.6 Hz, 1H) 7.71 (dd, J=1.6, 6.4 Hz, 1H) 7.96 (d, J=7.6 Hz, 1H) 8.19 (d, J=1.6 Hz, 1H).

Example 126f

3-(7-{[(2,4-Dichlorobenzoyl)amino]methyl}-2,3-dihydrobenzo[b]furan-5-yl)

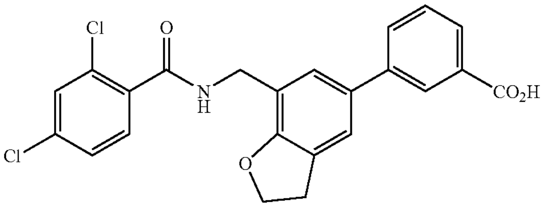

The title compound was obtained in the same way as Example 1e) except for using methyl 3-(7-{[(t-butoxycarbonyl)amino]methyl}-2,3-dihydrobenzo[b]furan-5-yl)benzoate.

Benzoic acid MS m/e (ESI) 442 ($MH^+$).

Example 127

3-(7-{[(4-Chloro-2-fluorobenzoyl)amino]-methyl}-2,3-dihydrobenzo[b]furan-5-yl)benzoic Acid

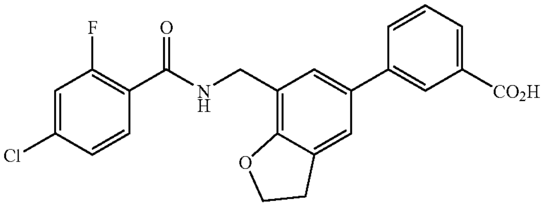

The title compound was obtained in the same way as Example 126f) except for using 4-chloro-2-fluorobenzoic acid.

MS m/e (ESI) 426 ($MH^+$).

Example 128

3-(7-{[(4-Trifluoromethyl-2-fluorobenzoyl)amino]methyl}-2,3-dihydrobenzo[b]furan-5-yl)benzoic Acid

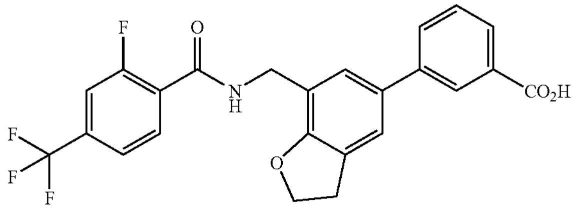

The title compound was obtained in the same way as Example 126f) except for using 4-trifluoromethyl-2-fluorobenzoic acid.

MS m/e (ESI) 460 ($MH^+$).

Example 129

3-(7-{[(4-Propoxy-2-chlorobenzoyl)amino]methyl}-2,3-dihydrobenzo[b]furan-5-yl)benzoic Acid

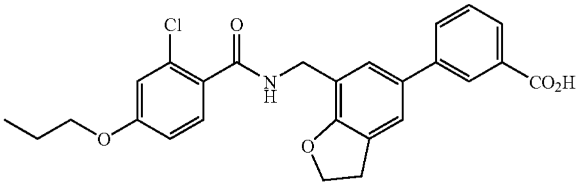

The title compound was obtained in the same way as Example 126f) except for using 4-propoxy-2-chlorobenzoic acid.

MS m/e (ESI) 466 ($MH^+$).

Example 130

3-(7-{[(4-Isopropoxy-2-chlorobenzoyl)amino]methyl}-2,3-dihydrobenzo[b]furan-5-yl)benzoic Acid

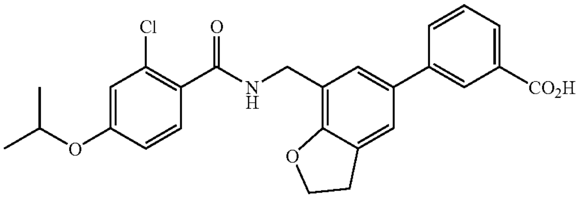

The title compound was obtained in the same way as Example 126f) except for using 4-isopropoxy-2-chlorobenzoic acid.

MS m/e (ESI) 466 ($MH^+$).

Example 131

3-(2-{[(2,4-Dichlorobenzoyl)amino]methyl}-4-pyridyl)benzoic Acid

Production Example 131a

Methyl 3-(4-pyridyl)benzoate

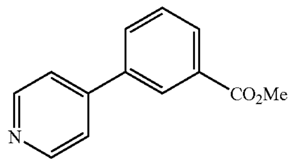

1.121 g of 4-pyridylboronic acid, 2.35 g of methyl 3-bromobenzoate, 7.5 g of cesium carbonate and 530 mg of tetrakistriphenyl phosphine palladium were dissolved in 40 ml of N,N-dimethylformamide, and the mixture was stirred at 120° C. overnight in a nitrogen atmosphere. The reaction mixture was diluted with ethyl acetate, washed with water and dried over anhydrous magnesium sulfate, and the solvent was removed. The residue was purified by silica gel column, to give 1.325 g of the title compound in the 4:3 hexane-ethyl acetate fraction.

$^1$H-NMR ($CDCl_3$).

δ: 3.97 (s, 3H) 7.56 (d, J=6.0 Hz, 1H) 7.59 (d, J=7.6 Hz, 1H) 7.84 (d, J=9.6 Hz, 2H) 8.12 (d, J=9.6 Hz, 2H) 8.33 (t, J=1.2 Hz, 1H) 8.70 (brd, J=4.4 Hz, 1H).

Production Example 131b

Methyl 3-(2-cyano-4-pyridyl)benzoate

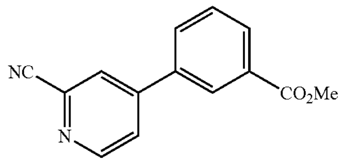

1.383 g of methyl 3-(4-pyridyl)benzoate was dissolved in 20 ml of dichloromethane, 2.2 g of 3-chloroperbenzoic acid was added thereto, and the mixture was stirred overnight at room temperature. The reaction mixture was concentrated, and the residue was purified by silica gel column to give 1.549 g of 1-oxy-4-[3-(methoxycarbonyl)phenyl]pyridium in the 3:1 hexane-methanol fraction. 716 mg of this product was dissolved in 7 ml of acetonitrile, 0.35 ml of dimethylcarbamoyl chloride and 0.5 ml of trimethylsilyl cyanide were added successively, and the mixture was stirred overnight at room temperature. The reaction mixture was diluted with ethyl acetate, washed with water and dried over anhydrous magnesium sulfate, and the solvent was removed. The residue was purified by silica gel column, to give 370 mg of the title compound in the 3:2 hexane-ethyl acetate fraction.

$^1$H-NMR ($CDCl_3$).

δ: 3.98 (s, 3H) 7.63 (t, J=7.6 Hz, 1H) 7.77 (dd, J=2.0, 5.2 Hz, 1H) 7.83 (dq, J=1.2, 8.0 Hz, 1H) 7.96 (q, J=0.8 Hz, 1H) 8.19 (dt, J=1.6, 8.0 Hz, 1H) 8.32 (t, J=1.2 Hz, 1H) 8.80 (dd, J=0.8, 5.2 Hz, 1H).

Production Example 131c

Methyl 3-(2-{[(t-butoxycarbonyl)amino]methyl}-4-pyridyl)benzoate

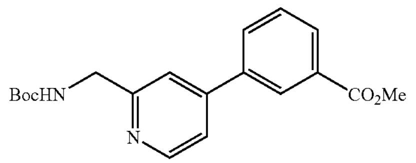

379mg of 3-(2-cyano-4-pyridyl)benzoate, 350 mg of t-butyl dicarbonate and 300 mg of 10% palladium-carbon were added to and dissolved in 16 ml of ethanol and 2 ml of ethyl acetate, and the mixture was stirred at room temperature for 3 hours in a hydrogen atmosphere. The reaction mixture was filtered, and the filtrate was evaporated. The residue was purified by silica gel column, to give 243 mg of the title compound in the 1:1 hexane-ethyl acetate fraction.

1H-NMR ($CDCl_3$)

δ: 1.48 (s, 9H) 3.97 (s, 3H) 4.53 (d, J=4.8 Hz, 2H) 5.60 (br, 1H) 7.44 (dd, J=1.6, 5.6 Hz, 1H) 7.52 (s, 1H) 7.57 (t, J=8.0 Hz, 1H) 7.82 (dd, J=1.2, 8.0 Hz, 1H) 8.12 (d, J=7.6 Hz, 1H) 8.31 (s, 1H) 8.61 (d, J=5.2 Hz, 1H).

Example 131d

3-(2-{[(2,4-Dichlorobenzoyl)amino]methyl}-4-pyridyl)benzoic Acid

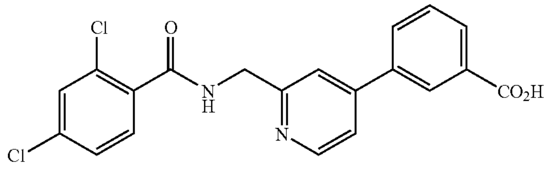

The title compound was obtained in the same way as Example 1e) except for using methyl 3-(2-{[(t-butoxycarbonyl)amino]methyl}-4-pyridyl)benzoate.

MS m/e (ESI) 401 ($MH^+$).

Example 132

3-(2-{[(4-Propoxy-2-chlorobenzoyl)amino]methyl}-4-pyridyl)benzoic Acid

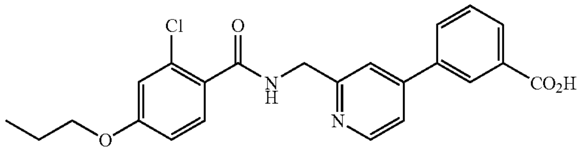

The title compound was obtained in the same way as Example 131d) except for using 4-propoxy-2-chlorobenzoic acid.

MS m/e (ESI) 425 ($MH^+$).

Example 133

3-{2-[({[4-Methyl-2-(4-methylphenyl)-1,3-thiazol-5-yl]-carbonyl}amino)methyl]-4-pyridyl}benzoic Acid

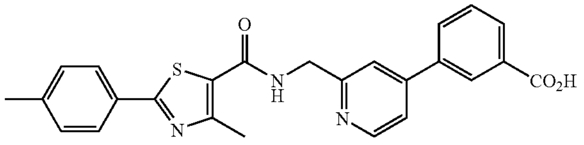

The title compound was obtained in the same way as Example 131d) except for using 4-methyl-2-(4-methylphenyl)-1,3-thiazol-5-carboxylic Acid.

MS m/e (ESI) 444 ($MH^+$).

Example 134

3-(2-{[(4-Cyclopentyloxy-2-chlorobenzoyl)amino] methyl}-4-pyridyl)benzoic Acid

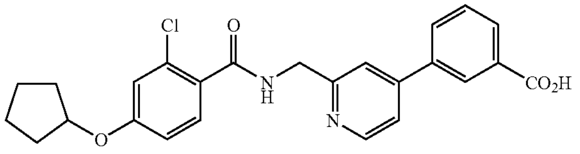

The title compound was obtained in the same way as Example 131d) except for using 4-cyclopentyloxy-2-chlorobenzoic acid.

MS m/e (ESI) 451 ($MH^+$).

Example 135

(E)-3-[3-(3-{[(2,4-Dichlorobenzoyl)amino]methyl}-4-methoxyphenyl)phenyl]-2-propenoic Acid Production Example 135a t-Butyl N-{5-[3-(hydroxymethyl)phenyl]-2-methoxybenzyl}carbamate

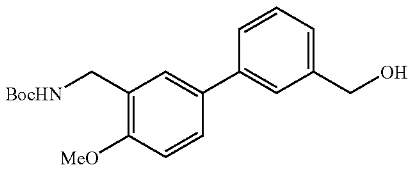

Methyl 3-(3-{[(t-butoxycarbonyl)amino]-methyl}-4-methoxyphenyl)benzoate (1.943 g) was dissolved in 30 ml of tetrahydrofuran, 250 mg of lithium borohydride was added thereto, and the mixture was stirred at room temperature for 2 weeks. 1N Hydrochloric acid was added to the reaction mixture which was then extracted with ethyl acetate. The organic layer was dried over anhydrous magnesium sulfate, and the solvent was removed. The residue was purified by silica gel column, to give 1.47 g of the title compound in the 3:1→1:1 hexane-ethyl acetate fraction.

$^1$H-NMR ($CDCl_3$).

δ: 1.45 (s, 9H) 3.89 (s, 3H) 4.36 (brd, J=6.0 Hz, 2H) 4.75 (s, 2H) 5.06 (br, 1H) 6.93 (d, J=8.4 Hz, 1H) 7.31 (d, J=7.6 Hz, 1H) 7.40 (t, J=7.6 Hz, 1H) 7.47-7.51 (m, 3H) 7.55 (s, 1H).

Production Example 135b t-Butyl N-[5-(3-formylphenyl)-2-methoxybenzyl]carbamate

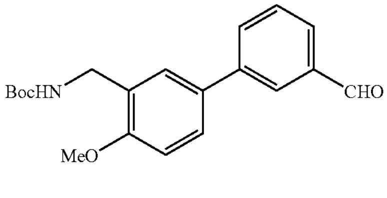

747 mg of t-Butyl N-{5-[3-(hydroxymethyl)-phenyl]-2-methoxybenzyl}carbamate, 510 mg of N-methylmorpholin-N-oxide, 76 mg of tetrapropyl ammonium perruthenate and 1 g of 4A molecular sieve powder were dissolved in 1 g of dichloromethane, and the mixture was stirred at room temperature for 2hours. The reaction mixture was filtered and the filtrate was evaporated. The residue was purified by silica gel column, to give 566 mg of the title compound in the 3:1→1:1 hexane-ethyl acetate fraction.

$^1$H-NMR ($CDCl_3$).

δ: 1.46 (s, 9H) 3.91 (s, 3H) 4.38 (brd, J=5.2 Hz, 2H) 5.08 (br, 1H) 6.96 (d, J=8.4 Hz, 1H) 7.52-7.60 (m, 3H) 7.82 (d, J=7.6 Hz, 2H) 8.06 (s, 1H) 10.08 (s, 1H).

Production Example 135c

Ethyl (E)-3-[3-(3-{[(t-butoxycarbonyl)amino]methyl}-4-methoxyphenyl)phenyl]-2-propenoate

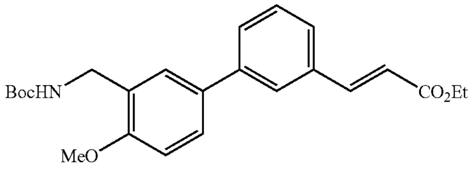

235 mg of Triethyl phosphonoacetate was dissolved in 4 ml of tetrahydrofuran, 40 mg of sodium hydride was added thereto and the mixture was stirred at room temperature for 0.5 hour. To this reaction mixture was added 1 ml of solution of 286 mg of t-butyl N-[5-(3-formylphenyl)-2-methoxybenzyl]carbamatein N,N-dimethylformamide, and the mixture was stirred at room temperature for 2 hours. The reaction mixture was diluted with ethyl acetate and washed with water, the organic layer was dried over anhydrous magnesium sulfate, and the solvent was removed. The residue was purified by silica gel column, to give 301 mg of the title compound in the 5:1 hexane-ethyl acetate fraction.

$^1$H-NMR ($CDCl_3$).

δ: 1.35 (t, J=7.2 Hz, 3H) 1.46 (s, 9H) 3.90 (s, 3H) 4.28 (q, J=7.2 Hz, 2H) 4.37 (brd, J=5.6 Hz, 2H) 5.07 (br, 1H) 6.50 (d, J=16.0 Hz, 1H) 6.94 (d, J=8.8 Hz, 1H) 7.41-7.51 (m, 4H) 7.56 (dt, J=1.2, 7.2 Hz, 1H) 7.68 (d, J=2.0 Hz, 1H) 7.74 (d, J=12.0 Hz, 1H).

Example 135d (E)-3-[3-(3-{[(2,4-Dichlorobenzoyl)amino]-methyl}-4-methoxyphenyl)phenyl]-2-propenoic Acid

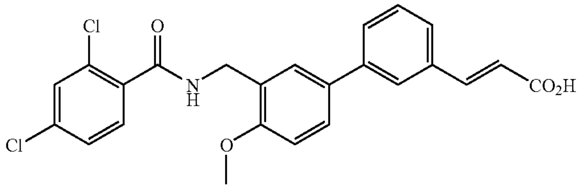

The title compound was obtained in the same way as Example 1e) except for using (E)-3-[3-(3-{[(t-butoxycarbonyl)amino]methyl}-4-methoxyphenyl)phenyl]-2-propenoate.

MS m/e (ESI) 456 ($MH^+$).

Example 136

(E)-3-[3-(3-{[(4-Trifluoromethyl-2-fluorobenzoyl)amino]methyl}-4-methoxyphenyl)phenyl]-2-propenoic Acid

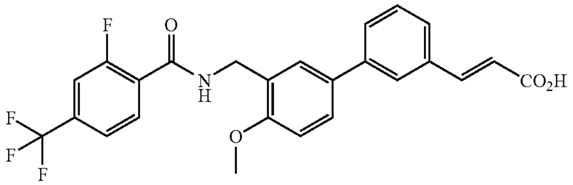

The title compound was obtained in the same way as Example 135d) except for using 4-trifluoromethyl-2-fluorobenzoic acid.

MS m/e (ESI) 474 ($MH^+$).

Example 137

(E)-3-[3-(3-{[(4-Propoxy-2-chlorobenzoyl)amino]methyl}-4-methoxyphenyl)phenyl]-2-propenoic Acid

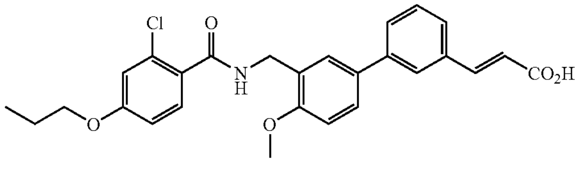

The title compound was obtained in the same way as Example 135d) except for using 4-propoxy-2-chlorobenzoic acid.

MS m/e (ESI) 480 ($MH^+$).

Example 138

(E)-3-(3-{4-Methoxy-3-[({[4-methyl-2-(4-methylphenyl)-1,3-thiazol-5-yl]carbonyl}amino)methyl]-phenyl}phenyl)-2-propenoic Acid

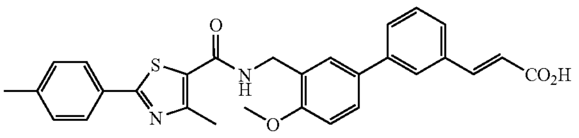

The title compound was obtained in the same way as Example 135d) except for using 4-methyl-2-(4-methylphenyl)-1,3-thiazol-5-carboxylic Acid.

MS m/e (ESI) 499 ($MH^+$).

Example 139

(E)-2-Ethyl-3-[3-(3-{[(2,4-dichlorobenzoyl)amino]methyl}-4-methoxyphenyl)phenyl]-2-propenoic Acid Production Example 139a Ethyl (E)-3-[3-(3-{[(t-butoxycarbonyl)amino]methyl}-4-methoxyphenyl)phenyl]-2-ethyl-2-propenoate

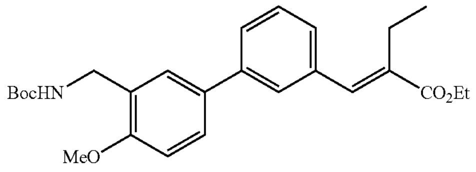

The title compound was obtained in the same way as Production Example 135c) except for using 260 mg of triethyl phosphonobutyrate.

$^1$H-NMR ($CDCl_3$).

δ: 1.20 (t, J=5.6 Hz, 3H) 1.37 (t, J=7.2 Hz, 3H) 1.45 (s, 9H) 2.59 (q, J=7.6 Hz, 2H) 3.89 (s, 3H) 4.29 (q, J=7.2 Hz, 2H) 4.37 (brd, J=5.2 Hz, 2H) 5.05 (br, 1H) 6.95 (d, J=8.8 Hz, 1H) 7.32 (d, J=7.6 Hz, 1H) 7.43 (t, J=7.6 Hz, 1H) 7.45-7.54 (m, 4H) 7.70 (s, 1H).

Example 139b (E)-2-Ethyl-3-[3-(3-{[(2,4-dichlorobenzoyl)amino]methyl}-4-methoxyphenyl)phenyl]-2-propenoic Acid

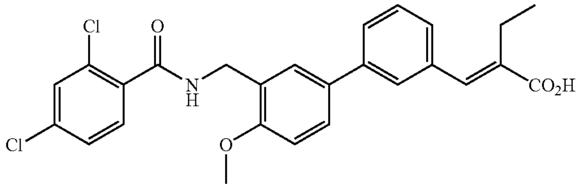

The title compound was obtained in the same way as Example 1e) except for using ethyl (E)-3-[3-(3-{[(t-butoxycarbonyl)amino]methyl}-4-methoxyphenyl)phenyl]-2-ethyl-2-propenoate MS m/e (ESI) 484 ($MH^+$). .

Example 140

(E)-2-Ethyl-3-[3-(3-{[(4-trifluoromethyl-2-fluorobenzoyl)amino]methyl}-4-methoxyphenyl)phenyl]-2-propenoic Acid

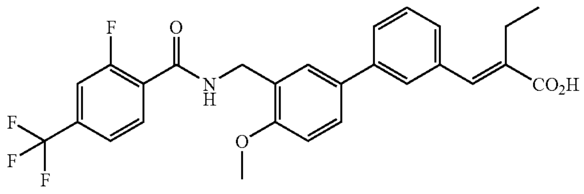

The title compound was obtained in the same way as Example 139b) except for using 4-trifluoromethyl-2-fluorobenzoic acid.

MS m/e (ESI) 502 ($MH^+$).

Example 141

(E)-2-Ethyl-3-[3-(3-{[(4-propoxy-2-chlorobenzoyl)amino]methyl}-4-methoxyphenyl)phenyl]-2-propenoic Acid

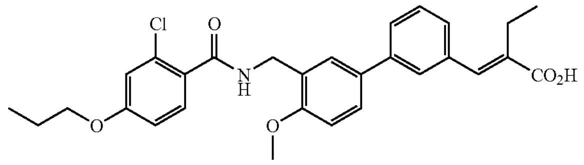

The title compound was obtained in the same way as Example 139b) except for using 4-propoxy-2-chlorobenzoic acid.

MS m/e (ESI) 508 ($MH^+$).

Example 142

(E)-2-Ethyl-3-(3-{4-methoxy-3-[({[5-methyl-2-(4-methylphenyl)-1,3-thiazol-4-yl]carbonyl}amino)methyl]-phenyl}phenyl)-2-propenoic Acid

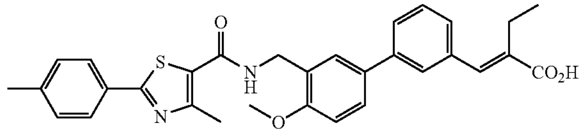

The title compound was obtained in the same way as Example 139b) except for using 4-methyl-2-(4-methylphenyl)-1,3-thiazol-5-carboxylic Acid.

MS m/e (ESI) 527 ($MH^+$).

Example 143

3-[3-(3-{[(2,4-Dichlorobenzoyl)amino]methyl}-4-methoxy-phenyl)phenyl]propanoic Acid Production Example 143a Ethyl 2-{[3-(3-{[(t-butoxycarbonyl)amino]methyl}-4-methoxyphenyl)phenyl]propanoate

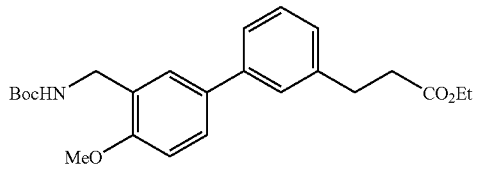

(E)-3-[3-(3-{[(t-Butoxycarbonyl)amino]methyl}-4-methoxyphenyl)phenyl]-2-propenoate (153 mg) was dissolved in ethanol, 20 mg of 10% palladium-carbon was added thereto, and the mixture was stirred at room temperature for 3 days in a hydrogen atmosphere. The reaction mixture was filtered, the filtrate was evaporated, and the residue was purified by silica gel column to give 157 mg of the title compound.

$^1$H-NMR ($CDCl_3$).

δ: 1.24 (t, J=7.2 Hz, 3H) 1.46 (s, 9H) 2.66 (dt, J=1.2, 6.8 Hz, 2H) 3.00 (t, J=8.4 Hz, 2H) 3.89 (s, 3H) 4.14 (q, J=7.2 Hz, 2H) 4.37 (d, J=5.6 Hz, 2H) 5.05 (br, 1H) 6.92 (d, J=8.4 Hz, 1H) 7.15 (d, J=7.2 Hz, 1H) 7.34 (dd, J=2.4, 7.6 Hz, 1H) 7.38-7.40 (m, 2H) 7.47 (dd, J=2.0, 8.4 Hz, 1H) 7.49 (s, 1H).

Example 143b

3-[3-(3-{[(2,4-Dichlorobenzoyl)amino]-methyl}-4-methoxyphenyl)phenyl]propanoic Acid

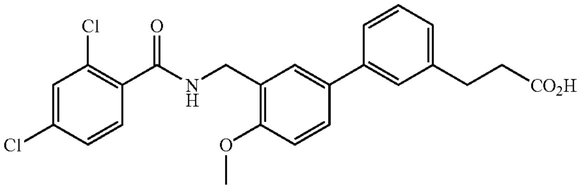

The title compound was obtained in the same way as Example 1e} except for using ethyl 2-{[3-(3-{[(t-butoxycarbonyl)amino]methyl}-4-methoxyphenyl)phenyl]propanoate.

MS m/e (ESI) 458 ($MH^+$).

Example 144

3-[3-(3-{[(4-Trifluoromethyl-2-fluorobenzoyl)amino]-methyl}-4-methoxyphenyl)phenyl]propanoic Acid

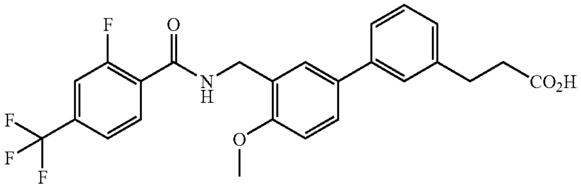

The title compound was obtained in the same way as Example 143b) except for using 4-trifluoromethyl-2-fluorobenzoic acid.

MS m/e (ESI) 476 ($MH^+$).

Example 145

3-[3-(3-{[(4-propoxy-2-chlorobenzoyl)amino]-methyl}-4-methoxyphenyl)phenyl]propanoic Acid

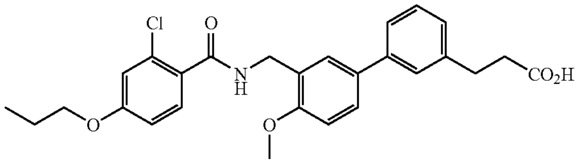

The title compound was obtained in the same way as Example 143b) except for using 4-propoxy-2-chlorobenzoic acid.

MS m/e (ESI) 482 ($MH^+$).

Example 146

3-(3-{4-Methoxy-3-[({[5-methyl-2-(4-methylphenyl)-1,3-thiazol-4-yl]carbonyl}amino)methyl]-phenyl}phenyl)propanoic Acid

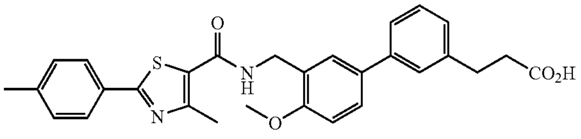

The title compound was obtained in the same way as Example 143b) except for using 4-methyl-2-(4-methylphenyl)-1,3-thiazol-5-carboxylic Acid.

MS m/e (ESI) 501 ($MH^+$).

Example 147

2-{[3-(3-{[(2,4-Dichlorobenzoyl)amino]-methyl}-4-methoxyphenyl)phenyl]methyl}butanoic Acid Production Example 147a Ethyl 2-{[3-(3-{[(t-butoxycarbonyl)amino]methyl}-4-methoxyphenyl)phenyl]-methyl}butanoate

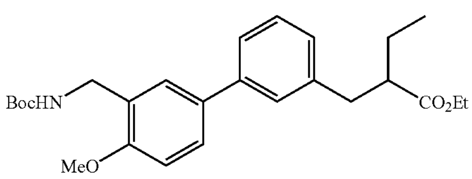

The title compound was obtained in the same way as Production Example 143a) except for using ethyl (E)-3-[3-(3-{[(t-butoxycarbonyl)amino]methyl}-4-methoxyphenyl)phenyl]-2-ethyl-2-propenoate.

$^1$H-NMR ($CDCl_3$).

δ: 0.93 (t, J=7.6 Hz, 3H) 1.15 (t, J=7.2 Hz, 3H) 1.46 (s, 9H) 1.55-1.72 (m, 2H) 2.60-2.66 (m, 1H) 2.79 (dd, J=6.8, 13.6 Hz, 1H) 2.98 (dd, J=8.0, 13.6 Hz, 1H) 3.87 (s, 3H) 4.08 (q, J=7.2 Hz, 2H) 4.37 (brd, J=5.6 Hz, 2H) 5.06 (br, 1H) 6.92 (d, J=8.4 Hz, 1H) 7.11 (d, J=7.2 Hz, 1H) 7.26-7.39 (m, 3H) 7.45-7.48 (m, 2H).

Example 147b

2-{[3-(3-{[(2,4-Dichlorobenzoyl)amino]-methyl}-4-methoxyphenyl)phenyl]methyl}butanoic Acid

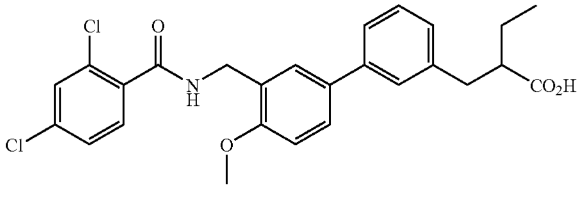

The title compound was obtained in the same way as Example 1e) except for using ethyl 2-{[3-(3-{[(t-butoxycarbonyl)amino]methyl}-4-methoxyphenyl)phenyl] methyl}butanoate.

MS m/e (ESI) 486 ($MH^+$).

Example 148

2-{[3-(3-{[(4-Trifluoromethyl-2-fluorobenzoyl) amino]methyl}-4-methoxyphenyl)phenyl]-methyl}butanoic Acid

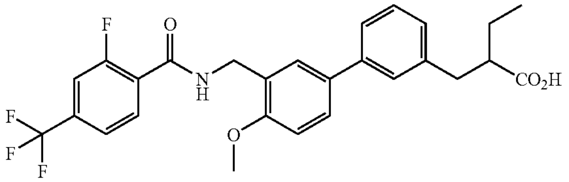

The title compound was obtained in the same way as Example 147b) except for using 4-trifluoromethyl-2-fluorobenzoic acid.

MS m/e (ESI) 504 ($MH^+$).

Example 149

2-{[3-(3-{[(4-Propoxy-2-chlorobenzoyl)amino]methyl)-4-methoxyphenyl)phenyl]methyl)butanoic Acid

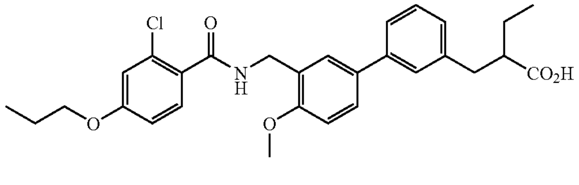

The title compound was obtained in the same way as Example 147b) except for using 4-propoxy-2-chlorobenzoic acid.

MS m/e (ESI) 510 ($MH^+$).

Example 150

2-[(3-{4-methoxy-3-[({[5-methyl-2-(4-methylphenyl)-1,3-thiazol-4-yl]carbonyl}amino)methyl]-phenyl}phenyl)methyl]butanoic Acid

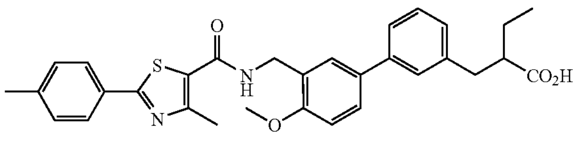

The title compound was obtained in the same way as Example 147b) except for using 4-methyl-2-(4-methylphenyl)-1,3-thiazol-5-carboxylic Acid.

MS m/e (ESI) 529 ($MH^+$).

Example 151

3-[4-Methoxy-3-({[4-(trifluoromethyl)benzyl]-amino)carbonyl)phenyl]benzoic Acid

Production Example 151a

2-Methoxy-5-[3-(methoxycarbonyl)phenyl]benzoic acid

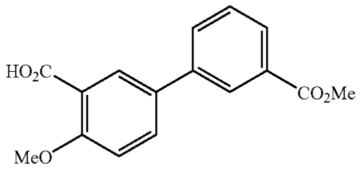

2.022 g of 5-Bromo-2-methoxybenzoic acid, 1.733 g of 3-carboxymethylboronic acid, 40 mg of palladium acetate and 2.5 g of sodium acetate were dissolved in 20 ml of water, and the mixture was stirred overnight at room temperature. The reaction mixture was extracted with ethyl acetate and the aqueous layer was acidified with hydrochloric acid, and the precipitated crystals were filtered. The crystals were washed with water and dried under reduced pressure to give 2.687 g of the title compound.

$^1H$-NMR ($CDCl_3$).

δ: 3.86 (s, 3H) 3.88 (s, 3H) 7.24 (d, J=8.8 Hz, 1H) 7.60 (t, J=8.0 Hz, 1H) 7.86 (dd, J=2.4, 8.8 Hz, 1H) 7.90-7.94 (m, 3H) 8.13 (s, 1H).

Example 151b

3-[4-Methoxy-3-({[4-(trifluoromethyl)benzyl]amino}carbonyl)phenyl]benzoic Acid

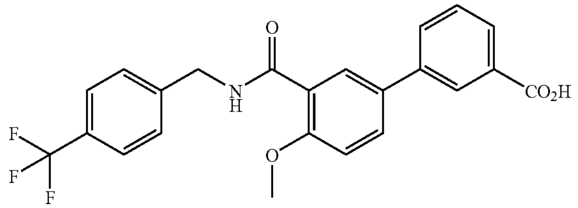

12 mg of 2-Methoxy-5-[3-(methoxycarbonyl)phenyl]benzoic acid and 9 mg of 4-trifluoromethylbenzylamine were dissolved in 0.2 ml of N,N-dimethylformamide, 9 ml of diethyl cyanophosphonate and 50 ml of triethylamine were added thereto, and the mixture was stirred at room temperature for 1 hour. Ethyl acetate was added to the reaction mixture which was then washed with water. The organic layer was evaporated, and the residue was dissolved in 0.4 ml of ethanol. 0.1 ml of 5N sodium hydroxide was added thereto, and the mixture was stirred at room temperature for 1 hour. 1 N hydrochloric acid was added to the reaction mixture which was then extracted with ethyl acetate. The organic layer was evaporated, and the residue was purified by HPLC using a reverse phase system column and a water-acetonitrile-trifluoroacetic acid eluent, to give the title compound.

MS m/e (ESI) 430 ($MH^+$).

Example 152

3-[4-Methoxy-3-({[2,4-dichlorobenzyl]amino}carbonyl)phenyl]benzoic Acid

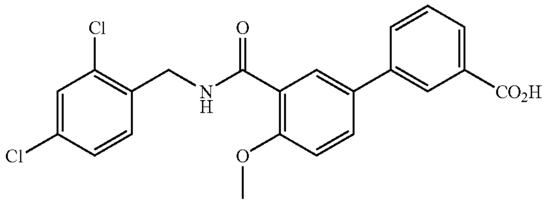

The title compound was obtained in the same way as Example 151b) except for using 2,4-dichlorobenzylamine.

MS m/e (ESI)430 ($MH^+$).

Example 153

3-[4-Methoxy-3-({[4-(trifluoromethyl)benzyl]oxy}methyl)phenyl]benzoic Acid

Production Example 153a

Methyl 3-[3-(hydroxymethyl)-4-methoxyphenyl]benzoate

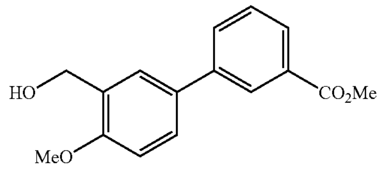

894 mg of 2-Methoxy-5-[3-(methoxycarbonyl)phenyl]benzoic acid was dissolved in 7 ml of tetrahydrofuran, 0.36 mg of triethylamine and 0.55 ml of ethyl chlorocarbonate were added successively, and the mixture was stirred at room temperature for 15 minutes. The precipitated crystals were filtered, and the filtrate was filtered. 2 ml aqueous solution of 180 mg sodium borohydride was added thereto, and the mixture was stirred at room temperature for 1 hour. 1 N hydrochloric acid was added to the reaction mixture which was then extracted with ethyl acetate. The organic layer was dried over anhydrous magnesium sulfate, and the solvent was removed. The residue was purified by a silica gel column, to give 496 mg of the title compound in the 5:3 hexane-ethyl acetate fraction.

$^1H$-NMR ($CDCl_3$).

δ: 3.92 (s, 3H) 3.95 (s, 3H) 4.76 (s, 2H) 6.98 (d, J=8.0 Hz, 1H) 7.49 (t, J=7.6 Hz, 1H) 7.54 (dd, J=2.4, 8.4 Hz, 1H) 7.57

(s, 1H) 7.75 (ddd, J=1.6, 2.0, 8.0 Hz, 1H) 7.98 (ddd, J=1.2, 1.6, 7.6 Hz, 1H) 8.24 (t, J=1.6 Hz, 1H).

Example 153b

3-[4-Methoxy-3-({[4-(trifluoromethyl)benzyl]oxy}methyl)phenyl]benzoic Acid

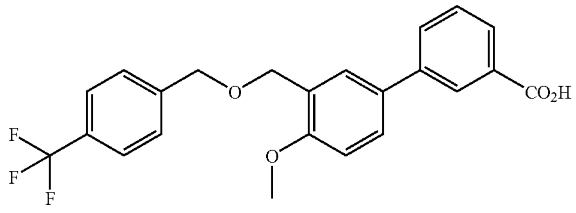

10 mg of 2-Methoxy-5-[3-(methoxycarbonyl)phenyl]benzoic acid was dissolved in 0.2 ml of THF, 20 mg of 4-trifluoromethylbenzylbromide and 5 mg of sodium hydride were added thereto, and the mixture was stirred overnight at room temperature. 0.1 ml of 5 N sodium hydroxide was added thereto, and the reaction mixture was heated with a dryer. The reaction mixture was neutralized with 1 N hydrochloric acid and extracted with ethyl acetate, and the solvent was concentrated. The residue was purified by HPLC using a reverse phase system column and a water-acetonitrile-trifluoroacetic acid eluent, to give 2.4 mg of the title compound.

MS m/e (ESI)417 ($MH^+$).

Example 154

3-[4-Methoxy-3-({[2,4-dichlorobenzyl]oxy}-methyl)phenyl]benzoic Acid

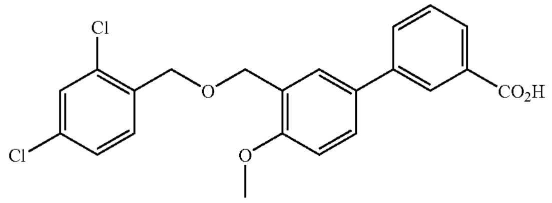

The title compound was obtained in the same way as Example 153b) except for using 2,4-dichlorobenzylbromide.

MS m/e (ESI)417 ($MH^+$).

Example 155

3-{3-[2-(2,4-Dichlorophenoxy)ethyl]-4-methoxyphenyl}benzoic Acid

Production Example 155a

Methyl 3-[3-(2-hydroxyethyl)-4-methoxyphenyl]benzoic Acid

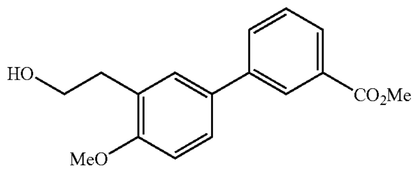

1.013 g of [(5-bromo-2-methoxyphenethyl)oxy](t-butyl)diphenyl silane, 580 mg of 3-carboxymethylboronic acid, 170 mg of tetrakistriphenyl phosphine palladium and 1.01 g of potassium carbonate were dissolved in 12 ml of toluene, and the mixture was stirred overnight at 90° C. in a nitrogen atmosphere. The reaction mixture was filtered through Celite, the filtrate was concentrated, and then the residue was dissolved in 15 ml of tetrahydrofuran. To this reaction mixture was added 5 ml of tetrabutyl ammonium fluoride solution (1M) in tetrahydrofuran, and the mixture was stirred at room temperature for 2 hours. The reaction mixture was diluted with ethyl acetate and successively washed with water and brine, dried over anhydrous magnesium sulfate, and the solvent was removed. The residue was purified by a silica gel column, and 197 mg methyl 3-[3-(2-hydroxyethyl)-4-methoxyphenyl]benzoic acid was obtained from a fraction eluted with hexane-ethyl acetate (2:1).

$^1$H-NMR ($CDCl_3$).

δ: 2.98 (t, J=6.4 Hz, 2H) 3.87-3.95 (m, 2H) 3.89 (s, 3H) 3.95 (s, 3H) 6.96 (d, J=8.8 Hz, 1H) 7.45-7.50 (m, 3H) 7.75 (dq, J=1.6, 8.0 Hz, 1H) 7.97 (dq, J=1.2, 7.6 Hz, 1H) 8.23 (t, J=1.2 Hz, 1H).

Example 155b

3-{3-[2-(2,4-Dichlorophenoxy)ethyl]-4-methoxyphenyl}benzoic Acid

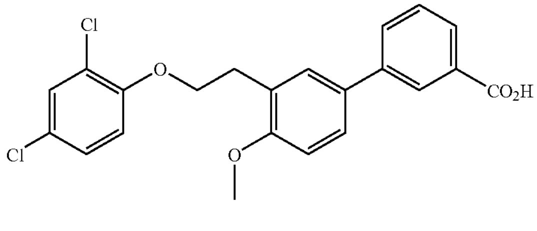

53 mg of 3-[3-(2-hydroxyethyl)-4-methoxyphenyl]benzoic acid, 45 mg of 2,4-dichlorophenol and 73 mg of triphenyl phosphine were dissolved in 2 ml of THF, and 73 ml of diisopropyl azodicarboxylate was added thereto. The mixture was stirred overnight at room temperature, and the solvent was evaporated. The residue was purified by silica gel column chromatography to give 84 mg of methyl-3-{3-[2-(2,4-dichlorophenoxy)ethyl]-4-methoxyphenyl}benzoate. This product was dissolved in 2 ml of of ethanol and 0.5 ml of 5N sodium hydroxide and then heated. The reaction mixture was neutralized with 1 N hydrochloric acid and extracted with ethyl acetate. The solvent was evaporated to give 42 mg of the title compound.

$^1$H-NMR ($CDCl_3$).

δ: 3.10 (t, J=7.6 Hz, 2H) 3.84 (s, 3H) 4.24 (t, J=7.6 Hz, 2H) 7.08 (d, J=8.8 Hz, 1H) 7.20 (d, J=8.8 Hz, 1H) 7.33 (dd, J=2.4, 8.8 Hz, 1H) 7.52-7.58 (m, 3H) 7.63 (d, J=2.4 Hz, 1H) 7.84-7.87 (m, 2H) 8.16 (t, J=1.6 Hz, 1H).

MS m/e (ESI)417 ($MH^+$).

Example 156

3-(3-{[(2,4-Dichlorobenzoyl)amino]methyl}-4-ethoxyphenyl)-6-methylbenzoic Acid

Production Example 156a

Methyl 3-(3-{[(t-butoxycarbonyl)amino]methyl}-4-hydroxyphenyl)benzoate

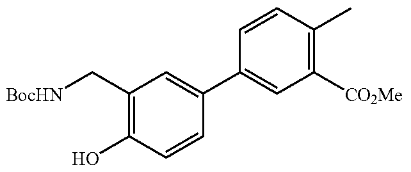

1.01 g of t-butyl N-[2-benzyloxy-5-(4,4,5,5-tetramethyl-1,3,2-dioxaborolan-2-yl)benzyl]carbamate, 593 mg of methyl 3-bromo-6-methylbenzoate, 130 mg of dichloro-bistriphenyl phosphinoferrocene palladium and 1 g of potassium carbonate were dissolved in 15 ml of dimethoxyethane, and the mixture was heated under reflux for 4 hours in a nitrogen atmosphere. The reaction mixture was filtered through Celite, and the filtrate was evaporated. The residue was purified by silica gel column, to give methyl 3-(3-{[(t-butoxycarbonyl)amino]methyl}-4-benzyloxyphenyl)-6-methylbenzoate in the 4:1 hexane-ethyl acetate fraction. This crude product was dissolved in 100 ml of methanol, then 500 mg of 10% Pd—C was added thereto, and the mixture was stirred overnight at room temperature in a hydrogen atmosphere. The reaction mixture was filtered through Celite, and the filtrate was concentrated. The residue was purified by silica gel column, to give 521 mg of the title compound in the 5:1 hexane-ethyl acetate fraction.

Production Example 156b

Methyl 3-(3-{[(t-butoxycarbonyl)amino]methyl}-4-ethoxyphenyl)-6-methylbenzoate

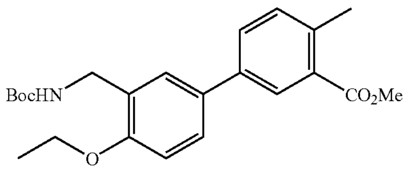

170 mg of Methyl 3-(3-{[(t-butoxycarbonyl)amino]-methyl}-4-hydroxyphenyl)-6-methylbenzoate was dissolved in 5 ml of acetonitrile, 0.5 ml of iodoethane and 500 mg of cesium carbonate were added successively thereto and the mixture was stirred overnight at 50° C. The reaction mixture was diluted with ethyl acetate and successively washed with water and brine, dried over magnesium sulfate, filtered, and the solvent was concentrated, to give 185 mg of the title compound.

Example 156c 3-(3-{[(2,4-Dichlorobenzoyl)amino]methyl}-4-ethoxyphenyl)-6-methylbenzoic Acid

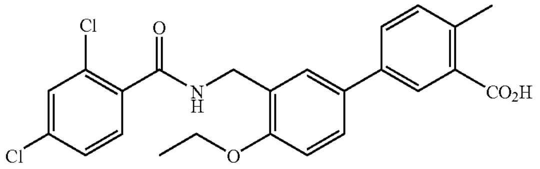

The title compound was obtained in the same way as Example 1e) except for using methyl 3-(3-{[(t-butoxycarbonyl)amino]methyl}-4-ethoxyphenyl)-6-methylbenzoate.

MS m/e (ESI) 458 ($MH^+$).

Example 157

3-(3-{[(4-Chloro-2-fluorobenzoyl)amino]-methyl}-4-ethoxyphenyl)-6-methylbenzoic Acid

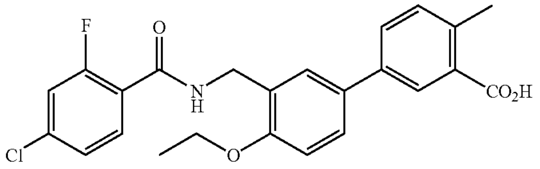

The title compound was obtained in the same way as Example 156c) except for using 4-chloro-2-fluorobenzoic acid.

MS m/e (ESI) 442 ($MH^+$).

Example 158

3-(3-{[(4-Bromo-2-fluorobenzoyl)amino]methyl}-4-ethoxyphenyl)-6-methylbenzoic Acid

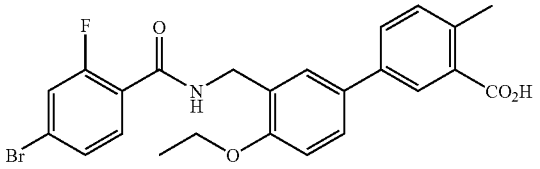

The title compound was obtained in the same way as Example 156c) except for using 4-bromo-2-fluorobenzoic acid.

MS m/e (ESI) 486 ($MH^+$).

Example 159

3-(3-{[(4-Trifluoromethyl-2-fluorobenzoyl)amino]methyl}-4-ethoxyphenyl)-6-methylbenzoic Acid

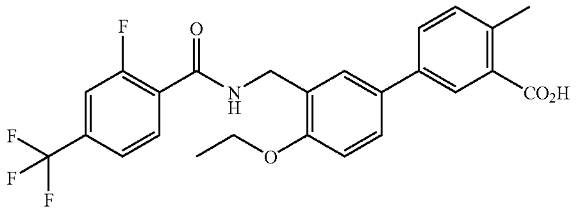

The title compound was obtained in the same way as Example 156c) except for using 4-trifluoromethyl-2-fluorobenzoic acid.

MS m/e (ESI) 476 ($MH^+$).

Example 160

3-(3-{[(4-Propoxy-2-chlorobenzoyl)amino]-methyl}-4-ethoxyphenyl)-6-methylbenzoic Acid

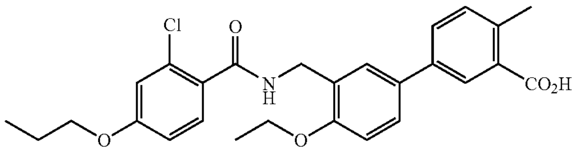

The title compound was obtained in the same way as Example 156c) except for using 4-propoxy-2-chlorobenzoic acid.

MS m/e (ESI) 482 ($MH^+$).

Example 161

3-(3-{[(4-Isopropoxy-2-chlorobenzoyl)amino]-methyl}-4-ethoxyphenyl)-6-methylbenzoic Acid

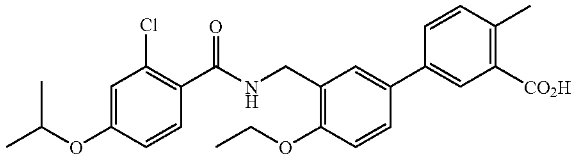

The title compound was obtained in the same way as Example 156c) except for using 4-isopropoxy-2-chlorobenzoic acid.

$^1$H-NMR ($CDCl_3$).

δ: 1.25 (d, J=6.0 Hz, 6H) 1.37 (t, J=6.8 Hz, 3H) 2.52 (s, 3H) 4.10 (q, J=7.2 Hz, 2H) 4.43 (d, J=5.6 Hz, 2H) 4.69 (sept, J=6.0 Hz, 1H) 6.95 (dd, J=2.4, 8.0 Hz, 1H) 7.02 (d, J=2.0 Hz, 1H) 7.06 (d, J=8.8 Hz, 1H) 7.34 (d, J=8.0 Hz, 1H) 7.39 (d, J=8.8 Hz, 1H) 7.53 (dd, J=2.4, 8.8 Hz, 1H) 7.59 (d, J=2.0 Hz, 1H) 7.65 (dd, J=2.0, 7.6 Hz, 1H) 8.03 (d, J=2.0 Hz, 1H) 8.75 (t, J=5.6 Hz, 1H).

MS m/e (ESI) 482 ($MH^+$).

Example 162

3-{4-Ethoxy-3-[({[4-methyl-2-(4-methylphenyl)-1,3-thiazol-5-yl]carbonyl}amino)methyl]-phenyl}-6-methylbenzoic Acid

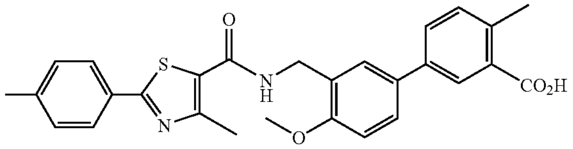

The title compound was obtained in the same way as Example 156c) except for using 4-methyl-2-(4-methylphenyl)-1,3-thiazol-5-carboxylic Acid.

MS m/e (ESI) 501 ($MH^+$).

Example 163

3-(3-{[(2,4-Dichlorobenzoyl)amino]methyl}-4-propoxyphenyl)-6-methylbenzoic Acid

Production Example 163a

Methyl 3-(3-{[(t-butoxycarbonyl)amino]methyl}-4-propoxyphenyl)-6-methylbenzoate

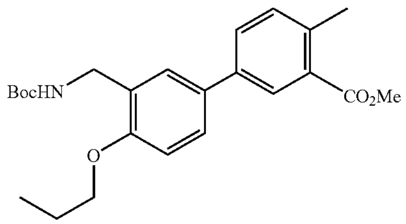

The title compound was obtained in the same way as Production Example 156b) except for using iodopropane.

Example 163b 3-(3-{[(2,4-Dichlorobenzoyl)amino]methyl}-4-propoxyphenyl)-6-methylbenzoic Acid

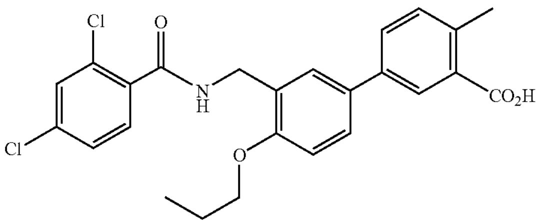

The title compound was obtained in the same way as Example 1e) except for using 3-(3-{[(t-butoxycarbonyl)amino]methyl}-4-propoxyphenyl)-6-methylbenzoate.

MS m/e (ESI) 472 ($MH^+$).

Example 164

3-(3-{[(4-Chloro-2-fluorobenzoyl)amino]-methyl}-4-propoxyphenyl)-6-methylbenzoic Acid

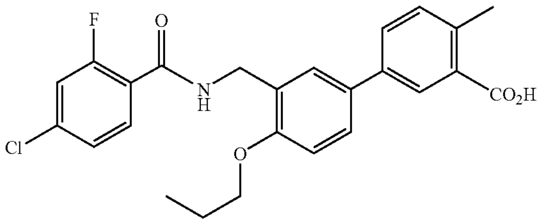

The title compound was obtained in the same way as Example 163b) except for using 4-chloro-2-fluorobenzoic acid.

MS m/e (ESI) 456 ($MH^+$).

Example 165

3-(3-{[(4-Bromo-2-fluorobenzoyl)amino]-methyl}-4-propoxyphenyl)-6-methylbenzoic Acid

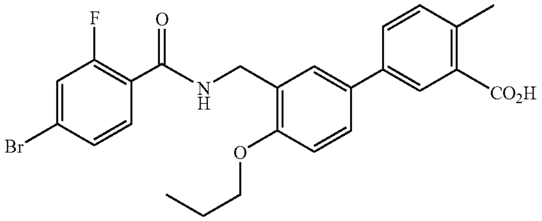

The title compound was obtained in the same way as Example 163b) except for using 4-bromo-2-fluorobenzoic acid.

MS m/e (ESI) 500 ($MH^+$).

Example 166

3-(3-{[(4-Trifluoromethyl-2-fluorobenzoyl)amino] methyl}-4-propoxyphenyl)-6-methylbenzoic Acid

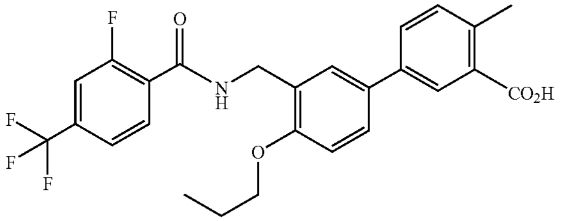

The title compound was obtained in the same way as Example 163b) except for using 4-trifluoromethyl-2-fluorobenzoic acid.

MS m/e (ESI) 490 ($MH^+$).

Example 167

3-(3-{[(4-Propoxy-2-chlorobenzoyl)amino]-methyl}-4-propoxyphenyl)-6-methylbenzoic Acid

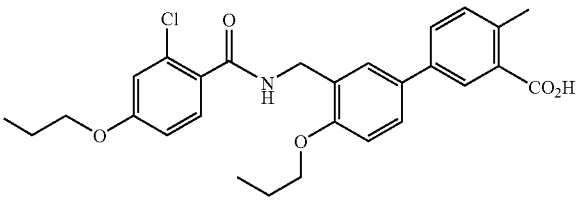

The title compound was obtained in the same way as Example 163b) except for using 4-propoxy-2-chlorobenzoic acid.

MS m/e (ESI) 496 ($MH^+$).

Example 168

3-(3-{[(4-Isopropoxy-2-chlorobenzoyl)amino]-methyl}-4-propoxyphenyl)-6-methylbenzoic Acid

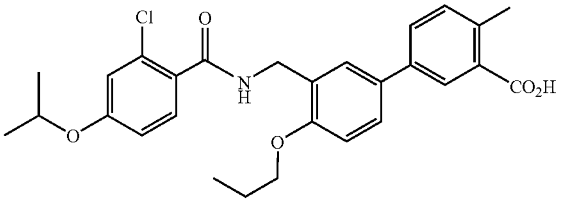

The title compound was obtained in the same way as Example 163b) except for using 4-isopropoxy-2-chlorobenzoic acid.

$^1$H-NMR ($CDCl_3$).

δ: 1.02 (t, J=7.6 Hz, 3H) 1.25 (d, J=6.0 Hz, 6H) 1.77 (q, J=7.6 Hz, 2H) 2.52 (s, 3H) 4.01 (t, J=6.4 Hz, 2H) 4.44 (d, J=6.0 Hz, 2H) 4.69 (sept, J=6.0 Hz, 1H) 6.95 (dd, J=2.4, 8.4 Hz, 1H) 7.02 (d, J=2.4 Hz, 1H) 7.06 (d, J=8.8 Hz, 1H) 7.34 (d, 8.0 Hz, 1H) 7.40 (d, J=8.0 Hz, 1H) 7.52 (dd, J=2.4, 8.8 Hz, 1H) 7.59 (d, J=2.0 Hz, 1H) 7.65 (dd, J=2.4, 8.4 Hz, 1H) 8.03 (d, J=2.0 Hz, 1H) 8.75 (t, J=6.0 Hz, 1H).

MS m/e (ESI) 496 ($MH^+$).

Example 169

3-{4-Propoxy-3-[({[4-methyl-2-(4-methylphenyl)-1,3-thiazol-5-yl]carbonyl}amino)methyl]-phenyl}-6-methylbenzoic Acid

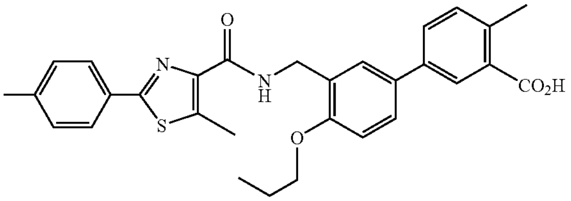

The title compound was obtained in the same way as Example 163b) except for using 4-methyl-2-(4-methylphenyl)-1,3-thiazol-5-carboxylic Acid.

MS m/e (ESI) 515 ($MH^+$).

Example 170

3-(3-{[(2,4-Dichlorobenzoyl)amino]methyl}-4-isopropoxyphenyl)-6-methylbenzoic Acid

Production Example 170a

Methyl 3-(3-{[(t-butoxycarbonyl)amino]methyl}-4-propoxyphenyl)-6-methylbenzoate

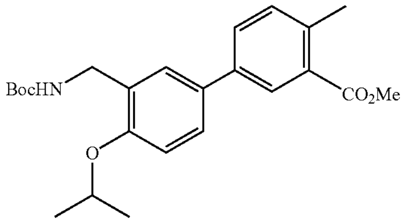

The title compound was obtained in the same way as Production Example 156b) except for using 2-iodopropane.

Example 170b

3-(3-{[(2,4-Dichlorobenzoyl)amino]methyl}-4-isopropoxyphenyl)-6-methylbenzoic Acid

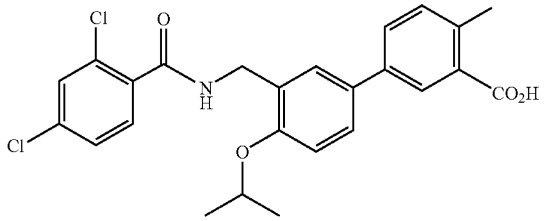

The title compound was obtained in the same way as Example 1e) except for using methyl 3-(3-{[(t-butoxycarbonyl)amino]methyl}-4-propoxyphenyl)-6-methylbenzoate.

MS m/e (ESI) 472 ($MH^+$).

Example 171

3-(3-{[(4-Chloro-2-fluorobenzoyl)amino]-methyl}-4-isopropoxyphenyl)-6-methylbenzoic Acid

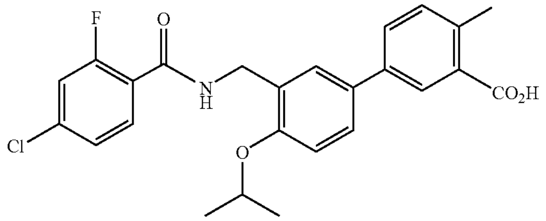

The title compound was obtained in the same way as Example 170b) except for using 4-chloro-2-fluorobenzoic acid.

MS m/e (ESI) 456 ($MH^+$).

Example 172

3-(3-{[(4-bromo-2-fluorobenzoyl)amino]methyl}-4-isopropoxyphenyl)-6-methylbenzoic Acid

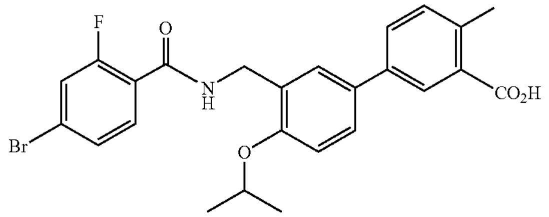

The title compound was obtained in the same way as Example 170b) except for using 4-bromo-2-fluorobenzoic acid.

MS m/e (ESI) 500 ($MH^+$).

Example 173

3-(3-{[(4-Trifluoromethyl-2-fluorobenzoyl)amino]methyl}-4-isopropoxyphenyl)-6-methylbenzoic Acid

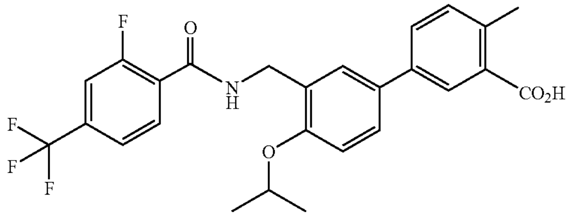

The title compound was obtained in the same way as Example 170b) except for using 4-trifluoromethyl-2-fluorobenzoic acid MS m/e (ESI) 490 ($MH^+$).

Example 174

3-(3-{[(4-Propoxy-2-chlorobenzoyl)amino]-methyl}-4-isopropoxyphenyl)-6-methylbenzoic Acid

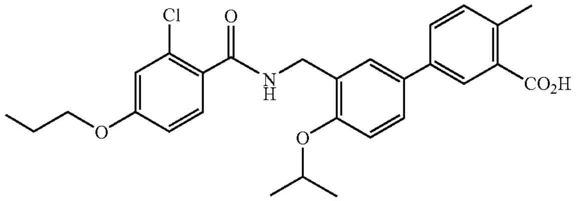

The title compound was obtained in the same way as Example 170b) except for using 4-propoxy-2-chlorobenzoic acid.

MS m/e (ESI) 496 ($MH^+$).

Example 175

3-(3-{[(4-Isopropoxy-2-chlorobenzoyl)amino]methyl}-4-isopropoxyphenyl)-6-methylbenzoic Acid

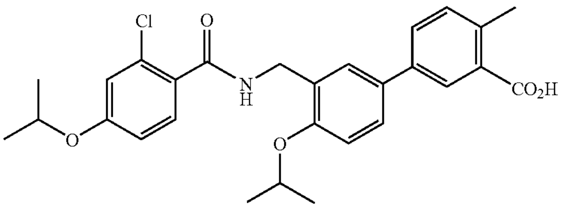

The title compound was obtained in the same way as Example 170b) except for using 4-isopropoxy-2-chlorobenzoic acid.

$^1$H-NMR ($CDCl_3$).

δ: 1.25 (d, J=6.0 Hz, 6H) 1.31 (d, J=6.0 Hz, 6H) 2.52 (s, 3H) 4.41 (d, J=5.6 Hz, 2H) 4.68 (sept, J=6.0 Hz, 2H) 6.95 (dd, J=2.4, 8.8 Hz, 1H) 7.02 (d, J=2.0 Hz, 1H) 7.08 (d, J=8.4 Hz, 1H) 7.34 (d, 8.0 Hz, 1H) 7.39 (d, J=8.4 Hz, 1H) 7.51 (d, J=8.8 Hz, 1H) 7.58 (s, 1H) 7.65 (dd, J=2.0, 8.0 Hz, 1H) 8.02 (s, 1H) 8.73 (t, J=6.0 Hz, 1H).

MS m/e (ESI) 496 ($MH^+$).

Example 176

3-{4-Isopropoxy-3-[({[4-methyl-2-(4-methylphenyl)-1,3-thiazol-5-yl]carbonyl}amino)methyl]-phenyl}-6-methylbenzoic Acid

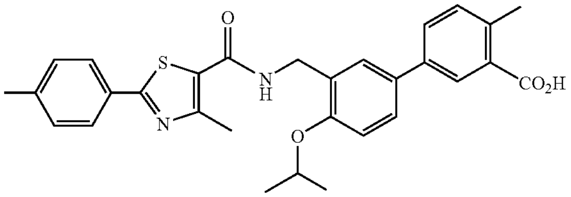

The title compound was obtained in the same way as Example 170b) except for using 4-methyl-2-(4-methylphenyl)-1,3-thiazol-5-carboxylic Acid.

MS m/e (ESI) 515 ($MH^+$).

Example 177

3-(3-{[(2,4-Dichlorobenzoyl)amino]methyl}-4-propoxyphenyl)-6-fluorobenzoic Acid

Production Example 177a t-Butyl N-[2-hydroxy-5-(4,4,5,5-tetramethyl-1,3,2-dioxaborolan-2-yl)benzyl]carbamate

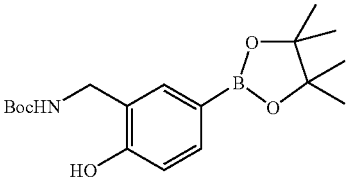

10.8 g of t-butyl N-[2-benzyloxy-5-(4,4,5,5-tetramethyl-1,3,2-dioxaborolan-2-yl) benzyl]carbamate was dissolved in 300 ml of ethanol, 2 g of 10% palladium-carbon was added thereto, and the mixture was stirred overnight at room temperature in a hydrogen atmosphere. The reaction mixture was filtered through Celite, and the filtrate was concentrated to give 8.2 g of the title compound.

$^1$H-NMR ($CDCl_3$).

δ: 1.33 (s, 12H) 1.44 (s, 9H) 4.24 (d, J=6.8 Hz, 2H) 5.20 (br, 1H) 6.94 (d, J=8.0 Hz, 1H) 7.53 (d, 1.2 Hz, 1H) 7.67 (dd, J=2.0, 8.0 Hz, 1H) 9.28(br, 1H).

Production Example 177b

Methyl 3-(3-{[(t-butoxycarbonyl)amino]methyl}-4-hydroxyphenyl)-6-fluorobenzoate

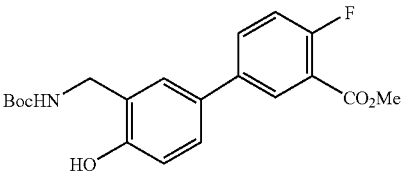

501 mg of t-butyl N-[2-hydroxy-5-(4,4,5,5-tetramethyl-1,3,2-dioxaborolan-2-yl)benzyl]carbamate, 370 mg of methyl 3-bromo-6-fluorobenzoate, 80 mg of dichlorobistriphenyl phosphinoferrocene palladium and 500 mg of potassium carbonate were dissolved in 8 ml of dimethoxyethane and stirred overnight at 80° C. in a nitrogen atmosphere. The reaction mixture was filtered through Celite, and the filtrate was evaporated. The residue was purified by silica gel column, to give 391 mg of the title compound in the 4:1 hexane-ethyl acetate fraction.

$^1$H-NMR ($CDCl_3$).

δ: 1.46 (s, 9H) 3.97 (s, 3H) 4.30 (d, J=7.2 Hz, 2H) 5.22 (brs, 1H) 7.02 (dd, J=2.8, 8.4 Hz, 1H) 7.15-7.20 (m, 1H) 7.26-7.28 (m, 1H) 7.40-7.44 (m, 1H) 7.63-7.67 (m, 1H) 8.06-8.09 (m, 1H) 9.15 (br, 1H).

Production Example 177c

Methyl 3-(3-{[(t-butoxycarbonyl)amino]methyl}-4-propoxyphenyl)-6-fluorobenzoate

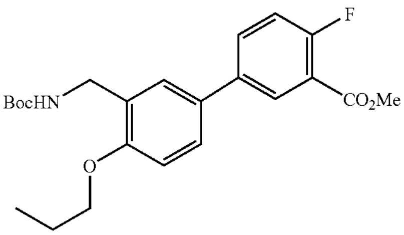

The title compound was obtained in the same way as Production Example 156b) except for using 3-(3-{[(t-butoxycarbonyl)amino]methyl}-4-hydroxyphenyl)-6-fluorobenzoate.

Example 177d 3-(3-{[(2,4-Dichlorobenzoyl)amino]methyl}-4-propoxyphenyl)-6-fluorobenzoic Acid

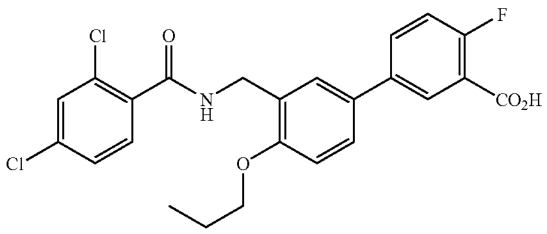

The title compound was obtained in the same way as Example 1e) except for using 3-(3-{[(t-butoxycarbonyl)amino]methyl}-4-propoxyphenyl)-6-fluorobenzoate.

MS m/e (ESI) 476 ($MH^+$).

Example 178

3-(3-{[(4-Chloro-2-fluorobenzoyl)amino]methyl}-4-propoxyphenyl)-6-fluorobenzoic Acid

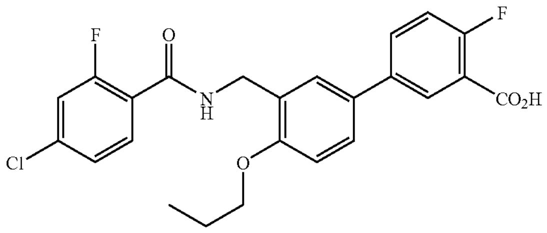

The title compound was obtained in the same way as Example 177d) except for using 4-chloro-2-fluorobenzoic acid.

MS m/e (ESI) 460 ($MH^+$).

Example 179

3-(3-{[(4-Trifluoromethyl-2-fluorobenzoyl)amino]methyl}-4-propoxyphenyl)-6-fluorobenzoic Acid

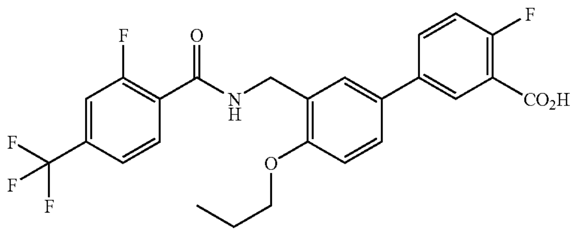

The title compound was obtained in the same way as Example 177d) except for using 4-trifluoromethyl-2-fluorobenzoic acid.

MS m/e (ESI) 494 ($MH^+$).

Example 180

3-(3-{[(4-Propoxy-2-chlorobenzoyl)amino]-methyl}-4-propoxyphenyl)-6-fluorobenzoic Acid

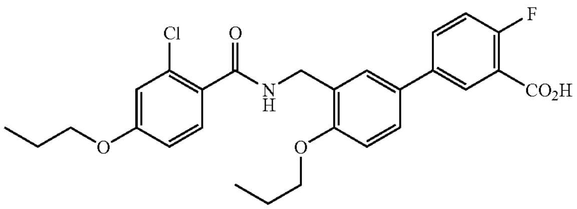

The title compound was obtained in the same way as Example 177d) except for using 4-propoxy-2-chlorobenzoic acid.

MS m/e (ESI) 500 ($MH^+$).

Example 181

3-(3-{[(4-Isopropoxy-2-chlorobenzoyl)amino]-methyl}-4-propoxyphenyl)-6-fluorobenzoic Acid

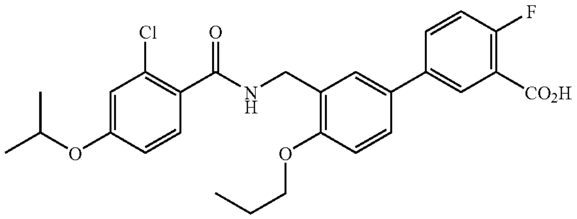

The title compound was obtained in the same way as Example 177d) except for using 4-isopropoxy-2-chlorobenzoic acid.

MS m/e (ESI) 500 ($MH^+$).

Example 182

3-(3-{[(2,4-Dichlorobenzoyl)amino]methyl}-4-propoxyphenyl)-2-fluorobenzoic Acid

Production Example 182a

Methyl 3-(3-{[(t-butoxycarbonyl)amino]methyl}-4-propoxyphenyl)-2-fluorobenzoate

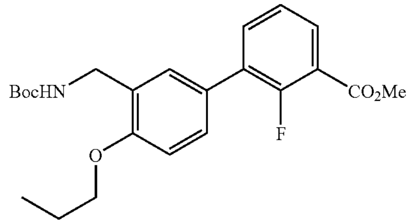

The title compound was obtained in the same way as Production Examples 156a) and 156b) except for using methyl 3-bromo-2-fluorobenzoate and iodopropane.

$^1H$-NMR ($CDCl_3$).

δ: 1.46 (s, 9H) 3.96 (s, 3H) 4.28 (d, J=6.8 Hz, 2H) 5.31 (br, 1H) 7.03 (dd, J=3.6, 6.8 Hz, 2H) 7.21-7.29 (m, 2H) 7.37-7.40 (m, 1H) 7.53-7.58 (m, 1H) 7.83-7.87 (m, 1H) 9.19 (br, 1H).

Example 182b 3-(3-{[(2,4-Dichlorobenzoyl)amino]methyl}-4-propoxyphenyl)-2-fluorobenzoic Acid

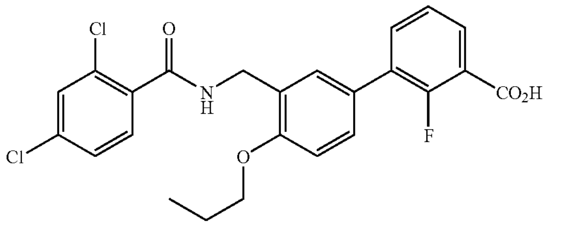

The title compound was obtained in the same way as Example 1e) except for using 3-(3-{[(t-butoxycarbonyl)amino]methyl}-4-propoxyphenyl)-2-fluorobenzoate.

MS m/e (ESI) 476 ($MH^+$).

Example 183

3-(3-{[(4-Chloro-2-fluorobenzoyl)amino]methyl}-4-propoxyphenyl)-2-fluorobenzoic Acid

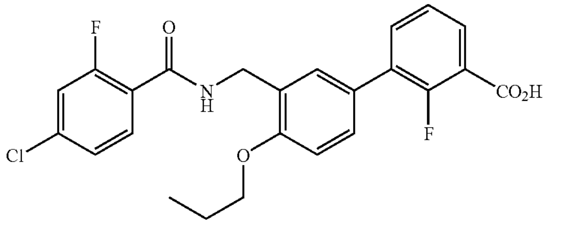

The title compound was obtained in the same way as Example 182b) except for using 4-chloro-2-fluorobenzoic acid.

MS m/e (ESI) 460 ($MH^+$).

Example 184

3-(3-{[(4-Trifluoromethyl-2-fluorobenzoyl)amino]methyl}-4-propoxyphenyl)-2-fluorobenzoic Acid

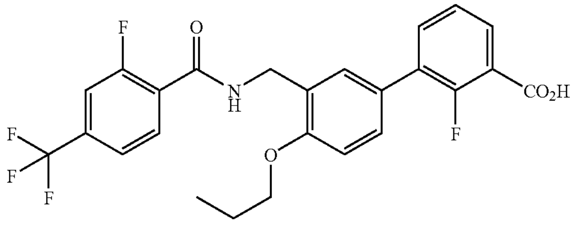

The title compound was obtained in the same way as Example 182b) except for using 4-trifluoromethyl-2-fluorobenzoic acid.

MS m/e (ESI) 494 ($MH^+$).

Example 185

3-(3-{[(4-Propoxy-2-chlorobenzoyl)amino]-methyl}-4-propoxyphenyl)-2-fluorobenzoic Acid

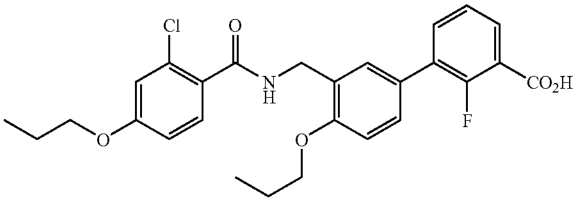

The title compound was obtained in the same way as Example 182b) except for using 4-propoxy-2-chlorobenzoic acid.

MS m/e (ESI) 500 ($MH^+$).

Example 186

3-(3-{[(4-Isopropoxy-2-chlorobenzoyl)amino]-methyl}-4-propoxyphenyl)-2-fluorobenzoic Acid

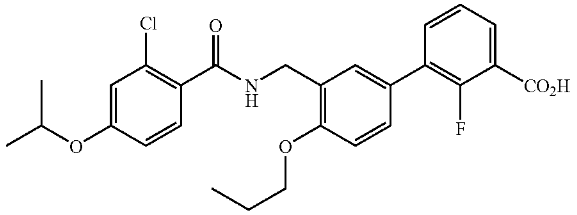

The title compound was obtained in the same way as Example 182b) except for using 4-isopropoxy-2-chlorobenzoic acid.

MS m/e (ESI) 500 ($MH^+$).

Example 187

3-(3-{[(2,4-Dichlorobenzoyl)amino]methyl}-4-propoxyphenyl)-5-fluorobenzoic Acid

Production Example 187a

Methyl 3-(3-{[(t-butoxycarbonyl)amino]methyl}-4-propoxyphenyl)-5-fluorobenzoate

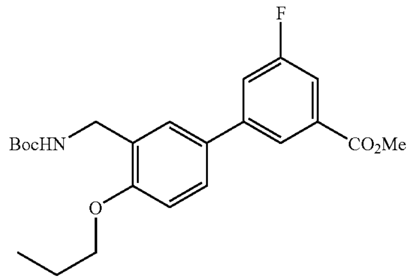

The title compound was obtained in the same way as Production Examples 156a) and 156b) except for using methyl 3-bromo-5-fluorobenzoate and iodopropane.

Example 187b 3-(3-{[(2,4-Dichlorobenzoyl)amino]methyl}-4-propoxyphenyl)-5-fluorobenzoic Acid

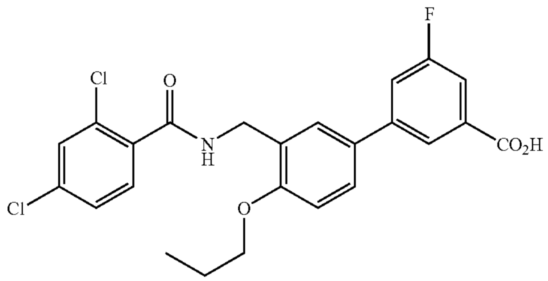

The title compound was obtained in the same way as Example 1e) except for using 3-(3-{[(t-butoxycarbonyl)amino]methyl}-4-propoxyphenyl)-5-fluorobenzoate.

MS m/e (ESI) 476 ($MH^+$).

Example 188

3-(3-{[(4-Chloro-2-fluorobenzoyl)amino]-methyl}-4-propoxyphenyl)-5-fluorobenzoic Acid

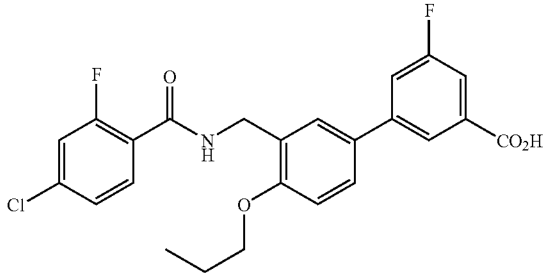

The title compound was obtained in the same way as Example 187b) except for using 4-chloro-2-fluorobenzoic acid.

MS m/e (ESI) 460 ($MH^+$).

Example 189

3-(3-{[(4-Trifluoromethyl-2-fluorobenzoyl)amino]methyl)-4-propoxyphenyl)-5-fluorobenzoic Acid

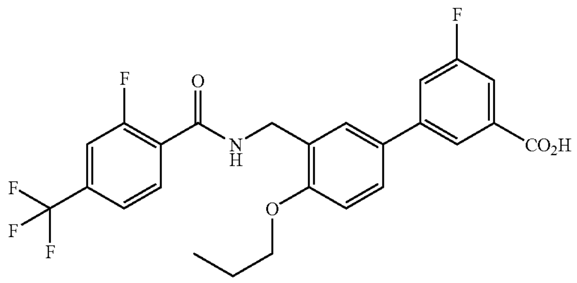

The title compound was obtained in the same way as Example 187b) except for using 4-trifluoromethyl-2-fluorobenzoic acid.

MS m/e (ESI) 494 ($MH^+$).

Example 190

3-(3-{[(4-Propoxy-2-chlorobenzoyl)amino]-methyl}-4-propoxyphenyl)-5-fluorobenzoic Acid

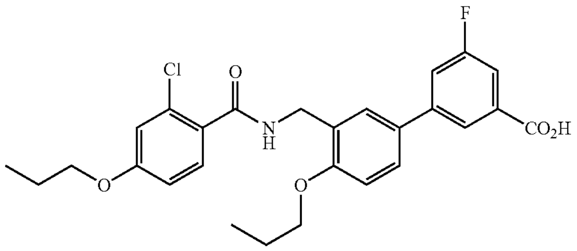

The title compound was obtained in the same way as Example 187b) except for using 4-propoxy-2-chlorobenzoic acid.

MS m/e (ESI) 500 ($MH^+$).

Example 191

3-(3-{[(4-Isopropoxy-2-chlorobenzoyl)amino]-methyl}-4-propoxyphenyl)-5-fluorobenzoic Acid

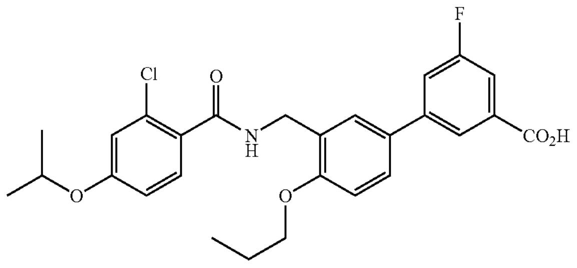

The title compound was obtained in the same way as Example 187b) except for using 4-propoxy-2-chlorobenzoic acid.

MS m/e (ESI) 500 ($MH^+$).

Example 192

3-(3-{[(2,4-Dichlorobenzoyl)amino]methyl}-4-propoxyphenyl)-4-fluorobenzoic Acid

Production Example 192a

Methyl 3-(3-{[(t-butoxycarbonyl)amino]methyl}-4-propoxyphenyl)-4-fluorobenzoate

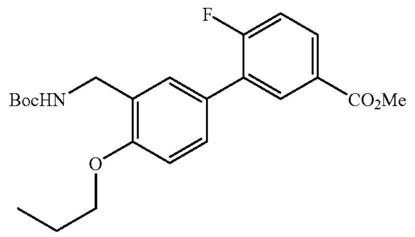

The title compound was obtained in the same way as Production Examples 156a) and 156b) except for using methyl 3-bromo-4-fluorobenzoate and iodopropane.

Example 192b 3-(3-{[(2,4-Dichlorobenzoyl)amino]methyl}-4-propoxyphenyl)-4-fluorobenzoic Acid

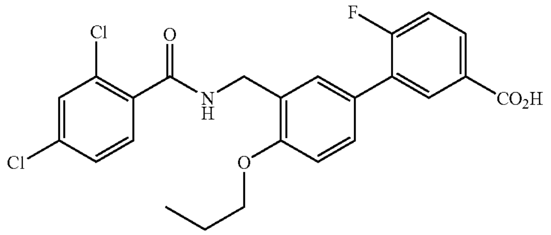

The title compound was obtained in the same way as Example 1e) except for using 3-(3-{[(t-butoxycarbonyl)amino]methyl}-4-propoxyphenyl)-4-fluorobenzoate.

MS m/e (ESI) 476 ($MH^+$).

Example 193

3-(3-{[(4-Chloro-2-fluorobenzoyl)amino]methyl}-4-propoxyphenyl)-4-fluorobenzoic Acid

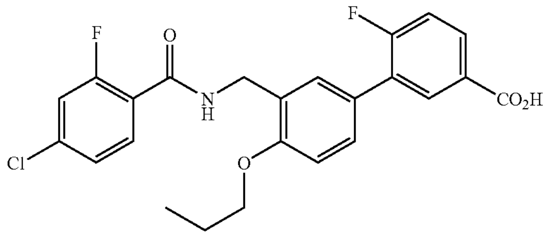

The title compound was obtained in the same way as Example 192b) except for using 4-chloro-2-fluorobenzoic acid.

MS m/e (ESI) 460 ($MH^+$).

Example 194

3-(3-{[(4-Trifluoromethyl-2-fluorobenzoyl)amino]methyl}-4-propoxyphenyl)-4-fluorobenzoic Acid

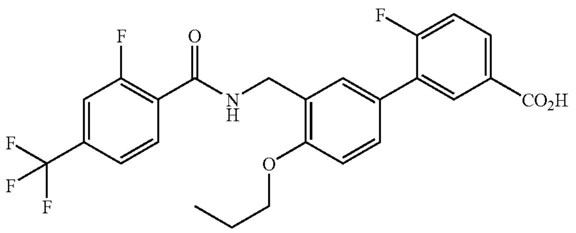

The title compound was obtained in the same way as Example 192b) except for using 4-trifluoromethyl-2-fluorobenzoic acid.

MS m/e (ESI) 494 ($MH^+$).

Example 195

3-(3-{[(4-Propoxy-2-chlorobenzoyl)amino]methyl}-4-propoxyphenyl)-4-fluorobenzoic Acid

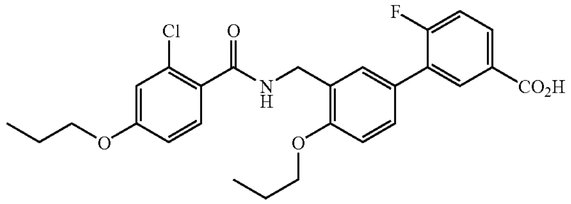

The title compound was obtained in the same way as Example 192b) except for using 4-propoxy-2-chlorobenzoic acid.

MS m/e (ESI) 500 ($MH^+$).

Example 196

3-(3-{[(4-Isopropoxy-2-chlorobenzoyl)amino]methyl}-4-propoxyphenyl)-4-fluorobenzoic Acid

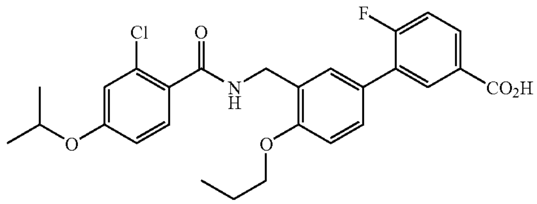

The title compound was obtained in the same way as Example 192b) except for using 4-isopropoxy-2-chlorobenzoic acid.

MS m/e (ESI) 500 ($MH^+$).

Example 197

3-(3-{[(2,4-Dichlorobenzoyl)amino]methyl}-4-propoxyphenyl)-4-chlorobenzoic Acid

Production Example 197a

Methyl 3-(3-{[(t-butoxycarbonyl)amino]methyl}-4-propoxyphenyl)-4-chlorobenzoate

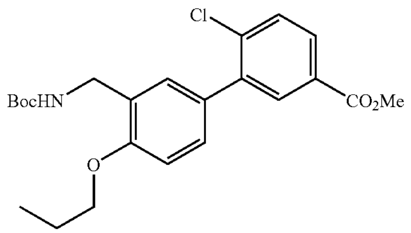

The title compound was obtained in the same way as Production Examples 156a) and 156b) except for using methyl 3-bromo-4-chlorobenzoate.

Example 197b 3-(3-{[(2,4-Dichlorobenzoyl)amino]methyl}-4-propoxyphenyl)-4-chlorobenzoic Acid

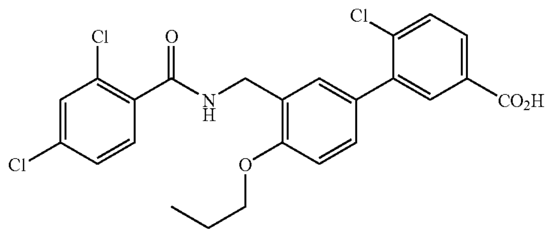

The title compound was obtained in the same way as Example 1e) except for using methyl 3-(3-{[(t-butoxycarbonyl)amino]methyl}-4-propoxyphenyl)-4-chlorobenzoate.

MS m/e (ESI) 492 ($MH^+$).

Example 198

3-(3-{[(4-Chloro-2-fluorobenzoyl)amino]-methyl}-4-propoxyphenyl)-4-chlorobenzoic Acid

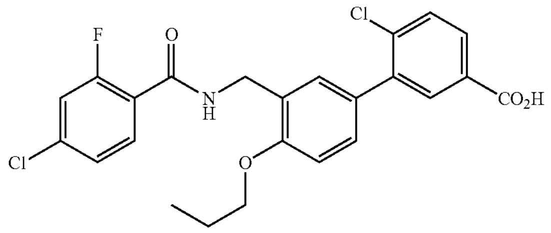

The title compound was obtained in the same way as Example 197b) except for using 4-chloro-2-fluorobenzoic acid.

MS m/e (ESI) 476 ($MH^+$).

Example 199

3-(3-{[(4-Trifluoromethyl-2-fluorobenzoyl)amino]methyl}-4-propoxyphenyl)-4-chlorobenzoic Acid

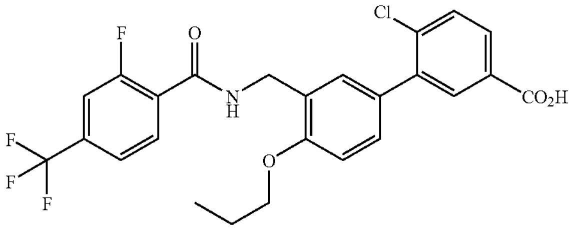

The title compound was obtained in the same way as Example 197b) except for using 4-trifluoromethyl-2-fluorobenzoic acid.

MS m/e (ESI) 510 ($MH^+$).

Example 200

3-(3-{[(4-Propoxy-2-chlorobenzoyl)amino]-methyl}-4-propoxyphenyl)-4-chlorobenzoic Acid

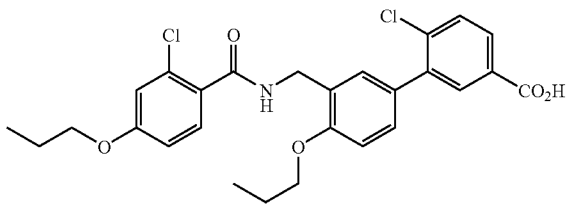

The title compound was obtained in the same way as Example 197b) except for using 4-propoxy-2-chlorobenzoic acid.

MS m/e (ESI) 516 ($MH^+$).

Example 201

3-(3-{[(4-Isopropoxy-2-chlorobenzoyl)amino]-methyl}-4-propoxyphenyl)-4-chlorobenzoic Acid

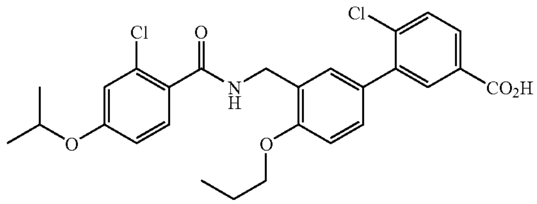

The title compound was obtained in the same way as Example 197b) except for using 4-isopropoxy-2-chlorobenzoic acid.

MS m/e (ESI) 516 ($MH^+$).

Example 202

3-(3-{[(2,4-Dichlorobenzoyl)amino]methyl}-4-propoxyphenyl)-4-methylbenzoic Acid

Production Example 202a

Methyl 3-(3-{[(t-butoxycarbonyl)amino]methyl}-4-propoxyphenyl)-4-methylbenzoate

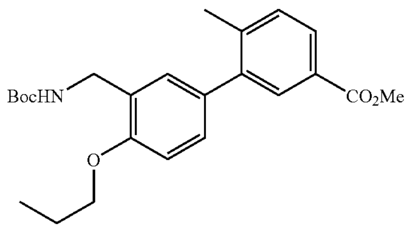

The title compound was obtained in the same way as Production Examples 156a) and 156b) except for using methyl 3-bromo-4-methylbenzoate.

Example 202b 3-(3-{[(2,4-Dichlorobenzoyl)amino]methyl}-4-propoxyphenyl)-4-methylbenzoic Acid

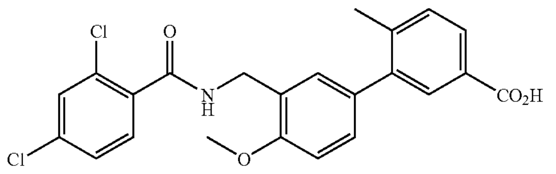

The title compound was obtained in the same way as Example 1e) except for using 3-(3-{[(t-butoxycarbonyl)amino]methyl}-4-propoxyphenyl)-4-methylbenzoate.

MS m/e (ESI) 472 ($MH^+$).

Example 203

3-(3-{[(4-Chloro-2-fluorobenzoyl)amino]-methyl}-4-propoxyphenyl)-4-methylbenzoic Acid

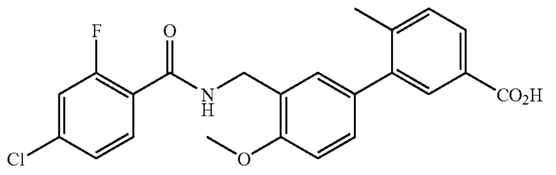

The title compound was obtained in the same way as Example 202b) except for using 4-chloro-2-fluorobenzoic acid.

MS m/e (ESI) 456 ($MH^+$).

Example 204

3-(3-{[(4-Trifluoromethyl-2-fluorobenzoyl)amino]methyl}-4-propoxyphenyl)-4-methylbenzoic Acid

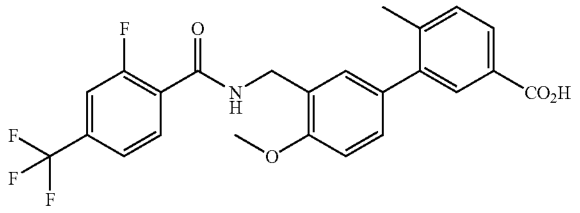

The title compound was obtained in the same way as Example 202b) except for using 4-trifluoromethyl-2-fluorobenzoic acid.

MS m/e (ESI) 490 ($MH^+$).

Example 205

3-(3-{[(4-Propoxy-2-chlorobenzoyl)amino]-methyl}-4-propoxyphenyl)-4-methylbenzoic Acid

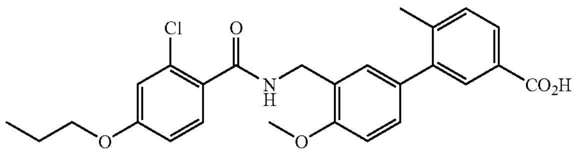

The title compound was obtained in the same way as Example 202b) except for using 4-propoxy-2-chlorobenzoic acid.

MS m/e (ESI) 496 ($MH^+$).

Example 206

3-(3-{[(4-Isopropoxy-2-chlorobenzoyl)amino]-methyl}-4-propoxyphenyl)-4-methylbenzoic Acid

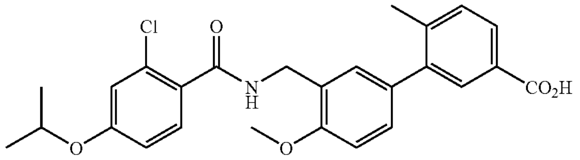

The title compound was obtained in the same way as Example 202b) except for using 4-isopropoxy-2-chlorobenzoic acid.

MS m/e (ESI) 496 ($MH^+$).

Example 207

4-(3-{[(2,4-Dichlorobenzoyl)amino]methyl}-4-propoxyphenyl)-2-thiophenecarboxylic Acid Production Example 207a Methyl 3-(3-{[(t-butoxycarbonyl)amino]methyl}-4-propoxyphenyl)-2-thiophenecarboxylate

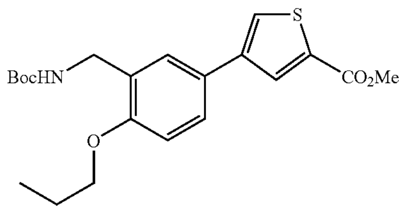

The title compound was obtained in the same way as Production Examples 156a) and 156b) except for using methyl 4-bromo-2-thiophenecarboxylate.

Example 207b 4-(3-{[(2,4-Dichlorobenzoyl)amino]methyl}-4-propoxyphenyl)-2-thiophenecarboxylic Acid

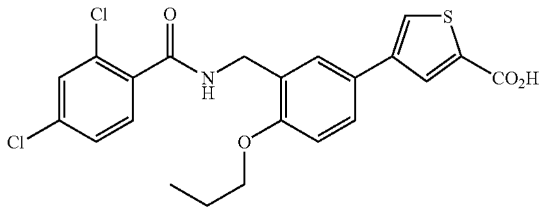

The title compound was obtained in the same way as Example 1e) except for using methyl 3-(3-{[(t-butoxycarbonyl)amino]methyl}-4-propoxyphenyl)-2-thiophenecarboxylate.

MS m/e (ESI) 464 ($MH^+$).

Example 208

4-(3-{[(4-Chloro-2-fluorobenzoyl)amino]-methyl}-4-propoxyphenyl)-2-thiophenecarboxylic Acid

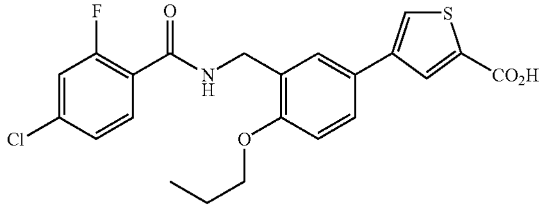

The title compound was obtained in the same way as Example 207b) except for using 4-chloro-2-fluorobenzoic acid.

MS m/e (ESI) 448 ($MH^+$).

Example 209

4-(3-{[(4-Trifluoromethyl-2-fluorobenzoyl)amino]methyl}-4-propoxyphenyl)-2-thiophenecarboxylic Acid

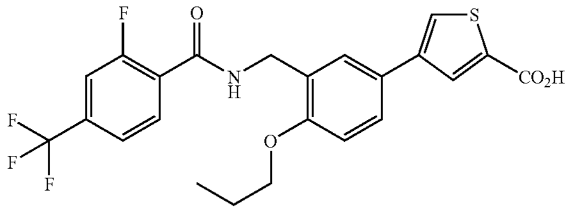

The title compound was obtained in the same way as Example 207b) except for using 4-trifluoromethyl-2-fluorobenzoic acid.

MS m/e (ESI) 482 ($MH^+$).

Example 210

4-(3-{[(4-Propoxy-2-fluorobenzoyl)amino]-methyl}-4-propoxyphenyl)-2-thiophenecarboxylic Acid

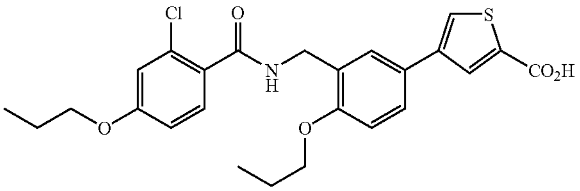

The title compound was obtained in the same way as Example 207b) except for using 4-propoxy-2-chlorobenzoic acid.

MS m/e (ESI) 488 ($MH^+$).

Example 211

4-(3-{[(4-Isopropoxy-2-fluorobenzoyl)amino]-methyl}-4-propoxyphenyl)-2-thiophenecarboxylic Acid

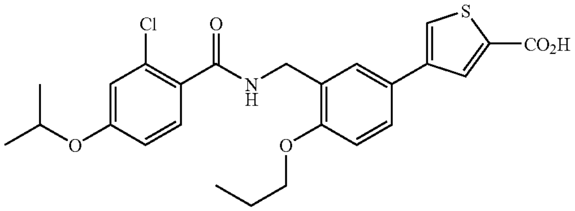

The title compound was obtained in the same way as Example 207b) except for using 4-isopropoxy-2-chlorobenzoic acid.

MS m/e (ESI) 488 ($MH^+$).

Example 212

3-(3-{[(2,4-Dichlorobenzoyl)amino]methyl}-4-propoxyphenyl)-4-methyl-6-fluorobenzoic Acid Production Example 212a Methyl 3-(3-{[(t-butoxycarbonyl)amino]methyl}-4-propoxyphenyl)-4-methyl-6-fluorobenzoate

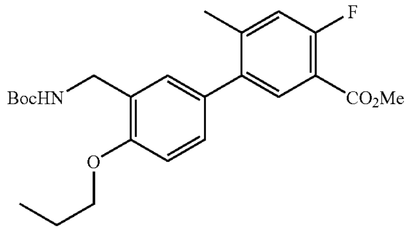

The title compound was obtained in the same way as Production Example 156a) and 156b) except for using methyl 3-bromo-4-methyl-6-fluorobenzoate.

Example 212b 3-(3-{[(2,4-Dichlorobenzoyl)amino]methyl}-4-propoxyphenyl)-4-methyl-6-fluorobenzoic Acid

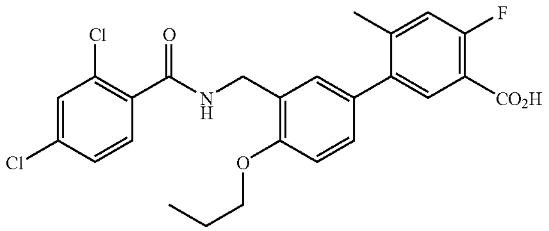

The title compound was obtained in the same way as Example 1e) except for using 3-(3-{[(t-butoxycarbonyl)amino]methyl}-4-propoxyphenyl)-4-methyl-6-fluorobenzoate.

MS m/e (ESI) 490 ($MH^+$).

Example 213

3-(3-{[(4-Chloro-2-fluorobenzoyl)amino]-methyl}-4-propoxyphenyl)-4-methyl-6-fluorobenzoic Acid

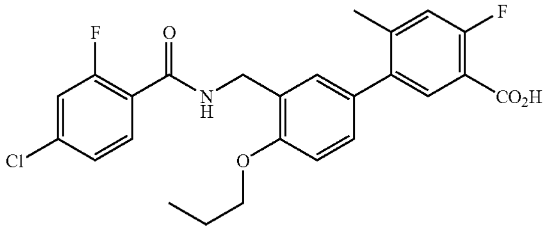

The title compound was obtained in the same way as Example 212b) except for using 4-chloro-2-fluorobenzoic acid.

MS m/e (ESI) 474 ($MH^+$).

Example 214

3-(3-{[(4-Trifluoromethyl-2-fluorobenzoyl)amino]methyl}-4-propoxyphenyl)-4-methyl-6-fluorobenzoic Acid

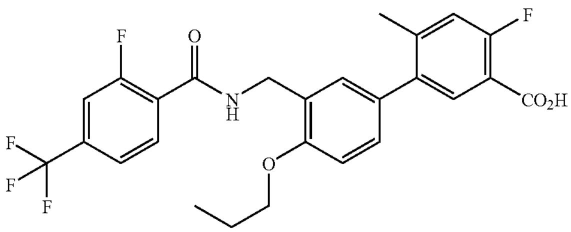

The title compound was obtained in the same way as Example 212b) except for using 4-trifluoromethyl-2-fluorobenzoic acid.

MS m/e (ESI) 508 ($MH^+$).

Example 215

3-(3-{[(4-Propoxy-2-chlorobenzoyl)amino]methyl}-4-propoxyphenyl)-4-methyl-6-fluorobenzoic Acid

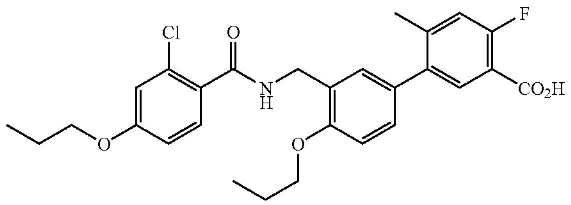

The title compound was obtained in the same way as Example 212b) except for using 4-propoxy-2-chlorobenzoic acid.

MS m/e (ESI) 514 ($MH^+$).

Example 216

3-(3-{[(4-Isopropoxy-2-chlorobenzoyl)amino]methyl}-4-propoxyphenyl)-4-methyl-6-fluorobenzoic Acid

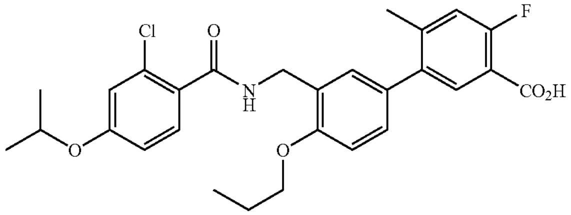

The title compound was obtained in the same way as Example 212b) except for using 4-isopropoxy-2-chlorobenzoic acid.

MS m/e (ESI) 514 ($MH^+$).

Example 217

3-(3-{[(2,4-Dichlorobenzoyl)amino]methyl}-4-methoxyphenyl)-3-phenylacetic Acid

Production Example 217a

Methyl 2-[5-(3-[(t-butoxycarbonyl)amino]methyl-4-methoxyphenyl)-3-phenyl]acetate

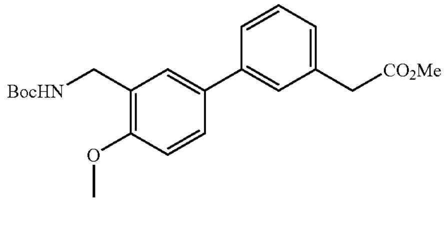

The title compound was obtained in the same way as Production Example 1d) except for using methyl 3-bromobenzoate.

Example 217b 3-(3-{[(2,4-Dichlorobenzoyl)amino]methyl}-4-methoxyphenyl)-3-phenylacetic Acid

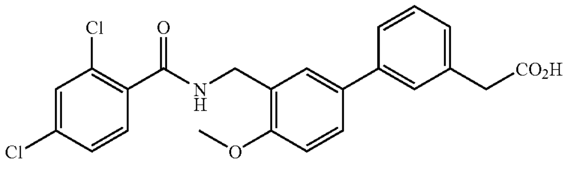

The title compound was obtained in the same way as Example 1e) except for using methyl 2-[5-(3-[(t-butoxycarbonyl)amino]-methyl-4-methoxyphenyl)-3-phenyl]acetate.

MS m/e (ESI) 444 ($MH^+$).

Example 218

3-(3-{[(4-Chloro-2-fluorobenzoyl)amino]-methyl}-4-methoxyphenyl)-3-phenylacetic Acid

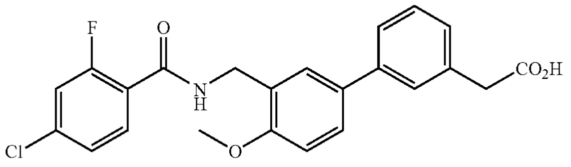

The title compound was obtained in the same way as Example 217b) except for using 4-chloro-2-fluorobenzoic acid.

MS m/e (ESI) 428($MH^+$).

Example 219

3-(3-{[(4-Bromo-2-fluorobenzoyl)amino]methyl}-4-methoxyphenyl)-3-phenylacetic Acid

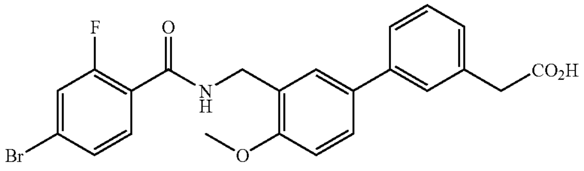

The title compound was obtained in the same way as Example 217b) except for using 4-bromo-2-fluorobenzoic acid.

MS m/e (ESI) 472 ($MH^+$).

Example 220

3-(3-{[(4-Trifluoromethyl-2-fluorobenzoyl)amino]methyl}-4-methoxyphenyl)-3-phenylacetic Acid

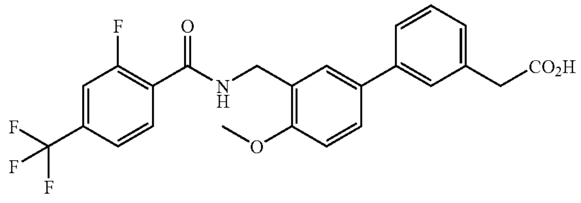

The title compound was obtained in the same way as Example 217b) except for using 4-trifluoromethyl-2-fluorobenzoic acid.

MS m/e (ESI) 462 ($MH^+$).

Example 221

3-(3-{[(4-Propoxy-2-chlorobenzoyl)amino]-methyl)-4-methoxyphenyl)-3-phenylacetic Acid

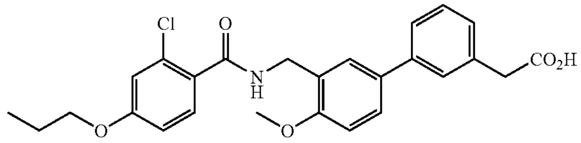

The title compound was obtained in the same way as Example 217b) except for using 4-propoxy-2-chlorobenzoic acid.

MS m/e (ESI) 468 ($MH^+$).

Example 222

3-(3-{[(4-Isopropoxy-2-chlorobenzoyl)amino]-methyl}-4-methoxyphenyl)-3-phenylacetic Acid

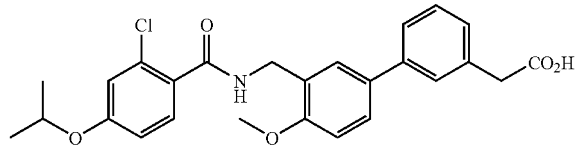

The title compound was obtained in the same way as Example 217b) except for using 4-isopropoxy-2-chlorobenzoic acid $^1$H-NMR ($CDCl_3$).

δ: 1.25 (d, J=6.0 Hz, 6H) 3.71 (s, 2H) 3.85 (s, 3H) 4.43 (d, J=4.8 Hz, 2H) 4.69 (sept, J=6.0 Hz, 1H) 6.94 (dd, J=2.4, 8.4 Hz, 1H) 7.03 (d, J=2.4 Hz, 1H) 7.08 (d, J=8.8 Hz, 1H) 7.19 (d, 7.6 Hz, 1H) 7.34-7.41 (m, 2H) 7.46 (d, J=1.6 Hz, 2H) 7.52 (dd, J=2.4, 8.4 Hz, 1H) 7.57 (d, J=2.0 Hz, 1H) 8.73 (t, J=6.0 Hz, 1H).

MS m/e (ESI) 468 ($MH^+$).

Example 223

3-{4-Methoxy-3-[({[4-methyl-2-(4-methylphenyl)-1,3-thiazol-5-yl]carbonyl)amino)methyl]-phenyl}-3-phenylacetic Acid

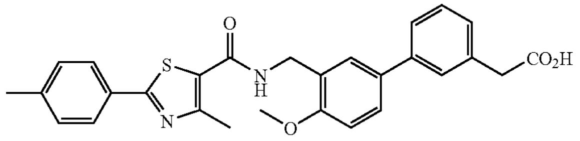

The title compound was obtained in the same way as Example 217b) except for using 4-methyl-2-(4-methylphenyl)-1,3-thiazol-5-carboxylic Acid.

MS m/e (ESI) 487 ($MH^+$).

Example 224

3-(3-{[(2,4-Dichlorobenzoyl)amino]methyl}-4-propoxyphenyl)-3-phenylacetic Acid

Production Example 224a

Methyl 2-[5-(3-[(t-butoxycarbonyl)amino]methyl-4-hydroxyphenyl)-3-phenyl]acetate

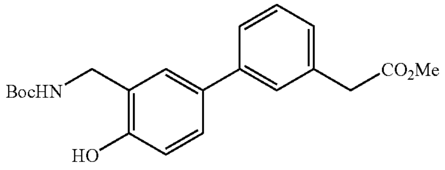

The title compound was obtained in the same way as Production Example 156a) except for using methyl 3-bromobenzoate.

$^1$H-NMR ($CDCl_3$).

δ: 1.46 (s, 9H) 3.67 (s, 2H) 3.71 (s, 3H) 4.79 (d, J=6.4 Hz, 2H) 5.29 (br, 1H) 7.01 (dd, J=1.2, 8.4 Hz, 1H) 7.21 (dd, J=1.2, 8.8 Hz, 1H) 7.28 (d, J=2.0 Hz, 1H) 7.36 (dt, J=1.2, 7.6 Hz, 1H) 7.42-7.46 (m, 3H) 9.04 (br, 1H).

Production Example 224b

Methyl 2-[5-(3-[(t-butoxycarbonyl)amino]methyl-4-propoxyphenyl)-3-phenyl]acetate

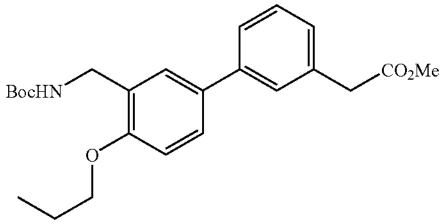

The title compound was obtained in the same way as Production Example 156b) except for using methyl 2-[5-(3-[(t-butoxycarbonyl)amino]methyl-4-hydroxyphenyl)-3-phenyl]acetate.

Example 224c 3-(3-{[(2,4-Dichlorobenzoyl)amino]methyl}-4-propoxyphenyl)-3-phenylacetic Acid

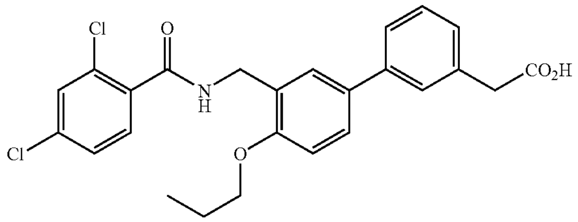

The title compound was obtained in the same way as Example 1e) except for using methyl 2-[5-(3-[(t-butoxycarbonyl)amino]-methyl-4-propoxyphenyl)-3-phenyl]acetate.

$^1$H-NMR ($CDCl_3$).

δ: 1.06 (t, J=7.2 Hz, 3H) 1.86 (q, J=6.4 Hz, 2H) 3.71 (s, 2H) 4.02 (t, J=6.4 Hz, 2H) 4.71 (d, J=6.0 Hz, 2H) 6.84 (brt, J=5.6 Hz, 1H) 6.93 (d, J=8.4 Hz, 1H) 7.23 (brd, J=7.6 Hz, 1H) 7.29 (dd, J=2.0, 8.4 Hz, 1H) 7.37 (t, J=8.4 Hz, 1H) 7.40 (d, J=2.0 Hz, 1H) 7.46-7.50 (m, 3H) 7.59 (d, J=2.0 Hz, 1H) 7.65 (d, J=8.4 Hz, 1H).

MS m/e (ESI) 472 ($MH^+$).

Example 225

3-(3-{[(4-Chloro-2-fluorobenzoyl)amino]-methyl}-4-propoxyphenyl)-3-phenylacetic Acid

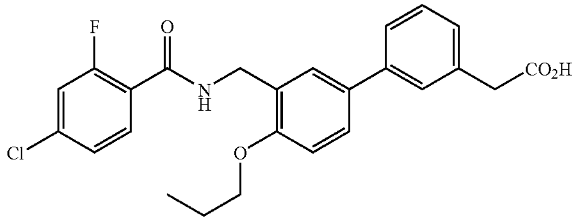

The title compound was obtained in the same way as Example 224c) except for using 4-chloro-2-fluorobenzoic acid.

$^1$H-NMR ($CDCl_3$).

δ: 1.06 (t, J=7.2 Hz, 3H) 1.86 (q, J=6.4 Hz, 2H) 3.71 (s, 2H) 4.04 (t, J=6.8 Hz, 2H) 4.72 (d, J=5.2 Hz, 2H) 6.94 (d, J=8.4 Hz, 1H) 7.13 (dd, J=2.0, 11.6 Hz, 1H) 7.21-7.25 (m, 2H) 7.36 (br, 1H) 7.37 (t, J=7.6 Hz, 1H) 7.45-7.49 (m, 3H) 7.57 (d, J=2.4 Hz, 1H) 8.07 (t, J=8.4 Hz, 1H).

MS m/e (ESI) 456($MH^+$).

Example 226

3-(3-{[(4-Trifluoromethyl-2-fluorobenzoyl)amino] methyl}-4-propoxyphenyl)-3-phenylacetic Acid

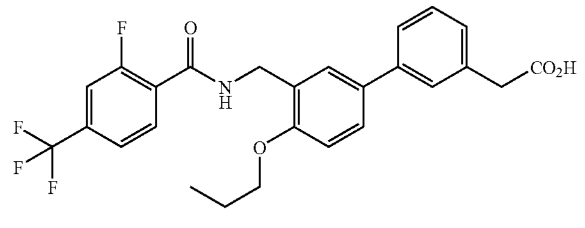

The title compound was obtained in the same way as Example 224c) except for using 4-trifluoromethyl-2-fluorobenzoic acid $^1$H-NMR ($CDCl_3$).

δ: 1.09 (t, J=7.2 Hz, 3H) 1.90 (q, J=7.2 Hz, 2H) 3.71 (s, 2H) 4.05 (t, J=7.6 Hz, 2H) 4.74 (d, J=4.8 Hz, 2H) 6.95 (d, J=8.4 Hz, 1H) 7.23 (brd, J=7.6 Hz, 1H) 7.38 (t, J=8.4 Hz, 1H) 7.39-7.42 (m, 1H) 7.45-7.53 (m, 5H) 7.58 (d, J=2.4 Hz, 1H) 8.25 (t, J=7.6 Hz, 1H).

MS m/e (ESI) 490 ($MH^+$).

Example 227

3-(3-{[(4-Propoxy-2-chlorobenzoyl)amino]-methyl}-4-propoxyphenyl)-3-phenylacetic Acid

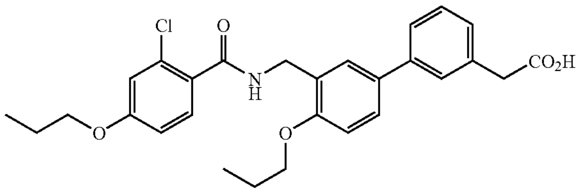

The title compound was obtained in the same way as Example 224c) except for using 4-propoxy-2-chlorobenzoic acid.

$^1$H-NMR ($CDCl_3$).

δ: 1.02 (t, J=7.6 Hz, 3H) 1.06 (t, J=7.6 Hz, 3H) 1.80 (q, J=6.8 Hz, 2H) 1.86 (q, J=6.8 Hz, 2H) 3.70 (s, 2H) 3.91 (t, J=6.4 Hz, 2H) 4.01 (t, J=6.4 Hz, 2H) 4.72 (d, J=6.0 Hz, 2H) 6.82 (dd, J=2.8, 8.8 Hz, 1H) 6.93 (d, J=8.8 Hz, 1H) 6.99 (brt, J=6.0 Hz, 1H) 7.22 (brd, J=7.6 Hz, 1H) 7.37 (t, J=8.4 Hz, 1H) 7.46-7.49 (m, 4H) 7.60 (d, J=2.4 Hz, 1H) 7.74 (d, J=8.8 Hz, 1H).

MS m/e (ESI) 496 ($MH^+$).

Example 228

3-(3-{[(4-Isopropoxy-2-chlorobenzoyl)amino]-methyl}-4-propoxyphenyl)-3-phenylacetic Acid

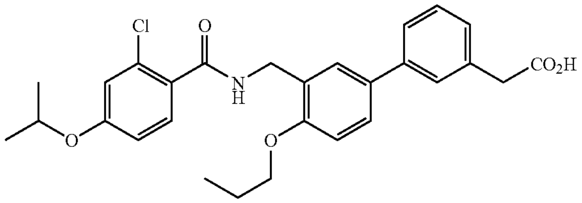

The title compound was obtained in the same way as Example 224c) except for using 4-isopropoxy-2-chlorobenzoic acid.

$^1$H-NMR ($CDCl_3$).

δ: 1.06 (t, J=7.6 Hz, 3H) 1.33 (d, J=6.0 Hz, 6H) 1.86 (q, J=6.8 Hz, 2H) 3.70 (s, 2H) 4.01 (t, J=6.8 Hz, 2H) 4.55 (sept, J=6.0 Hz, 1H) 4.72 (d, J=6.0 Hz, 2H) 6.80 (dd, J=2.4, 8.8 Hz, 1H) 6.87 (d, J=2.4 Hz, 1H) 6.93 (d, J=8.4 Hz, 1H) 6.99 (brt, J=6.0 Hz, 1H) 7.22 (brd, J=7.2 Hz, 1H) 7.37 (t, J=8.4 Hz, 1H) 7.46-7.48 (m, 3H) 7.60 (d, J=2.4 Hz, 1H) 7.74 (d, J=8.8 Hz, 1H).

MS m/e (ESI) 496 ($MH^+$).

Example 229

2-[3-(5-[(2,4-Dichlorobenzoyl)amino]methyl-6-ethoxy-3-pyridyl)phenyl]acetic Acid

Production Example 229a t-Butyl N-[2-ethoxy-5-(4,4,5,5-tetramethyl-1,3,2-dioxaborolan-2-yl)-3-pyridyl]methylcarbamate

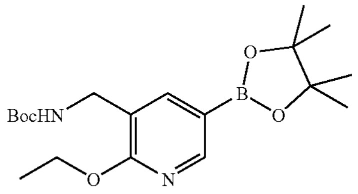

The title compound was obtained in the same way as Production Example 1c) except for using N-[(5-bromo-2-methoxy-3-pyridyl)methyl]carbamate.

$^1$H-NMR ($CDCl_3$).

δ: 1.33(s, 12H) 1.40 (t, J=6.8 Hz, 3H) 1.45 (s, 9H) 4.27 (d, J=5.2 Hz, 2H) 4.43 (q, J=6.8 Hz, 2H) 4.99 (br, 1H) 7.85 (d, J=1.2 Hz, 1H) 8.42 (d, J=1.6 Hz, 1H).

Production Example 229b

Methyl 2-[3-(5-[(t-butoxycarbonyl)amino]methyl-6-ethoxy-3-pyridyl)phenyl]acetate

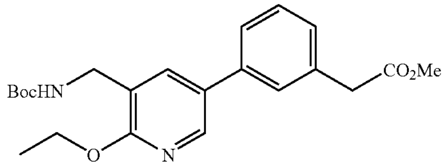

The title compound was obtained in the same way as Production Example 1d) except for using N-[2-ethoxy-5-(4,4,5,5-tetramethyl-1,3,2-dioxaborolan-2-yl)-3-pyridyl]methylcarbamate and methyl 3-bromophenylacetate.

Example 229c

2-[3-(5-[(2,4-dichlorobenzoyl)amino]methyl-6-ethoxy-3-pyridyl)phenyl]acetic Acid

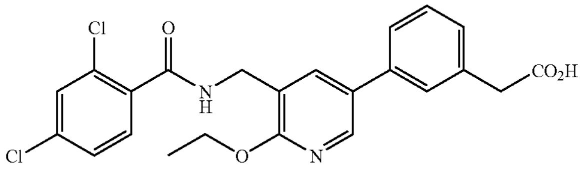

The title compound was obtained in the same way as Example 1e) except for using methyl 2-[3-(5-[(t-butoxycarbonyl)amino]-methyl-6-ethoxy-3-pyridyl)phenyl]acetate.

$^1$H-NMR ($CDCl_3$).

δ: 1.44 (t, J=6.8 Hz, 3H) 3.72 (s, 2H) 4.47 (q, J=7.2 Hz, 2H) 4.65 (d, J=6.0 Hz, 2H) 6.98 (br, 1H) 7.26-7.30 (m, 1H) 7.31 (dd, J=2.0, 8.4 Hz, 1H) 7.38-7.46 (m, 4H) 7.68 (d, J=8.4 Hz, 1H) 7.86 (d, J=2.4 Hz, 1H) 8.30 (d, J=2.4 Hz, 1H).

MS m/e (ESI) 459 ($MH^+$).

Example 230

2-[3-(5-[(2-Fluoro-4-dichlorobenzoyl)amino]-methyl-6-ethoxy-3-pyridyl)phenyl]acetic Acid

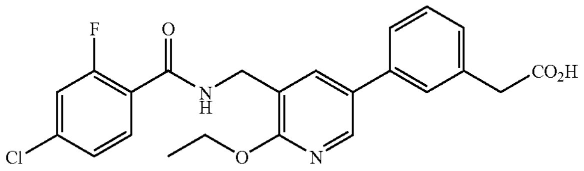

The title compound was obtained in the same way as Example 229c) except for using 4-chloro-2-fluorobenzoic acid.

$^1$H-NMR ($CDCl_3$).

δ: 1.47 (t, J=6.8 Hz, 3H) 3.71 (s, 2H) 4.49 (q, J=7.2 Hz, 2H) 4.67 (d, J=5.2 Hz, 2H) 7.16 (dd, J=2.7, 11.6 Hz, 1H) 7.23-7.29 (m, 2H) 7.37-7.51 (m, 4H) 7.83 (d, J=2.8 Hz, 1H) 8.07 (t, J=8.8 Hz, 1H) 8.29 (d, J=2.4 Hz, 1H).

MS m/e (ESI) 443 ($MH^+$).

Example 231

2-[3-(5-[(2-Fluoro-4-trifluoromethylbenzoyl)amino] methyl-6-ethoxy-3-pyridyl)phenyl]acetic Acid

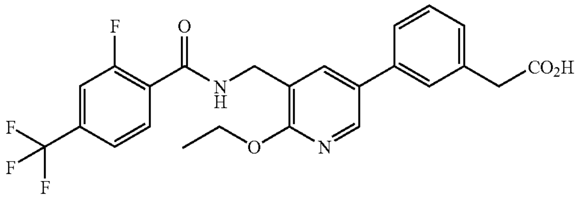

The title compound was obtained in the same way as Example 229c) except for using 4-trifluoromethyl-2-fluorobenzoic acid.

$^1$H-NMR ($CDCl_3$).

δ: 1.47 (t, J=7.2 Hz, 3H) 3.72 (s, 2H) 4.50 (q, J=6.8 Hz, 2H) 4.69 (d, J=4.8 Hz, 2H) 7.25-7.29 (m, 1H) 7.38-7.46 (m, 4H) 7.51-7.56 (m, 2H) 7.83 (d, J=2.4 Hz, 1H) 8.25 (t, J=7.2 Hz, 1H) 8.30 (d, J=2.4 Hz, 1H).

MS m/e (ESI) 477 ($MH^+$).

Example 232

2-[3-(5-[(2-Chloro-4-propoxybenzoyl)amino]-methyl-6-ethoxy-3-pyridyl)phenyl]acetic Acid

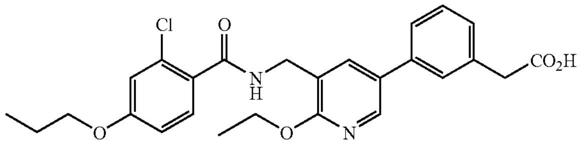

The title compound was obtained in the same way as Example 229c) except for using 4-propoxy-2-chlorobenzoic acid.

$^1$H-NMR ($CDCl_3$).

δ: 1.02 (t, J=7.2 Hz, 3H) 1.45 (t, J=6.8 Hz, 3H) 1.80 (q, 2H, J=7.2Hz) 3.71 (s, 2H) 3.92 (t, J=6.8 Hz, 2H) 4.47 (q, J=6.8 Hz, 2H) 4.66 (d, J=6.0 Hz, 2H) 6.84 (dd, J=2.8, 8.8 Hz, 1H) 6.90 (d, J=2.4 Hz, 1H) 7.14 (t, J=6.0 Hz, 1H) 7.27 (brd, J=6.4 Hz, 1H) 7.39 (t, J=8.0 Hz, 1H) 7.42-7.46 (m, 2H) 7.77 (d, J=8.8 Hz, 1H) 7.88 (d, J=2.4 Hz, 1H) 8.29 (d, J=2.4 Hz, 1H).

MS m/e (ESI) 483 ($MH^+$).

Example 233

2-[3-(5-[(2-Chloro-4-isopropoxybenzoyl)amino] methyl-6-ethoxy-3-pyridyl)phenyl]acetic Acid

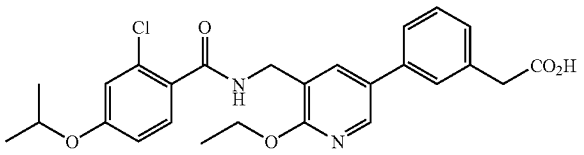

The title compound was obtained in the same way as Example 229c) except for using 4-isopropoxy-2-chlorobenzoic acid.

$^1$H-NMR ($CDCl_3$).

δ: 1.33 (d, J=6.0 Hz, 6H) 1.44 (t, J=7.2 Hz, 3H) 3.71 (s, 2H) 4.47 (q, J=7.2 Hz, 2H) 4.56 (sept, J=6.0 Hz, 1H) 4.66 (d, J=6.0 Hz, 2H) 6.82 (dd, J=2.4, 8.8 Hz, 1H) 6.88 (d, J=2.4 Hz, 1H) 7.13 (brt, J=6.0 Hz, 1H) 7.27 (brd, J=8.8 Hz, 1H) 7.39 (t, J=7.6 Hz, 1H) 7.43-7.47 (m, 2H) 7.76 (d, J=8.8 Hz, 1H) 7.87 (d, J=2.4 Hz, 1H) 8.29 (d, J=2.4 Hz, 1H).

MS m/e (ESI) 483 ($MH^+$).

Example 234

3-(2-[(2-Chloro-4-propoxybenzoyl)amino]methyl-4-methoxyphenyl)benzoic Acid

Production Example 234a t-Butyl N-(2-bromo-5-methoxybenzyl)carbamate

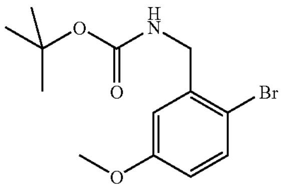

3-Methoxybenzylamine (23 g) was dissolved in 150 ml of tetrahydrofuran, and a solution of 32 g of t-butyl dicarbonate in tetrahydrofuran (50 ml) was added thereto. The mixture was stirred at room temperature for 1 hour, and then the solvent was evaporated. The residue was dissolved in ethyl acetate and successively washed with 1N hydrochloric acid and brine. The organic layer was dried over anhydrous magnesium sulfate, and the solvent was evaporated to give t-butyl N-(3-methoxybenzyl)carbamate. The resulting t-butyl N-(3-methoxybenzyl)carbamate was then dissolved in 250 ml of acetonitrile, 30 g of N-bromosuccinimide was added thereto under ice-cooling, the mixture was stirred at room temperature for 3 hours, and then the solvent was evaporated. The residue was dissolved in ethyl acetate and washed with water and then with brine. The organic layer was dried over anhydrous magnesium sulfate, and the solvent was evaporated. The residue was purified by a silica gel column, to give 36 g of the title compound in the 2:1 hexane-diethyl ether fraction.

$^1$H-NMR ($CDCl_3$).

δ: 1.43 (s, 9H) 3.78 (s, 3H) 4.34 (d, J=6.4 Hz, 2H) 5.00 (br, 1H) 6.69 (dd, J=3.2, 8.8 Hz, 1H) 6.93 (d, J=3.2 Hz, 1H) 7.41 (d, J=8.8 Hz, 1H).

Production Example 234b

Methyl 3-(2-{[(t-butoxycarbonyl)amino]methyl}-4-methoxyphenyl)benzoate

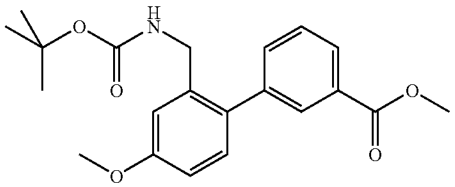

1.26 g of t-Butyl N-(2-bromo-5-methoxybenzyl)carbamate, 790 mg of 3-methoxycarbonylphenylboronic acid, 231 mg of tetrakistriphenyl phosphine palladium and 2.20 g of potassium carbonate were dissolved in 25 ml of toluene, and the mixture was heated at 100° C. for 7 hours in a nitrogen atmosphere. The reaction mixture was filtered through Celite, and the filtrate was evaporated. The residue was purified by silica gel column, to give 470 mg of the title compound in the 4:1 hexane-ethyl acetate fraction.

$^1$H-NMR ($CDCl_3$).

δ: 1.42 (s, 9H) 3.85 (s, 3H) 3.92 (s, 3H) 4.23 (brd, J=5.6 Hz, 2H) 4.65 (br, 1H) 6.86 (dd, J=2.8, 8.4 Hz, 1H) 7.00 (d, J=2.8 Hz, 1H) 7.16 (d, J=8.4 Hz, 1H) 7.46-7.48 (m, 2H) 7.88 (s, 1H) 7.94 (t, J=2.8 Hz, 1H).

Example 234c 3-(2-[(2-Chloro-4-propoxybenzoyl)amino]-methyl-4-methoxyphenyl)benzoic acid

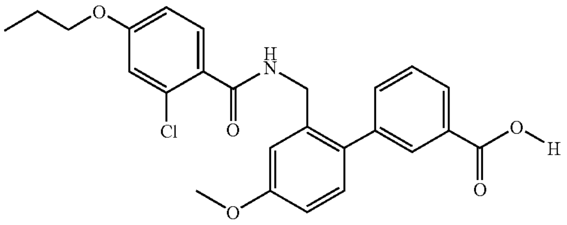

2 mL of 4N HCl/dioxane was added to 50 mg of methyl 3-(2-{[(t-butoxycarbonyl)amino]methyl}-4-methoxyphenyl)benzoate and stirred at room temperature for 1 hour. The reaction mixture was concentrated, and then the residue was dissolved in 2 mL of N,N-dimethylformamide, and to 1 mL of aliquot thereof were added 15 mg of 2-chloro-4-propoxybenzoic acid, 9 μL of diethyl cyanophosphonate and 17 μL of triethylamine, and the mixture was stirred at room temperature for 17 hours. The reaction mixture was diluted with water and extracted with ethyl acetate. The organic layer was concentrated, then the residue was dissolved in 0.4 mL of methanol, 0.1 mL of 5N aqueous sodium hydroxide was added thereto, and the mixture was stirred at room temperature for 5 hours. The reaction mixture was concentrated and then neutralized with 1 N hydrochloric acid. The reaction mixture was extracted with ethyl acetate and then purified by HPLC using a reverse phase system column and a water-acetonitrile-trifluoroacetic acid eluent, to give 7.14 mg of the title compound.

MS m/e (ESI) 454 ($MH^+$).

Example 235

3-[2-([2-Fluoro-4-(trifluoromethyl)benzoyl]-aminomethyl)-4-methoxyphenyl]benzoic Acid

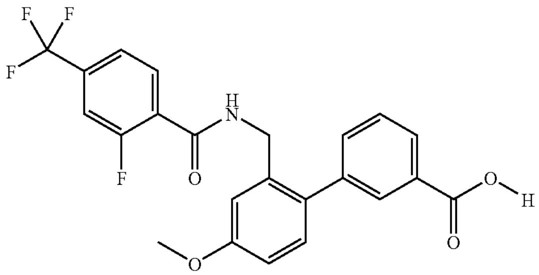

The title compound was obtained in the same way as Example 234c) except for using 2-fluoro-4-(trifluoromethyl) benzoic Acid.

MS m/e (ESI) 447 ($MH^+$).

Example 236

3-(4-Methoxy-2-[([4-methyl-2-(4-methylphenyl)-1,3-thiazol-5-yl]carbonylamino)methyl]phenyl)benzoic Acid

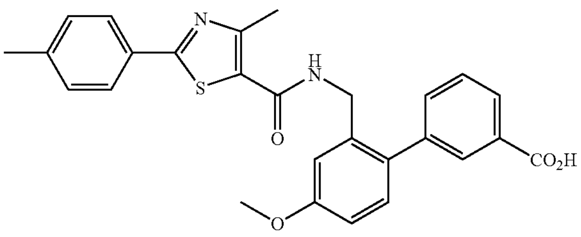

The title compound was obtained in the same way as Example 234c) except for using 2-(4-methylphenyl)-5-methyl-1,3-thiazol-4-carboxylic Acid.

MS m/e (ESI) 473 ($MH^+$).

Example 237

3-(2-[(2,4-Dichlorobenzoyl)amino]methyl-4-methoxyphenyl)benzoic Acid

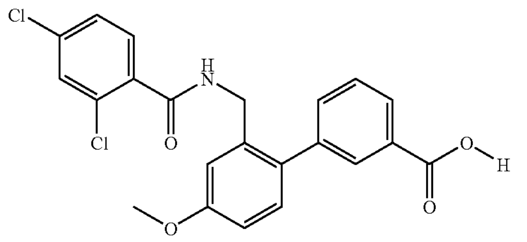

The title compound was obtained in the same way as Example 234c) except for using 2,4-dichlorobenzoic acid.

MS m/e (ESI) 430 ($MH^+$).

Example 238

3-[2-([2-Chloro-4-(4-chlorophenyl)benzoyl]amino)methyl-4-methoxyphenyl]benzoic Acid

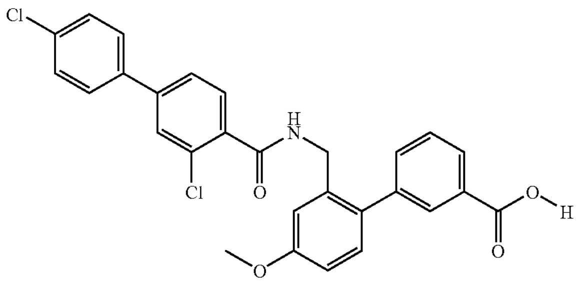

The title compound was obtained in the same way as Example 234c) except for using 2-chloro-4-(4'-chlorophenyl) benzoic Acid.

MS m/e (ESI) 506 ($MH^+$).

Example 239

3-[4-Methoxy-2-([(5-methyl-2-phenyl-1,3-thiazol-4-yl)carbonyl]aminomethyl)phenyl]benzoic Acid

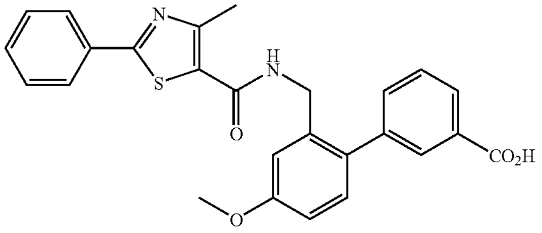

The title compound was obtained in the same way as Example 234c) except for using 4-methyl-2-phenyl-1,3-thiazol-5-carboxylic Acid.

MS m/e (ESI) 459 ($MH^+$).

Example 240

3-(2-[([2-(4-Chlorophenyl)-4-methyl-1,3-thiazol-5-yl]carbonylamino)methyl]-4-methoxyphenyl)benzoic Acid

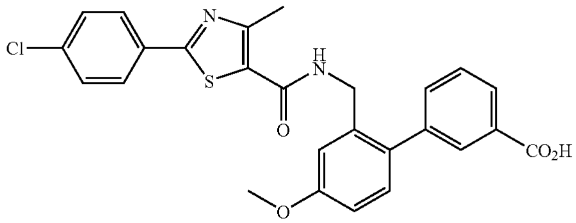

The title compound was obtained in the same way as Example 234c) except for using 2-(4-chlorophenyl)-4-methyl-1,3-thiazol-5-carboxylic Acid.

MS m/e (ESI) 493 ($MH^+$).

Example 241

3-(2-[([2-(4-Methoxyphenyl)-4-methyl-1,3-thiazol-5-yl]-carbonylamino)methyl]-4-methoxyphenyl) benzoic Acid

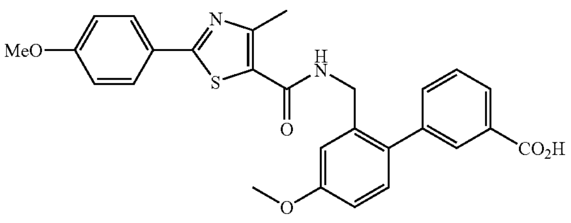

The title compound was obtained in the same way as Example 234c) except for using 2-(4-methoxy phenyl)-4-methyl-1,3-thiazol-5-carboxylic Acid.

MS m/e (ESI) 489 ($MH^+$).

Example 242

3-(2-[(2-Chloro-4-propoxybenzoyl)amino]methyl-4-methoxyphenyl)-6-methoxybenzoic Acid Production Example 242a Methyl 2-methoxy-5-(4,4,5,5-tetramethyl-1,3,2-dioxaborolan-2-yl)benzoate

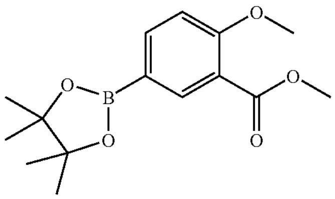

1.6 g of Methyl 3-bromo-5-methoxybenzoate, 1.9 g of bis(pinacolato)diboron, 160 mg of dichlorobistriphenyl phosphinoferrocene palladium and 1.9 of g potassium acetate were dissolved in 25 ml of dimethyl sulfoxide, and the mixture was stirred at 100° C. for 24 hours in a nitrogen atmosphere. The reaction mixture was diluted with ethyl acetate and water and, filtered through Celite. The filtrate was washed with water and brine, dried over anhydrous magnesium sulfate, and the solvent was evaporated. The residue was purified by silica gel column, to give 1.1 g of the title compound in the 4:1 hexane-ethyl acetate fraction.

$^1$H-NMR ($CDCl_3$).

δ: 1.34 (s, 12H) 3.88 (s, 3H) 3.93 (s, 3H) 6.96 (d, J=8.4 Hz, 1H) 7.90 (dd, J=1.6, 8.4 Hz, 1H) 8.22 (d, J=1.6 Hz, 1H).

Production Example 242b

Methyl 5-(2-{[(t-butoxycarbonyl)amino]methyl}-4-methoxyphenyl)-2-methoxybenzoate

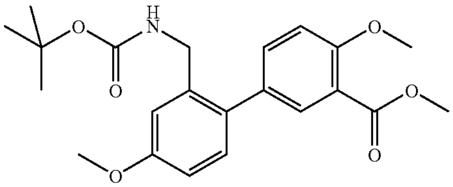

570 mg of t-butyl N-(2-bromo-5-methoxybenzyl)carbamate, 440 mg of methyl 2-methoxy-5-(4,4,5,5-tetramethyl-1,3,2-dioxaborolan-2-yl)benzoate, 86 mg of dichlorobistriphenyl phosphinoferrocene palladium and 1.0 g of potassium carbonate were dissolved in 15 ml of dimethoxyethane, and the mixture was heated at 80° C. for 24 hours in a nitrogen atmosphere. The reaction mixture was filtered through Celite, and the filtrate was evaporated. The residue was purified by silica gel column, to give 680 mg of the title compound in the 3:1 hexane-ethyl acetate fraction.

$^1$H-NMR ($CDCl_3$).

δ: 1.42 (s, 9H) 3.84 (s, 3H) 3.88 (s, 3H) 3.94 (s, 3H) 4.23 (brd, J=6.0 Hz, 2H) 4.65 (br, 1H) 6.84 (dd, J=2.8, 8.4 Hz, 1H) 6.97 (d, J=2.8 Hz, 1H) 7.01(d, J=8.8 Hz, 1H) 7.14 (d, J=8.4 Hz, 1H) 7.38 (dd, J=2.4, 8.8 Hz, 1H) 7.70 (d, J=2.4 Hz, 1H).

Example 242c 3-(2-[(2-Chloro-4-propoxybenzoyl)amino]-methyl-4-methoxyphenyl)-6-methoxybenzoic Acid

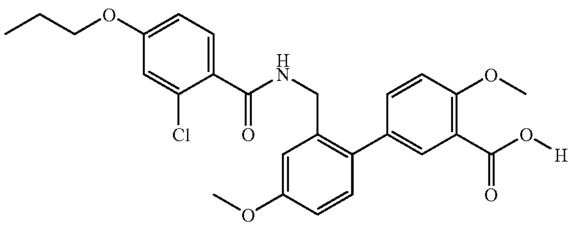

The title compound was obtained in the same way as Example 1e) except for using 2-chloro-4-propoxybenzoic acid and methyl 5-(2-{[(t-butoxycarbonyl)amino]methyl}-4-methoxyphenyl)-2-methoxybenzoate.

MS m/e (ESI) 484 ($MH^+$).

Example 243

6-Methoxy-3-(4-methoxy-2-[([4-methyl-2-(4-methylphenyl)-1,3-thiazol-5-yl]carbonylamino)methyl]phenyl)benzoic Acid

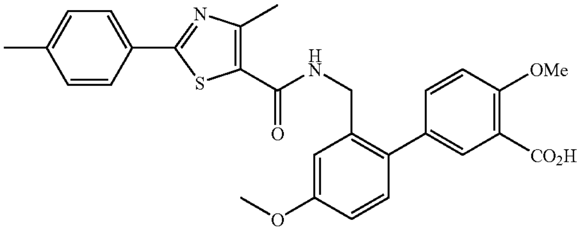

The title compound was obtained in the same way as Example 242c) except for using 2-(4-methylphenyl)-4-methyl-1,3-thiazol-5-carboxylic Acid.

MS m/e (ESI) 503 ($MH^+$).

Example 244

3-(2-[([2-(4-Chlorophenyl)-4-methyl-1,3-thiazol-5-yl]carbonylamino)methyl]-4-methoxyphenyl)-6-methoxybenzoic Acid

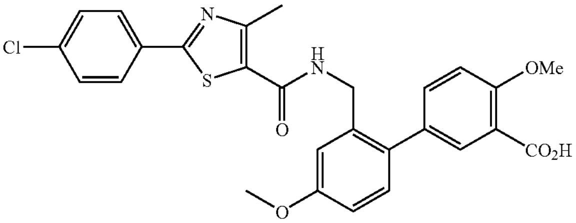

The title compound was obtained in the same way as Example 242c) except for using 2-(4-chlorophenyl)-4-methyl-1,3-thiazol-5-carboxylic Acid MS m/e (ESI) 523 ($MH^+$). .

Example 245

3-[2-([2-Chloro-4-(4-chlorophenyl)benzoyl]amino) methyl-4-methoxyphenyl]-6-methylbenzoic Acid Production Example 245a Methyl 2-methyl-5-(4,4,5,5-tetramethyl-1,3,2-dioxaborolan-2-yl)benzoate

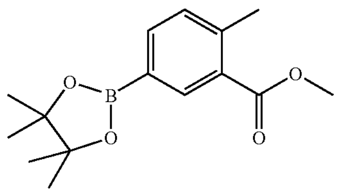

The title compound was obtained in the same way as Production Example 242a) except for using methyl 3-bromo-5-methylbenzoate.

$^1$H-NMR ($CDCl_3$).

δ: 1.35 (s, 12H) 2.61(s, 3H) 3.88 (s, 3H) 7.25 (d, J=7.6 Hz, 1H) 7.81 (dd, J=1.2, 7.6 Hz, 1H) 8.32 (d, J=1.2 Hz, 1H).

Production Example 245b

Methyl 3-(2-{[(t-butoxycarbonyl)amino]methyl}-4-methoxyphenyl)-6-methylbenzoate

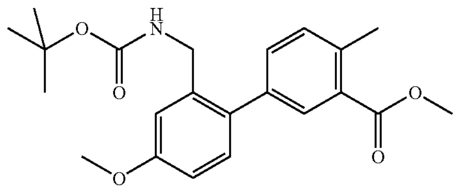

The title compound was obtained in the same way as Production Example 242b) except for using t-butyl N-(2-bromo-5-methoxybenzyl)carbamate and methyl 5-(4,4,5,5-tetramethyl-1,3,2-dioxaborolan-2-yl)benzoate.

$^1$H-NMR ($CDCl_3$).

δ: 1.42 (s, 9H) 2.63 (s, 3H) 3.84 (s, 3H) 3.88 (s, 3H) 4.23 (brd, J=6.0 Hz, 2H) 4.65 (br, 1H) 6.84 (dd, J=2.8, 8.4 Hz, 1H) 6.98 (d, J=2.8 Hz, 1H) 7.15 (d, J=8.4 Hz, 1H) 7.28-7.31 (m, 2H) 7.82 (d, J=2.0 Hz, 1H).

Example 245c

3-[2-([2-Chloro-4-(4-chlorophenyl)benzoyl]amino) methyl-4-methoxyphenyl]-6-methylbenzoic Acid

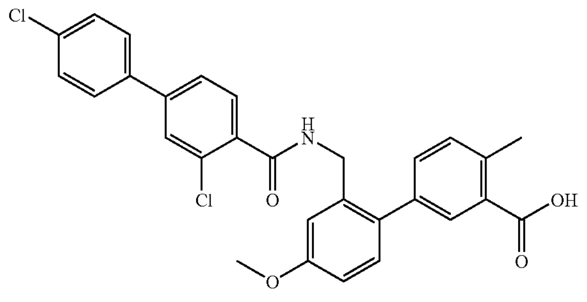

The title compound was obtained in the same way as Example 1e) except for using 2-chloro-4-(4'-chlorophenyl) benzoic acid and methyl 3-(2-{[(t-butoxycarbonyl)amino] methyl}-4-methoxyphenyl)-6-methylbenzoate.

MS m/e (ESI) 520 ($MH^+$).

Example 246

3-(2-[([2-(4-Chlorophenyl)-4-methyl-1,3-thiazol-5-yl]carbonylamino)methyl]-4-methoxyphenyl)-6-methylbenzoic Acid

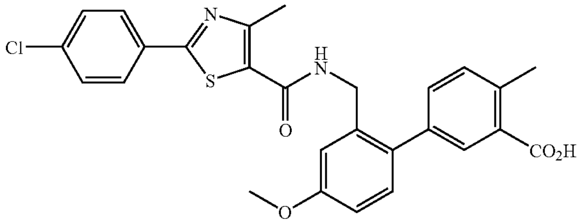

The title compound was obtained in the same way as Example 245c) except for using 2-(4-chlorophenyl)-4-methyl-1,3-thiazol-5-carboxylic Acid.

MS m/e (ESI) 507 ($MH^+$).

Example 247

2-[3-(2-[([2-(4-Chlorophenyl)-4-methyl-1,3-thiazol-5-yl]carbonylamino)methyl]-4-methoxyphenyl)phenyl]acetic Acid Production Example 247a Methyl 2-[3-(4,4,5,5-tetramethyl-1,3,2-dioxaborolan-2-yl)phenyl]acetate

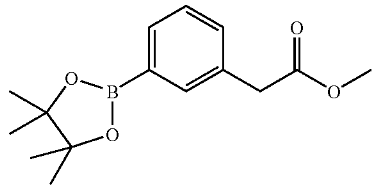

The title compound was obtained in the same way as Production Example 242a) except for using methyl 2-(3-bromophenyl)acetate.

$^1$H-NMR ($CDCl_3$).

δ: 1.34 (s, 12H) 3.64 (s, 2H) 3.68 (s, 3H) 6.96 (d, J=8.4 Hz, 1H) 7.34-7.39 (m, 2H) 7.70-7.72 (m, 2H).

Production Example 247b

Methyl 2-[3-(2-{[(t-butoxycarbonyl)amino]methyl}-4-methoxyphenyl)phenyl]acetate

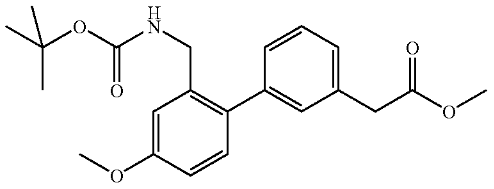

The title compound was obtained in the same way as Production Example 242b) except for using t-butyl N-(2-bromo-5-methoxybenzyl)carbamate and methyl 2-[3-(4,4,5,5-tetramethyl-1,3,2-dioxaborolan-2-yl)phenyl]acetate.

$^1$H-NMR ($CDCl_3$).

δ: 1.42 (s, 9H) 3.66 (s, 2H) 3.71 (s, 3H) 3.84 (s, 3H) 4.23 (brd, J=6.0 Hz, 2H) 4.72 (br, 1H) 6.85 (dd, J=2.8, 8.4 Hz, 1H) 7.00 (d, J=2.8 Hz, 1H) 7.15-7.19 (m, 4H) 7.35 (t, J=7.6 Hz, 1H).

Example 247c

2-[3-(2-[([2-(4-Chlorophenyl)-4-methyl-1,3-thiazol-5-yl]carbonylamino)methyl]-4-methoxyphenyl)phenyl]acetic Acid

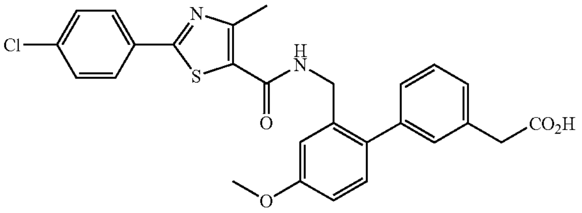

The title compound was obtained in the same way as Production Example 1e) except for using 2-(4-chlorophenyl)-4-methyl-1,3-thiazol-5-carboxylic acid and methyl 2-[3-(2-{[(t-butoxycarbonyl)amino]methyl}-4-methoxyphenyl)phenyl]acetate.

MS m/e (ESI) 507 ($MH^+$).

Example 248

2-[3-(2-[(2,4-Dichlorobenzoyl)amino]methyl-4-methoxyphenyl)phenyl]acetic Acid

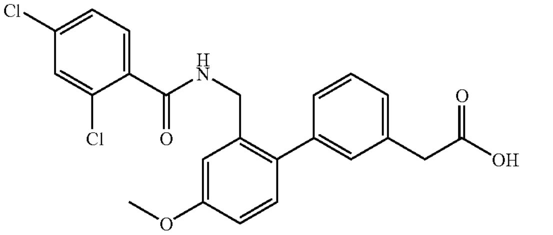

The title compound was obtained in the same way as Production Example 247c) except for using 2,4-dichlorobenzoic acid.

MS m/e (ESI) 444 ($MH^+$).

Example 249

2-[3-(2-[([2-(4-Chlorophenyl)-4-methyl-1,3-thiazol-5-yl]carbonylamino)methyl]-4-methoxyphenyl)-6-methoxyphenyl]acetic Acid Production Example 249a Methyl 2-[2-methoxy-5-(4,4,5,5-tetramethyl-1,3,2-dioxaborolan-2-yl)phenyl]acetate

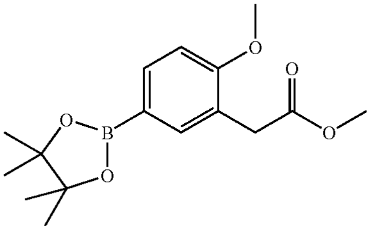

The title compound was obtained in the same way as Production Example 242a) except for using methyl 2-(3-bromo-6-methoxyphenyl)acetate.

$^1$H-NMR ($CDCl_3$).

δ: 1.33 (s, 12H) 3.63 (s, 2H) 3.67 (s, 3H) 3.83 (s, 3H) 6.87 (d, J=8.0 Hz, 1H) 7.61 (d, J=1.6 Hz, 1H) 7.73 (dd, J=1.6, 8.0 Hz, 1H).

Production Example 249b

Methyl 2-[3-(2-{[(t-butoxycarbonyl)amino]methyl}-4-methoxyphenyl)-6-methoxyphenyl]acetate

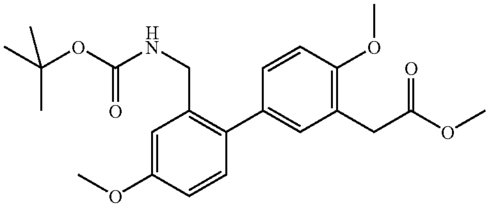

The title compound was obtained in the same way as Production Example 242b) except for using tertiary butyl N-(2-bromo-5-methoxybenzyl)carbamate and methyl 2-[2-methoxy-5-(4,4,5,5-tetramethyl-1,3,2-dioxaborolan-2-yl)phenyl]acetate.

$^1$H-NMR ($CDCl_3$).

δ: 1.42 (s, 9H) 3.66 (s, 2H) 3.70 (s, 3H) 3.83 (s, 3H) 3.85 (s, 3H) 4.24 (brd, J=6.0 Hz, 2H) 4.72 (br, 1H) 6.83 (dd, J=2.8, 8.4 Hz, 1H) 6.89 (d, J=8.4 Hz, 1H) 6.98 (d, J=2.8 Hz, 1H) 7.09 (d, J=2.8 Hz, 1H) 7.14 (dd, J=2.0, 8.4 Hz, 1H) 7.15 (d, J=8.4 Hz, 1H).

Example 249c

2-[3-(2-[([2-(4-Chlorophenyl)-4-methyl-1,3-thiazol-5-yl]carbonylamino)methyl]-4-methoxyphenyl)-6-methoxyphenyl]acetic Acid

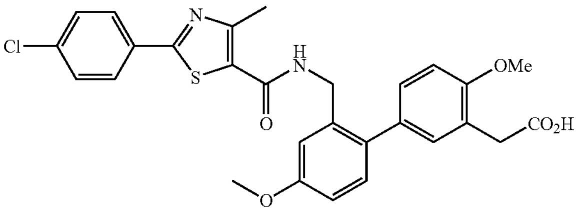

The title compound was obtained in the same way as Example 1e) except for using 2-(4-chlorophenyl)-4-methyl-1,3-thiazol-5-carboxylic acid and methyl 2-[3-(2-{[(t-butoxycarbonyl)amino]methyl}-4-methoxyphenyl)-6-methoxyphenyl]acetate.

MS m/e (ESI) 537 ($MH^+$).

Example 250

2-[3-(2-[(2,4-Dichlorobenzoyl)amino]methyl-4-methoxyphenyl)-6-methoxyphenyl]acetic Acid

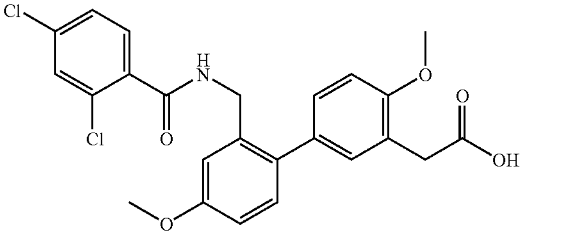

The title compound was obtained in the same way as Example 249c) except for using 2,4-dichlorobenzoic acid.

MS m/e (ESI) 474 ($MH^+$).

Example 251

2-(3-[2-([2-Chloro-4-(4-chlorophenyl)benzoyl]amino)methyl-4-methoxyphenyl]-6-methoxyphenyl)acetic Acid

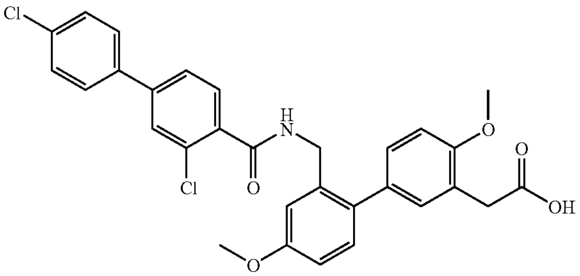

The title compound was obtained in the same way as Example 249c) except for using 2-chloro-4-(4'-chlorophenyl)benzoic AcidMS m/e (ESI) 550 ($MH^+$). .

Example 252

3-[2-([2-Chloro-4-(4-chlorophenyl)benzoyl]amino)methylphenyl]benzoic Acid

Production Example 252a t-Butyl N-(2-bromobenzyl)carbamate

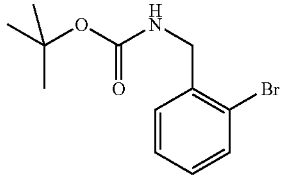

15.0 g of 2-Bromobenzylamine hydrochloride was dissolved in 100 ml of tetrahydrofuran, and a solution of 13 g of t-butyl dicarbonate in tetrahydrofuran (25 ml) was added thereto. The mixture was stirred at room temperature for 1 hour, and then the solvent was evaporated. The residue was dissolved in ethyl acetate, and washed successively with 1N hydrochloric acid and brine. The organic layer was dried over anhydrous magnesium sulfate, and the solvent was evaporated, to give 16.0 g of the title compound.

$^1H$-NMR ($CDCl_3$).

δ: 1.42 (s, 9H) 4.38 (d, J=6.0 Hz, 2H) 5.02 (br, 1H) 7.13 (dt, J=1.6, 7.6 Hz, 1H) 7.29 (dt, J=1.2, 8.0 Hz, 1H) 7.38 (dd, J=1.2, 7.6 Hz, 1H) 7.54 (dd, J=1.6, 8.0 Hz, 1H).

Production Example 252b

Methyl 3-(2-{[(t-butoxycarbonyl)amino]methyl}phenyl)benzoate

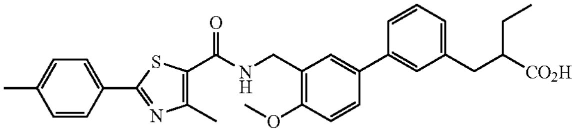

The title compound was obtained in the same way as Example 234b) except for using t-butyl N-(2-bromobenzyl)carbamate and 3-methoxycarbonylphenylboronic acid.

$^1H$-NMR ($CDCl_3$).

δ: 1.42 (s, 9H) 3.90 (s, 3H) 4.25 (brd, J=5.2 Hz, 2H) 4.63 (br, 1H) 7.22 (dd, J=1.6, 7.2 Hz, 1H) 7.33(t, J=7.6 Hz, 1H) 7.38 (t, J=7.6 Hz, 1H) 7.43-7.50 (m, 3H) 7.97 (s, 1H) 8.03 (t, J=1.6 Hz, 1H).

Example 252c

3-[2-([2-Chloro-4-(4-chlorophenyl)benzoyl]amino) methylphenyl]benzoic Acid

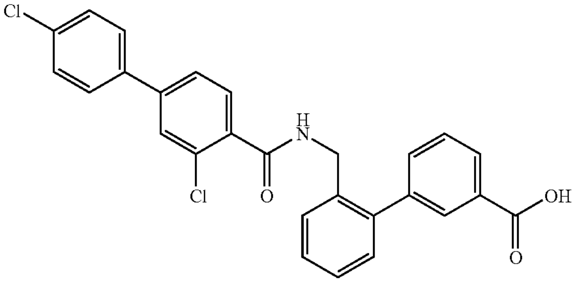

The title compound was obtained in the same way as Example 1e) except for using 2-chloro-4-(4'-chlorophenyl) benzoic acid and methyl 3-(2-{[(t-butoxycarbonyl)amino] methyl}phenyl)benzoate.

MS m/e (ESI) 476 ($MH^+$).

Example 253

3-(2-[([2-(4-Chlorophenyl)-4-methyl-1,3-thiazol-5-yl]carbonylamino)methyl]phenyl)benzoic Acid

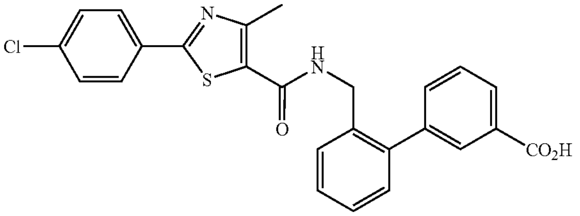

The title compound was obtained in the same way as Example 252c) except for using 2-(4-chlorophenyl)-4-methyl-1,3-thiazol-5-carboxylic Acid.

MS m/e (ESI) 463 ($MH^+$).

Example 254

3-[2-([2-Chloro-4-(4-chlorophenyl)benzoyl]-amino) methylphenyl]-6-methoxybenzoic Acid Production Example 254a Methyl 5-(2-{[(t-butoxycarbonyl)amino] methyl}phenyl)-2-methoxybenzoate

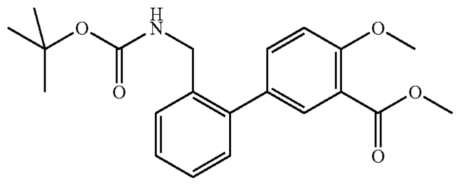

The title compound was obtained in the same way as Example 242b) except for using tertiary butyl N-(2-bromobenzyl)carbamate and methyl 2-methoxy-5-(4,4,5,5-tetramethyl-1,3,2-dioxaborolan-2-yl)benzoate.

1H-NMR ($CDCl_3$).

δ: 1.42 (s, 9H) 3.89 (s, 3H) 3.95 (s, 3H) 4.26 (brd, J=5.2 Hz, 2H) 4.63 (br, 1H) 7.03 (d, J=8.4 Hz, 1H) 7.22 (dd, J=2.0, 7.2 Hz, 1H) 7.31-7.35 (m, 2H) 7.41-7.43 (m, 2H) 7.74 (d, J=2.0 Hz, 1H).

Example 254b

3-[2-([2-Chloro-4-(4-chlorophenyl)benzoyl]-amino) methylphenyl]-6-methoxybenzoic Acid

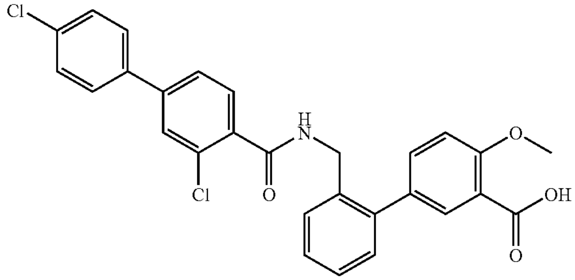

The title compound was obtained in the same way as Example 1e) except for using 2-chloro-4-(4'-chlorophenyl) benzoic acid and methyl 5-(2-{[(t-butoxycarbonyl)amino] methyl}phenyl)-2-methoxybenzoate.

MS m/e (ESI) 506 ($MH^+$).

Example 255

3-(2-[([2-(4-Chlorophenyl)-4-methyl-1,3-thiazol-5-yl]carbonylamino)methyl]phenyl)-6-methoxybenzoic Acid

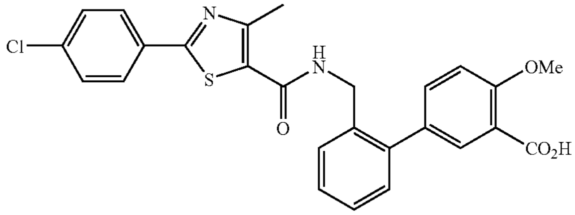

The title compound was obtained in the same way as Example 254b) except for using 2-(4-chlorophenyl)-4-methyl-1,3-thiazol-5-carboxylic Acid.

MS m/e (ESI) 493 ($MH^+$).

Example 256

3-[2-([2-Chloro-4-(4-chlorophenyl)benzoyl]-amino) methylphenyl]-6-methylbenzoic Acid Production Example 256a Methyl 3-(2-{[(t-butoxycarbonyl)amino] methyl}phenyl)-6-methylbenzoate

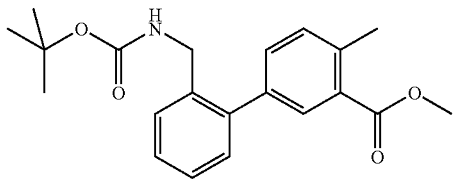

The title compound was obtained in the same way as Example 242b) except for using tertiary butyl N-(2-bromobenzyl)carbamate and methyl 2-methyl-5-(4,4,5,5-tetramethyl-1,3,2-dioxaborolan-2-yl)benzoate.

$^1$H-NMR ($CDCl_3$).

δ: 1.42 (s, 9H) 2.64 (s, 3H) 3.89 (s, 3H) 4.25 (brd, J=5.2 Hz, 2H) 4.63 (br, 1H) 7.22 (dd, J=1.6, 7.2 Hz, 1H) 7.29-7.36 (m, 4H) 7.43-7.46 (m, 1H) 7.85 (d, J=2.0 Hz, 1H).

Example 256b

3-[2-([2-Chloro-4-(4-chlorophenyl)benzoyl]-amino)methylphenyl]-6-methylbenzoic Acid

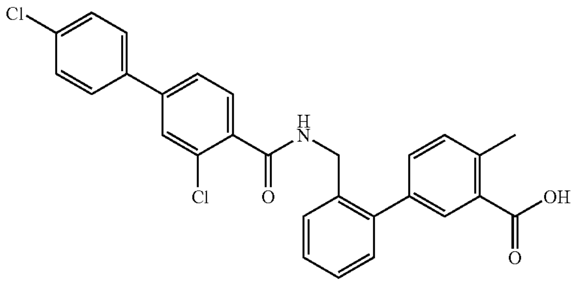

The title compound was obtained in the same way as Example 1e) except for using 2-chloro-4-(4'-chlorophenyl) benzoic acid and methyl 3-(2-{[(t-butoxycarbonyl)amino]methyl}phenyl)-6-methylbenzoate.

MS m/e (ESI) 490 ($MH^+$).

Example 257

3-(2-[([2-(4-Chlorophenyl)-4-methyl-1,3-thiazol-5-yl]carbonylamino)methyl]phenyl)-6-methylbenzoic Acid

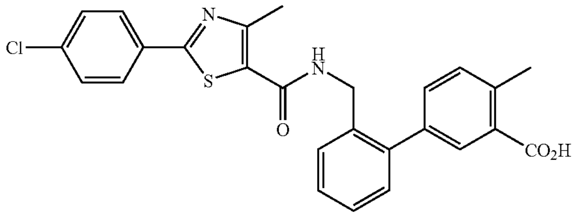

The title compound was obtained in the same way as Example 256b) except for using 2-(4-chlorophenyl)-4-methyl-1,3-thiazol-5-carboxylic Acid.

MS m/e (ESI) 477 ($MH^+$).

Example 258

2-[3-(2-[([2-(4-Chlorophenyl)-4-methyl-1,3-thiazol-5-yl]carbonylamino)methyl]phenyl)phenyl]acetic Acid Production Example 258a Methyl 2-[3-(2-{[(t-butoxycarbonyl)amino]methyl}phenyl)phenyl]acetate

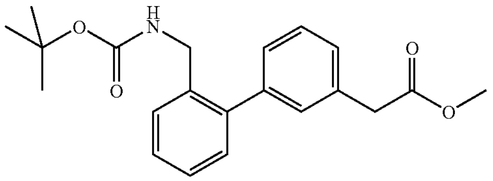

The title compound was obtained in the same way as Example 242b) except for using tertiary butyl N-(2-bromobenzyl)carbamate and methyl 2-[3-(4,4,5,5-tetramethyl-1,3,2-dioxaborolan-2-yl)phenyl]acetate.

$^1$H-NMR ($CDCl_3$).

δ: 1.42 (s, 9H) 3.67(s, 2H) 3.71 (s, 3H) 4.25 (brd, J=5.2 Hz, 2H) 4.71 (br, 1H) 7.20-7.46 (m, 8H).

Example 258b

2-[3-(2-[([2-(4-Chlorophenyl)-4-methyl-1,3-thiazol-5-yl]carbonylamino)methyl]phenyl)phenyl]acetic Acid

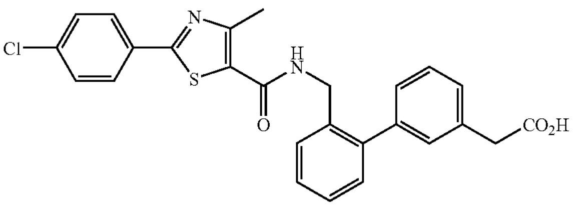

The title compound was obtained in the same way as Example 1e) except for using 2-(4-chlorophenyl)-4-methyl-1,3-thiazol-5-carboxylic acid and methyl 2-[3-(2-{[(t-butoxycarbonyl)amino]methyl}phenyl)phenyl]acetate.

MS m/e (ESI) 477 ($MH^+$).

Example 259

2-[3-(2-[(2,4-Dichlorobenzoyl)amino]methyl)phenyl]phenyl]acetic Acid

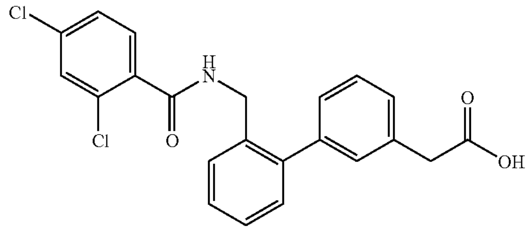

The title compound was obtained in the same way as Example 258b) except for using 2,4-dichlorobenzoic acid and methyl 2-[3-(2-{[(t-butoxycarbonyl)amino]methyl}phenyl)phenyl]-acetate MS m/e (ESI) 414 ($MH^+$). .

Example 260

2-[3-(2-[([2-(4-Chlorophenyl)-4-methyl-1,3-thiazol-5-yl]carbonylamino)methyl]phenyl)-6-methoxyphenyl]acetic Acid Production Example 260a Methyl 2-[5-(2-{[(t-butoxycarbonyl)amino]methyl}phenyl)-2-methoxyphenyl]acetate

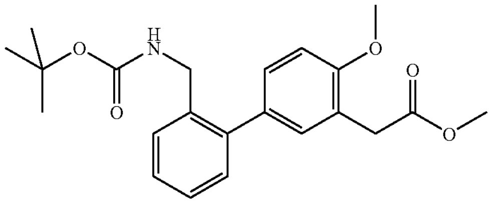

The title compound was obtained in the same way as Example 243b) except for using t-butyl N-(2-bromobenzyl) carbamate and methyl 2-[2-methoxy-5-(4,4,5,5-tetramethyl-1,3,2-dioxaborolan-2-yl)phenyl]acetate.

$^1$H-NMR ($CDCl_3$).

δ: 1.42 (s, 9H) 3.67(s, 2H) 3.70 (s, 3H) 3.86 (s, 3H) 4.27 (brd, J=5.2 Hz, 2H) 4.71 (br, 1H) 6.91 (d, J=8.0 Hz, 1H) 7.13 (d, J=2.0 Hz, 1H) 7.19 (dd, J=2.4, 8.4 Hz, 1H) 7.20-7.33 (m, 3H) 7.42-7.45 (m, 1H).

Example 260b

2-[3-(2-[([2-(4-Chlorophenyl)-4-methyl-1,3-thiazol-5-yl]carbonylamino)methyl]phenyl)-6-methoxyphenyl]acetic Acid

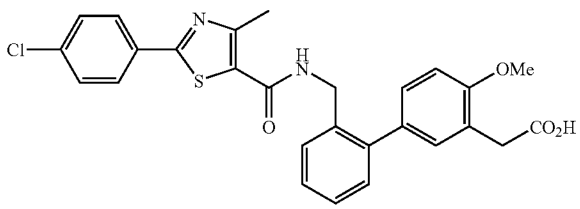

The title compound was obtained in the same way as Example 1e) except for using 2-(4-chlorophenyl)-4-methyl-1,3-thiazol-5-carboxylic acid and methyl 2-[5-(2-{[(t-butoxycarbonyl)amino]methyl}phenyl)-2-methoxyphenyl]acetate.

MS m/e (ESI) 507 (MH$^+$).

Example 261

2-[3-(2-[(2,4-Dichlorobenzoyl)amino]methyl)phenyl]-6-methoxyphenyl]acetic Acid

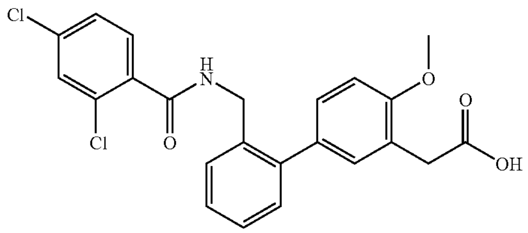

The title compound was obtained in the same way as Example 1e) except for using 2,4-dichlorobenzoic acid and methyl 2-[5-(2-{[(t-butoxycarbonyl)amino]methyl}phenyl)-2-methoxyphenyl]acetate.

MS m/e (ESI) 444 (MH$^+$).

Example 262

2-(3-[2-([2-Chloro-4-(4-chlorophenyl)benzoyl]amino)methylphenyl]-6-methoxyphenyl)acetic Acid

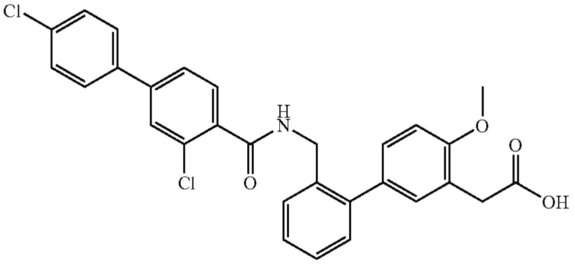

The title compound was obtained in the same way as Example 260b) except for using 2-chloro-4-(4'-chlorophenyl)benzoic acid.

MS m/e (ESI) 520 (MH$^+$).

Example 263

3-{3-[2-(2,4-Dichlorophenoxy)ethyl]-4-methoxyphenyl}phenylacetic Acid

Production Example 263a

Methyl 3-[3-(2-hydroxyethyl)-4-hydroxyphenyl]phenylacetate

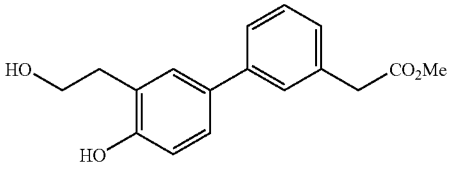

The title compound was obtained in the same way as Production Example 247b) except for using 5-bromo-2-hydroxyphenethyl alcohol and methyl 2-[3-(4,4,5,5-tetramethyl-1,3,2-dioxaborolan-2-yl)phenyl]acetate.

$^1$H-NMR ($CDCl_3$).

δ: 1.35 (s, 1H) 2.98 (t, J=7.2 Hz, 2H) 3.69 (s, 2H) 3.71 (s, 3H) 4.05 (t, J=5.2 Hz, 2H) 7.00 (d, J=8.4 Hz, 1H) 7.22 (d, J=7.6 Hz, 1H) 7.29 (dd, J=2.4, 12.8 Hz, 1H) 7.35-7.41 (m, 2H) 7.45 (d, J=4.0 Hz, 2H) 7.94 (br, 1H).

Production Example 263b

3-[3-(2-Hydroxyethyl)-4-methoxyphenyl]phenylacetate was obtained

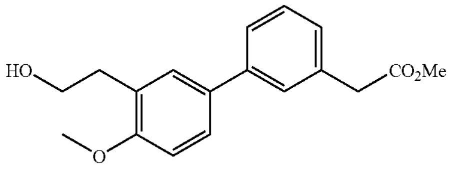

The title compound was obtained in the same way as Production Example 156b) except for using methyl 3-[3-(2-hydroxyethyl)-4-hydroxyphenyl]phenylacetate and iodomethane.

Example 263c

3-{3-[2-(2,4-Dichlorophenoxy)ethyl]-4-methoxyphenyl}phenylacetic Acid

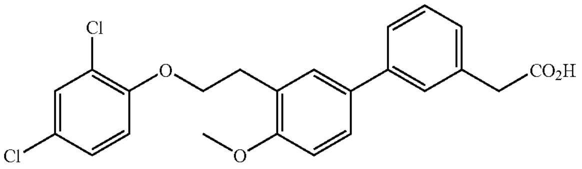

The title compound was obtained in the same way as Example 155b) except for using 3-[3-(2-hydroxyethyl)-4-methoxyphenyl]phenylacetate.

$^1$H-NMR ($CDCl_3$).

δ: 3.21 (t, J=7.6 Hz, 2H) 3.71 (s, 2H) 3.88 (s, 3H) 4.21 (t, J=7.2 Hz, 2H) 6.86 (d, J=8.8 Hz, 2H) 6.93 (d, J=8.8 Hz, 1H) 7.14 (dd, J=2.8 Hz, 8.8 Hz, 1H) 7.23 (d, J=7.6 Hz, 1H) 7.34 (d, J=2.4 Hz, 1H) 7.38 (t, J=7.6 Hz, 1H) 7.44 (dd, J=2.4, 8.4 Hz, 1H) 7.45-7.49 (m, 2H) 7.50 (d, J=2.4 Hz, 1H).

Example 264

3-{3-[2-(2,4-Dichlorophenoxy)ethyl]-4-propoxyphenyl}phenylacetic Acid

Production Example 264a

3-[3-(2-Hydroxyethyl)-4-propoxyphenyl]phenylacetate

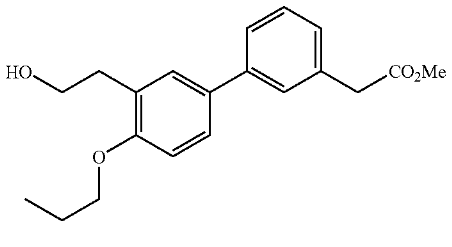

The title compound was obtained in the same way as Example 156b) except for using methyl 3-[3-(2-hydroxyethyl)-4-hydroxyphenyl]phenylacetate and iodopropane.

Production Example 264b

3-{3-[2-(2,4-Dichlorophenoxy)ethyl]-4-propoxyphenyl}phenylacetic Acid

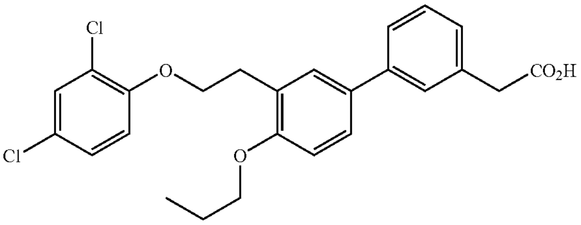

The title compound was obtained in the same way as Example 155b) except for using 3-[3-(2-hydroxyethyl)-4-propoxyphenyl]phenylacetate.

$^1$H-NMR ($CDCl_3$).

δ: 1.07 (t, J=7.2 Hz, 3H) 1.87 (q, J=6.8 Hz, 2H) 3.21 (t, J=7.2 Hz, 2H) 3.71 (s, 2H) 3.99 (t, J=6.4 Hz, 2H) 4.24 (t, J=6.8 Hz, 2H) 6.90 (d, J=8.8 Hz, 1H) 6.91 (d, J=8.4 Hz, 1H) 7.14 (dd, J=2.8 Hz, 8.8 Hz, 1H) 7.23 (d, J=7.6 Hz, 1H) 7.35 (d, J=2.4 Hz, 1H) 7.39 (t, J=7.6 Hz, 1H) 7.42 (dd, J=2.4, 8.4 Hz, 1H) 7.45-7.50 (m, 3H).

Example 265

2-[5-(3-{2-[(Anilinocarbonyl)oxy]ethyl}-4-methoxyphenyl)3-phenyl]acetic Acid

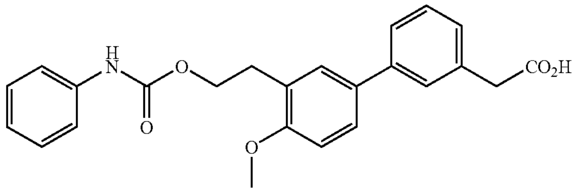

11 mg of 3-[3-(2-Hydroxyethyl)-4-methoxyphenyl]-phenylacetate was dissolved in 0.4 ml of toluene, 10 mg of phenylisocyanate and one drop of triethylamine were added thereto, and the mixture was stirred overnight at 60° C. The reaction mixture was concentrated, then the residue was dissolved in 0.4 ml of ethanol, 0.1 ml of 5N aqueous sodium hydroxide was added thereto, and the mixture was left at room temperature for 4 hours. The reaction mixture was acidified with 1N hydrochloric acid and extracted with ethyl acetate. The organic layer was concentrated, and the residue was purified by HPLC using a reverse phase system column and a water-acetonitrile-trifluoroacetic acid eluent to give 4.71 mg of the title compound.

MS m/e (ESI) 406 ($MH^+$).

Example 266

2-[5-(3-{2-[(4-Chloroanilinocarbonyl)oxy]ethyl}-4-methoxyphenyl)-3-phenyl]acetic Acid

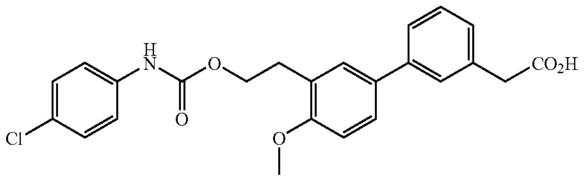

The title compound was obtained in the same way as Example 265 except for using 4-chlorophenyl isocyanate.

MS m/e (ESI) 440 ($MH^+$).

Example 267

2-[5-(3-{2-[(4-Trifluoromethylanilinocarbonyl)oxy]ethyl}-4-methoxyphenyl)-3-phenyl]acetic Acid

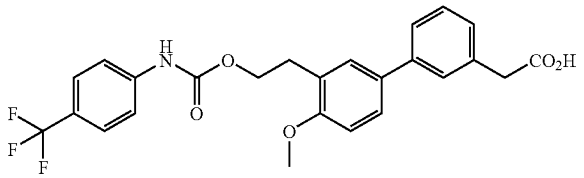

The title compound was obtained in the same way as Example 265 except for using 4-trifluoromethylphenylisocyanate.

MS m/e (ESI) 474 ($MH^+$).

Example 268

2-[5-(3-{2-[(4-Methylanilinocarbonyl)oxy]ethyl}-4-methoxyphenyl)-3-phenyl]acetic Acid

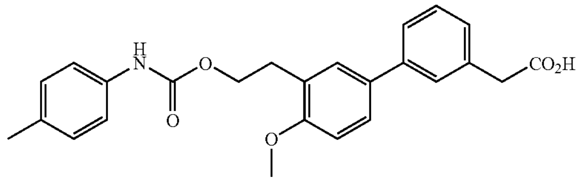

The title compound was obtained in the same way as Example 265 except for using 4-methylphenyl isocyanate.

MS m/e (ESI) 420 ($MH^+$).

Example 269

2-[5-(3-{2-[(4-Methoxyanilinocarbonyl)oxy]ethyl}-4-methoxyphenyl)-3-phenyl]acetic Acid

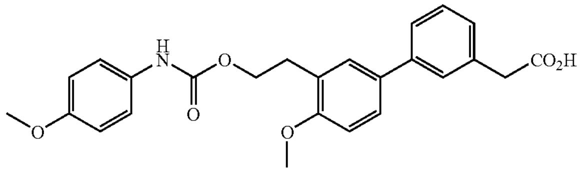

The title compound was obtained in the same way as Example 265 except for using 4-methoxyphenyl isocyanate.

MS m/e (ESI) 436 ($MH^+$).

Example 270

2-[5-(3-{2-[(2,4-Dichloroanilinocarbonyl)oxy]ethyl}-4-methoxyphenyl)-3-phenyl]acetic Acid

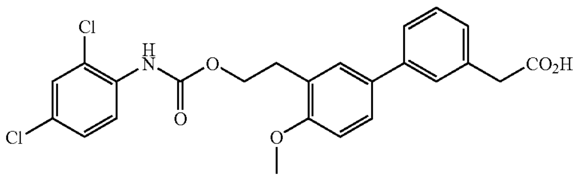

The title compound was obtained in the same way as Example 265 except for using 2,4-dichlorophenyl isocyanate.

MS m/e (ESI) 474 ($MH^+$).

Example 271

2-[5-(3-{[(2,4-Dichlorobenzoyl)amino]methyl}phenyl)-3-phenyl]acetic Acid

Production Example 271a

Methyl 2-[5-(3-{[(t-butoxycarbonyl)amino]methyl}phenyl)-3-phenyl]acetate

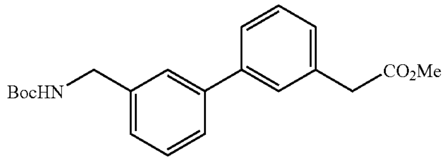

The title compound was obtained in the same way as Production Examples 1c) and 1d) except for using t-butyl N-(3-bromobenzyl)carbamate and methyl 3-bromophenylacetate.

$^1$H-NMR ($CDCl_3$).

δ: 1.47 (s, 9H) 3.69 (s, 3H) 3.71 (s, 2H) 4.38 (d, J=5.6 Hz, 2H) 7.27 (d, J=10.0 Hz, 2H) 7.40 (t, J=8.0 Hz, 2H) 7.46-7.51 (m, 4H)

Example 271b

2-[5-(3-{[(2,4-Dichlorobenzoyl)amino]methyl}phenyl)-3-phenyl]acetic Acid

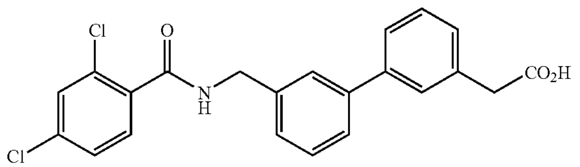

The title compound was obtained in the same way as Example 1e) except for using methyl 2-[5-(3-{[(t-butoxycarbonyl)amino]methyl}phenyl)-3-phenyl]acetate and 2,4-dichlorobenzoic acid MS m/e (ESI) 414 ($MH^+$). .

Example 272

2-[5-(3-{[(2-Fluoro-4-chlorobenzoyl)amino] methyl}phenyl)-3-phenyl]acetic Acid

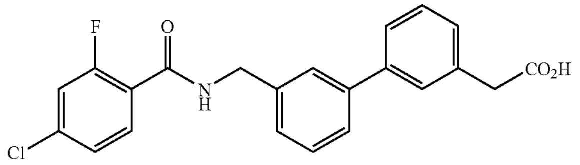

The title compound was obtained in the same way as Example 271 except for using 2-fluoro-4-chlorobenzoic acid.

MS m/e (ESI) 398 ($MH^+$).

Example 273

2-[5-(3-{[(2-Fluoro-4-trifluoromethylbenzoyl) amino]methyl}phenyl)-3-phenyl]acetic Acid

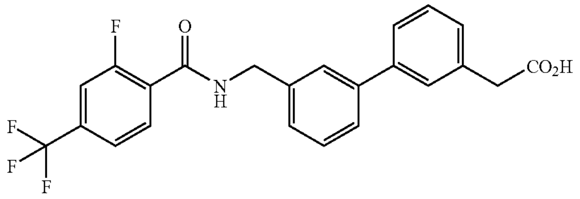

The title compound was obtained in the same way as Example 271 except for using 2-fluoro-4-trifluoromethyl-benzoic acid.

MS m/e (ESI) 432 ($MH^+$).

Example 274

2-[5-(3-{[(2-Chloro-4-propoxybenzoyl)amino] methyl}phenyl)-3-phenyl]acetic Acid

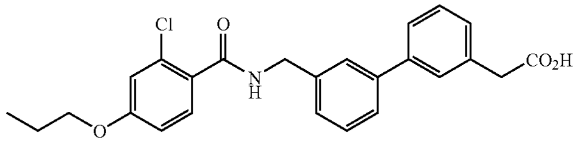

The title compound was obtained in the same way as Example 271 except for using 2-chloro-4-propoxybenzoic acid.

MS m/e (ESI) 438 ($MH^+$).

Example 275

2-[5-(3-{[(2-Chloro-4-isopropoxybenzoyl)amino] methyl}phenyl)-3-phenyl]acetic Acid

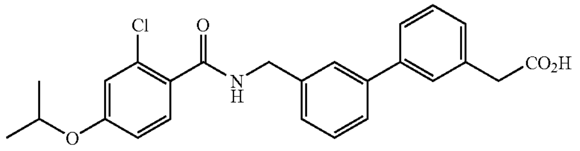

The title compound was obtained in the same way as Example 271 except for using 2-chloro-4-isopropoxybenzoic acid.

MS m/e (ESI) 438 ($MH^+$).

Example 276

2-[5-(3-{[({[4-(Trifluoromethyl)benzyl]oxy}-carbonyl)amino]methyl}phenyl)-3-phenyl]acetic Acid

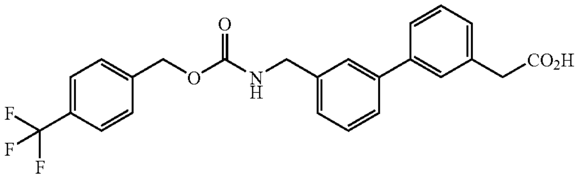

15 mg of Methyl 2-[5-(3-{[(t-butoxycarbonyl)amino]-methyl}phenyl)-3-phenyl]acetate was dissolved in 4N hydrogen chloride in dioxane and the solution was concentrated. The residue was dissolved in 1 ml N,N-dimethylformamide saturated previously with carbon dioxide by adding dry ice, and then 30 mg of tetrabutyl ammonium iodide, 40 mg of cesium carbonate and 30 mg of 4-trifluoromethylbenzyl bromide were added thereto, and the mixture was stirred overnight at room temperature. The reaction mixture was diluted with ethyl acetate and washed with water. The organic layer was concentrated, then the residue was dissolved in 0.4 ml of ethanol, 0.1 ml of 5N aqueous sodium hydroxide was added thereto, and the mixture was left at room temperature for 4 hours. The reaction mixture was neutralized with 1N hydrochloric acid and extracted with ethyl acetate, then the organic layer was concentrated, and the residue was purified by reverse phase high performance liquid chromatography to give 0.99 mg of the title compound.

MS m/e (ESI) 444 ($MH^+$).

Example 277

2-[5-(3-{[({[4-(Chloro)benzyl]oxy}carbonyl)amino] methyl}phenyl)-3-phenyl]acetic Acid

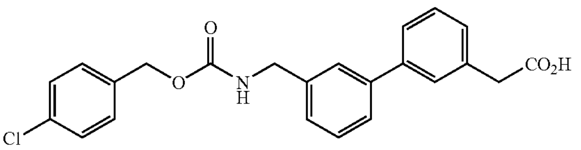

The title compound was obtained in the same way as Example 276 except for using 4-chlorobenzyl bromide.

MS m/e (ESI) 410 ($MH^+$).

Example 278

2-[5-(3-{[({[2,4-(Dichloro)benzyl]-oxy}carbonyl)amino]methyl}phenyl)-3-phenyl]acetic Acid

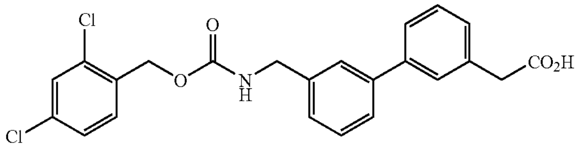

The title compound was obtained in the same way as Example 276 except for using 2,4-dichlorobenzyl chloride.

MS m/e (ESI) 444 ($MH^+$).

Example 279

2-[5-(3-{[({[2,6-(Dichloro)benzyl]-oxy}carbonyl)amino]methyl}phenyl)-3-phenyl]acetic Acid

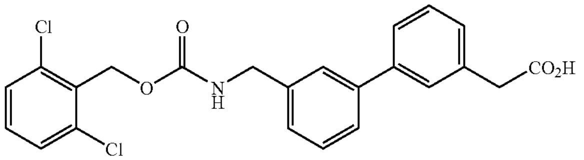

The title compound was obtained in the same way as Example 276 except for using 2,6-dichlorobenzylbromide.

MS m/e (ESI) 444 ($MH^+$).

Example 280

2-[5-(3-{[({[3,4-(Dichloro)benzyl]-oxy}carbonyl)amino]methyl}phenyl)-3-phenyl]acetic Acid

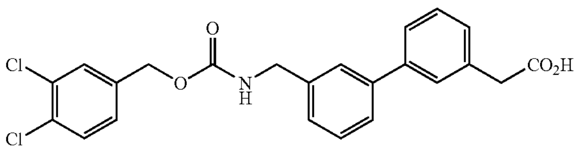

The title compound was obtained in the same way as Example 276 except for using 3,4-dichlorobenzyl bromide.

MS m/e (ESI) 444 ($MH^+$).

Example 281

{4'-Methoxy-3'-[(4-methylbenzyloxycarbonylamino)methyl]biphenyl-3-yl}acetic Acid Production Example 281a Methyl 2-[5-(3-aminomethyl-4-methoxyphenyl)-3-phenyl]acetate

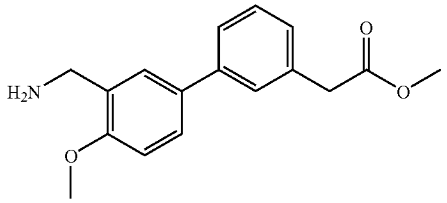

277 mg of Methyl 2-[5-(3-[(t-butoxycarbonyl)amino]methyl-4-hydroxyphenyl)-3-phenyl]acetate was dissolved in 4 ml of acetonitrile, 300 mg of cesium carbonate and 0.15 ml of methyliodide were added thereto, and the mixture was stirred overnight at room temperature. The reaction mixture was diluted with ethyl acetate and washed with water. The organic layer was dried over anhydrous magnesium sulfate and then filtered, and the filtrate was concentrated to give methyl 2-[5-(3-[(t-butoxycarbonyl)amino]methyl-4-methoxyphenyl)-3-phenyl]acetate. This product was dissolved in a solution of 4N hydrogen chloride in dioxane and left at room temperature for 1 hour, and the solvent was concentrated. The residue was neutralized and extracted with ethyl acetate and a saturated aqueous sodium bicarbonate solution. The organic layer was dried over anhydrous magnesium sulfate and then filtered, and the filtrate was concentrated to give 200 mg of the title compound.

Example 281b

{4'-Methoxy-3'-[(4-methylbenzyloxycarbonylamino)methyl]biphenyl-3-yl}acetic Acid

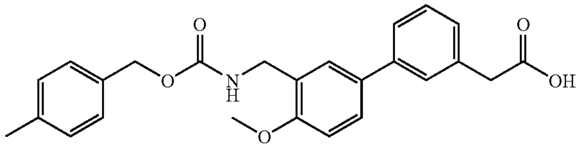

10 mg of 4-Methylbenzyl alcohol was dissolved in 0.25 ml of dichloromethane, 14 mg of carbonyl diimidazole was added thereto and the solution was stirred at room temperature for 1 hour. To this mixture was added a solution of 10 mg of methyl 2-[5-(3-aminomethyl-4-methoxyphenyl)-3-phenyl]acetate in 0.5 ml of dichloromethane, and the mixture was left overnight at room temperature. The reaction mixture was diluted with ethyl acetate and washed with water. The organic layer was concentrated to give methyl {4'-methoxy-3'-[(4-methylbenzyloxycarbonylamino)methyl]biphenyl-3-yl}acetate. This product was dissolved in 0.4 ml of ethanol, 0.1 ml of 5N aqueous sodium hydroxide was added thereto, and the mixture was left overnight at room temperature. The reaction mixture was neutralized with 1N hydrochloric acid, and the reaction mixture was extracted with ethyl acetate. The organic layer was concentrated, and the residue was purified by reverse phase high performance liquid chromatography to give 3.34 mg of the title compound MS m/e (ESI) 44.2 ($MNa^+$). .

Example 282

{4'-Methoxy-3'-[(4-ethylbenzyloxycarbonylamino)methyl]biphenyl-3-yl}acetic Acid

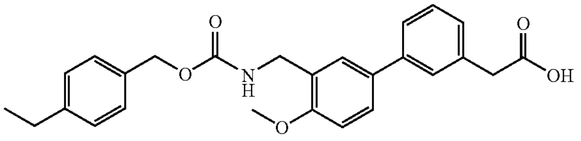

The title compound was obtained in the same way as Example 281 except for using 4-ethylbenzyl alcohol.

MS m/e (ESI) 456 (MNa$^+$).

Example 283

{4'-Methoxy-3'-[(4-chlorobenzyloxycarbonylamino)methyl]biphenyl-3-yl}acetic Acid

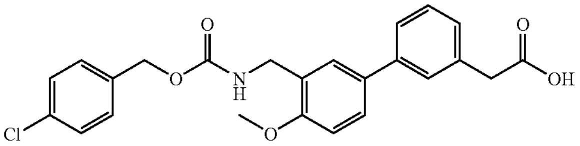

The title compound was obtained in the same way as Example 281 except for using 4-chlorobenzyl alcohol.

MS m/e (ESI) 462 (MNa$^+$).

Example 284

{4'-Methoxy-3'-[(4-trifluoromethylbenzyloxycarbonylamino)methyl]biphenyl-3-yl}acetic Acid

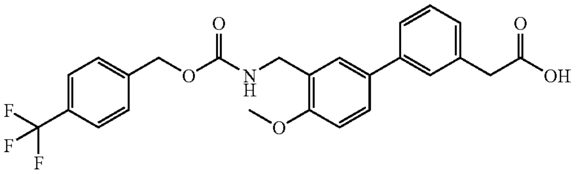

The title compound was obtained in the same way as Example 281 except for 4-trifluoromethylbenzyl alcohol.

MS m/e (ESI) 496 (MNa$^+$).

Example 285

{4'-Methoxy-3'-[(3-trifluoromethylbenzyloxycarbonylamino)methyl]biphenyl-3-yl}acetic Acid

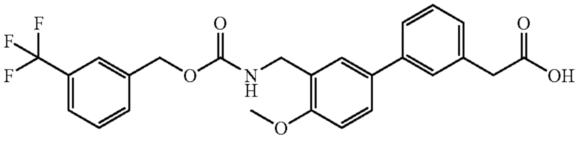

The title compound was obtained in the same way as Example 281 except for using 3-trifluoromethylbenzyl alcohol MS m/e (ESI) 496 (MNa$^+$) .

Example 286

{4'-Methoxy-3'-[(4-trifluoromethoxybenzyloxycarbonylamino)methyl]biphenyl-3-yl}acetic Acid

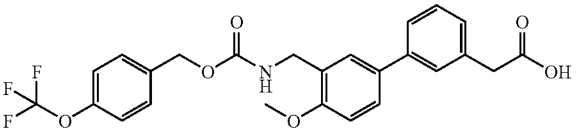

The title compound was obtained in the same way as Example 281 except for using 4-trifluoromethoxybenzyl alcohol.

MS m/e (ESI) 512 (MNa$^+$).

Example 287

{4'-Methoxy-3'-[(3-trifluoromethoxybenzyloxycarbonylamino)methyl]biphenyl-3-yl}acetic Acid

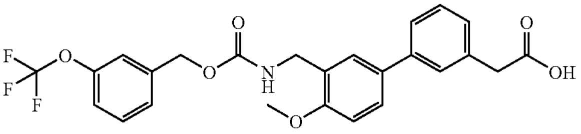

The title compound was obtained in the same way as Example 281 except for using 3-trifluoromethoxybenzyl alcohol.

MS m/e (ESI) 512 (MNa$^+$)

Example 288

{4'-Methoxy-3'-[(4-chloro-2-fluorobenzyloxycarbonylamino)methyl]biphenyl-3-yl}acetic Acid

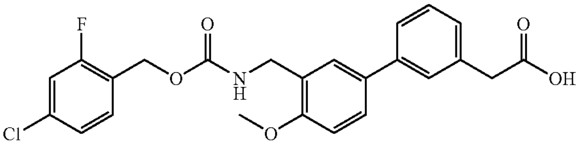

The title compound was obtained in the same way as Example 281 except for using 4-chloro-2-fluorobenzyl alcohol.

MS m/e (ESI) 480 (MNa$^+$).

Example 289

{4'-Methoxy-3'-[(2,4-dichlorobenzyloxycarbonylamino)methyl]biphenyl-3-yl}acetic Acid

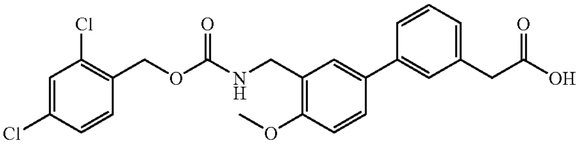

The title compound was obtained in the same way as Example 281 except for using 2,4-dichlorobenzyl alcohol MS m/e (ESI) 496 (MNa$^+$). .

Example 290

{4'-Methoxy-3'-[(3,4-dichlorobenzyloxycarbonylamino)methyl]biphenyl-3-yl}acetic Acid

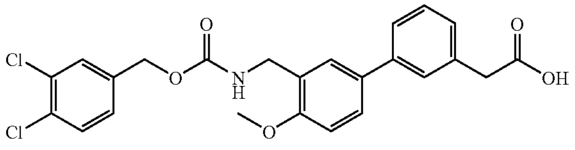

The title compound was obtained in the same way as Example 281 except for using 3,4-dichlorobenzyl alcohol.

MS m/e (ESI) 496 ($MNa^+$).

Example 291

{4'-Methoxy-3'-[(2-fluoro-4-trifluoromethylbenzyloxycarbonylamino)methyl]biphenyl-3-yl}acetic Acid

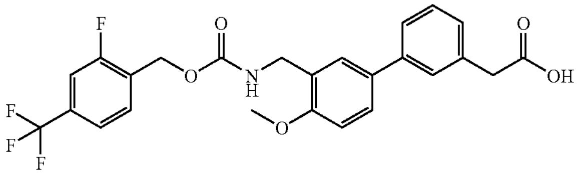

The title compound was obtained in the same way as Example 281 except for using 2-fluoro-4-trifluoromethylbenzyl alcohol.

MS m/e (ESI) 514($MNa^+$).

Example 292

{4'-Methoxy-3'-[(3-fluoro-4-trifluoromethylbenzyloxycarbonylamino)methyl]biphenyl-3-yl}acetic Acid

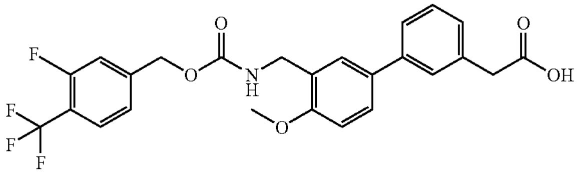

The title compound was obtained in the same way as Example 281 except for using 3-fluoro-4-trifluoromethylbenzyl alcohol.

MS m/e (ESI) 514($MNa^+$).

Example 293

{4'-Methoxy-3'-[(4-fluoro-3-trifluoromethylbenzyloxycarbonylamino)methyl]biphenyl-3-yl}acetic Acid

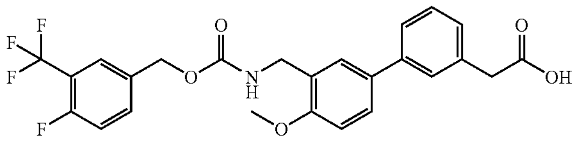

The title compound was obtained in the same way as Example 281 except for using 4-fluoro-3-trifluoromethylbenzyl alcohol.

MS m/e (ESI) 514($MNa^+$).

Example 294

{4'-Methoxy-3'-[(3,4-dimethylbenzyloxycarbonylamino)methyl]biphenyl-3-yl}acetic Acid

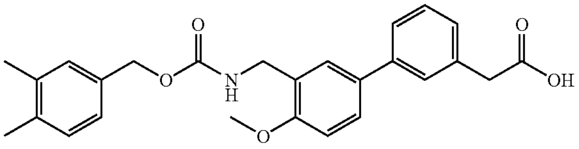

The title compound was obtained in the same way as Example 281 except for using 3,4-dimethylbenzyl alcohol.

MS m/e (ESI) 456($MNa^+$).

Example 295

{4'-Methoxy-3'-[(2-chloro-4-propoxybenzyloxycarbonylamino)methyl]biphenyl-3-yl}acetic Acid

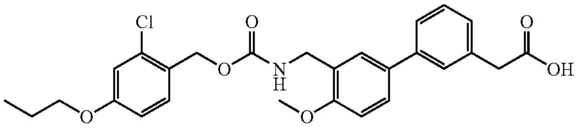

The title compound was obtained in the same way as Example 281 except for using 2-chloro-4-propoxybenzyl alcohol.

MS m/e (ESI) 520($MNa^+$).

Example 296

{3'-[(Benzo[1,3]dioxol-5-ylmethoxycarbonylamino)methyl]-4'-methoxybiphenyl-3-yl}acetic Acid

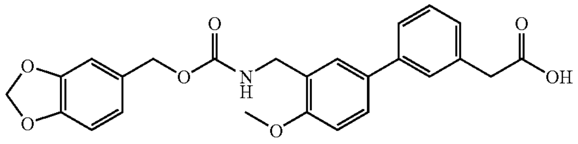

The title compound was obtained in the same way as Example 281 except for using piperonyl alcohol.

MS m/e (ESI) 472 ($MNa^+$).

Example 297

{3'-[(Biphenyl-4-ylmethoxycarbonylamino)methyl]-4'-methoxybiphenyl-3-yl}acetic Acid

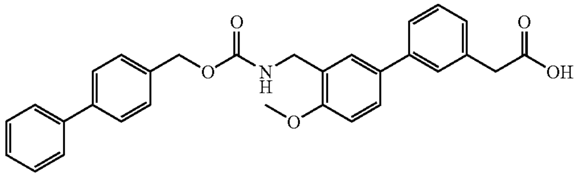

The title compound was obtained in the same way as Example 281 except for using 4-phenylbenzyl alcohol.

MS m/e (ESI) 504 ($MNa^+$).

Example 298

(3'-{[2-(4-Chlorophenyl)ethoxycarbonylamino]methyl}-4'-methoxybiphenyl-3-yl)acetic Acid

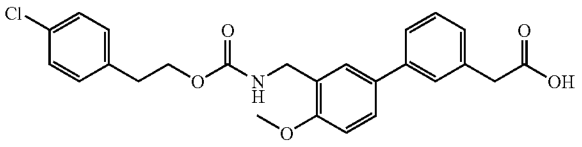

The title compound was obtained in the same way as Example 281 except for using 2-(4-chlorophenyl)ethanol.

MS m/e (ESI) 476 ($MNa^+$).

Example 299

(3'-{[2-(3-Chlorophenyl)ethoxycarbonylamino]-methyl}-4'-methoxybiphenyl-3-yl)acetic Acid

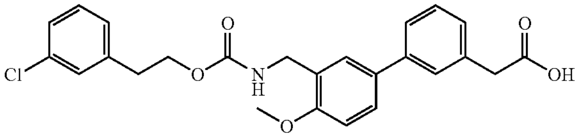

The title compound was obtained in the same way as Example 281 except for using 2-(3-chlorophenyl)ethanol.

MS m/e (ESI) 476 ($MNa^+$).

Example 300

(3'-{[2-(2,4-Dichlorophenyl)ethoxycarbonylamino] methyl}-4'-methoxybiphenyl-3-yl)acetic Acid

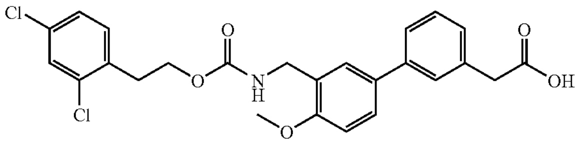

The title compound was obtained in the same way as Example 281 except for using 2-(2,4-dichlorophenyl)ethanol.

MS m/e (ESI) 510 ($MNa^+$).

Example 301

{4'-Ethoxy-3'-[(4-methylbenzyloxycarbonylamino) methyl]-biphenyl-3-yl}acetic Acid Production Example 301a Methyl 2-[5-(3-aminomethyl-4-ethoxyphenyl)-3-phenyl]acetate

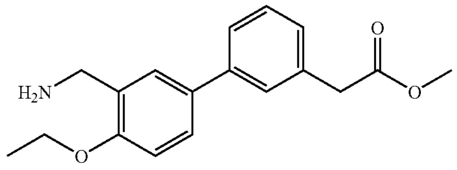

The title compound was obtained in the same way as Production Example 281a) except for using iodoethane.

Example 301b

{4'-Ethoxy-3'-[(4-methylbenzyloxycarbonylamino) methyl]-biphenyl-3-yl}acetic Acid

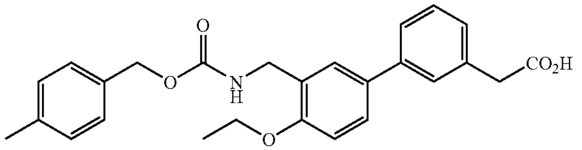

The title compound was obtained in the same way as Example 281b) except for using methyl 2-[5-(3-aminomethyl-4-ethoxyphenyl)-3-phenyl]acetate.

MS m/e (ESI) 456($MNa^+$).

Example 302

{4'-Ethoxy-3'-[(4-ethylbenzyloxycarbonylamino) methyl]-biphenyl-3-yl}acetic Acid

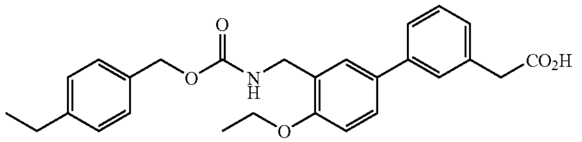

The title compound was obtained in the same way as Example 301 except for using 4-ethylbenzyl alcohol.

MS m/e (ESI) 470($MNa^+$).

Example 303

{4'-Ethoxy-3'-[(4-chlorobenzyloxycarbonylamino) methyl]-biphenyl-3-yl}acetic Acid

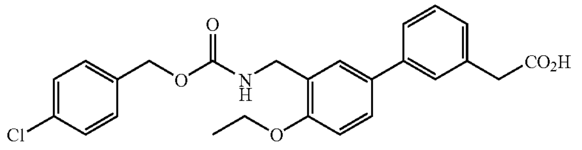

The title compound was obtained in the same way as Example 301 except for using 4-chlorobenzyl alcohol.

MS m/e (ESI) 476 ($MNa^+$).

Example 304

{4'-Ethoxy-3'-[(4-trifluoromethylbenzyloxycarbonyl) amino]-methyl]biphenyl-3-yl}-acetic Acid

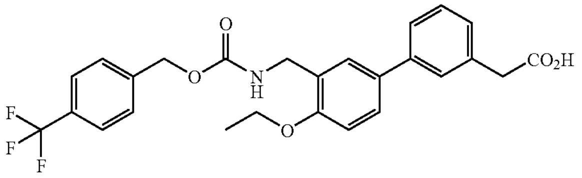

The title compound was obtained in the same way as Example 301 except for using 4-trifluoromethylbenzyl alcohol.

MS m/e (ESI) 510(MNa$^+$).

Example 305

{4'-Ethoxy-3'-[(3-trifluoromethylbenzyloxycarbonylamino)methyl]biphenyl-3-yl}acetic Acid

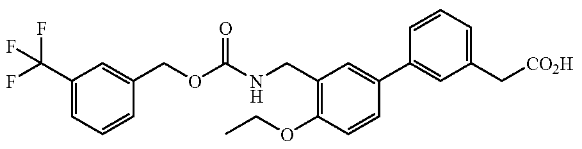

The title compound was obtained in the same way as Example 301 except for using 3-trifluoromethylbenzyl alcohol.

MS m/e (ESI) 510 (MNa$^+$).

Example 306

{4'-Ethoxy-3'-[(4-trifluoromethoxybenzyloxycarbonylamino)methyl]biphenyl-3-yl}acetic Acid

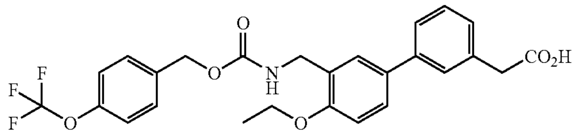

The title compound was obtained in the same way as Example 301 except for using 4-trifluoromethoxybenzyl alcohol.

MS m/e (ESI) 526 (MNa$^+$).

Example 307

{4'-Ethoxy-3'-[(3-trifluoromethoxybenzyloxycarbonylamino)methyl]biphenyl-3-yl}acetic Acid

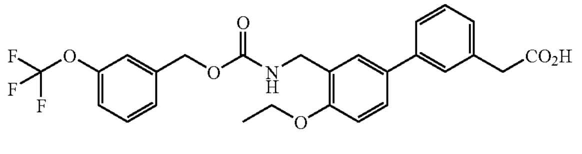

The title compound was obtained in the same way as Example 301 except for using 3-trifluoromethoxybenzyl alcohol MS m/e (ESI) 526 (MNa$^+$). .

Example 308

{4'-Ethoxy-3'-[(4-chloro-2-fluorobenzyloxycarbonylamino)methyl]biphenyl-3-yl}acetic Acid

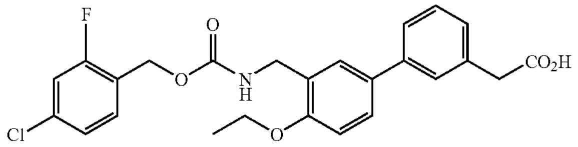

The title compound was obtained in the same way as Example 301 except for using 4-chloro-2-fluorobenzyl alcohol.

MS m/e (ESI) 494(MNa$^+$).

Example 309

{4'-Ethoxy-3'-[(2,4-dichlorobenzyloxycarbonylamino)methyl]biphenyl-3-yl }acetic Acid

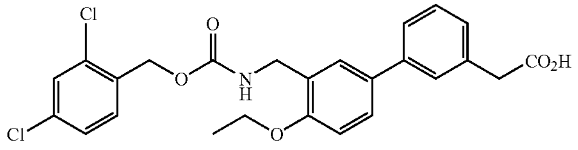

The title compound was obtained in the same way as Example 301 except for using 2,4-dichlorobenzyl alcohol.

MS m/e (ESI) 510(MNa$^+$).

Example 310

{4'-Ethoxy-3'-[(3,4-dichlorobenzyloxycarbonylamino)methyl]biphenyl-3-yl)acetic Acid

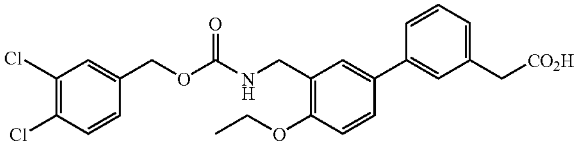

The title compound was obtained in the same way as Example 301 except for using 3,4-dichlorobenzyl alcohol.

MS m/e (ESI) 510(MNa$^+$).

Example 311

{4'-Ethoxy-3'-[(2-fluoro-4-trifluoromethylbenzyloxycarbonylamino)methyl]biphenyl-3-yl}acetic Acid

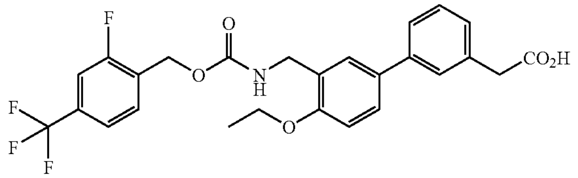

The title compound was obtained in the same way as Example 301 except for using 2-fluoro-4-trifluoromethylbenzyl alcohol.

MS m/e (ESI) 528(MNa$^+$).

Example 312

{4'-Ethoxy-3'-[(3-fluoro-4-trifluoromethylbenzyloxycarbonylamino)methyl]biphenyl-3-yl}-acetic Acid

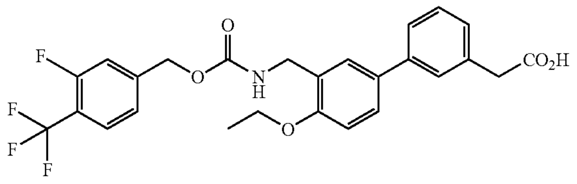

The title compound was obtained in the same way as Example 301 except for using 3-fluoro-4-trifluoromethylbenzyl alcohol.

MS m/e (ESI) 528($MNa^+$).

Example 313

{4'-Ethoxy-3'-[(4-fluoro-3-trifluoromethylbenzyloxycarbonylamino)methyl]biphenyl-3-yl}acetic Acid

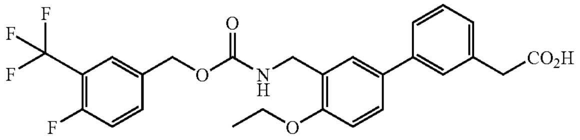

The title compound was obtained in the same way as Example 301 except for using 4-fluoro-3-trifluoromethylbenzyl alcohol.

MS m/e (ESI) 528($MNa^+$).

Example 314

{4'-Ethoxy-3'-[(3,4-dimethylbenzyloxycarbonylamino)lmethyl]biphenyl-3-yl}acetic Acid

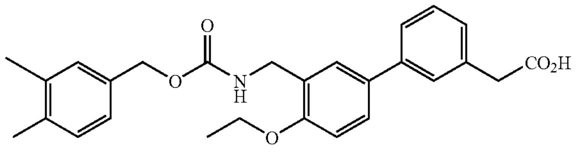

The title compound was obtained in the same way as Example 301 except for using 3,4-dimethylbenzyl alcohol.

MS m/e (ESI) 470($MNa^+$).

Example 315

{4'-Ethoxy-3'-[(2-chloro-4-propoxybenzyloxycarbonylamino)methyl]biphenyl-3-yl}acetic Acid

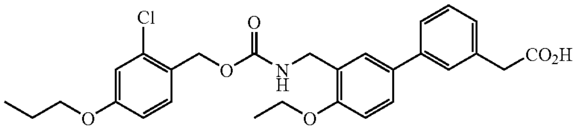

The title compound was obtained in the same way as Example 301 except for using 2-chloro-4-propoxybenzyl alcohol MS m/e (ESI) 534($MNa^+$). .

Example 316

{3'-[(Benzo[1,3]dioxol-5-ylmethoxycarbonylamino)methyl]-4'-ethoxybiphenyl-3-yl}acetic Acid

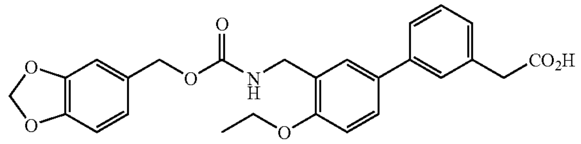

The title compound was obtained in the same way as Example 301 except for using piperonyl alcohol.

MS m/e (ESI) 486($MNa^+$).

Example 317

{3'-[(Biphenyl-4-ylmethoxycarbonylamino)methyl]-4'-ethoxybiphenyl-3-yl}acetic Acid

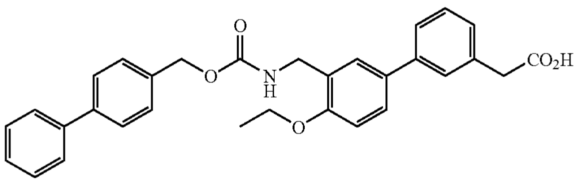

The title compound was obtained in the same way as Example 301 except for using 4-phenylbenzyl alcohol.

MS m/e (ESI) 518($MNa^+$).

Example 318

(3'-{[2-(4-Chlorophenyl)ethoxycarbonylamino]methyl}-4'-ethoxy-biphenyl-3-yl)acetic Acid

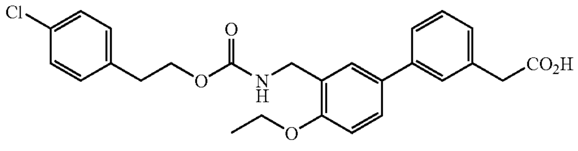

The title compound was obtained in the same way as Example 301 except for using 2-(4-chlorophenyl)ethanol.

MS m/e (ESI) 490 ($MNa^+$).

Example 319

(3'-{[2-(3-Chlorophenyl)ethoxycarbonylamino]-methyl}-4'-ethoxybiphenyl-3-yl)acetic Acid

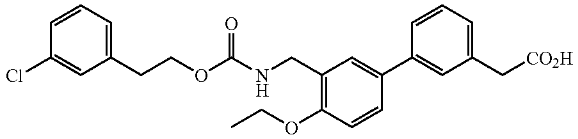

The title compound was obtained in the same way as Example 301 except for using 2-(3-chlorophenyl)ethanol.

MS m/e (ESI) 490 ($MNa^+$).

Example 320

(3'-{[2-(2,4-Dichlorophenyl)ethoxycarbonylamino]methyl}-4'-ethoxybiphenyl-3-yl)acetic Acid

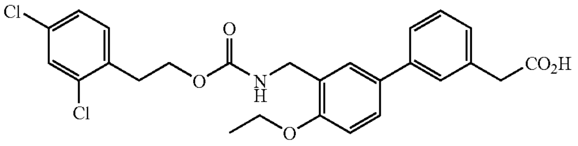

The title compound was obtained in the same way as Example 301 except for using 2-(2,4-dichlorophenyl)ethanol.

MS m/e (ESI) 524 ($MNa^+$).

Example 321

{4'-Propoxy-3'-[(4-ethyl-benzyloxycarbonylamino)methyl]biphenyl-3-yl}acetic Acid

Production Example 321a

Methyl 2-[5-(3-aminomethyl-4-propoxyphenyl)-3-phenyl]acetate

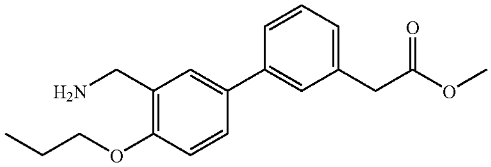

The title compound was obtained in the same way as Production Example 281a) except for using iodopropane.

Example 321b

{4'-Propoxy-3'-[(4-ethylbenzyloxycarbonylamino)methyl]-biphenyl-3-yl}acetic Acid

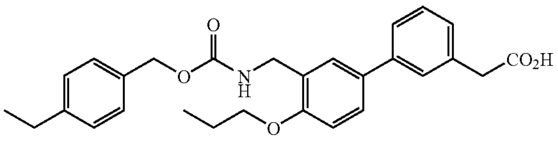

The title compound was obtained in the same way as Example 281b) except for using methyl 2-[5-(3-aminomethyl-4-propoxyphenyl)-3-phenyl]acetate and 4-ethylbenzyl alcohol.

MS m/e (ESI) 484($MNa^+$).

Example 322

{4'-Propoxy-3'-[(4-chlorobenzyloxycarbonylamino)methyl]-biphenyl-3-yl}acetic Acid

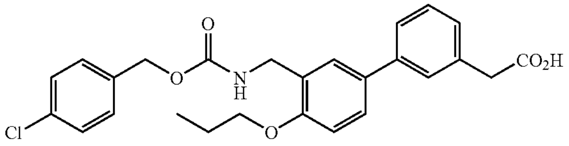

The title compound was obtained in the same way as Example 321 except for using 4-chlorobenzyl alcohol.

MS m/e (ESI) 490 ($MNa^+$).

Example 323

{4'-Propoxy-3'-[(4-trifluoromethylbenzyloxycarbonylamino)methyl]biphenyl-3-yl}acetic Acid

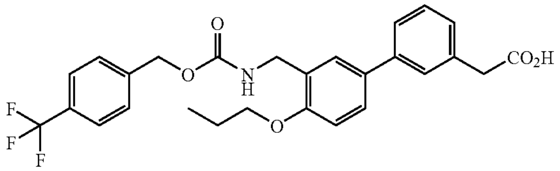

The title compound was obtained in the same way as Example 321 except for using 4-trifluoromethylbenzyl alcohol.

MS m/e (ESI) 524($MNa^+$).

Example 324

{4'-Propoxy-3'-[(4-trifluoromethoxybenzyloxycarbonylamino)methyl]biphenyl-3-yl}acetic Acid

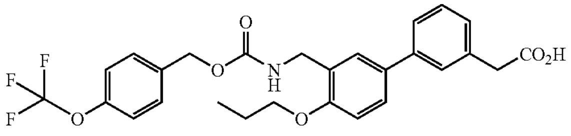

The title compound was obtained in the same way as Example 321 except for using 4-trifluoromethoxybenzyl alcohol.

MS m/e (ESI) 540($MNa^+$).

Example 325

{41-Propoxy-3'-[(3-trifluoromethoxybenzyloxycarbonylamino)methyl]biphenyl-3-yl}acetic Acid

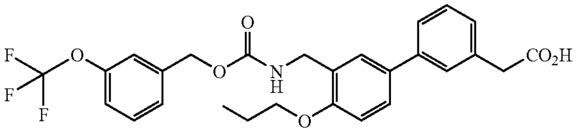

The title compound was obtained in the same way as Example 321 except for using 3-trifluoromethoxybenzyl alcohol.

MS m/e (ESI) 540($MNa^+$).

Example 326

{4'-Propoxy-3'-[(3,4-dichlorobenzyloxycarbonylamino)methyl]biphenyl-3-yl}acetic Acid

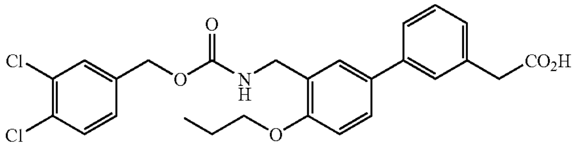

The title compound was obtained in the same way as Example 321 except for using 3,4-dichlorobenzyl alcohol.

MS m/e (ESI) 524($MNa^+$).

Example 327

{4'-Propoxy-3'-[(4-fluoro-3-trifluoromethylbenzyloxycarbonylamino)methyl]biphenyl-3-yl}acetic Acid

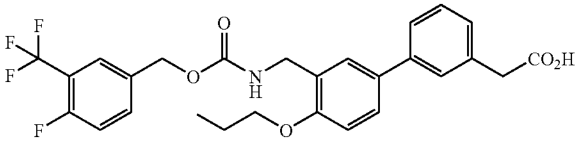

The title compound was obtained in the same way as Example 321 except for using 4-fluoro-3-trifluoromethylbenzyl alcohol.

MS m/e (ESI) 542($MNa^+$).

Example 328

{4'-Propoxy-3'-[(2-chloro-4-propoxybenzyloxycarbonylamino)methyl]biphenyl-3-yl}acetic Acid

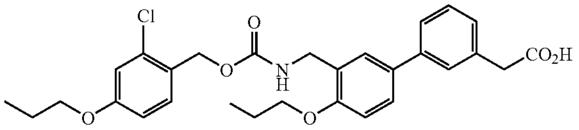

The title compound was obtained in the same way as Example 321 except for using 2-chloro-4-propoxybenzyl alcohol.

MS m/e (ESI) 548($MNa^+$).

Example 329

{3'-[(Biphenyl-4-ylmethoxycarbonylamino)methyl]-4'-propoxybiphenyl-3-yl}acetic Acid

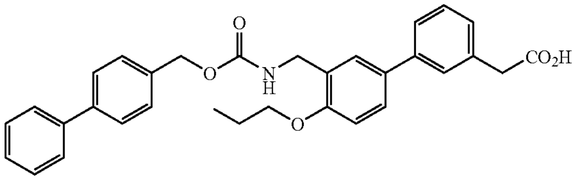

The title compound was obtained in the same way as Example 301 except for using 4-phenylbenzyl alcohol MS m/e (ESI) 532($MNa^+$). .

Example 330

(3'-{[2-(3-Chlorophenyl)-ethoxycarbonylamino]methyl}-4'-propoxybiphenyl-3-yl)acetic Acid

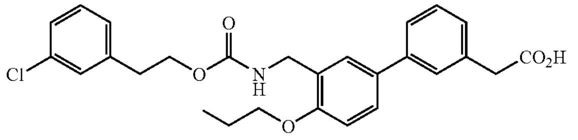

The title compound was obtained in the same way as Example 321 except for using 2-(3-chlorophenyl)ethanol.

MS m/e (ESI) 504($MNa^+$).

Example 331

2-{4'-Methoxy-3'-[(4-methylbenzyloxycarbonylamino)methyl]biphenyl-3-yl}propionic Acid Production Example 331a Methyl 2-[5-(3-aminomethyl-4-methoxyphenyl)-3-phenyl]propionate

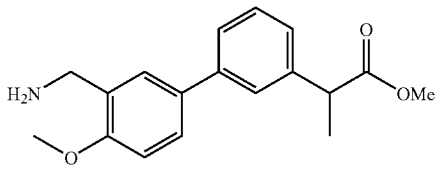

323 mg of Methyl 2-[5-(3-[(t-butoxycarbonyl)amino]methyl-4-hydroxyphenyl)-3-phenyl]acetate was dissolved in 2 ml of acetonitrile, 300 mg of cesium carbonate and 0.5 ml of methyl iodide were added thereto, and the mixture was stirred overnight at 50° C. The reaction mixture was diluted with ethyl acetate and washed with water. The organic layer was dried over anhydrous magnesium sulfate and then filtered, and the filtrate was concentrated to give methyl 2-[5-(3-[(t-butoxycarbonyl)amino]methyl-4-methoxyphenyl)-3-phenyl]propionate. This product was dissolved in 4N hydrogen chloride solution in dioxane and left at room temperature for 1 hour, and the solvent was concentrated. The residue was neutralized and extracted with ethyl acetate and a saturated aqueous sodium bicarbonate solution. The organic layer was dried over anhydrous magnesium sulfate and then filtered, and the filtrate was concentrated to give 150 mg of the title compound.

Example 331b

2-{4'-Methoxy-3'-[(4-methylbenzyloxycarbonylamino)methyl]biphenyl-3-yl}propionic Acid

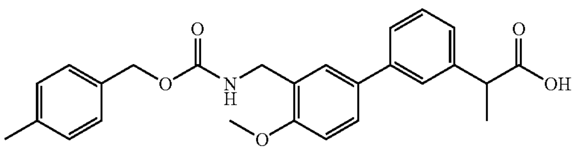

The title compound was obtained in the same way as Example 281b) except for using 4-methylbenzyl alcohol and methyl 2-[5-(3-aminomethyl-4-methoxyphenyl)-3-phenyl]propionate.

MS m/e (ESI) 456(MNa+).

Example 332

2-{4'-Methoxy-3'-[(4-ethylbenzyloxycarbonylamino) methyl]-biphenyl-3-yl}propionic Acid

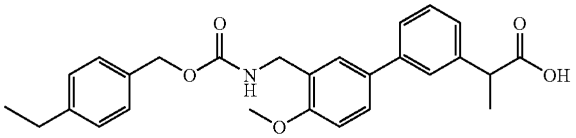

The title compound was obtained in the same way as Example 331 except for using 4-ethylbenzyl alcohol.

MS m/e (ESI) 470 (MNa+).

Example 333

2-{4'-Methoxy-3'-[(4-chlorobenzyloxycarbonylamino)methyl]biphenyl-3-yl)propionic Acid

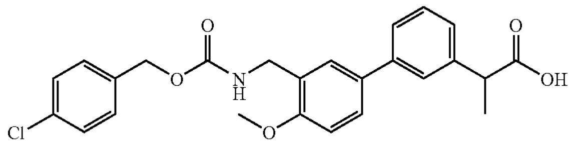

The title compound was obtained in the same way as Example 331 except for using 4-chlorobenzyl alcohol.

MS m/e (ESI) 476(MNa+).

Example 334

2-{4'-Methoxy-3'-[(4-trifluoromethylbenzyloxycarbonylamino)methyl]biphenyl-3-yl}propionic Acid

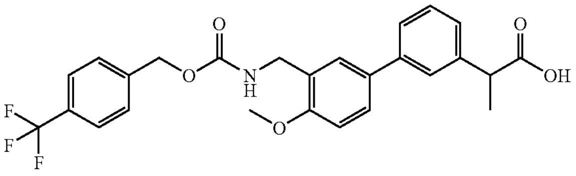

The title compound was obtained in the same way as Example 331 except for using 4-trifluoromethylbenzyl alcohol.

MS m/e (ESI) 510 (MNa+).

Example 335

2-{4'-Methoxy-3'-[(3-trifluoromethylbenzyloxycarbonylamino)methyl]biphenyl-3-yl}propionic Acid

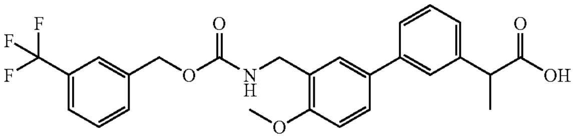

The title compound was obtained in the same way as Example 331 except for using 3-trifluoromethylbenzyl alcohol MS m/e (ESI) 510 (MNa+). .

Example 336

2-{4'-Methoxy-3'-[(4-trifluoromethoxybenzyloxycarbonylamino)methyl]biphenyl-3-yl}propionic Acid

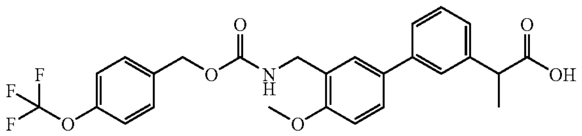

The title compound was obtained in the same way as Example 331 except for using 4-trifluoromethoxybenzyl alcohol.

MS m/e (ESI) 526 (MNa+).

Example 337

2-{4'-Methoxy-3'-[(3-trifluoromethoxybenzyloxycarbonylamino)methyl]biphenyl-3-yl}propionic Acid

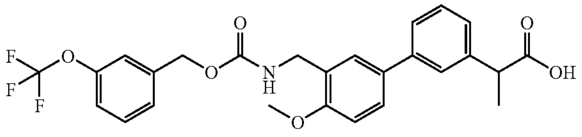

The title compound was obtained in the same way as Example 331 except for using 3-trifluoromethoxybenzyl alcohol.

MS m/e (ESI) 526 (MNa+).

Example 338

2-{4'-Methoxy-3'-[(4-chloro-2-fluorobenzyloxycarbonylamino)methyl]biphenyl-3-yl}propionic Acid

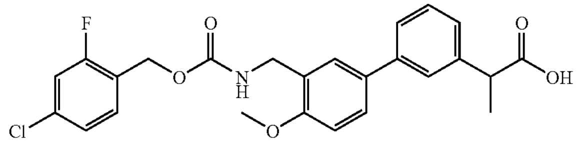

The title compound was obtained in the same way as Example 331 except for using 4-chloro-2-fluoro-benzyl alcohol.

MS m/e (ESI) 494 (MNa+).

Example 339

2-{4'-Methoxy-3'-[(2,4-dichlorobenzyloxycarbonylamino)methyl]biphenyl-3-yl}propionic Acid

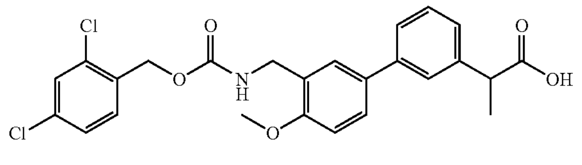

The title compound was obtained in the same way as Example 331 except for using 2,4-dichlorobenzyl alcohol MS m/e (ESI) 510 (MNa+). .

Example 340

2-{4'-Methoxy-3'-[(3,4-dichlorobenzyloxycarbonylamino)methyl]biphenyl-3-yl}propionic Acid

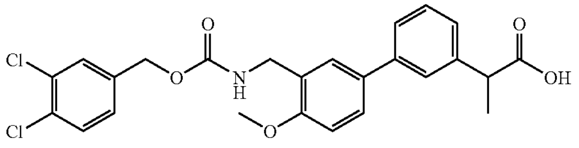

The title compound was obtained in the same way as Example 331 except for using 3,4-dichlorobenzyl alcohol.

MS m/e (ESI) 510 ($MNa^+$).

Example 341

2-{4'-Methoxy-3'-[(2-fluoro-4-trifluoromethylbenzyloxycarbonylamino)methyl]biphenyl-3-yl}propionic Acid

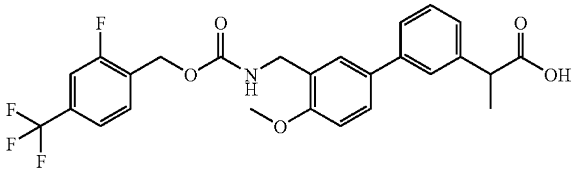

The title compound was obtained in the same way as Example 331 except for using 2-fluoro-4-trifluoromethylbenzyl alcohol.

MS m/e (ESI) 528($MNa^+$).

Example 342

2-{4'-Methoxy-3'-[(3-fluoro-4-trifluoromethylbenzyloxycarbonylamino)methyl]biphenyl-3-yl}propionic Acid

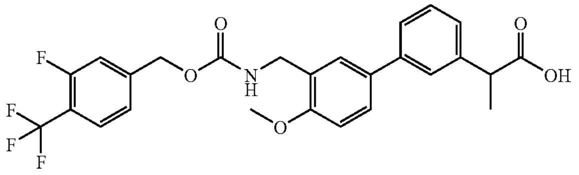

The title compound was obtained in the same way as Example 331 except for using 3-fluoro-4-trifluoromethylbenzyl alcohol.

MS m/e (ESI) 528($MNa^+$).

Example 343

2-{4'-Methoxy-3'-[(4-fluoro-3-trifluoromethylbenzyloxycarbonylamino)methyl]biphenyl-3-yl}propionic Acid

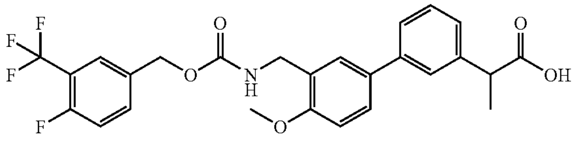

The title compound was obtained in the same way as Example 331 except for using 4-fluoro-3-trifluoromethylbenzyl alcohol.

MS m/e (ESI) 528($MNa^+$).

Example 344

2-{4'-Methoxy-3'-[(3,4-dimethylbenzyloxycarbonylamino)methyl]biphenyl-3-yl}propionic Acid

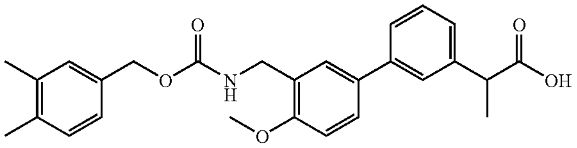

The title compound was obtained in the same way as Example 331 except for using 3,4-dimethylbenzyl alcohol.

MS m/e (ESI) 470($MNa^+$).

Example 345

2-{4'-Methoxy-3'-[(2-chloro-4-propoxybenzyloxycarbonylamino)methyl]biphenyl-3-yl}propionic Acid

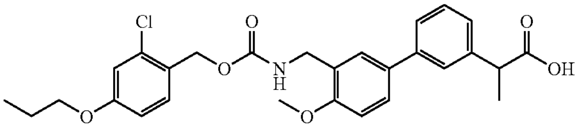

The title compound was obtained in the same way as Example 331 except for using 2-chloro-4-propoxybenzyl alcohol.

MS m/e (ESI) 534($MNa^+$).

Example 346

2-{3'-[(Benzo[1,3]dioxol-5-ylmethoxycarbonylamino)methyl]-4'-methoxybiphenyl-3-yl}propionic Acid

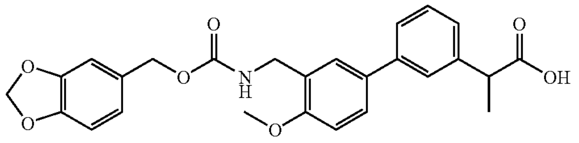

The title compound was obtained in the same way as Example 331 except for using piperonyl alcohol.

MS m/e (ESI) 486 ($MNa^+$).

Example 347

2-{3'-[(Biphenyl-4-ylmethoxycarbonylamino)methyl]-4'-methoxybiphenyl-3-yl}propionic Acid

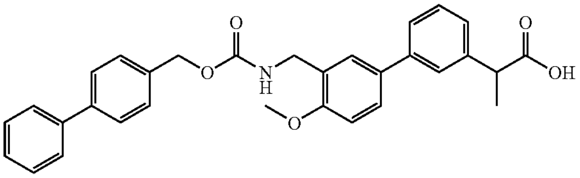

The title compound was obtained in the same way as Example 331 except for using 4-phenylbenzyl alcohol.

MS m/e (ESI) 518 ($MNa^+$).

Example 348

2-(3'-{[2-(4-Chlorophenyl)ethoxycarbonylamino]methyl}-4'-methoxybiphenyl-3-yl)propionic Acid

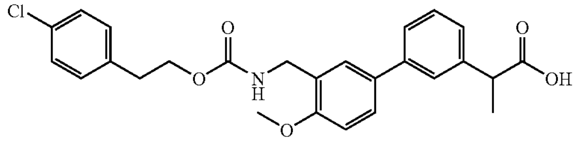

The title compound was obtained in the same way as Example 331 except for using 2-(4-chlorophenyl)ethanol.

MS m/e (ESI) 490 ($MNa^+$).

Example 349

2-(3'-{[2-(3-Chlorophenyl)ethoxycarbonylamino]methyl}-4'-methoxybiphenyl-3-yl)propionic Acid

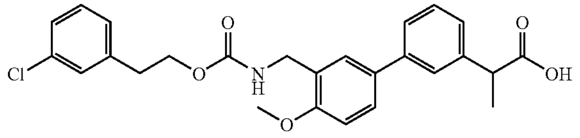

The title compound was obtained in the same way as Example 331 except for using 2-(3-chlorophenyl)ethanol.

MS m/e (ESI) 490 ($MNa^+$).

Example 350

2-(3'-{[2-(2,4-Dichlorophenyl)ethoxycarbonylamino]methyl}-4'-methoxybiphenyl-3-yl)propionic Acid

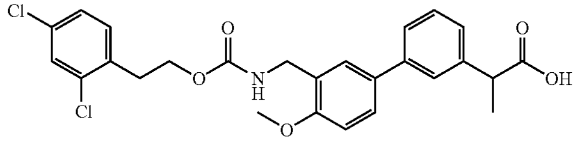

The title compound was obtained in the same way as Example 331 except for using 2-(2,4-dichlorophenyl)ethanol.

MS m/e (ESI) 524 ($MNa^+$).

Example 351

{4'-Methoxy-3'-[3-(4-trifluoromethylphenoxy)1-propynyl]biphenyl-3-yl}acetic Acid Production Example 351a 2-Benzyloxy-4-bromophenol

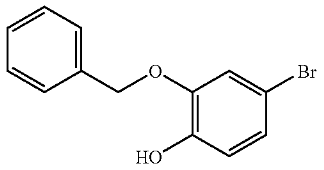

12 g of 2-Benzyloxyphenol was dissolved in 300 ml of acetonitrile, 10.7 g of N-bromosuccinimide was added thereto, and the mixture was stirred at room temperature for 2 hours. Additional N-bromosuccinimide (1 g) was added thereto and the mixture was stirred for 1 hour, and further additional N-bromosuccinimide (1 g) was added thereto and the mixture was stirred for 2 hours. The reaction mixture was concentrated, and the residue was diluted with ethyl acetate and washed with water. The organic layer was dried over anhydrous magnesium sulfate and then filtered, and the filtrate was concentrated. The residue was purified by silica gel column chromatography, to give 14.927 g of the title compound in the 10:1 hexane-ethyl acetate fraction.

$^1H$-NMR ($CDCl_3$).

δ: 5.08 (s, 2H) 5.60 (s, 1H) 6.82 (d, J=8.0 Hz, 1H) 7.01 (dd, J=2.4, 8.4 Hz, 1H) 7.06 (d, J=2.4 Hz, 1H) 7.36-7.42 (m, 5H).

Production Example 351b

2-Benzyloxy-4-bromo-1-methoxybenzene

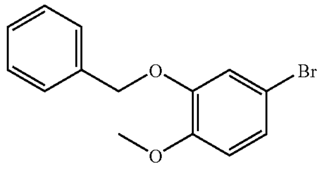

5.012 g of 2-Benzyloxy-2-bromophenol was dissolved in 50 ml of N,N-dimethylformamide, then 3.3 g of of potassium carbonate and 2 ml of methyl iodide were added thereto, and the mixture was stirred at room temperature for 3 hours. The reaction mixture was diluted with ethyl acetate and washed with water. The organic layer was dried over anhydrous magnesium sulfate and then filtered, and the filtrate was concentrated to give 4.86 g of the title compound.

Production Example 351c

2-Benzyloxy-1-methoxybenzeneboronic acid

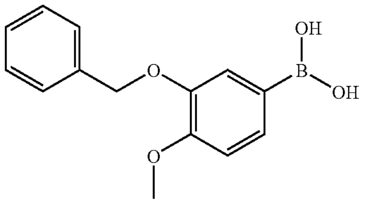

4.86 g of 2-Benzyloxy-4-bromo-1-methoxybenzene was dissolved in 100 ml of anhydrous tetrahydrofuran and cooled to −78° C. in a nitrogen atmosphere. 15 ml of 1.6 M n-butyl lithium in hexane was added dropwise, and the mixture was stirred for 30 minutes. 6 ml of Triisopropoxy borate was added all at once, and the mixture was allowed to warm overnight at room temperature. A saturated aqueous ammonium chloride solution was added to the reaction mixture which was then extracted with ethyl acetate. The organic layer was dried over anhydrous magnesium sulfate and then filtered, and the filtrate was concentrated. The residue was dissolved in 1N aqueous sodium hydroxide and extracted with diethyl ether. The aqueous layer was neutralized with 5N hydrochloric acid and extracted with ethyl acetate. The organic layer was dried over anhydrous magnesium sulfate and then filtered, and the filtrate was concentrated to give 1.76 of the title compound.

$^1$H-NMR ($CDCl_3$).

δ: 3.76 (s, 3H) 5.04 (s, 2H) 6.93 (d, J=8.0 Hz, 1H) 7.31-7.46 (m, 6H) 7.86 (s, 1H).

Production Example 351d

Methyl (3'-benzyloxy-4'-methoxybiphenyl-3-yl)acetate

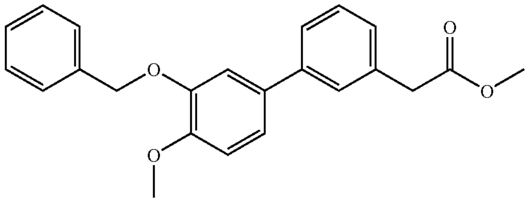

1.753 g of 2-Benzyloxy-1-methoxybenzeneboronic acid was suspended in 50 ml of diethyl ether, and 0.49 ml of propylene glycol was added thereto. The mixture was stirred at room temperature for 1 hour, and the solvent was removed to give 2-(3-benzyloxy-4-methoxyphenyl)-[1,3,2]dioxaborynane. This product was dissolved in 30 ml of 1,2-dimethoxyethane, then 1.5 g of potassium carbonate, 1.9 g of methyl 3-bromophenylacetate and 270 mg of dichlorodiphenyl phosphinoferrocene palladium were added thereto, and the mixture was stirred at 80° C. for 3 hours in a nitrogen atmosphere. The reaction mixture was neutralized with 1N hydrochloric acid and extracted with ethyl acetate. The organic layer was washed with water and dried over anhydrous magnesium sulfate and then filtered, and the filtrate was concentrated. The residue was purified by silica gel column chromatography, to give 1.356 g of the title compound in the 6:1→4:1 fraction.

$^1$H-NMR ($CDCl_3$).

δ: 3.67 (s, 2H) 3.70 (s, 3H) 3.92 (s, 3H) 5.21 (s, 2H) 6.96 (d, J=8.8 Hz, 1H) 7.15 (dd, J=2.4, 8.8 Hz, 1H) 7.22 (dt, J=2.4, 7.2 Hz, 1H) 7.33 (t, J=7.6 Hz, 1H) 7.36-7.40 (m, 5H) 7.48 (d, J=8.4 Hz, 1H).

Production Example 351e

Methyl (3'-hydroxy-4'-methoxy-biphenyl-3-yl)acetate

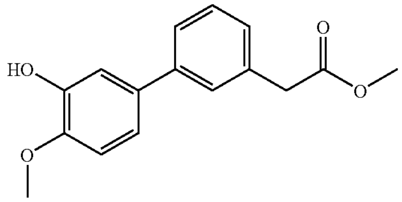

1.35 g of Methyl (3'-benzyloxy-4'-methoxybiphenyl-3-yl) acetate was dissolved in a mixed solvent of 10 ml of ethyl acetate and 30 ml of ethanol, then 500 mg of 10% palladium-carbon was added thereto, and the mixture was stirred overnight in a hydrogen atmosphere. The reaction mixture was filtered through Celite, and the filtrate was concentrated. The residue was purified by silica gel column chromatography, to give 970 mg of the title compound in the 3:1 hexane-ethyl acetate fraction.

$^1$H-NMR ($CDCl_3$).

δ: 3.67 (s, 2H) 3.70 (s, 3H) 3.93 (s, 3H) 5.65 (s, 1H) 6.91 (d, J=8.4 Hz, 1H) 7.08 (dd, J=2.4, 8.4 Hz, 1H) 7.18 (d, J=2.4 Hz, 1H) 7.22 (ddd, J=1.2, 2.0, 7.6 Hz, 1H) 7.36 (t, J=8.0 Hz, 1H) 7.43-7.46 (m, 2H).

Production Example 351f

Methyl (4'-methoxy-3'-trifluoromethanesulfonyloxy-biphenyl-3-yl)acetate

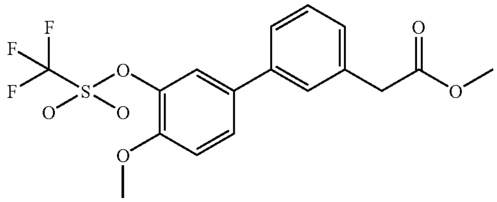

492 mg of Methyl (3'-hydroxy-4'-methoxybiphenyl-3-yl) acetate was dissolved in 5 ml of pyridine, 0.4 ml of trifluoromethanesulfonic anhydride was added thereto, and the mixture was stirred at room temperature for 3 days. The reaction mixture was diluted with ethyl acetate and washed with 1N hydrochloric acid. The organic layer was dried over anhydrous magnesium sulfate and then filtered, and the filtrate was concentrated to give 697 mg of the title compound.

Production Example 351g

Methyl [3'-(3-hydroxy-1-propynyl)-4'-methoxy-biphenyl-3-ylacetate

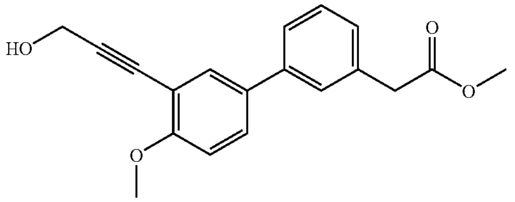

340 mg of Methyl (4'-methoxy-3'-trifluoromethanesulfonyloxybiphenyl-3-yl)acetate was dissolved in 3 ml of N,N-dimethylformamide, 100 mg of propargyl alcohol, 2.4 mg of copper iodide, 48 mg of tetrakistriphenyl phosphine palladium and 0.3 ml of triethylamine were added thereto, and the mixture was stirred at 80° C. overnight in a nitrogen atmosphere. The reaction mixture was diluted with ethyl acetate and washed with 1 N hydrochloric acid. The organic layer was dried over anhydrous magnesium sulfate and then filtered, and the filtrate was concentrated. The residue was purified by silica gel column chromatography, to give 149 mg of the title compound in the 3:2 hexane-ethyl acetate fraction.

$^{1}$H-NMR ($CDCl_3$).

δ: 2.81 (br, 1H) 3.68 (s, 2H) 3.71 (s, 3H) 3.93 (s, 3H) 4.56 (d, J=3.6 Hz, 2H) 6.94 (d, J=8.8 Hz, 1H) 7.24 (dt, J=1.6, 7.6 Hz, 1H) 7.38 (dd, J=7.6, 8.4 Hz, 1H) 7.43-7.46 (m, 2H) 7.52 (dd, J=2.0, 8.4 Hz, 1H) 7.66 (d, J=2.4 Hz, 1H).

Production Example 351h

Methyl [3'-(3-bromo-1-propynyl)-4'-methoxybiphenyl-3-ylacetate

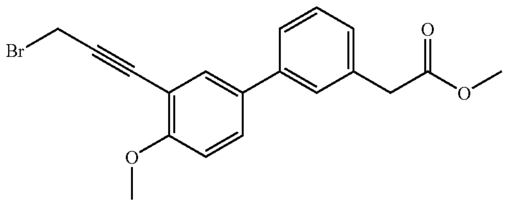

140 mg of Methyl [3'-(3-hydroxy-1-propynyl)-4'-methoxybiphenyl-3-ylacetate was dissolved in 3 ml of 1,2-dimethoxyethane, then 0.025 ml of phosphorastribromide was added thereto, and the mixture was stirred at room temperature for 3 days. The reaction mixture was diluted with ethyl acetate and washed with water. The organic layer was dried over anhydrous magnesium sulfate and then filtered, and the filtrate was concentrated. The residue was purified by silica gel column chromatography, to give 68 mg of the title compound in the 4:1 hexane-ethyl acetate fraction.

Example 351i

{4'-Methoxy-3'-[3-(4-trifluoromethylphenoxy)-1-propynyl]biphenyl-3-yl}acetic Acid

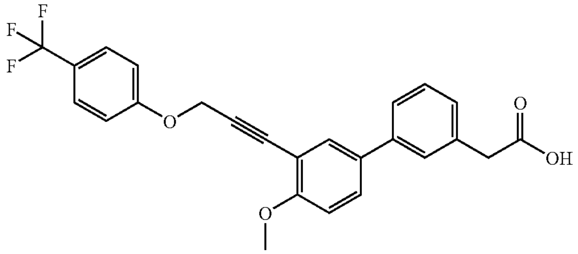

6.8 mg of Methyl [3'-(3-bromo-1-propynyl)-4'-methoxybiphenyl-3-yl acetate was dissolved in 0.2 ml of N,N-dimethylformamide, 10 mg of 4-trifluoromethylphenol and 10 mg of potassium carbonate were added thereto, and the mixture was stirred at room temperature for 3 days. The reaction mixture was diluted with ethyl acetate and washed with water. The organic layer was concentrated to give methyl {4'-methoxy-3'-[3-(4-trifluoromethylphenoxy)-1-propynyl]biphenyl-3-yl}acetate. This product was dissolved in 0.4 ml of ethanol, then 0.1 ml of 5N aqueous sodium hydroxide was added thereto, and the mixture was stirred overnight at room temperature. 1N hydrochloric acid was added to the reaction mixture which was then extracted with ethyl acetate. The organic layer was concentrated, and the residue was purified by reverse-phase high performance liquid chromatography to give 4.89 mg of the title compound.

MS m/e (ESI) 463 ($MNa^+$).

Example 352

{4'-Methoxy-3'-[3-(4-t-butylphenoxy)-1-propynyl] biphenyl-3-yl}acetic Acid

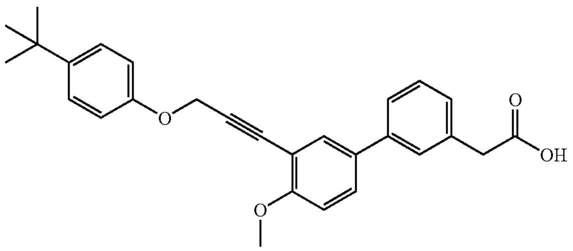

The title compound was obtained in the same way as Example 351i) except for using 4-t-butyl phenol.

MS m/e (ESI) 451 ($MNa^+$).

Example 353

{4'-Methoxy-3'-[3-(4-phenylphenoxy)-1-propynyl]biphenyl-3-yl}acetic Acid

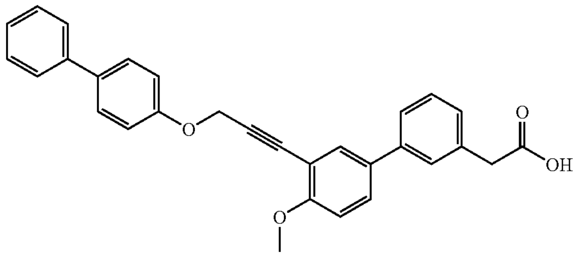

The title compound was obtained in the same way as Example 351i) except for using 4-phenyl phenol.

MS m/e (ESI) 471 ($MNa^+$).

Example 354

{4'-Methoxy-3'-[3-(4-chlorophenoxy)-1-propynyl]biphenyl-3-yl}acetic Acid

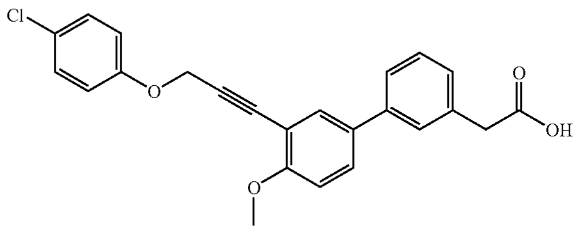

The title compound was obtained in the same way as Example 351i) except for using 4-chlorophenol.

MS m/e (ESI) 429($MNa^+$).

Example 355

{4'-Methoxy-3'-[3-(2,4-dichlorophenoxy)-1-propynyl]biphenyl-3-yl}acetic Acid

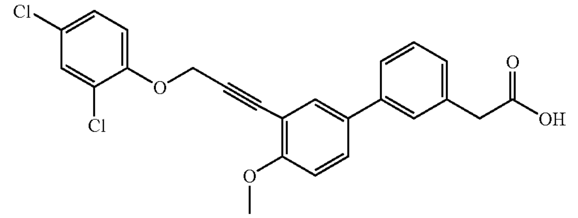

The title compound was obtained in the same way as Example 351i) except for using 4-chlorophenol.

MS m/e (ESI) 463($MNa^+$).

Example 356

{4'-Methoxy-3'-[3-(4-chloro-2-cyanophenoxy)-1-propynyl]biphenyl-3-yl}acetic Acid

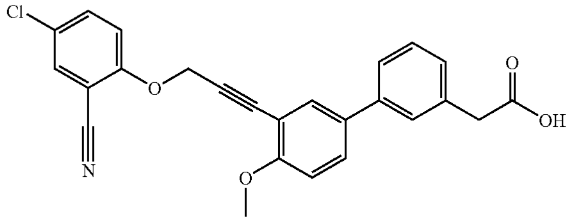

The title compound was obtained in the same way as Example 351i) except for using 4-chloro-2-cyanophenol.

MS m/e (ESI) 454($MNa^+$).

Example 357

{4'-Methoxy-3'-[3-(4-chloro-2-methylphenoxy)-1-propynyl]biphenyl-3-yl}acetic Acid

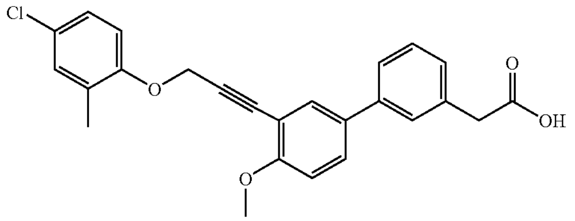

The title compound was obtained in the same way as Example 351i) except for using 4-chloro-2-methyl phenol.

MS m/e (ESI) 443($MNa^+$).

Example 358

{4'-Methoxy-3'-[3-(2-chloro-4-methylphenoxy)-1-propynyl]biphenyl-3-yl}acetic Acid

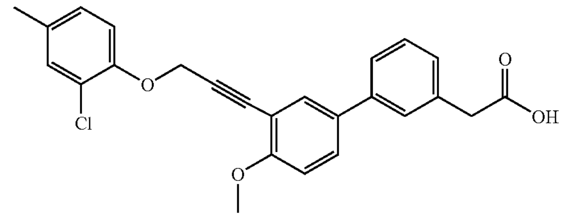

The title compound was obtained in the same way as Example 351i) except for using 2-chloro-4-methylphenol.

MS m/e (ESI) 441($MNa^+$).

Example 359

{4'-Methoxy-3'-[3-(2-trifluoromethylphenoxy)-1-propynyl]biphenyl-3-yl}acetic Acid

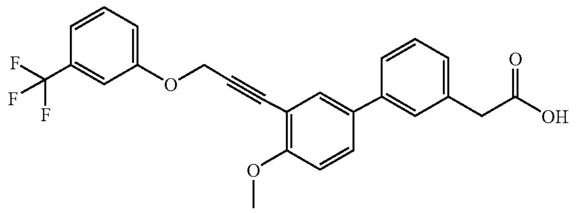

The title compound was obtained in the same way as Example 351i) except for using 3-trifluoromethyl phenol.

MS m/e (ESI) 463($MNa^+$).

Example 360

{4'-Methoxy-3'-[3-(3-chlorophenoxy)-1-propynyl]biphenyl-3-yl}acetic Acid

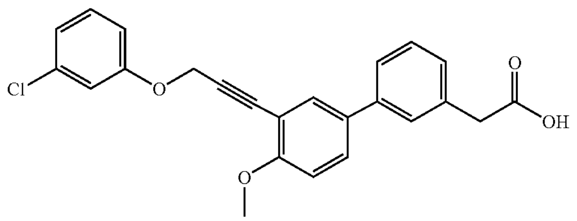

The title compound was obtained in the same way as Example 351i) except for using 3-chlorophenol.

MS m/e (ESI) 429($MNa^+$).

Example 361

{4'-Methoxy-3'-[1-(4-trifluoromethylbenzyloxy-imino)ethyl]-biphenyl-3-yl}acetic Acid Production Example 361a Methyl (3'-acetyl-4'-methoxybiphenyl-3-yl)acetate

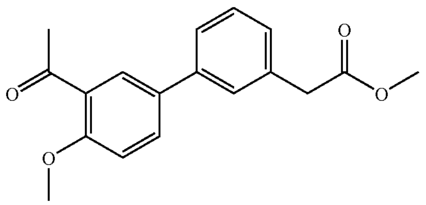

357 mg of Methyl (4'-methoxy-3'-trifluoromethanesulfonyloxybiphenyl-3-yl)acetate was dissolved in 3 ml of N,N-dimethylformamide, then 0.45 ml of butyl vinyl ether, 10 mg of palladium acetate, 20 mg of diphenyl phosphinopropane and 1 ml of triethylamine were added thereto, and the mixture was stirred at 80° C. overnight in a nitrogen atmosphere. The reaction mixture was diluted with ethyl acetate and washed with 1N hydrochloric acid. The organic layer was dried over anhydrous magnesium sulfate and then filtered, and the filtrate was concentrated. The residue was purified by silica gel column chromatography, to give 184 mg of the title compound in the 4:1 hexane-ethyl acetate fraction.

$^1H$-NMR ($CDCl_3$).

δ: 2.65 (s, 3H) 3.68 (s, 2H) 3.71 (s, 3H) 3.96 (s, 3H) 7.04 (d, J=8.4 Hz, 1H) 7.23-7.26 (m, 1H) 7.38 (t, J=8.4 Hz, 1H) 7.46-7.49 (m, 2H) 7.70 (dd, J=2.4, 8.8 Hz, 1H) 7.97 (d, J=2.4 Hz, 1H).

Production Example 361b

[3'-(1-Hydroxyiminoethyl)-4'-methoxybiphenyl-3-yl]acetic Acid

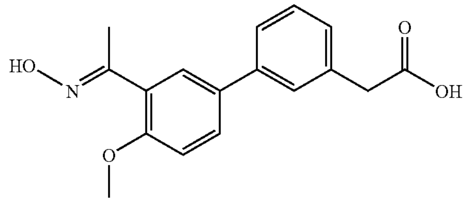

175 mg of Methyl (3'-acetyl-4'-methoxybiphenyl-3-yl)acetate was dissolved in 3 m of ethanol, then 55 mg of hydroxylamine hydrochloride and 65 mg of sodium acetate were added thereto, and the mixture was stirred at room temperature for 3 days. The reaction mixture was diluted with ethyl acetate and washed with 1N hydrochloric acid. The organic layer was dried over anhydrous magnesium sulfate and then filtered, and the filtrate was concentrated to give methyl [3'-(1-hydroxyiminoethyl)-4'-methoxybiphenyl-3-yl]acetate. This product was dissolved in 4 ml of ethanol, then 0.5 ml of 5N sodium hydroxide was added thereto, and the mixture was left at room temperature for 6 hours. The reaction mixture was neutralized with 1N hydrochloric acid and then extracted with ethyl acetate. The organic layer was dried over anhydrous magnesium sulfate and then filtered, and the filtrate was concentrated to give 166 mg of the title compound.

Example 361c

{4'-Methoxy-3'-[1-(4-trifluoromethylbenzyloxy-imino)ethyl]-biphenyl-3-yl}acetic Acid

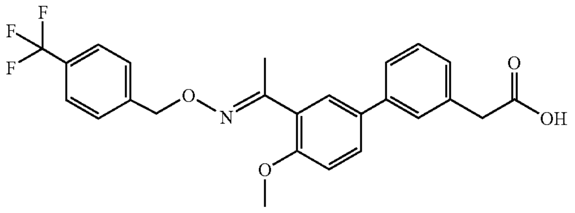

9 mg of [3'-(1-Hydroxyiminoethyl)-4'-methoxybiphenyl-3-yl]acetic acid was dissolved in 0.2 mg of tetrahydrofuran, then 25 mg of 4-trifluoromethylbenzyl bromide and 10 mg of sodium hydride were added thereto, and the mixture was stirred at room temperature for 3 days. The reaction mixture was neutralized with 1N hydrochloric acid and then extracted with ethyl acetate. The organic layer was concentrated, and the residue was purified by reverse-phase high performance liquid chromatography to give 5.21 mg of the title compound.

MS m/e (ESI) 450 ($MNa^+$).

Example 362

{4'-Methoxy-3'-[1-(3-chlorobenzyloxyimino)ethyl] biphenyl-3-yl}acetic Acid

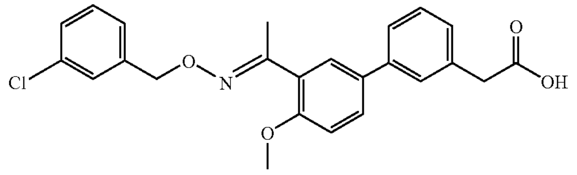

The title compound was obtained in the same way as Example 361c) except for using 3-chlorobenzyl bromide.

MS m/e (ESI) 446 ($MNa^+$).

Example 363

{4'-Methoxy-3'-[1-(3-trifluoromethylbenzyloxy-imino)ethyl]-biphenyl-3-yl}acetic Acid

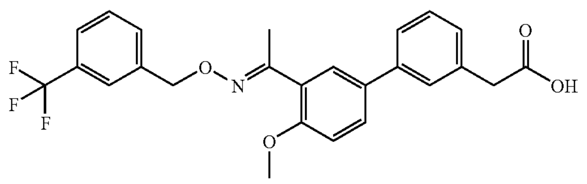

The title compound was obtained in the same way as Example 361c) except for using 3-trifluoromethylbenzylbromide.

MS m/e (ESI) 450 ($MNa^+$).

Example 364

{4'-Methoxy-3'-[1-(4-chlorobenzyloxyimino)ethyl] biphenyl-3-yl}acetic Acid

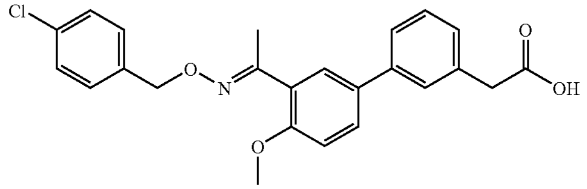

The title compound was obtained in the same way as Example 361c) except for using 4-chlorobenzyl bromide.

MS m/e (ESI) 446($MNa^+$).

Example 365

{3'-[2-Hydroxy-3-(4-t-butylphenoxy)propoxy]-4'-methoxybiphenyl-3-yl}acetic Acid

Production Example 365a

Methyl (4'-methoxy-3'-oxiranylmethoxybiphenyl-3-yl)acetate

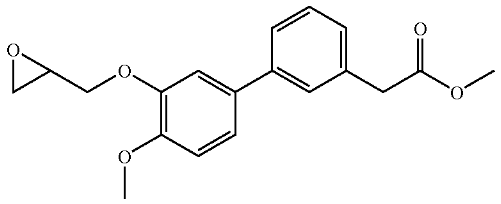

205 mg of Methyl (3'-hydroxy-4'-methoxybiphenyl-3-yl) acetate was dissolved in 3 ml of N,N-dimethylformamide, then 205 mg of glycidyl nocylate, 35 mg of cesium fluoride and 130 mg of potassium carbonate were added thereto, and the mixture was stirred at room temperature for 3 days. The reaction mixture was diluted with ethyl acetate and washed with 1N hydrochloric acid. The organic layer was dried over anhydrous magnesium sulfate and then filtered, and the filtrate was concentrated. The residue was purified by silica gel column chromatography, to give 79 mg of the title compound in the 4:1 hexane-ethyl acetate fraction.

$^1$H-NMR ($CDCl_3$).

δ: 2.77 (dd, J=2.4, 4.8 Hz, 1H) 2.92 (dd, J=4.4, 4.8 Hz, 1H) 3.40-3.45 (m, 1H) 3.69 (s, 2H) 3.71 (s, 3H) 3.91 (s, 3H) 4.11 (dd, J=5.6, 10.0 Hz, 1H) 4.32 (dd, J=2.4, 11.2 Hz, 1H) 7.65 (d, J=8.8 Hz, 1H) 7.17-7.20 (m, 2H) 7.23 (dt, J=1.2, 7.6 Hz, 1H) 7.37 (dd, J=7.6, 8.4 Hz, 1H) 7.43-7.47 (m, 2H).

Production Example 365b

{3'-[2-Hydroxy-3-(4-t-butylphenoxy)propoxy]-4'-methoxybiphenyl-3-yl}acetic Acid

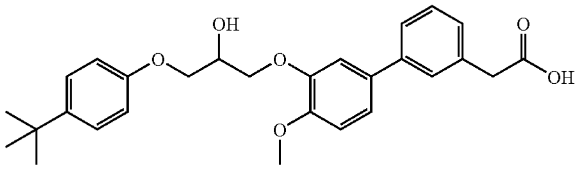

9 mg of Methyl (4'-methoxy-3'-oxiranylmethoxybiphenyl-3-yl)acetate was dissolved in 0.25 ml of ethanol, then 10 mg of 4-t-butyl phenol and 10 mg of potassium carbonate were added thereto, and the mixture was stirred at 50° C. for 3 days. The reaction mixture was diluted with ethyl acetate and washed with water. The organic layer was concentrated to give methyl-[3'-(1-hydroxyiminoethyl)-4-methoxybiphenyl-3-yl]acetate. This product was dissolved in 0.5 ml of ethanol, then 0.1 ml of 5N sodium hydroxide was added thereto, and the mixture was left overnight at room temperature. The reaction mixture was neutralized with 1 N hydrochloric acid and extracted with ethyl acetate. The organic layer was concentrated, and the residue was purified by reverse-phase high performance liquid chromatography to give 7.12 mg of the title compound.

MS m/e (ESI) 487($MNa^+$).

Example 366

{3'-[2-Hydroxy-3-(4-phenylphenoxy)propoxy]-4'-methoxybiphenyl-3-yl}acetic Acid

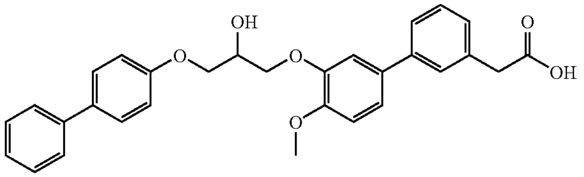

The title compound was obtained in the same way as Example 370b) except for using 4-phenyl phenol.

MS m/e (ESI) 507(MNa$^+$).

Example 367

{3'-[2-Hydroxy-3-(4-chlorophenoxy)propoxy]-4'-methoxybiphenyl-3-yl}acetic Acid

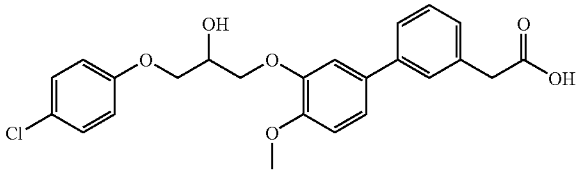

The title compound was obtained in the same way as Example 365b) except for using 4-chlorophenol.

MS m/e (ESI) 465(MNa$^+$).

Example 368

{3'-[2-Hydroxy-3-(2,4-dichlorophenoxy)propoxy]-4'-methoxybiphenyl-3-yl}acetic Acid

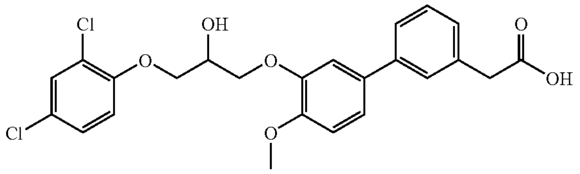

The title compound was obtained in the same way as Example 365b) except for using 2,4-dichlorophenol.

MS m/e (ESI) 499(MNa$^+$).

Example 369

{3'-[2-Hydroxy-3-(4-chloro-2-cyanophenoxy)propoxy]-4'-methoxybiphenyl-3-yl}acetic Acid

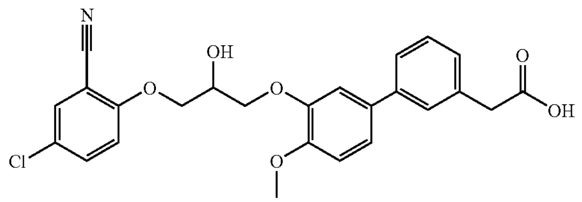

The title compound was obtained in the same way as Example 365b) except for using 4-chloro-2-cyanophenol.

MS m/e (ESI) 490(MNa$^+$).

Example 370

{3'-[2-Hydroxy-3-(4-chloro-2-methylphenoxy)propoxy]-4'-methoxybiphenyl-3-yl}acetic Acid

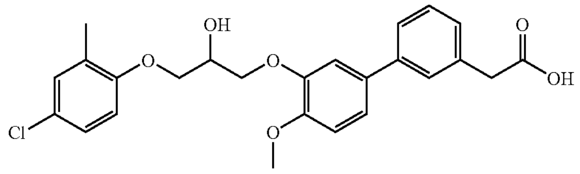

The title compound was obtained in the same way as Example 365b) except for using 4-chloro-2-methylphenol.

MS m/e (ESI) 479(MNa$^+$).

Example 371

{3'-[2-Hydroxy-3-(2-chloro-4-methylphenoxy)propoxy]-4'-methoxybiphenyl-3-yl}acetic Acid

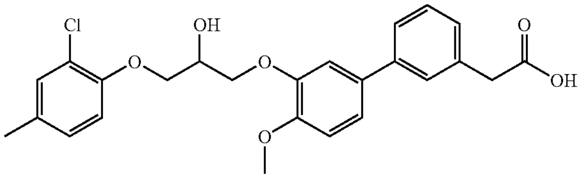

The title compound was obtained in the same way as Example 365b) except for using 2-chloro-4-methyl phenol.

MS m/e (ESI) 479(MNa$^+$).

Example 372

{3'-[2-Hydroxy-3-(3-trifluoromethylphenoxy)propoxy]-4'-methoxybiphenyl-3-yl}acetic Acid

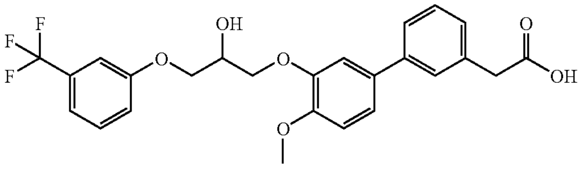

The title compound was obtained in the same way as Example 365b) except for using 3-trifluoromethyl phenol.

MS m/e (ESI) 490(MNa$^+$).

Example 373

{3'-[2-Hydroxy-3-(3-chlorophenoxy)propoxy]-4'-methoxybiphenyl-3-yl}acetic Acid

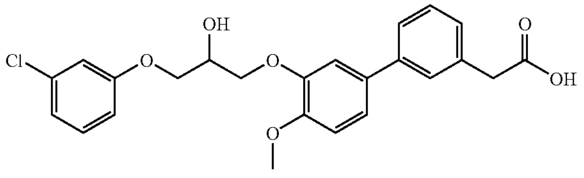

The title compound was obtained in the same way as Example 365b) except for using 3-chlorophenol.

MS m/e (ESI) 465(MNa+).

Example 374

{3'-[3-(2,4-Dichloro-phenyl)-2-propynyloxy]-4'-methoxybiphenyl-3-yl}acetic Acid

Production Example 374a

Methyl (4'-methoxy-3'-(2-propynyloxy)biphenyl-3-yl)acetate

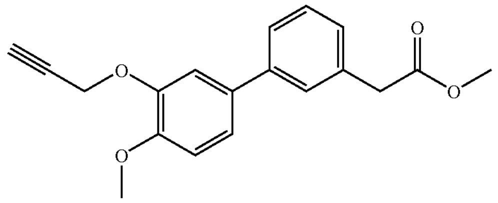

207 mg methyl (3'-hydroxy-4'-methoxybiphenyl-3-yl)acetate was dissolved in 3 ml N,N-dimethylformamide, 0.17 ml propargyl bromide and 150 mg potassium carbonate were added thereto, and the mixture was stirred at room temperature for 3 days. The reaction mixture was diluted with ethyl acetate and washed with 1 N hydrochloric acid. The organic layer was dried over anhydrous magnesium sulfate and then filtered, and the filtrate was concentrated. The residue was purified by silica gel column chromatography, to give 221 mg of the title compound in the 4:1 hexane-ethyl acetate fraction.

$^1$H-NMR ($CDCl_3$).

δ: 2.54 (s, 1H) 3.69 (s, 2H) 3.71 (s, 3H) 3.92 (s, 3H) 4.83 (d, J=2.4 Hz, 2H) 6.96 (d, J=8.4 Hz, 1H) 7.21 (dd, J=2.0, 8.4 Hz, 1H) 7.24 (brd, J=7.6 Hz, 1H) 7.28 (d, J=2.4 Hz, 1H) 7.37 (dd, J=7.6, 8.4 Hz, 1H) 7.45-7.48 (m, 2H).

Example 374b

{3'-[3-(2,4-Dichlorophenyl)-2-propynyloxy]-4'-methoxybiphenyl-3-yl}acetic Acid

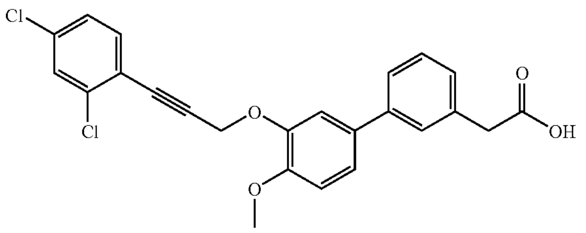

9 mg of methyl (4'-methoxy-3'-(2-propynyloxy)biphenyl-3-yl)acetate was dissolved in 0.1 ml of N,N-dimethylformamide, 30 mg of 2,4-dichloroiodobenzene, 2 mg of copper iodide, 2 mg of tetrakistriphenyl phosphine palladium and 0.05 ml of triethylamine were added thereto, and the mixture was stirred at room temperature for 3 days. The reaction mixture was diluted with ethyl acetate and washed with water. The organic layer was concentrated to give methyl {3'-[3-(2,4-dichlorophenyl)-2-propynyloxy]-4'-methoxybiphenyl-3-yl}acetate. This product was dissolved in 0.5 ml of ethanol, then 0.1 ml of 5N sodium hydroxide was added thereto, and the mixture was left overnight at room temperature. The reaction mixture was neutralized with 1N hydrochloric acid and extracted with ethyl acetate. The organic layer was concentrated, and the residue was purified by reverse-phase high performance liquid chromatography to give 4.24 mg of the title compound.

MS m/e (ESI) 463(MNa+).

Example 375

{3'-[3-(3-Trifluoromethylphenyl)-2-propynyloxy]-4'-methoxybiphenyl-3-yl}acetic Acid

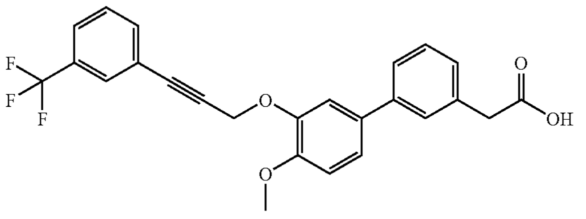

The title compound was obtained in the same way as Example 374b) except for using 3-trifluoromethyliodobenzene.

MS m/e (ESI) 463(MNa+).

Example 376

{3'-[3-(3,4-Dichlorophenyl)-2-propynyloxy]-4'-methoxybiphenyl-3-yl}acetic Acid

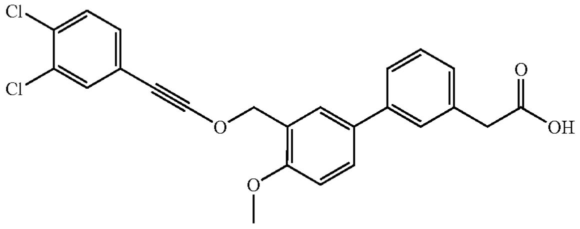

The title compound was obtained in the same way as Example 374b) except for using 3,4-dichloroiodobenzene.

MS m/e (ESI) 463(MNa+).

Example 377

{3'-[3-(4-Trifluoromethylphenyl)-2-propynyloxy]-4'-methoxybiphenyl-3-yl}acetic Acid

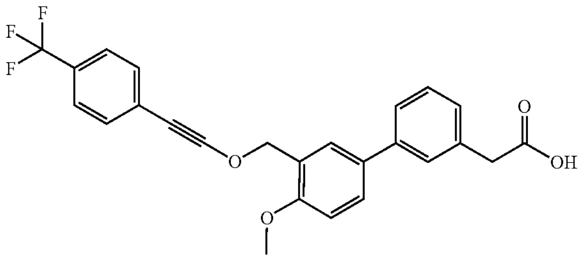

The title compound was obtained in the same way as Example 374b) except for using 4-trifluoromethyliodobenzene.

MS m/e (ESI) 463(MNa+).

Example 378

{4'-[3-(4-Trifluoromethylphenoxy)-1-propynyl]biphenyl-3-yl}acetic Acid

Production Example 378a

Methyl (4'-hydroxybiphenyl-3-yl)acetate

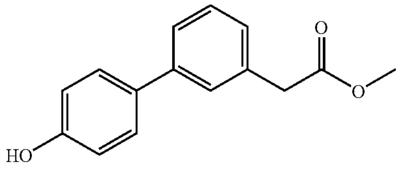

10 g of 4-(4,4,5,5-Tetramethyl-[1,3,2]dioxaborolan-2-yl) phenol and 12.5 g of methyl 3-bromophenylacetate were dissolved in 150 ml of 1,2-dimethoxyethane, then 14 g of potassium carbonate and 920 mg of dichlorodiphenyl phosphinoferrocene palladium were added thereto, and the mixture was stirred overnight at 70° C. in a nitrogen atmosphere. The reaction mixture was diluted with ethyl acetate and washed with 1N hydrochloric acid. The organic layer was dried over anhydrous magnesium sulfate and then filtered, and the filtrate was concentrated. The residue was purified by silica gel column chromatography, to give 10.336 g of the title compound in the 2:1 hexane-ethyl acetate fraction.

$^1$H-NMR ($CDCl_3$).

δ: 3.68 (s, 2H) 3.71 (s, 3H) 5.07 (s, 1H) 6.89 (d, J=8.8 Hz, 2H) 7.22 (d, J=6.0 Hz, 1H) 7.37 (t, J=8.4 Hz, 1H) 7.43-7.47 (m, 4H).

Production Example 378b

Methyl (4'-trifluoromethanesulfonyloxybiphenyl-3-yl)acetate

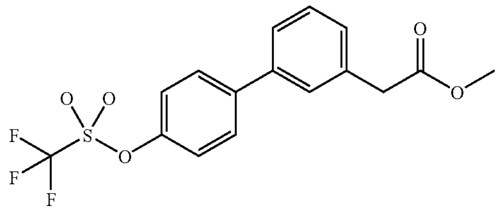

The title compound was obtained in the same way as Production Example 351f) except for using methyl (4'-hydroxybiphenyl-3-yl)acetate.

Production Example 378c

Methyl [4'-(3-hydroxy-1-propynyl)biphenyl-3-yl] acetate

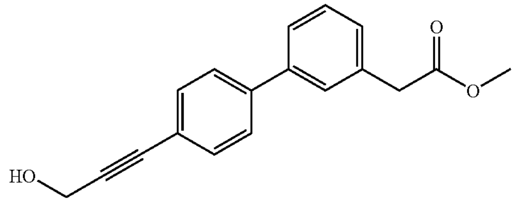

The title compound was obtained in the same way as Production Example 351g) except for using methyl (4'-trifluoromethanesulfonyloxybiphenyl-3-yl)acetate.

$^1$H-NMR ($CDCl_3$).

δ: 1.81 (br, 1H) 3.69 (s, 2H) 3.71 (s, 3H) 4.52 (d, J=5.2 Hz, 2H) 7.28 (dt, J=1.2, 7.6 Hz, 1H) 7.40 (dd, J=7.6, 8.0 Hz, 1H) 7.48-7.51 (m, 5H) 7.54 (d, J=9.2 Hz, 2H).

Production Example 378d

Methyl [4'-(3-bromo-1-propynyl)biphenyl-3-yl]acetate

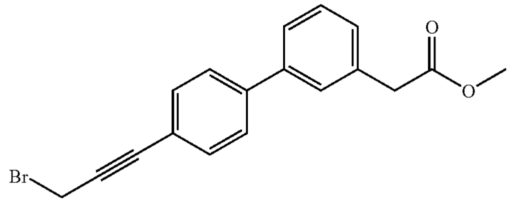

The title compound was obtained in the same way as Production Example 351h) except for using methyl [4'-(3-hydroxy-1-propynyl)biphenyl-3-yl]acetate.

Example 378e

{4'-[3-(4-Trifluoromethylphenoxy)-1-propynyl]biphenyl-3-yl}acetic Acid

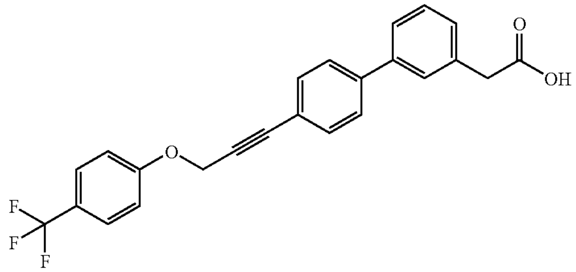

The title compound was obtained in the same way as Example 351i) except for using methyl [4'-(3-bromo-1-propynyl)biphenyl-3-yl]acetate.

MS m/e (ESI) 433($MNa^+$).

Example 379

{4'-[3-(4-t-Butylphenoxy)-1-propynyl]biphenyl-3-yl}acetic Acid

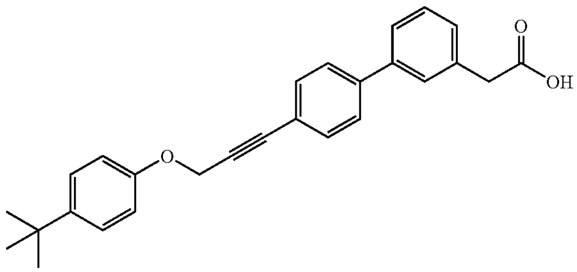

The title compound was obtained in the same way as Example 378e) except for using 4-t-butyl phenol.

MS m/e (ESI) 421($MNa^+$).

Example 380

{4'-[3-(4-Phenylphenoxy)-1-propynyl]biphenyl-3-yl}acetic Acid

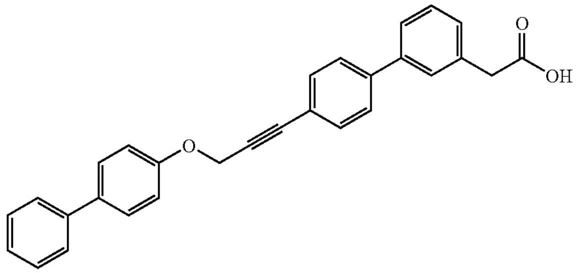

The title compound was obtained in the same way as Example 378e) except for using 4-phenylphenol.

MS m/e (ESI) 441($MNa^+$).

Example 381

{4'-[3-(4-Chlorophenoxy)-1-propynyl]biphenyl-3-yl}acetic Acid

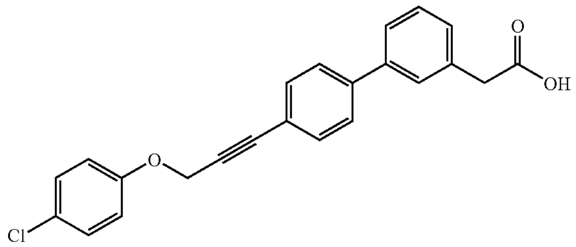

The title compound was obtained in the same way as Example 378e) except for using 4-chlorophenol.

MS m/e (ESI) 399($MNa^+$).

Example 382

{4'-[3-(2,4-Dichlorophenoxy)-1-propynyl]biphenyl-3-yl}acetic Acid

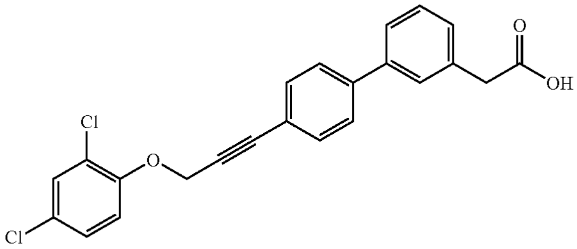

The title compound was obtained in the same way as Example 378e) except for using 2,4-dichlorophenol.

MS m/e (ESI) 433($MNa^+$).

Example 383

{4'-[3-(4-Chloro-2-cyanophenoxy)-1-propynyl]biphenyl-3-yl}acetic Acid

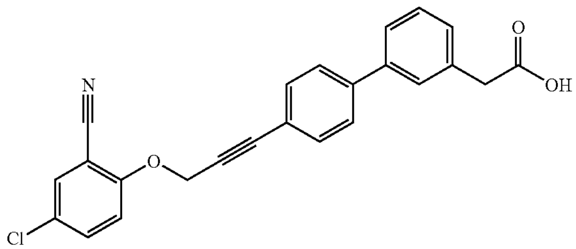

The title compound was obtained in the same way as Example 378e) except for using 4-chloro-2-cyanophenol.

MS m/e (ESI) 424($MNa^+$).

Example 384

{4'-[3-(4-Chloro-2-methylphenoxy)-1-propynyl]biphenyl-3-yl}acetic Acid

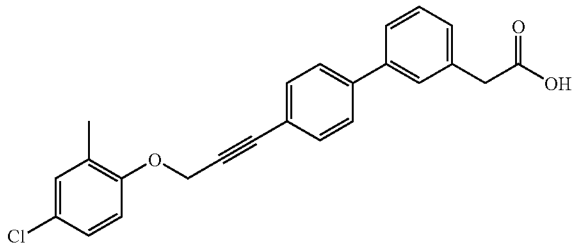

The title compound was obtained in the same way as Example 378e) except for using 4-chloro-2-methyl phenol.

MS m/e (ESI) 413(MNa$^+$).

Example 385

{4'-[3-(2-Chloro-4-methylphenoxy)-1-propynyl]biphenyl-3-yl}acetic Acid

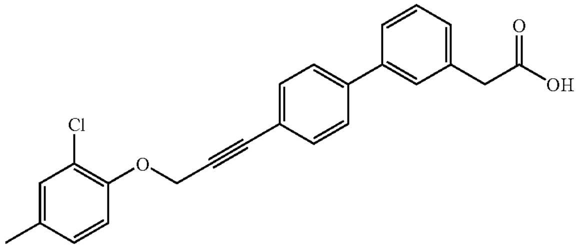

The title compound was obtained in the same way as Example 378e) except for using 2-chloro-4-methyl phenol.

MS m/e (ESI) 413(MNa$^+$).

Example 386

{4'-[3-(3-Trifluoromethylphenoxy)-1-propynyl]biphenyl-3-yl}acetic Acid

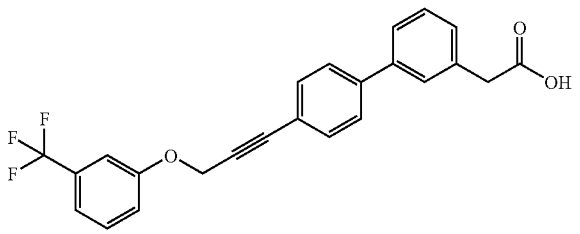

The title compound was obtained in the same way as Example 378e) except for using 3-trifluoromethyl phenol.

MS m/e (ESI) 413(MNa$^+$).

Example 387

{4'-[3-(3-Chlorophenoxy)-1-propynyl]biphenyl-3-yl}acetic Acid

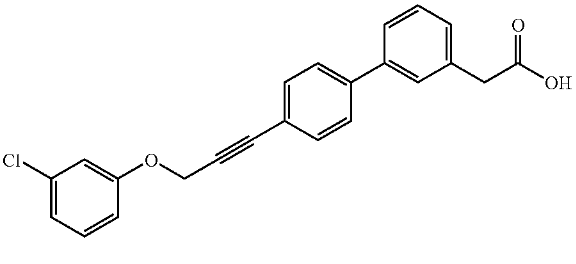

The title compound was obtained in the same way as Example 378e) except for using 3-chloro phenol.

MS m/e (ESI) 399(MNa$^+$).

Example 388

{4'-[1-(4-Trifluorobenzyloxyimino)ethyl]biphenyl-3-yl}acetic Acid

Production Example 388a

Methyl (4'-acetylbiphenyl-3-yl)acetate

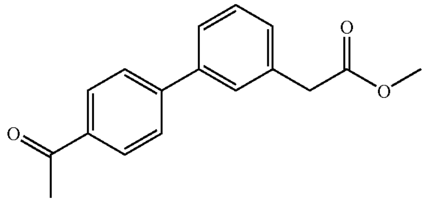

The title compound was obtained in the same way as Production Example 361a) except for using methyl (4'-trifluoromethanesulfonyloxybiphenyl-3-yl)acetate.

$^1$H-NMR ($CDCl_3$).

δ: 2.64 (s, 3H) 3.71 (s, 2H) 3.72 (s, 3H) 7.32 (d, J=7.6 Hz, 1H) 7.43 (t, J=8.0 Hz, 1H) 7.52-7.55 (m, 2H) 7.68 (d, J=8.0 Hz, 2H) 8.03 (d, J=8.4 Hz, 2H).

Production Example 388b

[4'-(1-Hydroxyiminoethyl)biphenyl-3-yl]acetic acid

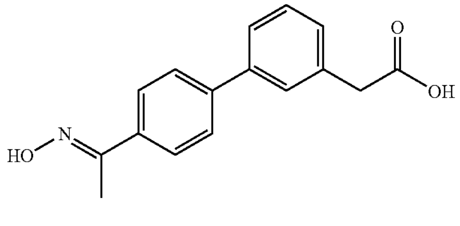

The title compound was obtained in the same way as Production Example 361b) except for using methyl (4'-acetylbiphenyl-3-yl)acetate.

Example 388c

{4'-[1-(4-Trifluoromethylbenzyloxyimino)ethyl]biphenyl-3-yl}acetic Acid

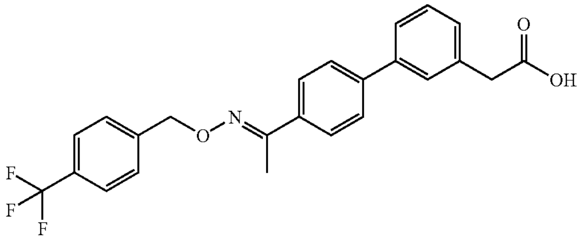

The title compound was obtained in the same way as Example 361c) except for using [4'-(1-hydroxyiminoethyl)biphenyl-3-yl]acetic acid.

MS m/e (ESI) 450 (MNa+).

Example 389

{4'-[1-(3-Chlorobenzyloxyimino)ethyl]biphenyl-3-yl}acetic Acid

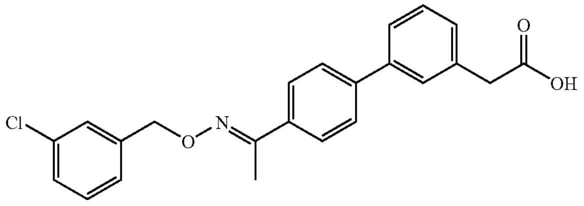

The title compound was obtained in the same way as Example 388c) except for using 3-chlorobenzyl bromide.

MS m/e (ESI) 416(MNa+).

Example 390

{4'-[1-(3-Trifluoromethylbenzyloxyimino)ethyl]biphenyl-3-yl}acetic Acid

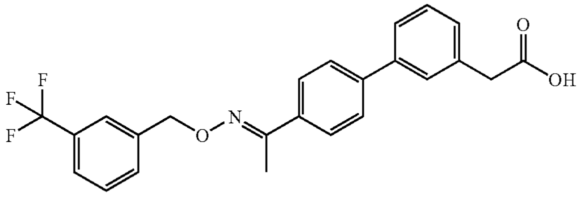

The title compound was obtained in the same way as Example 388c) except for using 3-trifluoromethylbenzylbromide.

MS m/e (ESI) 450(MNa+).

Example 391

{4'-[1-(4-Chlorobenzyloxyimino)ethyl]biphenyl-3-yl}acetic Acid

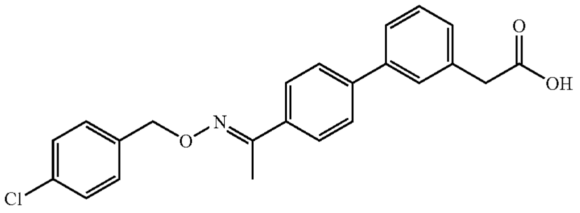

The title compound was obtained in the same way as Example 388c) except for using 4-chlorobenzyl bromide.

MS m/e (ESI) 416(MNa+).

Example 392

{4'-[1-(2-Naphthalenylmethyloxyimino)ethyl]biphenyl-3-yl}acetic Acid

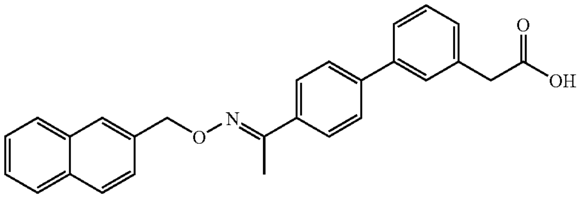

The title compound was obtained in the same way as Example 388c) except for using 2-bromomethylnaphthalene.

MS m/e (ESI) 432(MNa+).

Example 393

{4'-[1-(4-Phenylbenzyloxyimino)ethyl]biphenyl-3-yl}acetic Acid

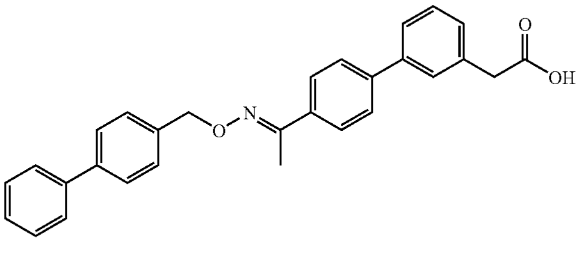

The title compound was obtained in the same way as Example 388c) except for using 4-phenyl benzyl bromide.

MS m/e (ESI) 458(MNa+).

Example 394

{4'-[1-(3,4-Dichlorobenzyloxyimino)ethyl]biphenyl-3-yl}acetic acid

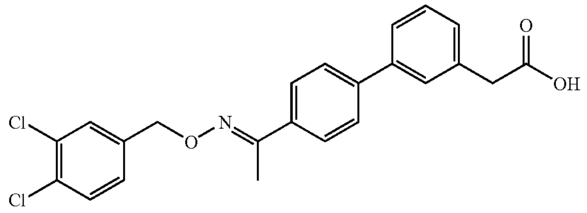

The title compound was obtained in the same way as Example 388c) except for using 3,4-dichlorobenzyl bromide.

MS m/e (ESI) 450($MNa^+$).

Example 395

{4'-[1-(2,4-Dichlorobenzyloxyimino)ethyl]biphenyl-3-yl}acetic Acid

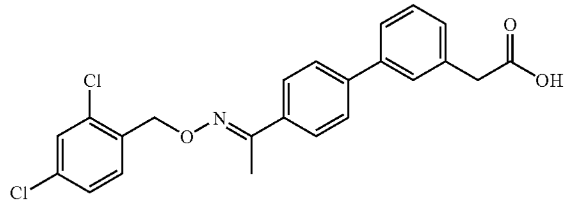

The title compound was obtained in the same way as Example 388c) except for using 2,4-dichlorobenzyl bromide.

MS m/e (ESI) 450($MNa^+$).

Example 396

{4'-[1-(4-Isopropylbenzyloxyimino)ethyl]biphenyl-3-yl}acetic Acid

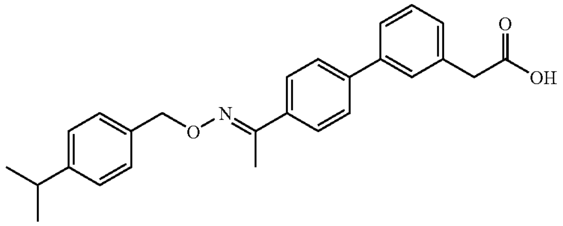

The title compound was obtained in the same way as Example 388c) except for using 4-isopropylbenzyl bromide.

MS m/e (ESI) 424($MNa^+$).

Example 397

{4'-[2-Hydroxy-3-(4-trifluoromethylphenoxy)propoxy]biphenyl-3-yl}acetic Acid

Production Example 397a

Methyl (4'-oxiranylmethoxybiphenyl-3-yl)acetate

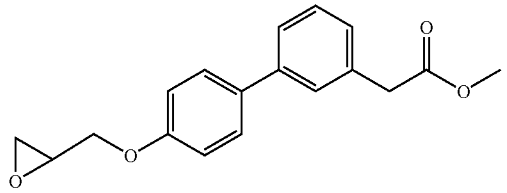

The title compound was obtained in the same way as Example 365a) except for using methyl (4'-hydroxybiphenyl-3-yl)acetate.

$^1$H-NMR ($CDCl_3$).

δ: 2.79 (dd, J=2.8, 4.8 Hz, 1H) 2.93 (dd, J=4.4, 4.8 Hz, 1H) 3.37-3.41 (m, 1H) 3.68 (s, 2H) 3.70 (s, 3H) 4.01 (dd, J=5.6, 10.8 Hz, 1H) 4.27 (dd, J=2.8, 10.8 Hz, 1H) 6.98 (d, J=9.2 Hz, 2H) 7.23 (d, J=7.2 Hz, 1H) 7.37 (t, J=7.6 Hz, 1H) 7.44-7.46 (m, 2H) 7.51 (d, J=9.6 Hz, 2H).

Production Example 397b

{4'-[2-Hydroxy-3-(4-trifluoromethylphenoxy)propoxy]biphenyl-3-yl}acetic Acid

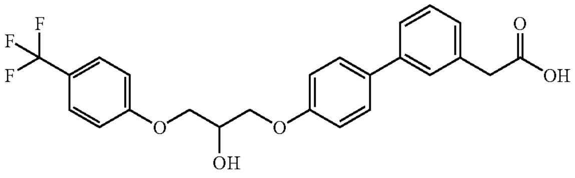

The title compound was obtained in the same way as Example 365b) except for using 4-trifluoromethyl phenol and methyl (4'-oxiranylmethoxy-biphenyl-3-yl)acetate.

MS m/e (ESI) 469($MNa^+$).

Example 398

{4'-[2-Hydroxy-3-(4-t-butylphenoxy)propoxy]biphenyl-3-yl}acetic Acid

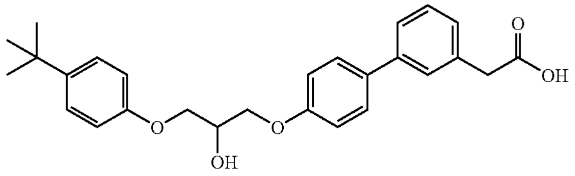

The title compound was obtained in the same way as Example 397b) except for using 4-tertiary butyl phenol MS m/e (ESI) 457($MNa^+$). .

Example 399

{4'-[2-Hydroxy-3-(4-phenylphenoxy)propoxy]biphenyl-3-yl}acetic Acid

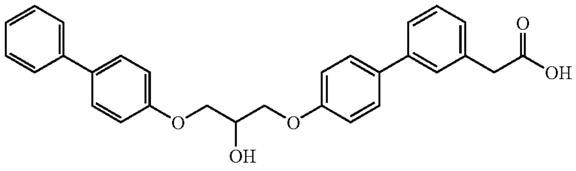

The title compound was obtained in the same way as Example 397b) except for using 4-phenyl phenol.

MS m/e (ESI) 477(MNa$^+$).

Example 400

{4'-[2-Hydroxy-3-(4-chlorophenoxy)propoxy]biphenyl-3-yl}acetic Acid

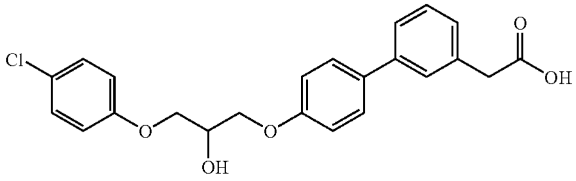

The title compound was obtained in the same way as Example 397b) except for using 4-chlorophenol.

MS m/e (ESI) 435(MNa$^+$).

Example 401

{4'-[2-Hydroxy-3-(2,4-dichlorophenoxy)propoxy]biphenyl-3-yl}acetic Acid

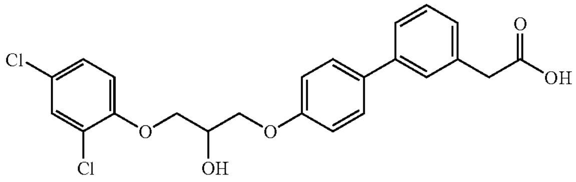

The title compound was obtained in the same way as Example 397b) except for using 2,4-dichlorophenol.

MS m/e (ESI) 469 (MNa$^+$).

Example 402

{4'-[2-Hydroxy-3-(4-chloro-2-cyanophenoxy)propoxy]biphenyl-3-yl}acetic Acid

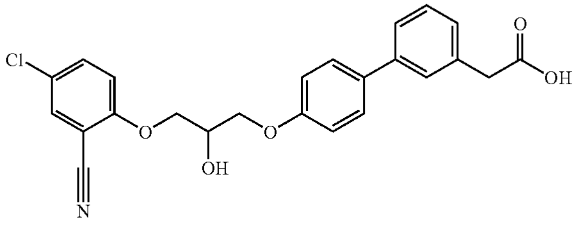

The title compound was obtained in the same way as Example 397b) except for using 4-chloro-2-cyanophenol.

MS m/e (ESI) 460(MNa$^+$).

Example 403

{4'-[2-Hydroxy-3-(4-chloro-2-methylphenoxy)propoxy]biphenyl-3-yl}acetic Acid

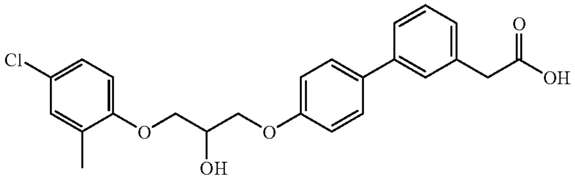

The title compound was obtained in the same way as Example 397b) except for using 4-chloro-2-methyl phenol.

MS m/e (ESI) 449(MNa$^+$).

Example 404

{4'-[2-Hydroxy-3-(2-chloro-4-methylphenoxy)propoxy]biphenyl-3-yl}acetic Acid

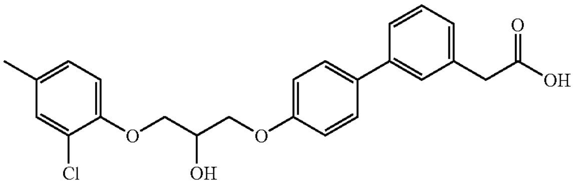

The title compound was obtained in the same way as Example 397b) except for using 2-chloro-4-methyl phenol.

MS m/e (ESI) 449(MNa$^+$).

Example 405

{4'-[2-Hydroxy-3-(3-trifluoromethylphenoxy)propoxy]biphenyl-3-yl}acetic Acid

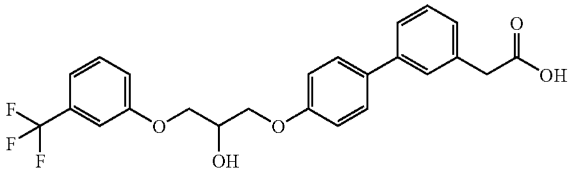

The title compound was obtained in the same way as Example 397b) except for using 3-trifluoromethyl phenol.

MS m/e (ESI) 469(MNa$^+$).

Example 406

{4'-[2-Hydroxy-3-(3-chloromethylphenoxy)propoxy] biphenyl-3-yl}acetic Acid

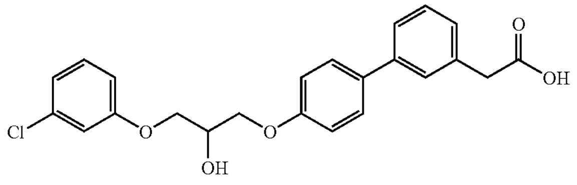

The title compound was obtained in the same way as Example 397b) except for using 3-chloro phenol.

MS m/e (ESI) 435($MNa^+$).

Example 407

{4'-[3-(2,4-Dichlorophenyl)-2-propynyloxy]biphenyl-3-yl}acetic Acid

Production Example 407a

Methyl [4'-(2-propynyloxy)biphenyl-3-yl]acetate

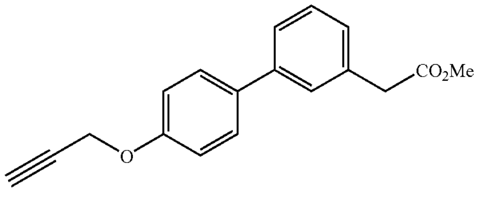

The title compound was obtained in the same way as Production Example 379a) except for using methyl (4'-hydroxybiphenyl-3-yl)acetate.

$^1$H-NMR ($CDCl_3$).

δ: 2.54 (t, J=2.4 Hz, 1H) 3.68 (s, 2H) 3.76 (s, 3H) 4.74 (d, J=2.4 Hz, 2H) 7.05 (d, J=8.8 Hz, 2H) 7.23 (dt, J=1.2, 7.2 Hz, 1H) 7.38 (t, J=8.4 Hz, 1H) 7.44-7.47 (m, 2H) 7.53 (d, J=9.2 Hz, 2H).

Example 407b

{4'-[3-(2,4-Dichlorophenyl)-2-propynyloxy]biphenyl-3-yl}acetic Acid

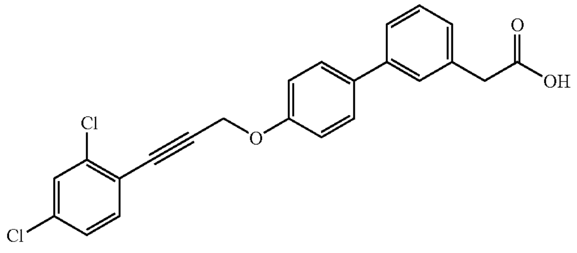

The title compound was obtained in the same way as Example 379b) except for using methyl [4'-(2-propynyloxy) biphenyl-3-yl]acetate.

MS m/e (ESI) 433($MNa^+$).

Example 408

{4'-[3-(3-Trifluoromethylphenyl)-2-propynyloxy] biphenyl-3-yl}acetic Acid

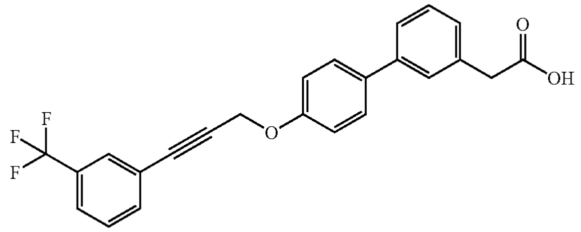

The title compound was obtained in the same way as Example 406b) except for using 3-trifluoromethyliodobenzene.

MS m/e (ESI) 433($MNa^+$).

Example 409

{4'-[3-(2-Methylphenyl)-2-propynyloxy]biphenyl-3-yl}acetic Acid

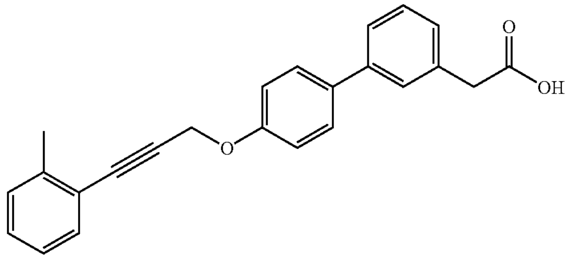

The title compound was obtained in the same way as Example 406b) except for using 2-methyliodobenzene.

MS m/e (ESI) 479($MNa^+$).

Example 410

{4'-[3-(1-Naphthalenyl)-2-propynyloxy]biphenyl-3-yl}acetic Acid

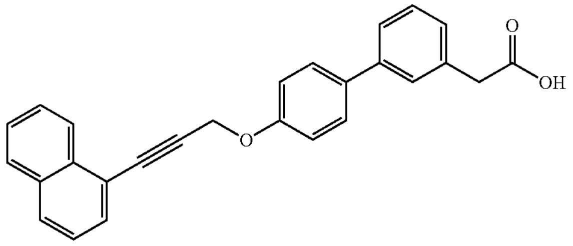

The title compound was obtained in the same way as Example 406b) except for using 1-iodonaphthalene.

MS m/e (ESI) 415($MNa^+$).

Example 411

{4'-[3-(3,4-Dichlorophenyl)-2-propynyloxy]biphenyl-3-yl}acetic Acid

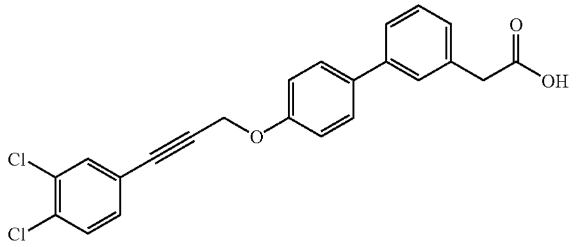

The title compound was obtained in the same way as Example 406b) except for using 3,4-dichloroiodobenzene.

MS m/e (ESI) 433(MNa$^+$).

Example 412

{4'-[3-(4-Methylphenyl)-2-propynyloxy]biphenyl-3-yl}acetic Acid

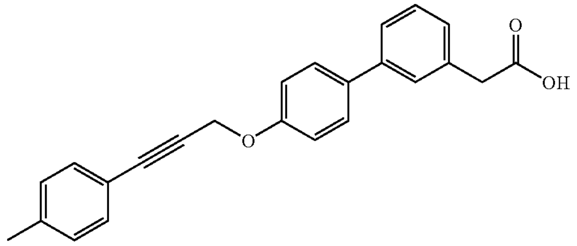

The title compound was obtained in the same way as Example 406b) except for using 4-methyliodobenzene.

MS m/e (ESI) 379(MNa$^+$).

Example 413

{4'-[3-(3-Methylphenyl)-2-propynyloxy]biphenyl-3-yl}acetic Acid

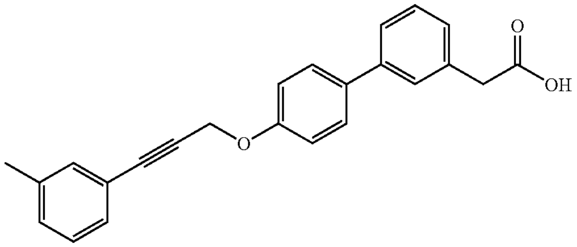

The title compound was obtained in the same way as Example 406b) except for using 3-methyliodobenzene.

MS m/e (ESI) 379(MNa$^+$).

Example 414

{4'-[3-(4-Ethoxyphenyl)-2-propynyloxy]biphenyl-3-yl}acetic Acid

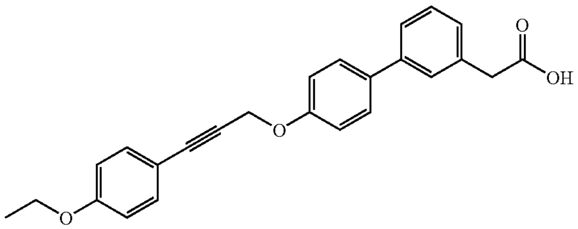

The title compound was obtained in the same way as Example 406b) except for using 4-ethoxyiodobenzene MS m/e (ESI) 409(MNa$^+$).

The invention claimed is:

1. A carboxylic acid compound represented by the formula:

(I)

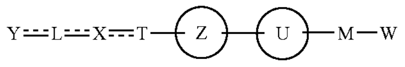

wherein L represents a single bond, a C1 to C6 alkylene group or a C2 to C6 alkynylene group; M represents a C1 to C6 alkylene group; T represents a single bond, a C1 to C3 alkylene group, or a C2 to C3 alkynylene group; W represents a carboxyl group; - - - represents a single bond; X represents an oxygen atom or a group represented by —$NR^{X1}CQ^1O$—, wherein $Q^1$ represents an oxygen atom; and $R^{X1}$ represents a hydrogen atom, —$OCQ^1NR^{X1}$, wherein $Q^1$ and $R^{X1}$ each represent the same groups as defined above, and —$CQ^1NR^{X1}$—, wherein $Q^1$ and $R^{X1}$ each represent the same groups as defined above; Y represents a 5 to 14-membered aromatic group which may have one or more substituents selected from the following substituent group and one or more hetero atoms wherein:

the substituent group is selected from the group consisting of:

a halogen atom, an alkyl group which may be substituted with 1 to 3 halogen atoms, an alkoxyl around which may be substituted with 1 to 3 halogen atoms, a C3 to C8 cycloalkyl group, a C3 to C8 cycloalkyloxy group, a methylenedioxy group, a thienyl group which is substituted with a C1 to C6 alkyl group, and a phenyl group which may be substituted with 1 to 3 halogen atoms, a C1 to C6 alkyl group or a C1 to C6 alkoxyl group;

the ring Z represents a 5 to 14-membered aromatic group which may have 1 to 4 substituent groups selected from the group consisting of a halogen atom, a hydroxyl group and a C1 to C6 alkoxyl group, and one or more hetero atoms, and the ring U represents a 5 to 14-membered aromatic group which may have 1 to 4 substituent groups selected from the group consisting of a halogen atom, a hydroxyl group, a C1 to C6 alkyl group, and a C1 to C6 alkoxyl group, and one or more hetero atoms.

2. The carboxylic acid compound according to claim 1, a wherein in the formula (I), Y is a 5 to 14-membered aromatic group which may have 1 to 4 substituents and 1 or more hetero atoms.

3. The carboxylic acid compound according to claim 1, wherein in the formula (I), L represents a single bond; X represents an oxygen atom; and T represents a C2 to C3 alkynylene group.

4. The carboxylic acid compound according to claim 1, wherein in the formula (I), L represents a C2 to C6 alkynylene group; X represents an oxygen atom; and T represents a single bond.

5. The carboxylic acid compound according to claim 1, wherein in the formula (I), X represents —$NR^{X1}CQ^1O$—, wherein $Q^1$ and $R^{X1}$ represent the same groups as defined above or —$OCQ^1NR^{X1}$, wherein $Q^1$ and $R^{X1}$ represent the same groups as defined above; L represents a single bond or C1 to C3 alkylene group; and T represents a C1 to C3 alkylene group.

6. The carboxylic acid compound according to claim 3, wherein in the formula (I), the ring U represents a phenylene group which may have 1 to 4 substituents.

7. The carboxylic acid compound according to claim 3, wherein in the formula (I), the ring Z represents a phenylene group which may have 1 to 4 substituents.

8. The carboxylic acid compound according to claim 3, wherein in the formula (I), the ring Z and the ring U each represent a 1,3-phenylene group which may have 1 to 4 substituents.

9. The carboxylic acid compound according to claim 1, wherein in the formula (I), X represents —$CQ^1NR^{X1}$, wherein $Q^1$ and $R^{X1}$ represent the same groups as defined above; L represents a single bond or a C1 to C3 alkylene group; and T represents a C1 to C3 alkylene group.

10. The carboxylic acid compound according to claim 1, wherein in the formula (I), L represents a single bond; X represents an oxygen atom; and T represents a C1 to C3 alkylene group.

11. The carboxylic acid compound according to claim 9, wherein in the formula (I), the ring U represents a phenylene group which may have 1 to 4 substituents.

12. The carboxylic acid compound according to claim 9, wherein in the formula (I), the ring Z represents a phenylene group which may have 1 to 4 substituents.

13. The carboxylic acid compound according to claim 9, wherein in the formula (I), the ring Z and the ring U each represent a 1,3-phenylene group which may have 1 to 4 substituents.

14. A medicament comprising a carboxylic acid compound represented by the formula:

(I)

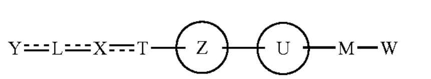

wherein L represents a single bond, C1 to C3 alkylene group, or a C2 to C6 alkynylene group; M represents a C1 to C6 alkylene group; T represents a single bond, a C1 to C3 alkylene group, or a C2 to C3 alkynylene group; W represents a carboxyl group; $\overline{---}$ represents a single bond; X represents an oxygen atom, or a group represented by —$NR^{X1}CQ^1O$—, wherein $Q^1$ represents an oxygen atom and $R^{X1}$ represents a hydrogen atom, —$OCQ^1NR^{X1}$, wherein $Q^1$ and $R^{X1}$ each represent the same groups as defined above or —$CQ^1NR^{X1}$, wherein $Q^1$ and $R^{X1}$ each represent the same groups as defined above; Y represents a 5 to 14-membered aromatic group which may have one or more substituents selected from the following substituent group and one or more hetero atoms wherein:

the substituent group is selected from the group consisting of:

a halogen atom, an alkyl group which may be substituted with 1 to 3 halogen atoms, an alkoxyl group which may be substituted with 1 to 3 halogen atoms, a C3 to C8 cycloalkyl group, a C3 to C8 cycloalkyloxy group, a methylenedioxy group, a thienyl group which is substituted with a C1 to C6 alkyl group, and a phenyl group which may be substituted with 1 to 3 halogen atoms, a C1 to C6 alkyl group or a C1 to C6 alkoxyl group;

the ring Z represents a 5 to 14-membered aromatic group which may have 1 to 4 substituent groups selected from the group consisting of a halogen atom, a hydroxyl group and a C1 to C6 alkoxyl group, and one or more hetero atoms, and the ring U represents a 5 to 14-membered aromatic group which may have 1 to 4 substituent groups selected from the group consisting of a halogen atom, a hydroxyl group, a C1 to C6 alkyl group, and a C1 to C6 alkoxyl group, and one or more hetero atoms.

15. A method of treating a disease against which an insulin sensitizing action is efficacious, which comprises administering to a patient a pharmaceutically effective amount of the carboxylic acid compound according to claim 1.

16. A pharmaceutical composition comprising a pharmacologically effective amount of the carboxylic acid compound according to claim 1, and a pharmaceutically acceptable carrier.

17. A pharmaceutical composition comprising the compound of claim 14 and additional pharmaceutically acceptable ingredients selected from the group consisting of fillers, binders, lubricants, coloring agents, flavoring agents, stabilizers, emulsifiers, absorption promoters, surfactants and other known pharmaceutical adjuvants.

18. A method of treating diabetes mellitus comprising administering to a patient a pharmaceutically effective amount of the pharmaceutical composition of claim 17.

19. A method of treating syndrome X comprising administering to a patient a pharmaceutically effective amount of the pharmaceutical composition of claim 17.

20. A method of treating hyperlipemia comprising administering to a patient a pharmaceutically effective amount of the pharmaceutical composition of claim 17.

21. A method of treating obesity comprising administering to a patient a pharmaceutically effective amount of the pharmaceutical composition of claim 17.

22. A composition according to claim 17, wherein the medicament compound is present in an amount effective to act as an insulin sensitizer.

23. A composition according to claim 17, wherein the medicament compound is present in an amount effective to act as a lipid-lowering agent.

24. A carboxylic acid compound according to claim 1, wherein Y represents furyl, thienyl, isoxazolyl, thiazolyl, phenyl or pyridyl which may have 1 to 4 substituents selected from the group consisting of a halogen atom, C1 to C6 alkyl, trifluoromethyl, C1 to C6 alkoxy, trifluoromethoxy, C3 to C6 cycloalkyl, C3 to C6 cycloalkyloxy, thienyl and phenyl which may be substituted with 1 to 3 halogen atoms a C1 to C6 alkyl group or a C1 to C6 alkoxy group;

the ring Z represents furan, thiophene, thiazole, benzene, pyridine or 2,3-dihydrobenzofuran which may have one to four substituents selected from the group consisting of halogen and C1 to C6 alkoxy, and the ring U represents furan, thiophene, thiazole, benzene, pyridine or 2,3-dihydrobenzofuran which may have one to four substituents selected from the group consisting of halogen, C1 to C6 alkyl and C1 to C6 alkoxy.

25. A carboxylic acid compound according to claim 14, wherein Y represents furyl, thienyl, isoxazolyl, thiazolyl, phenyl or pyridyl which may have 1 to 4 substituents selected from the group consisting of a halogen atom, C1 to C6 alkyl, trifluoromethyl, C1 to C6 alkoxy, trifluoromethoxy, C3 to C6 cycloalkyl, C3 to C6 cycloalkyloxy, thienyl and phenyl which may be substituted with 1 to 3 halogen atoms a C1 to C6 alkyl group or a C1 to C6 alkoxy group;

the ring Z represents furan, thiophene, thiazole, benzene, pyridine or 2,3-dihydrobenzofuran which may have one to four substituents selected from the group consisting of halogen, C1 to C6 alkyl and C1 to C6 alkoxy, and the ring U represents furan, thiophene, thiazole, benzene, pyridine or 2,3-dihydrobenzofuran which may have one to four substituents selected from the group consisting of halogen, C1 to C6 alkyl and C1 to C6 alkoxy.

* * * * *